US012790339B2

(12) United States Patent
Kawas et al.

(10) Patent No.: US 12,790,339 B2
(45) Date of Patent: Nov. 10, 2026

(54) BICYCLIC COMPOUNDS AND USES THEREOF FOR THE TREATMENT OF DISEASES

(71) Applicant: LeonaBio, Inc., Bothell, WA (US)

(72) Inventors: Leen Kawas, Lynnwood, WA (US); Kevin Church, Mountlake Terrace, WA (US); Robert Taylor, Seattle, WA (US); Jewel Johnston, Seattle, WA (US); Douglas Boatman, Portland, OR (US)

(73) Assignee: LeonaBio, Inc., Bothell, WA (US)

( * ) Notice: Subject to any disclaimer, the term of this patent is extended or adjusted under 35 U.S.C. 154(b) by 637 days.

(21) Appl. No.: 18/032,918

(22) PCT Filed: Nov. 1, 2021

(86) PCT No.: PCT/US2021/057563

§ 371 (c)(1),
(2) Date: Apr. 20, 2023

(87) PCT Pub. No.: WO2022/094400

PCT Pub. Date: May 5, 2022

(65) Prior Publication Data

US 2024/0025903 A1 Jan. 25, 2024

Related U.S. Application Data

(60) Provisional application No. 63/108,660, filed on Nov. 2, 2020.

(51) Int. Cl.
*C07D 487/04* (2006.01)
*A61P 25/28* (2006.01)

(52) U.S. Cl.
CPC ............ *C07D 487/04* (2013.01); *A61P 25/28* (2018.01)

(58) Field of Classification Search
CPC ............................ C07D 487/04; A61K 31/519
See application file for complete search history.

(56) References Cited

U.S. PATENT DOCUMENTS

| | | | |
|---|---|---|---|
| 4,477,440 | A | 10/1984 | Boger et al. |
| 4,639,456 | A | 1/1987 | Trouet et al. |
| 5,180,816 | A | 1/1993 | Dean |
| 5,378,691 | A | 1/1995 | Raddatz et al. |
| 5,382,569 | A | 1/1995 | Cody et al. |
| 5,430,062 | A | 7/1995 | Cushman et al. |
| 5,484,811 | A | 1/1996 | Hanson et al. |
| 5,484,812 | A | 1/1996 | Hanson et al. |
| 5,618,652 | A | 4/1997 | Ueda et al. |
| 5,661,129 | A | 8/1997 | Feelisch et al. |
| 5,686,419 | A | 11/1997 | Powers et al. |
| 5,763,576 | A | 6/1998 | Powers |
| 5,789,383 | A | 8/1998 | Wirth et al. |
| 5,817,757 | A | 10/1998 | Adams et al. |
| 5,831,004 | A | 11/1998 | Campbell et al. |
| 5,840,698 | A | 11/1998 | Campbell et al. |
| 5,854,388 | A | 12/1998 | Harding et al. |
| 6,013,458 | A | 1/2000 | Kahn et al. |
| 6,022,696 | A | 2/2000 | Harding et al. |
| 6,121,489 | A | 9/2000 | Dorner et al. |
| 6,184,223 | B1 | 2/2001 | Kahn et al. |
| 6,242,563 | B1 | 6/2001 | Dong |
| 6,348,570 | B1 | 2/2002 | Chapman et al. |
| 6,468,977 | B1 | 10/2002 | Karimian et al. |
| 6,867,192 | B1 | 3/2005 | Armour et al. |
| 7,118,747 | B2 | 10/2006 | Harding et al. |
| 7,795,378 | B2 | 9/2010 | Sharma et al. |
| 7,879,898 | B1 | 2/2011 | He |
| 7,910,555 | B2 | 3/2011 | Harding et al. |
| 7,981,862 | B2 | 7/2011 | Zamora et al. |
| 8,236,761 | B2 | 8/2012 | Harding et al. |
| 8,450,481 | B2 | 5/2013 | Masliah et al. |
| 8,598,118 | B2 | 12/2013 | Harding et al. |
| 9,051,351 | B2 | 6/2015 | Harding et al. |
| 9,066,901 | B2 | 6/2015 | Harding et al. |
| 9,150,613 | B2 | 10/2015 | Harding et al. |
| 9,475,854 | B2 | 10/2016 | Coffin et al. |
| 9,611,297 | B1 | 4/2017 | Leger et al. |
| 9,765,099 | B2 | 9/2017 | McMurray et al. |
| 9,877,898 | B2 | 1/2018 | Moszner et al. |
| 9,962,388 | B2 | 5/2018 | Ding et al. |
| 9,969,719 | B2 | 5/2018 | Ding et al. |
| 10,385,080 | B2 | 8/2019 | McMurray et al. |
| 10,526,320 | B2 | 1/2020 | Yuan et al. |
| 10,597,398 | B2 | 3/2020 | Shiota et al. |
| 2001/0046668 | A1 | 11/2001 | Levine et al. |

(Continued)

FOREIGN PATENT DOCUMENTS

| | | | |
|---|---|---|---|
| CA | 2016355 | A1 | 11/1990 |
| CA | 2075662 | A1 | 2/1993 |

(Continued)

OTHER PUBLICATIONS

STN CAS Registry Database Entry for 2089298-25-7, date entered STN: Apr. 11, 2017 (1 page).*
Athira Pharma Press Release, "Athira Pharma Announces Topline Results from Phase 2/3 LIFT-AD Clinical Trial of Fosgonimeton for Mild-to-Moderate Alzheimer's Disease", Sep. 3, 2024, 3 pages.
Athira Pharma Press Release, "Athira Pharma to Focus on Advancement of ATH-1105 for the Treatment of Neurodegenerative Diseases", Sep. 17, 2024, 2 pages.
Blasco, H., et al., "The Glutamate Hypothesis in ALS: Pathophysiology and Drug Development", Current Medicinal Chemistry, 2014, 21, 3551-3575 (25 pgs).
Brooks, B., et al., "El Escorial revisited: Revised criteria for the diagnosis of amyotrophic lateral sclerosis", Amyotrophic Lateral Sclerosis and Other Motor Neuron Disorders, 1:5, 200, 293-299 (8 pgs).

(Continued)

*Primary Examiner* — Sahar Javanmard
(74) *Attorney, Agent, or Firm* — McNeill PLLC

(57) ABSTRACT

Provided herein are compounds and compositions thereof for modulating hepatocyte growth factors. In some embodiments, the compounds and compositions are provided for treatment of diseases, including neurological disorders.

24 Claims, No Drawings

(56) References Cited

U.S. PATENT DOCUMENTS

| | | | |
|---|---|---|---|
| 2004/0001801 | A1 | 1/2004 | Madison et al. |
| 2004/0029868 | A1 | 2/2004 | Kahn et al. |
| 2005/0209256 | A1 | 9/2005 | Andres et al. |
| 2005/0238993 | A1 | 10/2005 | Watanabe et al. |
| 2005/0250780 | A1 | 11/2005 | Qabar et al. |
| 2006/0063803 | A1 | 3/2006 | Ruggeri et al. |
| 2006/0172952 | A1 | 8/2006 | Powers et al. |
| 2006/0233748 | A1 | 10/2006 | Merzouk et al. |
| 2006/0241057 | A1 | 10/2006 | Powers et al. |
| 2007/0116669 | A1 | 5/2007 | Merzouk et al. |
| 2007/0117821 | A1 | 5/2007 | Ding et al. |
| 2007/0160574 | A1 | 7/2007 | Merzouk et al. |
| 2008/0293634 | A1 | 11/2008 | Harding et al. |
| 2009/0048238 | A1 | 2/2009 | Aebi et al. |
| 2009/0111152 | A1 | 4/2009 | Sherman et al. |
| 2009/0186902 | A1 | 7/2009 | Merla et al. |
| 2009/0270423 | A1 | 10/2009 | Blackwell et al. |
| 2010/0228004 | A1 | 9/2010 | Prabhakaran |
| 2013/0023475 | A1 | 1/2013 | Harding et al. |
| 2013/0165392 | A1 | 6/2013 | Harding et al. |
| 2013/0178497 | A1 | 7/2013 | Koike et al. |
| 2014/0051633 | A1 | 2/2014 | Harding et al. |
| 2014/0051706 | A1 | 2/2014 | Kouji et al. |
| 2014/0094413 | A1 | 4/2014 | Harding et al. |
| 2014/0162937 | A1 | 6/2014 | Vaara et al. |
| 2014/0228373 | A1 | 8/2014 | Koike et al. |
| 2015/0337024 | A1 | 11/2015 | Coffin et al. |
| 2015/0357204 | A1 | 12/2015 | Ogihara et al. |
| 2016/0009763 | A1 | 1/2016 | Lin et al. |
| 2016/0074400 | A1 | 3/2016 | Kahn et al. |
| 2016/0122386 | A1 | 5/2016 | Wisniewski et al. |
| 2017/0022149 | A1 | 1/2017 | Nguyen |
| 2017/0196830 | A1 | 7/2017 | Shanahan et al. |
| 2018/0000897 | A1 | 1/2018 | Rusanescu |
| 2018/0072717 | A1 | 3/2018 | Liu et al. |
| 2018/0291063 | A1 | 10/2018 | Cai et al. |
| 2018/0340008 | A1 | 11/2018 | Bassiri et al. |
| 2019/0055249 | A1 | 2/2019 | Shiota et al. |
| 2025/0041307 | A1 | 2/2025 | Kawas et al. |

FOREIGN PATENT DOCUMENTS

| | | | |
|---|---|---|---|
| CN | 102838523 | A | 12/2012 |
| CN | 104788537 | A | 7/2015 |
| CN | 108117582 | A | 6/2018 |
| DE | 3320175 | A1 | 12/1984 |
| DE | 3915361 | A1 | 11/1990 |
| DE | 4122885 | A1 | 1/1993 |
| DE | 4321306 | A1 | 1/1995 |
| DE | 19914474 | A1 | 10/1999 |
| DE | 10305885 | A1 | 8/2004 |
| EP | 0163237 | A2 | 4/1988 |
| EP | 0126974 | A1 | 6/1988 |
| EP | 0355065 | A1 | 2/1990 |
| EP | 0393445 | A2 | 10/1990 |
| EP | 0412350 | A2 | 3/1992 |
| EP | 0497366 | A2 | 8/1992 |
| EP | 0457195 | A2 | 11/1992 |
| EP | 0498940 | A2 | 1/1993 |
| EP | 0528487 | A2 | 2/1993 |
| EP | 0519748 | A2 | 5/1993 |
| EP | 0547699 | A1 | 6/1993 |
| EP | 0600832 | A1 | 6/1994 |
| EP | 0661058 | A1 | 7/1995 |
| EP | 0731107 | A1 | 9/1996 |
| EP | 1059302 | A1 | 12/2000 |
| EP | 0443429 | A1 | 6/2002 |
| EP | 0987251 | A1 | 5/2004 |
| EP | 1947085 | A1 | 7/2008 |
| EP | 1932852 | A1 | 10/2008 |
| EP | 1867667 | A1 | 10/2012 |
| EP | 2746262 | A1 | 6/2014 |
| EP | 3150207 | A1 | 4/2017 |
| EP | 3345917 | A1 | 7/2018 |
| EP | 3366687 | A1 | 8/2018 |
| FR | 2778406 | A1 | 5/2003 |
| GB | 2292149 | A | 2/1996 |
| GB | 2324529 | A | 10/1998 |
| JP | 05117169 | A | 5/1993 |
| JP | 05178890 | A | 7/1993 |
| JP | 06192199 | A | 7/1994 |
| JP | 08262673 | A | 10/1996 |
| JP | 2000250182 | A | 9/2000 |
| JP | 2002145898 | A | 5/2002 |
| JP | 2006513221 | A | 4/2006 |
| JP | 2007524598 | A | 8/2007 |
| JP | 2007530003 | A | 11/2007 |
| JP | 2008514636 | A | 5/2008 |
| JP | 2014511858 | A | 5/2014 |
| JP | 2015151458 | A | 8/2015 |
| TW | 201825493 | A | 7/2018 |
| WO | 8704349 | A1 | 7/1987 |
| WO | 9005531 | A1 | 5/1990 |
| WO | 9213952 | A1 | 8/1992 |
| WO | 9220706 | A1 | 11/1992 |
| WO | 9221361 | A1 | 12/1992 |
| WO | 9312076 | A1 | 6/1993 |
| WO | 9314777 | A1 | 8/1993 |
| WO | 9316710 | A1 | 9/1993 |
| WO | 9323357 | A1 | 11/1993 |
| WO | 94000492 | | 1/1994 |
| WO | 9406451 | A1 | 3/1994 |
| WO | 9414817 | A1 | 7/1994 |
| WO | 9422491 | A1 | 10/1994 |
| WO | 9422906 | A1 | 10/1994 |
| WO | 9428012 | A1 | 12/1994 |
| WO | 9513289 | A1 | 5/1995 |
| WO | 9616079 | A2 | 5/1996 |
| WO | 9633209 | A1 | 10/1996 |
| WO | 9633268 | A1 | 10/1996 |
| WO | 9640204 | A1 | 12/1996 |
| WO | 9640738 | A1 | 12/1996 |
| WO | 9703093 | A1 | 1/1997 |
| WO | 9708193 | A1 | 3/1997 |
| WO | 9716410 | A1 | 5/1997 |
| WO | 9740071 | A1 | 10/1997 |
| WO | 981221 | F4 | 3/1998 |
| WO | 9812219 | A1 | 3/1998 |
| WO | 9822496 | A2 | 5/1998 |
| WO | 9827094 | A1 | 6/1998 |
| WO | 9829435 | A1 | 7/1998 |
| WO | 9931052 | A1 | 6/1999 |
| WO | 9932509 | A2 | 7/1999 |
| WO | 0005260 | A1 | 2/2000 |
| WO | 0100210 | A1 | 1/2001 |
| WO | 2001025210 | A2 | 10/2001 |
| WO | 2001079263 | A1 | 10/2001 |
| WO | 02040016 | A2 | 5/2002 |
| WO | 02055543 | A2 | 7/2002 |
| WO | 02060432 | A1 | 8/2002 |
| WO | 02092010 | A2 | 11/2002 |
| WO | 02095007 | A2 | 11/2002 |
| WO | 2003053988 | A2 | 12/2003 |
| WO | 2004005270 | A1 | 1/2004 |
| WO | 2004005324 | A2 | 3/2004 |
| WO | 2004018644 | A2 | 3/2004 |
| WO | 2004035587 | A1 | 4/2004 |
| WO | 2004072077 | A1 | 8/2004 |
| WO | 2004078778 | A3 | 11/2004 |
| WO | 2004099124 | A2 | 11/2004 |
| WO | 2005017107 | A2 | 2/2005 |
| WO | 2005039617 | A1 | 5/2005 |
| WO | 2005014623 | A2 | 9/2005 |
| WO | 2005080353 | A1 | 9/2005 |
| WO | 2005105829 | A2 | 11/2005 |
| WO | 2005113580 | A1 | 12/2005 |
| WO | 2006061714 | A2 | 6/2006 |
| WO | 2007031343 | A1 | 3/2007 |
| WO | 2007047991 | A1 | 4/2007 |
| WO | 2007048642 | A1 | 5/2007 |
| WO | 2007144196 | A2 | 12/2007 |
| WO | 2008000512 | A2 | 1/2008 |
| WO | 2008000513 | A2 | 1/2008 |
| WO | 2008005531 | A2 | 6/2008 |

(56) References Cited

FOREIGN PATENT DOCUMENTS

| | | | |
|---|---|---|---|
| WO | 2008068487 | A1 | 6/2008 |
| WO | 2007070372 | A2 | 7/2008 |
| WO | 2007144195 | A2 | 9/2008 |
| WO | 2008120098 | A2 | 10/2008 |
| WO | 2008157425 | A2 | 12/2008 |
| WO | 2009003003 | A2 | 12/2008 |
| WO | 2009003861 | A1 | 1/2009 |
| WO | 2009099677 | A2 | 8/2009 |
| WO | 2009103652 | A1 | 8/2009 |
| WO | 2009105782 | A1 | 8/2009 |
| WO | 2009114950 | A1 | 9/2009 |
| WO | 2010014179 | A1 | 2/2010 |
| WO | 2010022171 | A1 | 2/2010 |
| WO | 2010044485 | A1 | 4/2010 |
| WO | 2010039461 | A2 | 7/2010 |
| WO | 2010080605 | A1 | 7/2010 |
| WO | 2010080609 | A1 | 7/2010 |
| WO | 2010042212 | A2 | 9/2010 |
| WO | 2010138659 | A1 | 12/2010 |
| WO | 2010138685 | A1 | 12/2010 |
| WO | 2010138695 | A1 | 12/2010 |
| WO | 2010138706 | A1 | 12/2010 |
| WO | 2010138758 | A1 | 12/2010 |
| WO | 2010138652 | A1 | 1/2011 |
| WO | 2011011303 | A1 | 1/2011 |
| WO | 2011038066 | A2 | 3/2011 |
| WO | 2010151644 | A2 | 5/2011 |
| WO | 2011038061 | A2 | 7/2011 |
| WO | 2011088345 | A1 | 7/2011 |
| WO | 2011075471 | A2 | 1/2012 |
| WO | 2012020219 | A2 | 2/2012 |
| WO | 2012026988 | A2 | 3/2012 |
| WO | 2012032085 | A1 | 3/2012 |
| WO | 2012068299 | A2 | 5/2012 |
| WO | 2012115286 | A1 | 8/2012 |
| WO | 2012122422 | A2 | 9/2012 |
| WO | 2012138599 | A2 | 1/2013 |
| WO | 2013001297 | A1 | 1/2013 |
| WO | 2013063468 | A1 | 5/2013 |
| WO | 2013030569 | A2 | 6/2013 |
| WO | 2013123456 | A1 | 8/2013 |
| WO | 2013128003 | A1 | 9/2013 |
| WO | 2013152298 | A1 | 10/2013 |
| WO | 2013170113 | A1 | 11/2013 |
| WO | 2013170115 | A1 | 11/2013 |
| WO | 2013190520 | A2 | 12/2013 |
| WO | 2013170077 | A2 | 3/2014 |
| WO | 2012122420 | A2 | 4/2014 |
| WO | 2014049610 | A2 | 4/2014 |
| WO | 2014052766 | A1 | 4/2014 |
| WO | 2014067746 | A1 | 5/2014 |
| WO | 2014074789 | A1 | 5/2014 |
| WO | 2014091268 | A1 | 6/2014 |
| WO | 2014139008 | A1 | 9/2014 |
| WO | 2014143241 | A1 | 9/2014 |
| WO | 2014145090 | A1 | 9/2014 |
| WO | 2014207556 | A1 | 12/2014 |
| WO | 2014182928 | A2 | 1/2015 |
| WO | 2015023898 | A1 | 2/2015 |
| WO | 2015073769 | A1 | 5/2015 |
| WO | 2015091795 | A1 | 6/2015 |
| WO | 2015124797 | A1 | 8/2015 |
| WO | 2015166348 | A1 | 11/2015 |
| WO | 2016001319 | A1 | 1/2016 |
| WO | 2016008946 | A1 | 1/2016 |
| WO | 2016023511 | A1 | 2/2016 |
| WO | 2016049174 | A1 | 3/2016 |
| WO | 2016097405 | A1 | 6/2016 |
| WO | 2016123576 | A1 | 8/2016 |
| WO | 2016141881 | A1 | 9/2016 |
| WO | 2016150576 | A1 | 9/2016 |
| WO | 2016178979 | A1 | 11/2016 |
| WO | 2016182898 | A1 | 11/2016 |
| WO | 2017005902 | A1 | 1/2017 |
| WO | 2017106643 | A1 | 6/2017 |
| WO | 2017129331 | A1 | 8/2017 |
| WO | 2017151587 | A1 | 9/2017 |
| WO | 2017151886 | A1 | 9/2017 |
| WO | 2017172881 | A1 | 10/2017 |
| WO | 2017181004 | A1 | 10/2017 |
| WO | 2017201433 | A1 | 11/2017 |
| WO | 2017210188 | A1 | 12/2017 |
| WO | 2017210489 | A1 | 12/2017 |
| WO | 2017217855 | A1 | 12/2017 |
| WO | 2018010656 | A1 | 1/2018 |
| WO | 2018014862 | A1 | 1/2018 |
| WO | 2018035615 | A1 | 3/2018 |
| WO | 2018035617 | A1 | 3/2018 |
| WO | 2018060216 | A1 | 4/2018 |
| WO | 2018122419 | A1 | 7/2018 |
| WO | 2018136646 | A1 | 7/2018 |
| WO | 2018152633 | A1 | 8/2018 |
| WO | 2018174831 | A1 | 9/2018 |
| WO | 2019199800 | A1 | 10/2019 |
| WO | 2022094400 | A1 | 5/2022 |
| WO | 2023114456 | A1 | 6/2023 |
| WO | 2023163971 | A1 | 8/2023 |
| WO | 2023215376 | A1 | 11/2023 |
| WO | 2023215377 | A1 | 11/2023 |
| WO | 2023215378 | A1 | 11/2023 |
| WO | 2024108090 | A1 | 5/2024 |

OTHER PUBLICATIONS

Brooks, B., et al., "Intravenous edaravone treatment in ALS and survival: An exploratory, retrospective, administrative claims analysis", www.thelancet.com, vol. 52, Oct. 2022, 11 pages.

Brown, R. H., et al., "Amyotrophic Lateral Sclerosis", New England Journal of Medicine, 377(2), 2017 162-172 (12 pgs).

Buck, E., et al., "Increased NF-L levels in the TDP-43G298S Als mouse model resemble NF-L levels in ALS patients", Acta Neuropathologica (2022) 144:161-164 (4 pages).

Buratti, E., "Functional Significance of TDP-43 Mutations in Disease", Advances in Genetics, vol. 91, 2015, 53 pages.

Buratti, E., et al., "Multiple roles of TDP-43 in gene expression, splicing regulation, and human disease", Frontiers in Bioscience 13, 867-878, Jan. 1, 2008, 12 pages.

Cappello, V., et al., "Neuromuscular Junction Dismantling in Amyotrophic Lateral Sclerosis", Int. J. Mol. Sci. 2017, 16 pages.

Chu, et al: "An updated patent review of small-molecule c-Met kinase inhibitors (2018-present)", Expert Opinion on Therapeutic Patents, vol. 32, No. 3, Nov. 29, 2021 (Nov. 29, 2021), pp. 279-298, 21 pages.

Cohen, T., et al., "TDP-43 functions and pathogenic mechanisms implicated in TDP-43 proteinopathies", Trends in Molecular Medicine, Nov. 2011, vol. 17, No. 11, 9 pages.

Cruz, M., et al., "Edaravone (Radicava)—A Novel Neuroprotective Agent for the Treatment of Amyotrophic Lateral Sclerosis", P & T Drug Forecast, vol. 43, No. 1, Jan. 2018, 4 pages.

De Carvalho, M., "Electrodiagnosis of Amyotrophic Lateral Sclerosis: A Review of Existing Guidelines", Journal of Clinical Neurophysiology, vol. 37, No. 4, Jul. 2020, 5 pages.

De Carvalho, M., et al., "Electrodiagnostic criteria for diagnosis of ALS", Clinical Neurophysiology, 119 (2008), 497-503 (7 pages).

Desole, C., et al., "HGF and MET: From Brain Development to Neurological Disorders", Frontiers in Cell and Developmental Biology, Jun. 2021, 21 pages.

Doble, A., "The pharmacology and mechanism of action of riluzole", Neurology, Dec. 1996, 9 pages.

Feldman, E., et al., "Amyotrophic lateral sclerosis", www.thelancet.com, vol. 400, Oct. 15, 2022, 18 pages.

Foran, E., et al., "Glutamate Transporters and the Excitotoxic Path to Motor Neuron Degeneration in Amyotrophic Lateral Sclerosis", Antioxidants & Redox Signaling, vol. 11, No. 7, 2009, 26 pages.

Gaetani, L., et al., "Neurofilament light chain as a biomarker in neurological disorders", J Neurol Neurosurg Psychiatry, 2019, 90:870-881, 12 pages.

Gong, Z., et al., "Dysfunction of the oligodendrocytes in amyotrophic lateral sclerosis", The Journal of Biomedical Research, 2022 36(5): 336-342 (7 pages).

(56) References Cited

OTHER PUBLICATIONS

Goutman, Stephen A., et al., "Recent advances in the diagnosis and prognosis of amyotrophic lateral sclerosis", www.thelancet.com/neurology, vol. 21, May 2022, 14 pages.
Hinchcliffe, M., et al., "Riluzole: real-world evidence supports significant extension of median survival times in patients with amyotrophic lateral sclerosis", Degenerative Neurological and Neuromuscular Disease 2017:7, 10 pages.
Hulisz, D., "Amyotrophic Lateral Sclerosis: Disease State Overview", The American Journal of Managed Care® Supplement, vol. 24, No. 15, 7 pages.
Ishigaki, A., et al., "Intrathecal Delivery of Hepatocyte Growth Factor From Amyotrophic Lateral Sclerosis Onset Suppresses Disease Progression in Rat Amyotrophic Lateral Sclerosis Model", J Neuropathol Exp Neurol, vol. 66, No. 11, Nov. 2007, 8 pages.
Jankovska, N. et al., "Molecular Pathology of ALS: What We Currently Know and What Important Information Is Still Missing", Diagnostics 2021, 11, 1365; 18 pages.
Jeon G. S., et al. "Pathological Modification of TDP-43 in Amyotrophic Lateral Sclerosis with SOD1 Mutations", Molecular Neurobiology (2019) 56:2007-2021 (15 pages).
Jo, M., et al., "The role of TDP-43 propagation in neurodegenerative diseases: integrating insights from clinical and experimental studies", Official journal of the Korean Society for Biochemistry and Molecular Biology, Experimental & Molecular Medicine (2020) 52:1652-1662 (11 pages).
Kabashi, E., et al., "TARDBP mutations in individuals with sporadic and familial amyotrophic lateral sclerosis", Nature Genetics, vol. 40, No. 5, May 2008, 3 pages.
Kadoyama, K., et al., "Hepatocyte growth factor (HGF) attenuates gliosis and motoneuronal degeneration in the brainstem motor nuclei of a transgenic mouse model of ALS", Neuroscience Research 59 (2007) 446-456 (11 pages).
Kim, et al: "Solution-phase Synthesis and Preliminary Evaluation of 1,6,8-Trisubstituted Tetrahydro-2H-pyrazio[1,2-a] pyrimidin-4,7-dione Derivatives as a NF-κB Inhibitor", Bulletin of the Korean Chemical Society, vol. 27, No. 12, Dec. 20, 2006 (Dec. 20, 2006), pp. 2087-2090, 4 pages.
Ko, K. R., et al., "Hepatocyte Growth Factor (HGF) Promotes Peripheral Nerve Regeneration by Activating Repair Schwann Cells", Scientific Reports, 2018, 14 pages.
Le Gall, L., et al., "Molecular and Cellular Mechanisms Affected in ALS", J. Pers. Med. 2020, 10, 101, 34 pages.
Lee, et al., "Intrathecal delivery of recombinant AAV1 encoding hepatocyte growth factor improves motor functions and protects neuromuscular system in the nerve crush and SOD1-G93A transgenic mouse models", Acta Neuropathologica Communications (2019), 18 pages.
Lépine, et al., "TDP-43 dysregulation and neuromuscular junction disruption in amyotrophic lateral sclerosis", Translational Neurodegeneration (2022) 11:56, 24 pages.
Liu, et al., "Role of Neuroinflammation in Amyotrophic Lateral Sclerosis: Cellular Mechanisms and Therapeutic implications", Frontiers in Immunology; Aug. 2017, vol. 8, Article 1005, 12 pages.
Loeffler, et al., "Neurofilament-Light Chain as Biomarker of Neurodegenerative and Rare Diseases With High Translational Value", Frontiers in Neuroscience, vol. 14, Article 579, Jun. 2020, 7 pages.
Marin, et al., "Stratification of ALS patients' survival: a population-based study", J Neurol (2016) 263:100-111 (12 pages).
Masrori, et al., "Amyotrophic lateral sclerosis: a clinical review", European Journal of Neurology published by John Wiley & Sons Ltd on behalf of European Academy of Neurology, 2020, 12 pages.
Mead, et al., "Amyotrophic lateral sclerosis: a neurodegenerative disorder poised for successful therapeutic translation", Nature Reviews Drug Discovery, vol. 22, Mar. 2023, 185-212 (28 pages).
Miller, et al., "Riluzole for amyotrophic lateral sclerosis (ALS)/motor neuron disease (MND) (Review)", Cochrane Database of Systematic Reviews 2012, Issue 3. Art. No. CD001447, 30 pages.
Miller, et al., "Trial of Antisense Oligonucleotide Tofersen for SOD1 ALS", N Engl J Med 2022; 387:1099-110 (12 pages).
Obrador, et al., "Oxidative Stress, Neuroinflammation and Mitochondria in the Pathophysiology of Amyotrophic Lateral Sclerosis", Antioxidants 2020, 9, 901, 16 pages.
Organ, et al., "An overview of the c-MET signaling pathway", Therapeutic Advances in Medical Oncology 3 (1), http://tam.sagepub.com, 2011, 14 pages.
Paganoni, et al., "Analysis of sodium phenylbutyrate and taurursodiol survival effect in ALS using external controls", Annals of Clinical and Translational Neurology published by Wiley Periodicals LLC on behalf of American Neurological Association, 2023, 8 pages.
Paganoni, et al., "Trial of Sodium Phenylbutyrate-Taurursodiol for Amyotrophic Lateral Sclerosis", N Engl J Med 2020;383:919-30 (12 pages).
Palomo, et al., "TDP-43: A Key Therapeutic Target beyond Amyotrophic Lateral Sclerosis", ACS Chem. Neurosci. 2019, 10, 1183-1196 (14 pages).
Prasad, et al., "Molecular Mechanisms of TDP-43 Misfolding and Pathology in Amyotrophic Lateral Sclerosis", Frontiers in Molecular Neuroscience, www.frontiersin.org, vol. 12, Article 25, Feb. 2019, 36 pages.
Radicava, "Highlights of Prescribing Information", Patient Information, Mitsubishi Tanabe Pharma Corporation, Reference ID: 4094543, 2017, 11 pages.
Relyvrio, "Highlights of Prescribing Information—Full Prescribing Information", Amylyx Pharmaceuticals, Inc., 2022, 10 pages.
Eguchi, M. et al., "Solid-Phase Synthesis and Structural Analysis of Bicyclic β-Turn Mimetics Incorporating Functionality at the i to i + 3 Positions", J. Am. Chem. Soc. 1999, 121, 12204-12205, 2 pages.
Eguchi, M., et al., "Design, Synthesis, and Evaluation of Opioid Analogues with Non-Peptidic β-Turn Scaffold: Enkephalin and Endomorphin Mimetics", Journal of Medicinal Chemistry, 2002, vol. 45, No. 7 Letters, 4 pages.
International Preliminary Report on Patentability of PCT/US2021/057563 dated May 11, 2023, 7 pages.
International Search Report and Written Opinion of PCT/US2021/057563 dated Mar. 2, 2022, 10 pages.
international Search Report and Written Opinion of PCT/US2022/053113 dated Apr. 12, 2023, 10 pages.
International Search Report and Written Opinion of PCT/US2023/020830 dated Jul. 27, 2023, 14 pages.
International Search Report and Written Opinion of PCT/US2023/020832 dated Jul. 31, 2023, 12 pages.
International Search Report and Written Opinion of PCT/US2023/020833 dated Aug. 4, 2023, 15 pages.
Min, B., et al., "Synthesis of a novel benzyl-octahydropyrazino[1,2-a]pyrimidin-6-one derivative as a convenient internal bicyclic peptidomimetic", Tetrahedron Lett. Mar. 31, 2008; 49(14):2316-2319, 9 pages.
Pubchem, SID 246457262, Modify Date: Jan. 25, 2017 [retrieved on Feb. 7, 2023]., Retrieved from the Internetentire document. 6 pages.
Ueda, H., et al., "A mimetic of the mSin3-binding helix of NRSF/REST ameliorates abnormal pain behavior in chronic pain models", Bioorganic & Medicinal Chemistry Letters, vol. 27, No. 20, Oct. 15, 2017, pp. 4705-4709 (5 pages.).
Jia, Y., et al., "HGF Mediates Clinical-Grade Human Umbilical Cord-DerivedMesenchymal Stem Cells Improved Functional Recovery in aSenescence-Accelerated Mouse Model of Alzheimer's Disease", Adv Sci7, 1903809, 2020, 17 pgs.
Johnston, J.L., et al., "Fosgonimeton, a Novel Positive Modulator of the HGF/METSystem, Promotes Neurotrophic and Procognitive Effects in Models ofDementia", Neurotherapeutics, 2022, 21 pgs. Available from:https://pubmed.ncbi.nlm.nih.gov/36538176/. Accessed Mar. 23, 2023.
Kawas et al., "Development of Angiotensin IV Analogs as Hepatocyte Growth Factor/Met Modifiers," The Journal of Pharmacology and Experimental Therapeutics, vol. 340, No. 3, 2012, pp. 539-548.
Kawas et al., "Mimics of the Dimerization Domain of Hepatocyte Growth Factor Exhibit Anti-Met and Anticancer Activity," The

(56) References Cited

OTHER PUBLICATIONS

Journal of Pharmacology and Experimental Therapeutics, vol. 339, No. 2, Aug. 2011, pp. 509-518 and supplemental figures 1-3 and Erratum.
Kawas et al., "Nanoscale mapping of the Met receptor on hippocampal neurons by AFM and confocal microscopy," Nanomedicine: Nanotechnology, Biology and Medicine, vol. 9, Issue 3, Apr. 2013, pp. 428-438.
Kennedy, R., et al., "Association of Concomitant Use of Cholinesterase Inhibitorsor Memantine With Cognitive Decline in Alzheimer Clinical TrialsA Meta-analysis", JAMA Network Open, 2018, 10 pages. Downloaded From: https://jamanetwork.com/ on May 23, 2023.
Knopman, D.S., et al., "Alzheimer disease", Nat Rev Dis Primers 7, 33, 2021, 47 pgs.
Koffie, R.M., et al., "Alzheimer's disease: synapses gone cold", MolecularNeurodegeneration 6, 63, 2011, 9 pgs.
Koike, H., et al., "Prevention of onset of Parkinson's disease by in vivo gene transfer of human hepatocyte growth factor in rodent model: a model of gene therapy for Parkinson's disease", Gene Ther 13, 2006, 1639-1644 (6 pgs).
Kraska, A., et al., "In Vivo Cross-sectional Characterization of Cerebral AlterationsInduced by Intracerebroventricular Administration of Streptozotocin", Plosone 7, e46196, 2012, 9 pgs.
Kulczynska-Przybik, A., et al. "Cerebrospinal Fluid and Blood CX3CL1 as a PotentialBiomarker in Early Diagnosis and Prognosis of Dementia", Curr Alzheimer Res17, 2020, 709-721 (13 pgs.).
LeBlanc, C. A., "The Role of Apoptotic Pathways in Alzheimer's Disease Neurodegeneration and Cell Death", Current Alzheimer Research 2, 2005, 389-402 (14 pgs.).
Lewczuk, P., et al., "Plasma neurofilament light as a potential biomarker ofneurodegeneration in Alzheimer's disease", Alzheimers Res Ther 10, 71, 2018, 10 pgs.
Liu, J., et al., "The Role of NMDA Receptors in Alzheimer's Disease", Front Neurosci8, 43, 2019, 22 pgs.
Liu, X.S., et al., "Human umbilical cord mesenchymal stem cells infected withadenovirus expressing HGF promote regeneration of damaged neuron cells in aParkinson's disease model", Biomed Research International, 2014, Article ID: 909657, 7 pages.
Lloret, A., et al., "Amyloid-β toxicity and tau hyperphosphorylation are linked via RCAN1 in Alzheimer's disease", Journal of Alzheimer's disease, JAD 27, 2011, 701-9 (9 pgs.).
Maina, F., et al., "Hepatocyte growth factor, a versatile signal for developingneurons", Nature Neuroscience 2, 1999, 213-217 (5 pgs).
Mattsson, N., et al., "Association Between Longitudinal Plasma Neurofilament Lightand Neurodegeneration in Patients With Alzheimer Disease", JAMA Neurol76, 2019, 791-799 (9 pgs.).
McCoy et al., "Evaluation of Metabolically Stabilized Angiotensin IV Analogs as Procognitive/Antidementia Agents," Journal of Pharmacology and Experimental Therapeutics (Jan. 31, 2013), 344(1), pp. 141-154.
McKhann G.M., et al., "The diagnosis of dementia due to Alzheimer's disease:recommendations from the National Institute on Aging-Alzheimer'sAssociation workgroups on diagnostic guidelines for Alzheimer's disease",Alzheimers Dement 7, 2011, 263-9 (11 pgs.).
Mehta, C.R., et al., "Adaptive increase in sample size when interim resultsare promising: A practical guide with examples", Statist. Med., 30, 2000, 3267-3284 (20 pgs.).
Meraz-Rios, M.A., et al., "Inflammatory process in Alzheimer's Disease", Front IntegrNeurosci 7 (article 59), 2013, 1-15 (15 pgs).
Moebius et al., "ACT-AD: Fosgonimeton in Mild-to-Moderate Alzheimer's Disease—First Results of a Randomized, Placebo-Controlled, 26-Week, Phase 2 Proof-of-Concept Trial", 2022, 13 pages.
Moebius, et al., "The Case for a Novel Therapeutic Approach to Dementia: Small Molecule Hepatocyte Growth Factor (HGF/MET) Positive Modulators", Journal of Alzheimer's Disease 92, (2023), pp. 1-12 (12 pgs).
Moebius, H., et al., "Fosgonimeton Provides Congruent Benefit on Diverse Biomarkersof Neurodegeneration, Significantly Correlating With a CompositeClinical Score of Cognition and Function in Alzheimer's Disease", 2022, 2 pages.
Molnarfi, N., et al., "Hepatocyte growth factor: A regulator of inflammation andautoimmunity", Autoimmun Rev 14, 2015, 293-303 (12 pgs.).
Muir, J.L., "Acetylcholine, aging, and Alzheimer's disease", Pharmacol Biochem Behav56, 1997, 687-696 (10 pgs).
Nazem, A., et al., "Rodent models of neuroinflammation for Alzheimer's disease", J Neuroinflammation 12, 74, 2015, 15 pgs.
Noh, J., et al., "Kojic acid-tripeptide amide as a new tyrosinase inhibitor", Biopolymers, vol. 88, No. 2, Jan. 1, 2007 (Jan. 1, 2007), pp. 300-307, XP55649603, US ISSN: 0006-3525, DOI: 10.1002/bip.20670.
Noh, M.Y., et al., "Neuroprotective effects of donepezil through inhibition of GSK-3activity in amyloid-beta-induced neuronal cell death", J Neurochem 108, 2009, 1116-1125 (10 pgs.).
Okaichi, H., et al., "Scopolamine impairs both working and reference memory in rats: areplication and extension", Pharmacol Biochem Behav 34, 1989, 599-602 (4 pgs.).
Olichney, J.M., et al., "Predictive Power of Cognitive Biomarkers inNeurodegenerative Disease Drug Development: Utility of the P300 Event-Related Potential", Neural Plast 2104880, 2022, 13 pgs.
Osborn, L.M., et al., "Astrogliosis: An integral player in the pathogenesis ofAlzheimer's disease", Prog Neurobiol 144, 2016, 121-141 (21 pgs.).
Pacofsky et al., "Potent Dipeptide Inhibitors of the pp60 c=src domain," J. Med. Chem 1998, 41, pp. 1894-1908, 15 pages.
Park, SA., et al., "Promising Blood Biomarkers for Clinical Use in Alzheimer'sDisease: A Focused Update", J Clin Neurol 18, 2022, 401-409 (9 pgs.).
Pasqualetti, G., et al., "The Role of Neuroinflammation in Dementias", Curr NeurolNeurosci Rep 15, 17, 2015, 11 pgs.
Pasricha, "Athira Pharma's shares plunge after Bothell company's CEO placed on leave," Jun. 18, 2021, The Seattle Times, pp. 1-3.
PubPeer, Jul. 13, 2021 [online]. Retrieved from the internet: https://pubpeer.com/publications/01199F548BE82EE44C7D395568982B, "Development of angiotensin IV analogs as hepatocyte growth factor/Met modifiers," pp. 1-5.
PubPeer, Jul. 13, 2021 [online]. Retrieved from the internet: https://pubpeer.com/publications/36F84FDB31C718C8CF8F52C717D15C, "Nanoscale mapping of the Met receptor on hippocampal neurons by AFM and confocal microscopy," pp. 1-8.
PubPeer, Jul. 13, 2021 [online]. Retrieved from the internet: https://pubpeer.com/publications/4D8EFBD349D1A779627479FB694F7C, "Evaluation of metabolically stabilized angiotensin IV analogs as procognitive/antidementia agents," pp. 1-2.
PubPeer, Jul. 13, 2021 [online]. Retrieved from the internet: https://pubpeer.com/publications/51C554512CE22267B2E62172DF3DDE, "Mimics of the dimerization domain of hepatocyte growth factor exhibit anti-Met and anticancer activity," pp. 1-8.
PubPeer, Jul. 13, 2021 [online]. Retrieved from the internet: https://pubpeer.com/publications/56408F27C1C94294C69E8466C44C2B, "Plasma phospholipids identify antecedent memory impairment in older adults," pp. 1-3.
PubPeer, Jul. 13, 2021 [online]. Retrieved from the internet: https://pubpeer.com/publications/D5375331091A7EF887CDC02B813ACA, "The Procognitive and Synaptogenic Effects of Angiotensin IV-Derived Peptides Are Dependent on Activation of the Hepatocyte Growth Factor/c-Met System," pp. 1-6.
PubPeer, Jul. 13, 2021 [online]. Retrieved from the internet: https://pubpeer.com/publications/D803673763EF5404FAE8CC546CC028, "Hepatocyte growth factor mimetic protects lateral line hair cells from aminoglycoside exposure," pp. 1-2.
PubPeer, Jun. 16, 2021 [online]. Retrieved from the internet: https://pubpeer.com/search?q=Kawas, pp. 1-2.
Ramesh, V., et al., "Biphasic responses in cell signalling: A unifiedapproach", bioRxiv, 2023, 28 pgs.

(56) References Cited

OTHER PUBLICATIONS

Raz, L., et al., "The neuropathology and cerebrovascular mechanisms of dementia", J Cereb Blood Flow Metab. 1, 2016, 172-186 (15 pgs.).
Riekkinen, P., et al., "Effects of scopolamine infusions into the anterior and posteriorcingulate on passive avoidance and water maze navigation", Brain Res685, 1995, 46-54 (9 pgs.).
Salvadó G., et al., "Specific associations between plasma biomarkers and post-mortemamyloid plaque and neurofibrillary tau tangle loads", medRxiv, 2022, 38 pgs.
Schneider, "For Better Science," Jun. 15, 2021, 32 pages.
Eguchi, Masakatsu, et al., "Solid-phase synthesis and solution structure of bicyclic β-turn peptidomimetics: diversity at the i position," Tetrahedron Letters, 42.7, (2001): 1237-1239 (3 pages).
International Search Report and Written Opinion for International Application No. PCT/US2023/080224; mailed Mar. 13, 2024, 11 pages.
La Venia et al., "Regioselective Incorporation of Backbone Constraints Compatible with Traditional Solid-Phase Peptide Synthesis," ACS Combinatorial Science, 15.1, (2013): 59-72.
STN CAS Registry Database Entry for 949893-44-1, 949893-45-2, date entered STN: Oct. 10, 2007 (1 page).
Akimoto, M., et al., "Hepatocyte growth factor as an enhancer of NMDA currents andsynaptic plasticity in the hippocampus", Neuroscience 128, 2004, 155-162 (8 pgs).
Akita, H., et al., "Hepatocyte growth factor improves synaptic localization of theNMDA receptor and intracellular signaling after excitotoxic injury in culturedhippocampal neurons", Expimental Neurology 210, 2008, 83-94 (12 pgs).
Alberts B., et al., "General Principles of Cell Communication", Molecular Biology of the Cell, 4th edition, New York: GarlandScience, 2002. (19 pgs). Available from:https://www.ncbi.nlm.nih.gov/books/NBK26813/. Accessed Mar. 23, 2023.
Ally, B.A., et al., "The P300 component in patients with Alzheimer's disease and their biological children", Biological Psychology 72, 2006 180-7 (8 pgs).
Anonymous, "2022 Alzheimer's disease facts and figures", Alzheimers and Dementia 2022, 18, 700-789 (90 pgs).
Anonymous, "ATH-1017 Treatment in Subjects with Parkinson's Disease Dementia or Dementia with Lewy Bodies (SHAPE Trial)" ClinicalTrials.gov, ID: NCT04831281, dated Jul. 24, 2023, 11 pages.
Anonymous, "Athira Pharma Corporate Presentation—Advancing New Therapies for Neuronal Health", Jan. 2024, 36 pages.
Anonymous, "Athira Pharma Highlights Therapeutic Potential of Fosgonimeton in Presentation of Additional Biomarker Data in Mild-to-Moderate Alzheimer's Disease Patients from ACT-AD Phase 2 Study atCTAD Conference", Nov. 29, 2022, 2 pages.
Anonymous, "Athira Pharma R&D Day—Enhancing the HGF/MET System to Fight Neurodegenerative Diseases", Dec. 7, 2022, 51 pages.
Anonymous, "Form S-1 Registration Statement of Athira Pharma, Inc.," filed with United States Securities and Exchange Commission Sep. 14, 2020, 285 pages.
Anonymous, "WHO Drug Information", vol. 35, No. 2, 2021, 4 pages.
Armada-Moreira, A., et al., "Going the Extra (Synaptic) Mile: Excitotoxicity as theRoad Toward Neurodegenerative Diseases", Frontiers in Cellular Neuroscience 14, 90, 2020, (27 pgs.).
Arneson, D., et al., "Shared mechanisms among neurodegenerative diseases: fromgenetic factors to gene networks", Journals of Genetics 97, 2018, 795-806 (12 pgs.).
Asomugha, C.O., et al., "ACh receptors link two signaling pathways to neuroprotectionagainst glutamate-induced excitotoxicity in isolated RGCs", J Neurochem112, 2010, 214-26 (25 pgs.).
Athira Pharma Inc., United States Securities and Exchange Commission, Form 8-K, Oct. 18, 2021, 7 pages.
Athira Pharma Press Release, "Athira Pharma Announces Encouraging Results from SHAPE Phase 2 Clinical Trial of Fosgonimeton for the Treatment of Parkinson's Disease Dementia and Dementia with Lewy Bodies", Dec. 12, 2023, 2 pages.
Athira Pharma Press Release, "Athira Pharma Provides 2023 Pipeline Outlook," Jan. 5, 2023, 2 pages.
Athira Pharma Press Release, Retrieved from the internet: https://www.athira.com/athira-pharma-announces-leadership-changes//, "Athira Pharma Announces Leadership Changes," Oct. 21, 2021, 5 pages.
Baiardi, S., et al., "Diagnostic value of plasma p-tau181, NfL, and GFAP in a clinicalsetting cohort of prevalent neurodegenerative dementias", Alzheimer's Research& Therapy 14, 153, 2022 (12 pgs).
Batista, C.R.A., et al., "Lipopolysaccharide-Induced Neuroinflammation as a Bridge toUnderstand Neurodegeneration", Int. J. Mol. Sci 20, 2293, 2019, (31 pgs).
Benoist et al., "The Procognitive and Synaptogenic Effects of Angiotensin IV-Derived Peptides Are Dependent on Activation of the Hepatocyte Growth Factor/c-Met System," The Journal of Pharmacology and Experimental Therapeutics, 351:390-402, Nov. 2014, 13 pages.
Chen, Y., et al., "A non-transgenic mouse model (ICV-STZ mouse) of Alzheimer'sdisease: similarities to and differences from the transgenic model (3xTg-ADmouse)", Mol Neurobiol 47, 2013, 711-25 (15 pgs).
Chitnis, T. et al., "CNS inflammation and neurodegeneration", J Clin Invest127, 2017, 3577-3587 (11 pgs).
Cummings, J., et al., "Advances in designs for Alzheimer's disease clinical trials", Am J Neurodegener Dis 2012, 1 (3):205-216, 12 pgs.
Das, J.R., et al., "Additive protective effects of donepezil and nicotine againstsalsolinol-induced cytotoxicity in SH-SY5Y cells", Neurotox Res 16, 2009, 194-204 (11 pgs.).
De Strooper, B., et al., "The Cellular Phase of Alzheimer's Disease", Cell164, 2016, 603-15 (13 pgs.).
Desole, C., et al., "HGF and MET: From Brain Development to Neurological Disorders", Front Cell Dev Biol 9, 683609, 2021 (21 pgs.).
Eagleson, K.L, et al., "Distinct intracellular signaling mediates c-MET regulation ofdendritic growth and synaptogenesis", Developmental Neurobiology76, 2016, 1160-81 (22 pgs.).
European Search Report corresponding to European Patent Application No. 17807519.8, mailed Jan. 10, 2020, Examiner A. Schleifenbaum, 7 pages.
Faes, S., et al., "PI3K and AKT: Unfaithful Partners in Cancer", Int J Mol Sci 16, 2015, 21138-21152 (15 pgs.).
Funakoshi, H., et al., "Hepatocyte growth factor: from diagnosis toclinical applications", Clin Chim Acta 327, 2003, 1-23 (23 pgs.).
Funakoshi, H., et al. "Hepatocyte Growth Factor (HGF): Neurotrophicfunctions and therapeutic implications for neuronal injury/diseases", Current Signal Transduction Therapy, 6, 2011, 156-167 (12 pgs).
Gao, B.L., et al., "Neuroprotective effects of donepezil against Aβ25-35-inducedneurotoxicity", Eur J Med Res 27, 219, 2022, (8pgs.).
Ghosh et al., "Organic Carbamates in Drug Design and Medicinal Chemistry," J. Med. Chem., 2015, 58:2895-2940.
Götze, K., et al., "Plasma neurofilament light chain in memory clinic practice:Evidence from a real-life study", Neurobiol Dis. 176, 105937, 2023, 7 pages.
He, F., et al., "HGF protects cultured cortical neurons against hypoxia/reoxygenationinduced cell injury via ERK1/2 and PI-3K/Akt pathways", Colloids Surf B Biointerfaces 61, 2008, 290-297 (8 pgs.).
Hewett, S.J., et al., "Interleukin-1β in Central Nervous System Injury and Repair", Eur J Neurodegener Dis 1, 2012, 195-211 (21 pgs.).
Heyl, D. et al., "Peptide Inhibitors of a-Amylase Based on Tendamistat: Development of Analogues with [pi]-Amino Acids Linking Critical Binding Segments", Protein and Peptide Letters: international journal for rapid publication of short papers in protein and peptide science, vol. 12, No. 3, Apr. 1, 2005 (Apr. 1, 2005), pp. 275-280.
Higgins, J. "Prodrugs in Drug Discovery", ACS Webinars, Nov. 19, 2015, 27 pgs.
Hua, X., et al., "Safety, Tolerability, Pharmacokinetics, and Pharmacodynamics of thePositive Modulator of HGF/MET,

(56) References Cited

OTHER PUBLICATIONS

Fosgonimeton, in Healthy Volunteers andSubjects with Alzheimer's Disease: Randomized, Placebo-Controlled, Double-Blind, Phase I Clinical Trial", J Alzheimers Dis 86, 2022, 1399-1413 (15 pgs.).
Hwang, J., et al., "Microglia signaling as a target of donepezil", Neuropharmacology 58, 2010, 1122-1129 (8 pgs.).
Hynd, M.R., et al., "Glutamate-mediated excitotoxicity and neurodegeneration in Alzheimer's disease", Neurochem Int 45, 2004, 583-595 (13 pgs.).
International Search Report and Written Opinion for International Application No. PCT/US2017/035547 dated Oct. 18, 2017, 11 pages.
Ishihara, N., et al., "Inhibition of apoptosis-inducing factor translocation is involved inprotective effects of hepatocyte growth factor against excitotoxic cell death incultured hippocampal neurons", Journal of Neurochemistry 95, 2005, 1277-1286 (10 pgs.).
Ito, K., et al., "Artificial human Met agonists based on macrocycle scaffolds", Nat Commun 11, 2015, 63-73 (12 pgs.).
Jack Jr, C.R., et al., "A/T/N: An unbiased descriptive classification scheme forAlzheimer disease biomarkers", Neurology 87, 2016, 539-547 (9 pgs).
Jack Jr, C.R., et al., "NIA-AA Research Framework: Toward a biological definition ofAlzheimer's disease", Alzheimer's & Dementia 14, 2018, 535-562 (28 pgs).
Jayaraman, A., et al., "TNF-mediated neuroinflammation is linked to neuronalnecroptosis in Alzheimer's disease hippocampus", Acta Neuropathol Commun9, 159, 2021, 21 pgs.
Jeong, J., "EEG dynamics in patients with Alzheimer's disease", Clin Neurophysiol115, 2004, 1490-1505 (16 pgs).
Selkoe, D. J., "Alzheimer's disease is a synaptic failure", Science 298, 2002, 789-91 (3 pgs.).
Serrano-Pozo, A., et al., "Neuropathological alterations in Alzheimer disease", ColdSpring Harb Perspect Med 1, a006189, 2011, 24 pages.
Shang, J., et al., "Strong neurogenesis, angiogenesis, synaptogenesis, and antifibrosisof hepatocyte growth factor in rats brain after transient middle cerebral arteryocclusion", J Neurosci Res 89, 2011, 86-95 (10 pgs.).
Shen, H., et al., "Neuroprotection by donepezil against glutamate excitotoxicityinvolves stimulation of alpha7 nicotinic receptors and internalization of NMDAreceptors", Br J Pharmacol 161, 2010, 127-39 (13 pgs.).
Shulman, Y., et al., "ATP binding to synaspsin IIa regulates usage and clustering ofvesicles in terminals of hippocampal neurons", J Neurosci 35, 2015, 985-98 (14 pgs.).
Stancu, I.C, et al., "Models of β-Amyloid Induced Tau-Pathology: The Long and 'Folded' Road to Understand the Mechanism", Molecular Neurodegeneration, 9, 51, 2014, 14 pgs.
Stoiljkovic, M., et al., "Therapy for Alzheimer's disease: Missing targets andfunctional markers?", Ageing Res Rev 68, 101318, 2021, 15 pgs.
Sun, et al., "AngIV-Analog Dihexa Rescues Cognitive Impairment and Recovers Memory in the APP/PS1 Mouse via the PI3K/AKT Signaling Pathway", Brain Sci. 2021, 11, 1487, 13 pgs.
Sun, W., et al., "Overexpression of HGF retards disease progression and prolongs lifespan in a transgenic mouse model of Als", J Neurosci. 22, 2002, 6537-6548 (12 pgs.).
Takada-Takatori, Y., et al., "Acetylcholinesterase inhibitors used in treatment of Alzheimer's disease prevent glutamate neurotoxicity via nicotinic acetylcholine receptors and phosphatidylinositol 3-kinase cascade", Neuropharmacology 51, 2006, 474-486 (13 pgs.).
Takada-Takatori, Y., et al., "Mechanism of neuroprotection by donepezil pretreatment in rat cortical neurons chronically treated with donepezil", J Neurosci Res86, 2008, 3575-3583 (9 pgs.).
Takeuchi, D., et al., "Alleviation of AB-induced cognitive impairment byultrasound-mediated gene transfer of HGF in a mouse model", Gene Ther15, 2008, 561-571 (11 pgs.).
Tancredi, V., et al., "The inhibitory effects of interleukin-6 on synaptic plasticity in therat hippocampus are associated with an inhibition of mitogen-activated proteinkinase Erk", J Neurochem 75, 2000, 634-43 (10 pgs).
Taylor, R. et al., "Development of Stable, Orally Bioavailable, Small-Molecule Positive Modulators of HGF/MET Signaling for the Treatment of Cognitive Impairment", Presented at the 2022 AAIC Annual Meeting; Jul. 31-Aug. 4, 2022; San Diego, California, 1 page.
Thomas, A., et al., "Donepezil, rivastigmine, and vitamin E in Alzheimer disease: acombined P300 event-related potentials/neuropsychologic evaluation over6 months", Clin Neuropharmacol 24, 2001, 31-42 (12 pgs.).
Tulasne, D., et al., "The shadow of death on the MET tyrosine kinasereceptor", Cell Death Differ 15, 2008, 427-34 (8 pgs.).
Tyndall, S.J., et al., "Hepatocyte growth factor-induced enhancement of dendriticbranching is blocked by inhibitors of N-methyl-D-aspartate receptors andcalcium/calmodulin-dependent kinases", J Neurosci Res 85, 2007, 2343-2351 (9 pgs.).
Wang, T., et al., "Hepatocyte growth factor acts as a mitogen and chemoattractant forpostnatal subventricular zone-olfactory bulb neurogenesis", Mol Cell Neurosci48, 2011, 38-50 (24 pgs.).
Wilczynska, K, et al., "Diagnostic Utility of Selected Serum Dementia Biomarkers: Amyloid β-40, Amyloid β-42, Tau Protein, and YKL-40: A Review", J Clin Med 9, 3452, 2020, 26 pgs.
Xiao, G.H., et al., "Anti-apoptotic signaling by hepatocyte growth factor/Met via thephosphatidylinositol 3-kinase/Akt and mitogen-activated protein kinasepathways", Proc Natl Acad Sci U S A 98, 2001, 247-52 (6 pgs.).
Yaari, R., et al., "Alzheimer's disease clinical trials: pastfailures and future opportunities", Clin. Invest. (Lond.) 2015 5(3), 297-309 (13 pgs.).
Yuan, A., et al., "Neurofilament Proteins as Biomarkers to MonitorNeurological Diseases and the Efficacy of Therapies", Front Neurosci 15,689938, 2021, 28 pgs.
Yuan, J., et al., "Severity Distribution of Alzheimer's Disease Dementia and MildCognitive Impairment in the Framingham Heart Study",. J Alzheimers Dis79, 2021, 807-817 (11 pgs.).
Zhang et al., "Structural analysis of angiotensin IV receptor (AT4) from selected bovine tissues," Journal of Pharmacology and Experimental Therapeutics (1999), 289(2), pp. 1075-1083.
Rilutek®, "Rilutek®—(riluzole) Tablets—Rx only", Prescribing information, Sanofi-Aventis U.S. LLC, 2008, 12 pages.
Rosenblum, et al., "EAAT2 and the Molecular Signature of Amyotrophic Lateral Sclerosis", Springer International Publishing AG 2017, A. Ortega, A. Schousboe (eds.), Glial Amino Acid Transporters, Advances in Neurobiology 16, 117-135 (20 pages).
Rubio, et al., "Sensory Involvement in Amyotrophic Lateral Sclerosis", Int. J. Mol. Sci. 2022, 23, 15521, 32 pages.
Scotter, et al., "TDP-43 Proteinopathy and ALS: Insights into Disease Mechanisms and Therapeutic Targets", Neurotherapeutics (2015) 12:352-363 (12 pages).
Seki, et al., "Characteristics of Sensory Neuron Dysfunction in Amyotrophic Lateral Sclerosis (ALS): Potential for ALS Therapy", Biomedicines 2023, 11, 2967, 20 pages.
Shefner, et al., "Opinion Paper—A proposal for new diagnostic criteria for ALS", Clinical Neurophysiology 131 (2020) 1975-1978 (4 pages).
Staats, et al., "Blood-based biomarkers of inflammation in amyotrophic lateral sclerosis", Molecular Neurodegeneration, (2022) 17:11, 19 pages.
Stetkarova, et al., "Diagnostics of Amyotrophic Lateral Sclerosis: Up to Date", Diagnostics 2021, 11,231, 13 pages.
Sufit, et al., "Open label study to assess the safety of VM202 in subjects with amyotrophic lateral sclerosis", Amyotrophic Lateral Sclerosis and Frontotemporal Degeneration, 2017, 18:3-4, 269-278 (11 pages).
Talbott, et al., "The epidemiology of amyotrophic lateral sclerosis", Handbook of Clinical Neurology, vol. 138 (3rd series), Neuroepidemiology, 2016, 14 pages.
The Writing Group on behalf of the Edaravone (MCI-186) Als 19 Study Group, "Safety and efficacy of edaravone in well defined

(56) References Cited

OTHER PUBLICATIONS patients with amyotrophic lateral sclerosis: a randomised, double-blind, placebo-controlled trial", Lancet Neurol 2017; 16: 505-12 (8 pages).
Thompson, et al., "Multicentre appraisal of amyotrophic lateral sclerosis biofluid biomarkers shows primacy of blood neurofilament light chain", Brain Communications, https://doi.org/10.1093/braincomms/fcac029, 2022, 11 pages.
Tortelli, et al., "Elevated cerebrospinal fluid neurofilament light levels in patients with amyotrophic lateral sclerosis: a possible marker of disease severity and progression", European Journal of Neurology 2012, 19: 1561-1567 (7 pages).
Tortelli, et al., "Plasma Inflammatory Cytokines Are Elevated in ALS", Frontiers in Neurology, vol. 11, Article 552295, Nov. 2020, 8 pages.
Turner, et al., "Mimics and chameleons in motor neurone disease", Pract Neurol 2013; 13: 153-164 (12 pages).
Vallarola, et al., "A Novel HGF/SF Receptor (MET) Agonist Transiently Delays the Disease Progression in an Amyotrophic Lateral Sclerosis Mouse Model by Promoting Neuronal Survival and Dampening the Immune Dysregulation", Int. J. Mol. Sci. 2020, 21, 8542, 19 pages.
Van Den Bos, et al., "Pathophysiology and Diagnosis of ALS: Insights from Advances in Neurophysiological Techniques", Int. J. Mol. Sci. 2019, 20, 2818, 16 pages.
Vaughan, et al., "The ALS-inducing factors, TDP43A315T and SOD1G93A, directly affect and sensitize sensory neurons to stress", Scientific Reports, (2018) 8:16582, 12 pages.
Vaz, et al., "Astrocytes in Amyotrophic Lateral Sclerosis", NCBI Bookshelf, https://www.ncbi.nlm.nih.gov/books/NBK573422/?report=printable, 2021, 21 pages.
Verde, et al., "Neurofilament light chain in serum for the diagnosis of amyotrophic lateral sclerosis", J. Neurol Neurosurg Psychiatry 2019;90:157-164 (8 pages).
Verma, et al., "Neuromuscular Junction Dysfunction in Amyotrophic Lateral Sclerosis", Molecular Neurobiology (2022) 59:1502-1527 (26 pages).
Vucic, et al., "Gold Coast diagnostic criteria: Implications for ALS diagnosis and clinical trial enrollment", Muscle & Nerve, 2021, 64:532-537 (6 pages).
Warita, et al., "Safety, tolerability, and pharmacodynamics of intrathecal injection of recombinant human HGF (KP-100) in subjects with amyotrophic lateral sclerosis: A phase I trial", Author Manuscript, doi:10.1002/jcph.1355, 42 pages.
Wegorzewska, et al., "TDP-43 mutant transgenic mice develop features of ALS and frontotemporal lobar degeneration", PNAS, Nov. 3, 2009, vol. 106, No. 44, 8809-18814 (6 pages).
Xu, et al., "Global variation in prevalence and incidence of amyotrophic lateral sclerosis: a systematic review and meta-analysis", Journal of Neurology (2020) 267:944-953 (10 pages).
Yang, et al., "Low-level overexpression of wild type TDP-43 causes late-onset, progressive neurodegeneration and paralysis in mice", Plos One, https://doi.org/10.1371/journal.pone.0255710, Feb. 3, 2022, 29 pages.
Yoshihara, et al., "Differential expression of inflammation- and apoptosis-related genes in spinal cords of a mutant SOD1 transgenic mouse model of familial amyotrophic lateral sclerosis", Journal of Neurochemistry, 2002, 80, 158-167 (10 pages).
Zhang, et al: "c-Met kinase 1-23 inhibitors: an update patent review (2014-2017)", Expert Opinion On Therapeutic Patents, vol. 29, No. 1, Dec. 12, 2018 (Dec. 12, 2018), pp. 25-41, 18 pages.
Extended European Search Report corresponding to European Patent Application No. 21887720.7, mailed Aug. 7, 2024, 8 pages.
Extended European Search Report corresponding to European Patent Application No. 22908476.9, mailed Sep. 23, 2025, M. Lo Giudice, 14 pages.
Kasper, S., et al., "Management of mild cognitive impairment (MCI): The need for national and international guidelines", World Journal of Biological Psychiatry, vol. 21, No. 8, Feb. 5, 2020 (Feb. 5, 2020), pp. 579-594 (16 pages).
Zhao, LJ., et al., "Associations of the cerebrospinal fluid hepatocyte growth factor with Alzheimer's disease pathology and cognitive function", BMC Neurology, vol. 21, No. 1, Oct. 6, 2021 (Oct. 6, 2021) (9 pages).
STN CAS Registry No. 1087792-35-5, Date Entered STN: 2008.12.21, 1 page.

* cited by examiner

BICYCLIC COMPOUNDS AND USES THEREOF FOR THE TREATMENT OF DISEASES

CROSS-REFERENCE TO RELATED APPLICATIONS

This application is a national stage entry pursuant to 35 U.S.C. § 371 of International Application No. PCT/US2021/057563, filed Nov. 1, 2021, which claims priority to U.S. Provisional Application No. 63/108,660, filed on Nov. 2, 2020, the disclosure of each of which is hereby incorporated by reference in its entirety.

FIELD

The present disclosure relates generally to compounds, compositions, and methods for their preparation and use for treating diseases, such as neurodegenerative diseases.

BACKGROUND

Hepatocyte growth factor (HGF) is a pleiotropic protein factor involved in numerous biological processes including embryonic and organ development, regeneration, and inflammation. HGF is a critical contributor to cortical, motor, sensory, sympathetic, and parasympathetic neuronal development and maturation. HGF is translated and secreted as inactive pro-HGF, but following cleavage, the resultant α and β-subunits are joined by a disulfide linkage to form the active heterodimer. Expression of HGF predominantly occurs in mesenchymal cells such as fibroblasts, chondroblasts, adipocytes, and the endothelium. Expression has also been demonstrated in the central nervous system (CNS) including neurons, astrocytes, and ependymal cells (Nakamura and Mizuno, 2010). All biological activities of HGF are mediated through MET, a transmembrane receptor tyrosine kinase that serves as the sole known receptor for HGF. MET has known involvement in a variety of biological processes, with demonstrated roles in development, regeneration, and response to injury. Upon binding of HGF to the extracellular domain of MET, homo-dimerization of the MET protein leads to auto-phosphorylation of the intracellular domain. Phosphorylation of MET intracellular domains leads to recruitment and phosphorylation of a variety of effector proteins including Gab1, GRB2, Phospholipase C, and Stat3 (Gherardi et al., 2012; Organ and Tsao, 2011). These effector proteins then interact with downstream signaling pathways including PI3K/Akt, Ras/Raf/MAPK, RAC1/CDC42, RAP/FAK among others to influence an array of cellular components including gene regulation, cytoskeletal rearrangements, cell cycle progression, cell adhesion, survival, and proliferation (Organ and Tsao, 2011).

Because HGF has a demonstrated role in development (Nakamura et al., 2011), homeostasis (Funakoshi and Nakamura, 2003), suppression of cell death, and regeneration (Matsumoto et al., 2014), stimulation of the HGF/MET signaling system is an ideal target for therapeutics for a range of disease states. Therapeutics involving HGF activity modulation have been proposed for disease and injury in many diverse tissue types including liver, kidney, gastrointestinal tract, cardiovascular components, lung, skin, nervous system, and musculature (Matsumoto et al., 2014). However, highly efficacious compounds useful for the modulation of HGF/MET signaling activity are yet to be explored and discovered.

Although progress has been made in this field, there remains a need for improved compounds and methods for treatment of HGF-modulated diseases. Accordingly, in one aspect, provided herein are compounds which modulate HGF for use in treating neurodegenerative diseases.

SUMMARY

Described herein, in certain embodiments, are compounds and compositions thereof for modulating hepatocyte growth factor (HGF) for treatment of diseases. Nonlimiting exemplary embodiments include:

Embodiment 1. A compound of Formula (I):

(I)

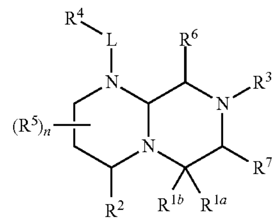

or a pharmaceutically acceptable salt thereof, wherein:

L is a direct bond, —C(=O)—, —$(CR^aR^b)_m$—C(=O)—, —C(=O)—$(CR^aR^b)_m$—, or —$(CR^aR^b)_m$—;

each $R^a$ and $R^b$ is independently H, $C_1$-$C_6$ alkyl, $C_2$-$C_6$ alkenyl, or $C_2$-$C_6$ alkynyl;

$R^{1a}$ and $R^{1b}$ are independently H, $C_1$-$C_6$ alkyl, $C_2$-$C_6$ alkenyl, $C_2$-$C_6$ alkynyl, $C_1$-$C_6$ alkoxy, halo, or $C_6$-$C_{10}$ arylalkyl;

$R^2$ is H, oxo, or thioxo;

$R^3$ is $C_2$-$C_6$ alkyl, $C_3$-$C_6$ alkenyl, $C_3$-$C_6$ alkynyl, $C_3$-$C_{12}$ cycloalkyl, $C_3$-$C_6$ cycloalkylalkyl, $C_6$-$C_{10}$ arylalkyl, 5- to 10-membered heteroarylalkyl, or 5- to 10-membered heterocyclylalkyl, wherein the 5- to 10-membered heteroarylalkyl or 5- to 10-membered heterocyclylalkyl contains 1-3 heteroatoms selected from nitrogen and oxygen;

$R^4$ is $C_6$-$C_{10}$ aryl, 5- to 10-membered heteroaryl, or 5- to 10-membered heterocyclyl, wherein the 5- to 10-membered heteroaryl or 5- to 10-membered heterocyclyl contains 1-3 heteroatoms selected from nitrogen and oxygen;

each $R^5$ is independently $C_1$-$C_6$ alkyl, oxo, or halo;

$R^6$ is H, $C_1$-$C_6$ alkyl, or oxo;

$R^7$ is H or oxo;

m is 1 or 2; and n is an integer from 0 to 3;

wherein each $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkylalkyl, $C_6$-$C_{10}$ aryl, $C_6$-$C_{10}$ arylalkyl, 5- to 10-membered heteroaryl, 5- to 10-membered heteroarylalkyl, 5- to 10-membered heterocyclyl, and 5- to 10-membered heterocyclylalkyl is optionally substituted with one to five substituents selected from hydroxyl, halo, amino, $C_1$-$C_6$ haloalkyl, $C_1$-$C_6$ alkoxy, $C_1$-$C_6$ haloalkoxy, cyano, —(C=O)$NH_2$, nitro, —$SO_2$($C_1$-$C_6$ alkyl), and —$CO_2$H.

Embodiment 2. The compound of embodiment 1, or a pharmaceutically acceptable salt thereof, wherein L is —C(=O)— or —$(CR^aR^b)_m$—.

Embodiment 3. The compound of embodiment 1 or 2, or a pharmaceutically acceptable salt thereof, wherein L is a —C(=O)—.

Embodiment 4. The compound of embodiment 1 or 2, or a pharmaceutically acceptable salt thereof, wherein L is $—(CR^aR^b)_m—$.

Embodiment 5. The compound of embodiment 4, or a pharmaceutically acceptable salt thereof, wherein $R^a$ and $R^b$ are each H, and m is 1.

Embodiment 6. The compound of any one of embodiments 1-5, or a pharmaceutically acceptable salt thereof, wherein $R^{1a}$ and $R^{1b}$ are each independently H; $C_1$-$C_6$ alkyl optionally substituted with 1-3 substituents selected from halo, $—CO_2H$, and $—C(═O)NH_2$; $C_1$-$C_6$ alkoxy; halo; or $C_6$-$C_{10}$ arylalkyl optionally substituted by 1-3 substituents selected from halo and amino.

Embodiment 7. The compound of embodiment 6, or a pharmaceutically acceptable salt thereof, wherein $R^{1a}$ and $R^{1b}$ are each independently H, methyl, fluoro, 2-methylbutyl, $—CH_2F$, methoxy, $—CH_2CO_2H$, $—CH_2C(═O)NH_2$, benzyl, or 4-aminobenzyl.

Embodiment 8. The compound of embodiment 6, or a pharmaceutically acceptable salt thereof, wherein $R^{1a}$ and $R^{1b}$ are each independently H or $C_1$-$C_3$ alkyl.

Embodiment 9. The compound of embodiment 8, or a pharmaceutically acceptable salt thereof, wherein $R^{1a}$ is methyl and $R^{1b}$ is H.

Embodiment 10. The compound of embodiment 8, or a pharmaceutically acceptable salt thereof, wherein $R^{1a}$ and $R^{1b}$ are each H.

Embodiment 11. The compound of any one of embodiments 1-10, or a pharmaceutically acceptable salt thereof, wherein $R^2$ is H.

Embodiment 12. The compound of any one of embodiments 1-10, or a pharmaceutically acceptable salt thereof, wherein $R^2$ is thioxo.

Embodiment 13. The compound of any one of embodiments 1-10, or a pharmaceutically acceptable salt thereof, wherein $R^2$ is oxo.

Embodiment 14. The compound of any one of embodiments 1-13, or a pharmaceutically acceptable salt thereof, wherein $R^3$ is $C_3$-$C_6$ alkyl, $C_3$-$C_6$ alkenyl, $C_3$-$C_6$ alkynyl, $C_3$-$C_{12}$ cycloalkyl, $C_3$-$C_6$ cycloalkylalkyl, $C_6$-$C_{10}$ arylalkyl, 5- to 10-membered heteroarylalkyl, or 5- to 10-membered heterocyclylalkyl, wherein the alkyl, alkenyl, alkynyl, cycloalkyl, cycloalkylalkyl, arylalkyl, heteroarylalkyl, or heterocyclylalkyl is optionally substituted with one to five substituents selected from hydroxyl, halo, amino, $C_1$-$C_6$ haloalkyl, $C_1$-$C_6$ alkoxy, $C_1$-$C_6$ haloalkoxy, cyano, $—(C═O)NH_2$, nitro, $—SO_2(C_1$-$C_6$ alkyl), and $—CO_2H$.

Embodiment 15. The compound of any one of embodiments 1-13, or a pharmaceutically acceptable salt thereof, wherein $R^3$ is $C_2$-$C_6$ alkyl optionally substituted by 1-3 substituents selected from halo, $C_1$-$C_3$ alkoxy, hydroxy, $—NH_2$, $—SO_2(C_1$-$C_3$ alkyl), and $—C(═O)NH_2$; $C_2$-$C_6$ alkenyl; $C_3$-$C_6$ cycloalkylalkyl; 5- to 6-membered heteroarylalkyl; 5- to 6-membered heterocyclylalkyl; or $C_6$ arylalkyl.

Embodiment 16. The compound of embodiment 15, or a pharmaceutically acceptable salt thereof, wherein $R^3$ is $C_2$ alkyl substituted by 1-3 substituents selected from $C_1$-$C_3$ alkoxy, hydroxy, $—NH_2$, and $—SO_2(C_1$-$C_3$ alkyl).

Embodiment 17. The compound of any one of embodiments 14-16, or a pharmaceutically acceptable salt thereof, wherein $R^3$ is:

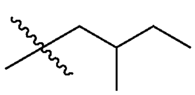,
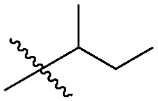,

-continued

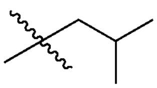,
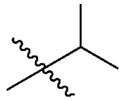,
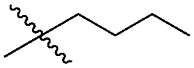,
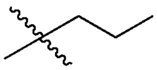,
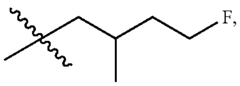
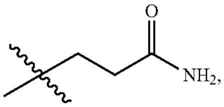
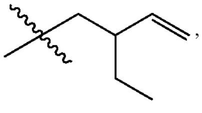,
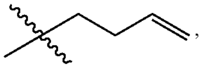,
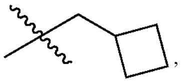,
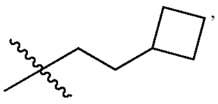,
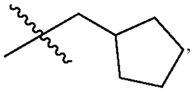,
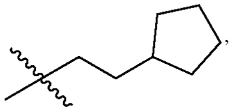,
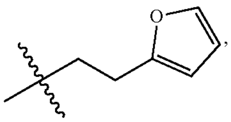,
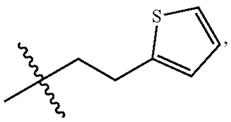,
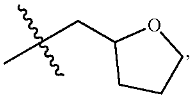,
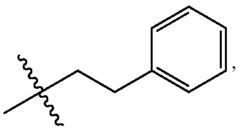,
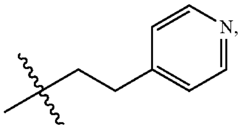
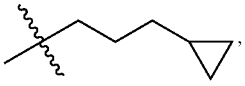,
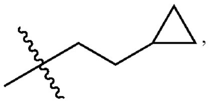,
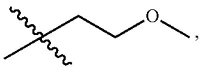,
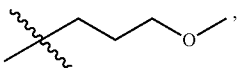,
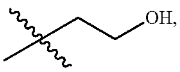
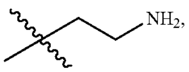,
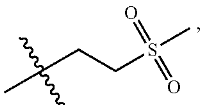, or
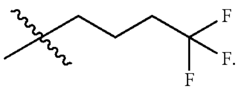.

Embodiment 18. The compound of embodiment 17, or a pharmaceutically acceptable salt thereof, wherein $R^3$ is:

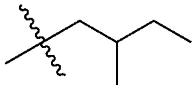,
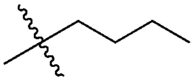,
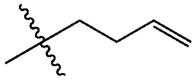,
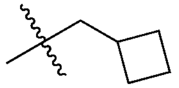,
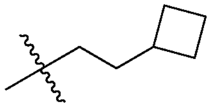,
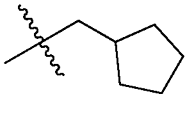,
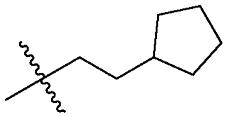, or
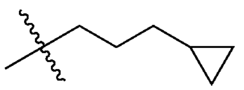.

Embodiment 19. The compound of any one of embodiments 1-18, or a pharmaceutically acceptable salt thereof, wherein $R^4$ is $C_6$-$C_{10}$ aryl optionally substituted with 1-3 substituents selected from halo, hydroxyl, $C_1$-$C_6$ haloalkyl, and $C_1$-$C_6$ haloalkoxy.

Embodiment 20. The compound of embodiment 19, or a pharmaceutically acceptable salt thereof, wherein $R^4$ is phenyl substituted with 1-3 substituents selected from —$CF_3$, —$OCHF_2$, —OH, fluoro, and chloro.

Embodiment 21. The compound of embodiment 20, or a pharmaceutically acceptable salt thereof, wherein $R^4$ is:

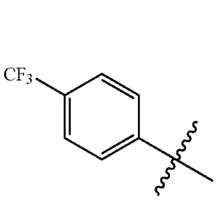,
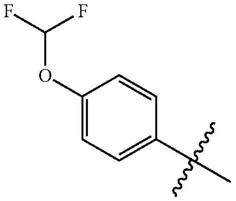,
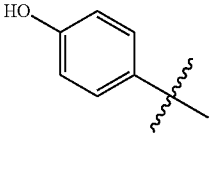,
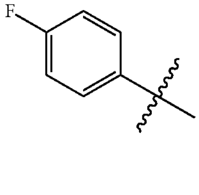,
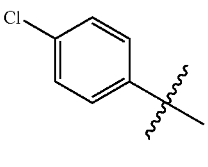, or
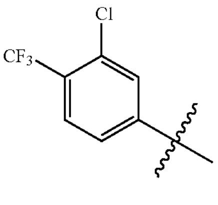.

Embodiment 22. The compound of embodiment 21, or a pharmaceutically acceptable salt thereof, wherein $R^4$ is:

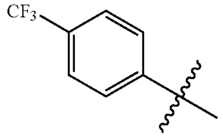,
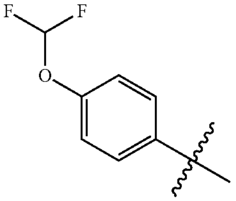,
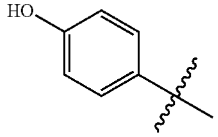,
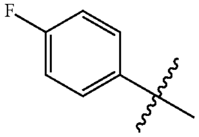, or
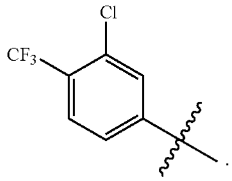.

Embodiment 23. The compound of any one of embodiments 1-18, or a pharmaceutically acceptable salt thereof, wherein $R^4$ is 5- to 10-membered heteroaryl optionally substituted with 1-3 substituents selected from halo, hydroxyl, $C_1$-$C_6$ haloalkyl, and $C_1$-$C_6$ haloalkoxy.

Embodiment 24. The compound of embodiment 23, or a pharmaceutically acceptable salt thereof, wherein $R^4$ is pyridyl or indolyl optionally substituted with 1-3 substituents selected from halo, hydroxyl, $C_1$-$C_6$ haloalkyl, and $C_1$-$C_6$ haloalkoxy.

Embodiment 25. The compound of embodiment 24, or a pharmaceutically acceptable salt thereof, wherein $R^4$ is

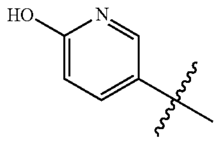 or 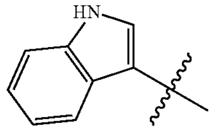.

Embodiment 26. The compound of embodiment 25, or a pharmaceutically acceptable salt thereof, wherein $R^4$ is

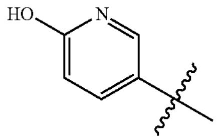.

Embodiment 27. The compound of any one of embodiments 1-18, or a pharmaceutically acceptable salt thereof, wherein $R^4$ is 5- to 10-membered heterocyclyl optionally substituted with 1-3 substituents selected from halo, hydroxyl, $C_1$-$C_6$ haloalkyl, and $C_1$-$C_6$ haloalkoxy.

Embodiment 28. The compound of embodiment 27, or a pharmaceutically acceptable salt thereof, wherein $R^4$ is indolinyl.

Embodiment 29. The compound of embodiment 28, or a pharmaceutically acceptable thereof, wherein $R^4$ is

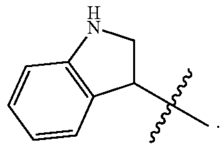 [SMILES: *C1CNc2ccccc21]

Embodiment 30. The compound of any one of embodiments 1-26, or a pharmaceutically acceptable salt thereof, wherein -L-$R^4$ is:

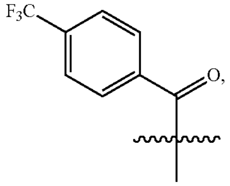
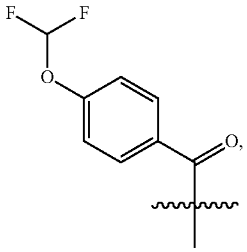
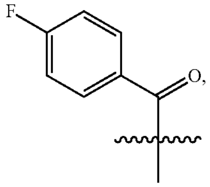
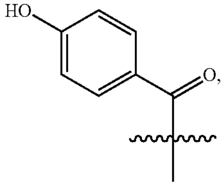
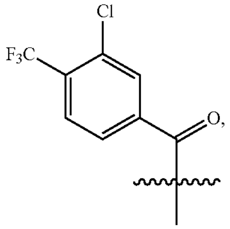
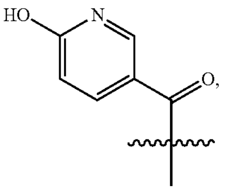
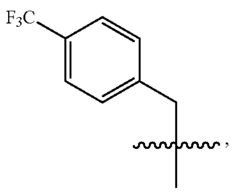
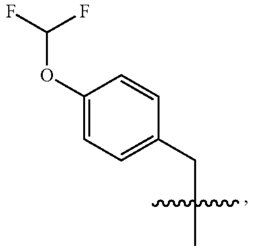
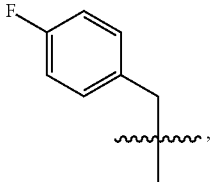
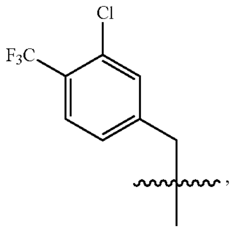
or -continued

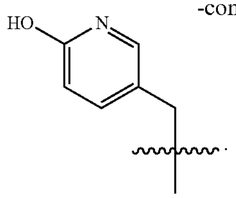

Embodiment 31. The compound of any one of embodiments 1-30, or a pharmaceutically acceptable salt thereof, wherein n is 0.

Embodiment 32. The compound of any one of embodiments 1-30, or a pharmaceutically acceptable salt thereof, wherein n is 1.

Embodiment 33. The compound of embodiment 32, or a pharmaceutically acceptable salt thereof, wherein $R^5$ is oxo or halo.

Embodiment 34. The compound of embodiment 33, or a pharmaceutically acceptable salt thereof, wherein $R^5$ is oxo or fluoro.

Embodiment 35. The compound of any one of embodiments 1-34, or a pharmaceutically acceptable salt thereof, wherein $R^6$ is H.

Embodiment 36. The compound of any one of embodiments 1-35, or a pharmaceutically acceptable salt thereof, wherein $R^7$ is oxo.

Embodiment 37. The compound of any one of embodiments 1-10, 13-31, 35, and 36, or a pharmaceutically acceptable salt thereof, wherein the compound is of Formula (V):

(V)

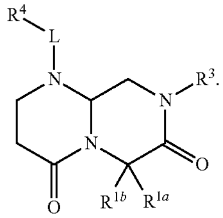

Embodiment 38. The compound of embodiment 37, or a pharmaceutically acceptable salt thereof, wherein:

L is —C(═O)— or —$CH_2$—;

$R^{1a}$ and $R^{1b}$ are independently H or $C_1$-$C_3$ alkyl optionally substituted with —$CO_2H$;

$R^3$ is $C_4$-$C_5$ alkyl, $C_4$-$C_5$ alkenyl, or $C_1$-$C_3$ alkyl substituted with $C_3$-$C_5$ cycloalkyl; and $R^4$ is phenyl or pyridyl substituted with 1-3 substituents selected from —$CF_3$, —$OCHF_2$, —OH, fluoro, and chloro.

Embodiment 39. A compound selected from the compounds of Table 1A and pharmaceutically acceptable salts thereof.

Embodiment 40. A pharmaceutical composition comprising the compound of any one of embodiments 1-39, or a pharmaceutically acceptable salt thereof, and a pharmaceutically acceptable carrier.

Embodiment 41. A method for modulating hepatocyte growth factor in a subject in need thereof, the method comprising administering to the subject an effective amount of the compound of any one of embodiments 1-39, or a pharmaceutically acceptable salt thereof, or the pharmaceutical composition of embodiment 40.

Embodiment 42. The method of embodiment 41, wherein the modulating comprises treating a disease, condition, or injury.

Embodiment 43. The method of embodiment 42, wherein the disease, condition, or injury is a neurodegenerative disease, a spinal cord injury, a traumatic brain injury, or a sensorineural hearing loss.

Embodiment 44. The method of embodiment 42 or 43, wherein the disease, condition, or injury is a neurodegenerative disease.

Embodiment 45. The method of embodiment 44, wherein the neurodegenerative disease is Alzheimer's disease, Parkinson's disease, Huntington's disease, or amyotrophic lateral sclerosis (ALS).

Embodiment 46. The method of embodiment 45, wherein the neurodegenerative disease is Alzheimer's disease or Parkinson's disease.

Embodiment 47. A method for treating or slowing progression of dementia in a subject in need thereof, the method comprising administering to the subject an effective amount of the compound of any one of embodiments 1-39, or a pharmaceutically acceptable salt thereof, or the pharmaceutical composition of embodiment 40.

Embodiment 48. The method of embodiment 47, wherein the dementia is associated P with Alzheimer's disease or Parkinson's disease.

Embodiment 49. A method for preventing cognitive dysfunction in a subject in need thereof, the method comprising administering to the subject an effective amount of the compound of any one of embodiments 1-39, or a pharmaceutically acceptable salt thereof, or the pharmaceutical composition of embodiment 40.

Embodiment 50. A method for treating, repairing or preventing a disease, condition or injury related to nerve tissue in a subject in need thereof, the method comprising administering to the subject an effective amount of the compound of any one of embodiments 1-39, or a pharmaceutically acceptable salt thereof, or the pharmaceutical composition of embodiment 40.

Embodiment 51. A method of treating or preventing a disease or disorder of the central nervous system, a disease or disorder of the peripheral nervous system, neuropathic pain, anxiety, or depression in a subject in need thereof, the method comprising administering to the subject an effective amount of the compound of any one of embodiments 1-39, or a pharmaceutically acceptable salt thereof, or the pharmaceutical composition of embodiment 40.

DETAILED DESCRIPTION

Definitions

Unless defined otherwise, all technical and scientific terms used herein have the same meaning as is commonly understood by one of skill in the art to which this disclosure belongs. In the following description, certain specific details are set forth in order to provide a thorough understanding of various embodiments of the disclosure. It is to be understood that the foregoing general description and the following detailed description are exemplary and explanatory only and are not restrictive of any subject matter claimed. To the extent any material incorporated herein by reference is inconsistent with the express content of this disclosure, the express content controls. In this application, the use of the singular includes the plural unless specifically stated otherwise. It must be noted that, as used in the specification and the appended claims, the singular forms "a," "an", and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless the context requires otherwise, throughout the present specification and claims, the word "comprise" and variations thereof, such as, "comprises" and "comprising" are to be construed in an open, inclusive sense, that is, as "including, but not limited to".

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the terms "about" and "approximately" mean±20%, ±10%, ±5%, or ±1% of the indicated range, value, or structure, unless otherwise indicated.

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the $—NH_2$ radical.

"Carboxy" or "carboxyl" refers to the $—CO_2H$ radical.

"Cyano" refers to the —CN radical.

"Hydroxy" or "hydroxyl" refers to the —OH radical.

"Nitro" refers to the $—NO_2$ radical.

"Oxo" refers to the =O substituent.

"Thioxo" refers to the =S substituent.

"Thiol" refers to the —SH substituent.

"Alkyl" refers to an unbranched or branched saturated hydrocarbon chain radical consisting solely of carbon and hydrogen atoms, having from one to twelve carbon atoms ($C_1$-$C_{12}$ alkyl), preferably one to eight carbon atoms ($C_1$-$C_8$ alkyl), one to six carbon atoms ($C_1$-$C_6$ alkyl), or one to three carbon atoms ($C_1$-$C_3$ alkyl) and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. Unless stated otherwise specifically in the specification, an alkyl group is optionally substituted.

"Alkenyl" refers to an unbranched or branched unsaturated hydrocarbon chain radical consisting solely of carbon and hydrogen atoms, which contains one or more carbon-carbon double bonds, having from two to twelve carbon atoms ($C_2$-$C_{12}$ alkenyl), preferably two to eight carbon atoms ($C_2$-$C_8$ alkenyl) or two to six carbon atoms ($C_2$-$C_6$ alkenyl), and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group is optionally substituted.

"Alkynyl" refers to an unbranched or branched unsaturated hydrocarbon chain radical consisting solely of carbon and hydrogen atoms, which contains one or more carbon-carbon triple bonds, having from two to twelve carbon atoms ($C_2$-$C_{12}$ alkynyl), preferably two to eight carbon atoms ($C_2$-$C_8$ alkynyl) or two to six carbon atoms ($C_2$-$C_6$ alkynyl), and which is attached to the rest of the molecule by a single bond, e.g., ethynyl, propynyl, butynyl, pentynyl, hexynyl, and the like. Unless stated otherwise specifically in the specification, an alkynyl group is optionally substituted.

"Alkoxy" refers to a radical of the formula —OR$^a$ where R$^a$ is an alkyl radical as defined above containing one to twelve carbon atoms. Preferred alkoxy groups have one to six carbon atoms (i.e., $C_1$-$C_6$ alkoxy) or one to three carbon atoms (i.e., $C_1$-$C_3$ alkoxy) in the alkyl radical. Unless stated otherwise specifically in the specification, an alkoxy group is optionally substituted.

"Aromatic ring" refers to a cyclic planar portion of a molecule (i.e., a radical) with a ring of resonance bonds that exhibits increased stability relative to other connective arrangements with the same sets of atoms. Generally, aromatic rings contain a set of covalently bound co-planar atoms and comprise a number of π-electrons (for example, alternating double and single bonds) that is even but not a multiple of 4 (i.e., 4n+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an aromatic ring includes all radicals that are optionally substituted.

"Aryl" refers to a carbocyclic ring system radical comprising 6 to 18 carbon atoms and at least one aromatic ring (i.e., $C_6$-$C_{18}$ aryl), preferably having 6 to 10 carbon atoms (i.e., $C_6$-$C_{10}$ aryl). For purposes of embodiments of this disclosure, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, phenyl, pleiadene, pyrene, and triphenylene. Unless stated otherwise specifically in the specification, an aryl group is optionally substituted.

"Arylalkyl" refers to a radical of the formula —$R_b$—$R_c$ where $R_b$ is an alkylene chain and $R_c$ is one or more aryl radicals as defined above, for example, benzyl, diphenylmethyl and the like. An arylalkyl group may contain a $C_1$-$C_{10}$ alkylene chain connected to a $C_6$-$C_{10}$ aryl radical (i.e., $C_6$-$C_{10}$ arylalkyl). Unless stated otherwise specifically in the specification, an arylalkyl group is optionally substituted.

"Cycloalkyl" refers to a stable non-aromatic monocyclic or polycyclic carbocyclic radical consisting solely of carbon and hydrogen atoms, which may include fused or bridged ring systems, having from three to fifteen carbon atoms (i.e., $C_3$-$C_{15}$ cycloalkyl), preferably having from three to ten carbon atoms (i.e., $C_3$-$C_{10}$ cycloalkyl) or three to six carbon atoms (i.e., $C_3$-$C_6$ cycloalkyl), and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Cycloalkyl also includes "spiro cycloalkyl" when there are two positions for substitution on the same carbon atom. Polycyclic radicals include, for example, adamantyl, norbornyl, decalinyl, 7,7-dimethyl-bicyclo [2.2.1]heptanyl, and the like. Unless otherwise stated specifically in the specification, a cycloalkyl group is optionally substituted.

"Cycloalkylalkyl" refers to a radical of the formula —$R_b$—$R_c$ where $R_b$ is an alkylene chain and $R_c$ is one or more cycloalkyl radicals as defined above, for example, cyclopropyl, cyclobutyl, cyclopentyl, cyclohexyl, cycloheptyl, and cyclooctyl and the like. A cycloalkylalkyl group may contain a $C_1$-$C_{10}$ alkylene chain connected to a $C_3$-$C_{12}$ cycloalkyl radical (i.e., $C_3$-$C_{12}$ cycloalkylalkyl) or a $C_1$-$C_{10}$ alkylene chain connected to a $C_3$-$C_6$ cycloalkyl radical (i.e., $C_3$-$C_6$ cycloalkylalkyl). Unless stated otherwise specifically in the specification, a cycloalkylalkyl group is optionally substituted.

"Fused" refers to any ring structure described herein which is fused to an existing ring structure in the compounds of the disclosure. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro, or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. A preferred haloalkyl group includes an alkyl group having one to six carbon atoms and that is substituted by one or more halo radicals (i.e., $C_1$-$C_6$ haloalkyl). The halo radicals may be all the same or the halo radicals may be different. Unless stated otherwise specifically in the specification, a haloalkyl group is optionally substituted.

"Haloalkoxy" refers to a radical of the formula —OR$^a$ where R$^a$ is a haloalkyl radical as defined herein containing one to twelve carbon atoms. A preferred haloalkoxy group includes an alkoxy group having one to six carbon atoms (i.e., $C_1$-$C_6$ haloalkoxy) or having one to three carbon atoms ($C_1$-$C_3$ haloalkoxy) and that is substituted by one or more halo radicals. The halo radicals may all be the same or the halo radicals may all be different. Unless stated otherwise specifically in the specification, a haloalkoxy group is optionally substituted.

"Heteroaryl" refers to an aromatic group (e.g., a 5-14 membered ring system) having a single ring, multiple rings, or multiple fused rings, with one or more ring heteroatoms independently selected from nitrogen, oxygen and sulfur. As used herein, heteroaryl includes 1 to 10 ring carbon atoms and 1 to 4 heteroatoms independently selected from nitrogen, oxygen and sulfur within the ring. Preferred heteroaryl groups have a 5- to 10-membered ring system containing one to four heteroatoms selected from nitrogen, oxygen, and sulfur (i.e., a 5- to 10-membered heteroaryl) and a 5- to 6-membered ring system containing one to four heteroatoms selected from nitrogen, oxygen, and sulfur (i.e., a 5- to 6-membered heteroaryl). For purposes of embodiments of this disclosure, the heteroaryl radical may be a monocyclic, bicyclic, tricyclic or tetracyclic ring system, which may include fused or bridged ring systems. Examples of heteroaryl groups include pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). A heteroaryl may comprise one or more N-oxide (N—O—) moieties, such as pyridine-N-oxide. Unless stated otherwise specifically in the specification, a heteroaryl group is optionally substituted.

"Heteroarylalkyl" refers to a radical of the formula —$R_b$—$R_c$ where $R_b$ is an alkylene chain and $R_c$ is one or more heteroaryl radicals as defined above. A heteroarylalkyl group may contain a $C_1$-$C_{10}$ alkylene chain connected to a 5- to 10-membered heteroaryl group (i.e., 5- to 10-membered heteroarylalkyl) or a $C_1$-$C_{10}$ alkylene chain connected to a 5- to 6-membered heteroaryl group (i.e., 5- to 6-membered heteroarylalkyl). Unless stated otherwise specifically in the specification, a heteroarylalkyl group is optionally substituted.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e., the heterocyclyl group having at least one double bond), bridged-heterocyclyl groups, fused-heterocyclyl groups and spiro-heterocyclyl groups. A heterocyclyl may be a single ring or multiple rings wherein the multiple rings may be fused, bridged or spiro, and may comprise one or more oxo (C═O) or N-oxide (N—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 1 to 10 ring carbon atoms, 1 to 8 carbon atoms, 1 to 6 carbon atoms, or 1 to 4 carbon atoms, and 1 to 5 ring heteroatoms, 1 to 4 heteroatoms, 1 to 3 heteroatoms, or 1 to 2 heteroatoms independently selected from nitrogen, sulfur and oxygen. Preferred heterocyclyls have five to 10 members in the ring system including one to four heteroatoms selected from nitrogen and oxygen (i.e., 5- to 10-membered heterocyclyl) or five to eight members in the ring system including one to four heteroatoms selected from nitrogen and oxygen (i.e., 5- to 8-membered heterocyclyl). Examples of heterocyclyl groups include dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl and 1,1-dioxo-thiomorpholinyl. Unless stated otherwise specifically in the specification, a heterocyclyl group is optionally substituted.

"Heterocyclylalkyl" refers to a radical of the formula $—R_b—R_c$ where $R_b$ is an alkylene chain and $R_c$ is one or more heterocyclyl radicals as defined above. A heterocyclylalkyl group may contain a $C_1$-$C_{10}$ alkylene chain connected to a 5- to 10-membered heterocyclyl radical (i.e., 5- to 10-membered heterocyclylalkyl) or a $C_1$-$C_{10}$ alkylene chain connected to a 5- to 8-membered heterocyclyl radical (i.e., 5- to 8-membered heterocyclylalkyl). Unless stated otherwise specifically in the specification, a heterocyclylalkyl group is optionally substituted.

In some embodiments, the term "substituted" as used herein means any of the above groups, or other substituents (e.g., $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkylalkyl, aryl, and heteroaryl) wherein at least one hydrogen atom (e.g., 1, 2, 3, or all hydrogen atoms) is replaced by a bond to a non-hydrogen atom such as, but not limited to: a halogen atom such as F, Cl, Br, and I (i.e., "halo"); an oxygen atom in groups such as hydroxyl groups or alkoxy groups (e.g., alkoxy or haloalkoxy); a nitrogen atom in groups such as amines (e.g., $—NH_2$), amides (e.g., $—(C═O)NH_2$), and nitro; alkyl groups including one or more halogen, such as F, Cl, Br, and I (e.g., haloalkyl); and cyano.

It is understood that each choice for L, $R^{1a}$, $R^{1b}$, $R^2$, $R^3$, $R^4$, $R^5$, $R^6$, and $R^7$ is optionally substituted as described above unless specifically stated otherwise, and provided that all valences are satisfied by the substitution. Specifically, each choice for L, $R^{1a}$, $R^{1b}$, $R^2$, $R^3$, $R^4$, $R^5$, $R_6$, and $R^7$ is optionally substituted unless specifically stated otherwise, and provided such substitution results in a stable molecule (e.g., groups such as H and halo are not optionally substituted).

"Effective amount" or "therapeutically effective amount" of a compound or a composition refers to that amount of the compound or the composition that results in an intended result as desired based on the disclosure herein. Effective amounts can be determined by standard pharmaceutical procedures in cell cultures or experimental animals including, without limitation, by determining the $ED_{50}$ (the dose therapeutically effective in 50% of the population) and the $LD_{50}$ (the dose lethal to 50% of the population). In some embodiments, an effective amount of a compound results in reduction or inhibition of symptoms or a prolongation of survival in a subject (i.e., a human patient). The results may require multiple doses of the compound.

"Treating" or "treatment" of a disease in a subject refers to 1) preventing the disease from occurring in a patient that is predisposed or does not yet display symptoms of the disease; 2) inhibiting the disease or arresting its development; or 3) ameliorating or causing regression of the disease. As used herein, "treatment" or "treating" is an approach for obtaining beneficial or desired results including clinical results. For the purposes of this disclosures, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a subject. Also encompassed by "treatment" is a reduction of pathological consequence of the disease or disorder. The methods of the invention contemplate any one or more of these aspects of treatment.

As used herein, the terms "individual(s)", "subject(s)" and "patient(s)" mean any mammal. Examples include, but are not limited to, mice, rats, hamsters, guinea pigs, pigs, rabbits, cats, dogs, goats, sheep, cows, and humans. In some embodiments, the mammal is a human.

A "therapeutic effect", as that term is used herein, encompasses a therapeutic benefit and/or a prophylactic benefit as described herein. A therapeutic effect includes delaying or eliminating the appearance of a disease or condition; delaying or eliminating the onset of symptoms of a disease or condition; slowing, halting, or reversing the progression of a disease or condition; causing partial or complete regression of a disease or condition; or any combination thereof.

The terms "co-administration", "administered in combination with", and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable" refers to compounds, salts, compositions, dosage forms and other materials which are useful in preparing a pharmaceutical composition that is suitable for veterinary or human pharmaceutical use.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline, and caffeine.

In some embodiments, pharmaceutically acceptable salts include quaternary ammonium salts such as quaternary amine alkyl halide salts (e.g., methyl bromide).

As used herein, "therapeutic agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

The term "in vivo" refers to an event that takes place in a subject's body.

Embodiments of the disclosure are also meant to encompass all pharmaceutically acceptable compounds of Formula (I) being isotopically-labelled by having one or more atoms replaced by an atom having a different atomic mass or mass number (i.e., an "isotopic form" of a compound of Formula (I)). Examples of isotopes that can be incorporated into the compounds of Formula (I) include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action. Certain isotopically-labeled compounds of Formula (I), for example, those incorporating a radioactive isotope, are useful in drug and/or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with heavier isotopes such as deuterium, i.e., $^{2}H$, may afford certain therapeutic advantages resulting from greater metabolic stability, for example, increased in vivo half-life or reduced dosage requirements, and hence are preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) can generally be prepared by conventional techniques known to those skilled in the art or by processes analogous to those described in the Examples as set out below using an appropriate isotopically-labeled reagent in place of the non-labeled reagent previously employed.

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments include compounds produced by a process comprising administering a compound of this disclosure to a mammal for a period of time sufficient to yield a metabolic product thereof. Such products are typically identified by administering a radiolabeled compound of the disclosure in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the disclosure. As used herein, the term "solvate" refers to an aggregate that comprises one or more molecules of a compound of Formula (I) with one or more molecules of solvent. In some embodiments, the solvent is water, in which case the solvate is a hydrate. Alternatively, in other embodiments, the solvent is an organic solvent. Thus, the compounds of Formula (I) may exist as a hydrate, including a monohydrate, dihydrate, hemihydrate, sesquihydrate, trihydrate, tetrahydrate and the like, as well as the corresponding solvated forms. In some aspects, the compound of Formula (I) is a true solvate, while in other cases, the compound of the disclosure merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan.

A "pharmaceutical composition" or "pharmaceutically acceptable composition" refers to a formulation of a compound of the disclosure and a medium generally accepted in the art for the delivery of the biologically active compound to mammals, e.g., humans. Such a medium includes all pharmaceutically acceptable carriers, diluents, or excipients therefor.

"Pharmaceutically acceptable carrier, diluent or excipient" includes, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of Formula (I), or a pharmaceutically acceptable salt or isotopic form thereof, may contain one or more centers giving rise to geometric asymmetry and may thus provide enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Diastereoisomers" are stereoisomers that have at least two asymmetric atoms, but which are not mirror-images of each other.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Compounds

In one aspect, provided herein is a compound of Formula (I):

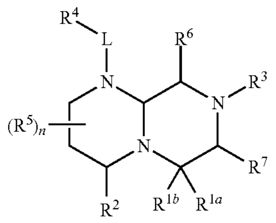

(I)

or a pharmaceutically acceptable salt thereof, wherein:

L is a direct bond, —C(═O)—, —$(CR^aR^b)_m$—C(═O)—, —C(═O)—$(CR^aR^b)_m$—, or —$(CR^aR^b)_m$—;

each $R^a$ and $R^b$ is independently H, $C_1$-$C_6$ alkyl, $C_2$-$C_6$ alkenyl, or $C_2$-$C_6$ alkynyl;

$R^{1a}$ and $R^{1b}$ are independently H, $C_1$-$C_6$ alkyl, $C_2$-$C_6$ alkenyl, $C_2$-$C_6$ alkynyl, $C_1$-$C_6$ alkoxy, halo, or $C_6$-$C_{10}$ arylalkyl;

$R^2$ is H, oxo, or thioxo;

$R^3$ is $C_2$-$C_6$ alkyl, $C_3$-$C_6$ alkenyl, $C_3$-$C_6$ alkynyl, $C_3$-$C_{12}$ cycloalkyl, $C_3$-$C_6$ cycloalkylalkyl, $C_6$-$C_{10}$ arylalkyl, 5- to 10-membered heteroarylalkyl, or 5- to 10-membered heterocyclylalkyl, wherein the 5- to 10-membered heteroarylalkyl or 5- to 10-membered heterocyclylalkyl contains 1-3 heteroatoms selected from nitrogen and oxygen;

$R^4$ is $C_6$-$C_{10}$ aryl, 5- to 10-membered heteroaryl, or 5- to 10-membered heterocyclyl, wherein the 5- to 10-membered heteroaryl or 5- to 10-membered heterocyclyl contains 1-3 heteroatoms selected from nitrogen and oxygen;

each $R^5$ is independently $C_1$-$C_6$ alkyl, oxo, or halo;

$R^6$ is H, $C_1$-$C_6$ alkyl, or oxo;

$R^7$ is H or oxo;

m is 1 or 2; and n is an integer from 0 to 3;

wherein each $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkylalkyl, $C_6$-$C_{10}$ aryl, $C_6$-$C_{10}$ arylalkyl, 5- to 10-membered heteroaryl, 5- to 10-membered heteroarylalkyl, 5- to 10-membered heterocyclyl, and 5- to 10-membered heterocyclylalkyl is optionally substituted with one to five substituents selected from hydroxyl, halo, amino, $C_1$-$C_6$ haloalkyl, $C_1$-$C_6$ alkoxy, $C_1$-$C_6$ haloalkoxy, cyano, —(C═O)$NH_2$, nitro, —$SO_2$($C_1$-$C_6$ alkyl), and —$CO_2$H.

In some embodiments, L is a direct bond. In some embodiments, L is —C(═O)— or —$(CR^aR^b)_m$—. In some embodiments, L is —C(═O)—. In some embodiments, L is —$(CR^aR^b)_m$—. In some embodiments, L is —$(CR^aR^b)_m$—C(═O)— or —C(═O)—$(CR^aR^b)_m$—. In some embodiments, L is —$(CR^aR^b)_m$—C(═O)—. In some embodiments, L is —C(═O)—$(CR^aR^b)_m$—.

In some embodiments, each $R^a$ and $R^b$ is independently H, $C_1$-$C_6$ alkyl, $C_2$-$C_6$ alkenyl, or $C_2$-$C_6$ alkynyl. In some embodiments, each $R^a$ and $R^b$ is independently H, $C_1$-$C_3$ alkyl, $C_2$-$C_4$ alkenyl, or $C_2$-$C_4$ alkynyl. In some embodiments, $R^a$ and $R^b$ are each H. In some embodiments, $R^a$ is H. In some embodiments, $R^a$ is $C_1$-$C_6$ alkyl, such as methyl, ethyl, or propyl. In some embodiments, $R^a$ is $C_2$-$C_6$ alkenyl, such as vinyl or propenyl. In some embodiments, $R^a$ is $C_2$-$C_6$ alkynyl, such as ethynyl or propynyl. In some embodiments, $R^b$ is H. In some embodiments, $R^b$ is $C_1$-$C_6$ alkyl, such as methyl, ethyl, or propyl. In some embodiments, $R^b$ is $C_2$-$C_6$ alkenyl, such as vinyl or propenyl. In some embodiments, $R^b$ is $C_2$-$C_6$ alkynyl, such as ethynyl or propynyl.

In some embodiments, $R^{1a}$ and $R^{1b}$ are independently H, $C_1$-$C_6$ alkyl, $C_2$-$C_6$ alkenyl, $C_2$-$C_6$ alkynyl, $C_1$-$C_6$ alkoxy, halo, or $C_6$-$C_{10}$ arylalkyl. In some embodiments, $R^{1a}$ is H. In some embodiments, $R^{1a}$ is $C_1$-$C_6$ alkyl, such as methyl, ethyl, or propyl. In some embodiments, $R^{1a}$ is $C_2$-$C_6$ alkenyl, such as vinyl or propenyl. In some embodiments, $R^{1a}$ is $C_2$-$C_6$ alkynyl, such as ethynyl or propynyl. In some embodiments, $R^{1a}$ is $C_1$-$C_6$ alkoxy, such as methoxy, ethoxy, or propoxy. In some embodiments, $R^{1a}$ is halo, such as fluoro, chloro, or bromo. In some embodiments, $R^{1a}$ is $C_6$-$C_{10}$ arylalkyl, such as benzyl. In some embodiments, $R^{1b}$ is H. In some embodiments, $R^{1b}$ is $C_1$-$C_6$ alkyl, such as methyl, ethyl, or propyl. In some embodiments, $R^{1b}$ is $C_2$-$C_6$ alkenyl, such as vinyl or propenyl. In some embodiments, $R^{1b}$ is $C_2$-$C_6$ alkynyl, such as ethynyl or propynyl. In some embodiments, $R^{1b}$ is $C_1$-$C_6$ alkoxy, such as methoxy, ethoxy, or propoxy. In some embodiments, $R^{1b}$ is halo, such as fluoro, chloro, or bromo. In some embodiments, $R^{1b}$ is $C_6$-$C_{10}$ arylalkyl, such as benzyl.

In some embodiments, $R^{1a}$ and $R^{1b}$ are each independently H; $C_1$-$C_6$ alkyl optionally substituted with 1-3 substituents selected from halo, —$CO_2$H, and —C(═O)$NH_2$; $C_1$-$C_6$ alkoxy; halo; or $C_6$-$C_{10}$ arylalkyl optionally substituted by 1-3 substituents selected from halo and amino. In some embodiments, $R^{1a}$ is $C_1$-$C_6$ alkyl substituted with 1-3 halo, such as fluoro or chloro. In some embodiments, $R^{1a}$ is $C_1$-$C_6$ alkyl substituted with 1-3 —$CO_2$H groups. In some variations, $R^{1a}$ is $C_1$-$C_3$ alkyl substituted with 1-2 $CO_2$H groups, such as —$CH_2CO_2$H or —$CH_2CH_2CO_2$H. In some embodiments, $R^{1a}$ is $C_1$-$C_6$ alkyl substituted with 1-3 —C(═O)$NH_2$ groups. In some embodiments, $R^{1a}$ is $C_1$-$C_3$ alkyl substituted with 1-2 —C(═O)$NH_2$ groups, such as —$CH_2$C(═O)$NH_2$ or —$CH_2CH_2$C(═O)$NH_2$. In some embodiments, $R^{1a}$ is $C_6$-$C_{10}$ arylalkyl substituted by 1-3 substituents selected from halo and amino. In some embodiments, $R^{1a}$ is $C_6$-$C_{10}$ arylalkyl substituted by 1-3 halo, such as fluoro, chloro, or bromo. In some embodiments, $R^{1a}$ is $C_6$-$C_{10}$ arylalkyl substituted by 1-3 amino. In some embodiments, $R^{1b}$ is $C_1$-$C_6$ alkyl substituted with 1-3 halo, such as fluoro or chloro. In some embodiments, $R^{1b}$ is $C_1$-$C_6$ alkyl substituted with 1-3 —$CO_2$H groups. In some variations, $R^{1b}$ is $C_1$-$C_3$ alkyl substituted with 1-2 $CO_2$H groups, such as —$CH_2CO_2$H or —$CH_2CH_2CO_2$H. In some embodiments, $R^{1b}$ is $C_1$-$C_6$ alkyl substituted with 1-3 —C(═O)$NH_2$ groups. In some embodiments, $R^{1b}$ is $C_1$-$C_3$ alkyl substituted with 1-2 —C(═O)$NH_2$ groups, such as —$CH_2$C(═O)$NH_2$ or —$CH_2CH_2$C(═O)$NH_2$. In some embodiments, $R^{1b}$ is $C_6$-$C_{10}$ arylalkyl substituted by 1-3 substituents selected from halo and amino. In some embodiments, $R^{1b}$ is $C_6$-$C_{10}$ arylalkyl substituted by 1-3 halo, such as fluoro, chloro, or bromo. In some embodiments, $R^{1b}$ is $C_6$-$C_{10}$ arylalkyl substituted by 1-3 amino. In some embodiments, $R^{1a}$ and $R^{1b}$ are each independently H, methyl, fluoro, 2-methylbutyl, —$CH_2$F, methoxy, —$CH_2CO_2$H, —$CH_2$C(═O)$NH_2$, benzyl, or 4-aminobenzyl. In some embodiments, $R^{1a}$ and $R^{1b}$ are each independently H or $C_1$-$C_3$ alkyl. In some embodiments, $R^{1a}$ is methyl and $R^{1b}$ is H. In some embodiments, $R^{1a}$ and $R^{1b}$ are each H. In some embodiments, one of $R^{1a}$ and $R^{1b}$ is H and the other is $C_1$-$C_3$ alkyl, such as methyl.

In some embodiments, $R^2$ is H, oxo, or thioxo. In some embodiments, $R^2$ is H. In some embodiments, $R^2$ is oxo. In some embodiments, $R^2$ is thioxo.

In some embodiments, $R^3$ is $C_3$-$C_6$ alkyl, $C_3$-$C_6$ alkenyl, $C_3$-$C_6$ alkynyl, $C_3$-$C_{12}$ cycloalkyl, $C_3$-$C_6$ cycloalkylalkyl, $C_6$-$C_{10}$ arylalkyl, 5- to 10-membered heteroarylalkyl, or 5- to 10-membered heterocyclylalkyl, wherein the 5- to 10-membered heteroarylalkyl or 5- to 10-membered heterocyclylalkyl contains 1-3 heteroatoms selected from nitrogen and oxygen. In some embodiments, $R^3$ is $C_3$-$C_6$ alkyl, such as propyl, butyl, pentyl, or hexyl. In some embodiments, $R^3$ is $C_4$-$C_6$ alkyl. In some embodiments, $R^3$ is $C_3$-$C_6$ alkenyl. In some embodiments, $R^3$ is $C_4$-$C_6$ alkenyl. In some embodiments, $R^3$ is $C_3$-$C_6$ alkynyl. In some embodiments, $R^3$ is $C_4$-$C_6$ alkynyl. In some embodiments, $R^3$ is $C_3$-$C_{12}$ cycloalkyl, such as cyclopropyl, cyclobutyl, cyclopentyl, or cyclohexyl. In some embodiments, $R^3$ is $C_3$-$C_6$ cycloalkyl. In some embodiments, $R^3$ is $C_3$-$C_6$ cycloalkylalkyl, such as —$(CH_2)_{1-3}$($C_3$-$C_6$ cycloalkyl). In some embodiments, $R^3$ is $C_6$-$C_{10}$ arylalkyl, such as benzyl. In some embodiments, $R^3$ is 5- to 10-membered heteroarylalkyl, such as —$(CH_2)_{1-3}$ (5- to 10-membered heteroaryl) or —$(CH_2)_{1-3}$ (5- to 6-membered heteroaryl). In some embodiments, the 5- to 10-membered heteroarylalkyl contains 1-2 nitrogen atoms. In some embodiments, $R^3$ is 5- to 10-membered heterocyclylalkyl, such as —$(CH_2)_{1-3}$ (5- to 10-membered heterocyclyl) or —$(CH_2)_{1-2}$(5- to 6-membered heterocyclyl). In some embodiments, the 5- to 10-membered heterocyclylalkyl contains 1-2 nitrogen atoms.

In some embodiments, $R^3$ is $C_3$-$C_6$ alkyl optionally substituted by 1-3 substituents selected from halo and —C(═O)$NH_2$, $C_2$-$C_6$ alkenyl, or $C_3$-$C_6$ cycloalkylalkyl. In some embodiments, $R^3$ is $C_2$-$C_6$ alkyl optionally substituted by 1-3 substituents selected from halo, $C_1$-$C_3$ alkoxy, hydroxy, —$NH_2$, —$SO_2$($C_1$-$C_3$ alkyl), and —C(═O)$NH_2$; $C_2$-$C_6$ alkenyl; $C_3$-$C_6$ cycloalkylalkyl; 5- to 6-membered heteroarylalkyl; 5- to 6-membered heterocyclylalkyl; or $C_6$ arylalkyl. In some embodiments, $R^3$ is $C_2$ alkyl substituted by 1-3 substituents selected from $C_1$-$C_3$ alkoxy, hydroxy, —$NH_2$, and —$SO_2$($C_1$-$C_3$ alkyl). In some embodiments, $R^3$ is:

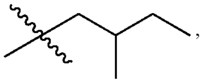, 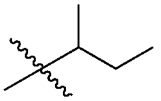,

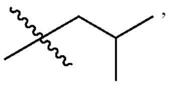, 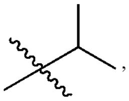,

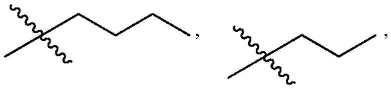,

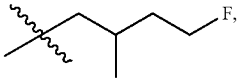, 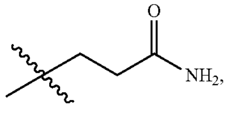,

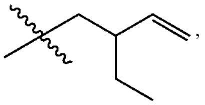, 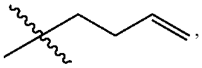,

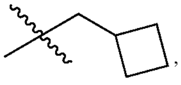, 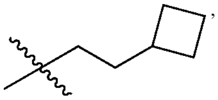,

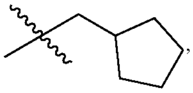, 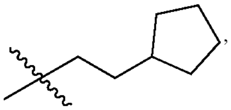,

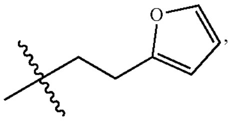, 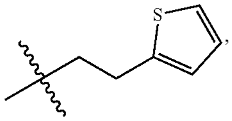,

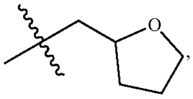, 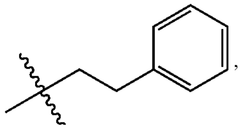,

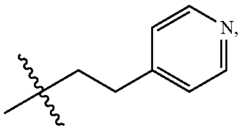, 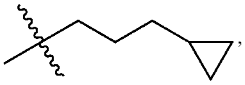,

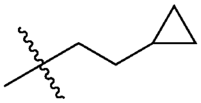, 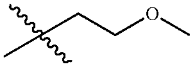,

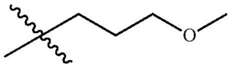, 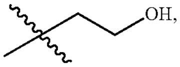,

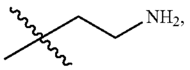, 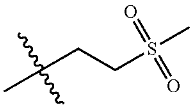, or

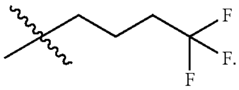.

In some embodiments, $R^3$ is:

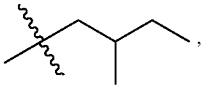, 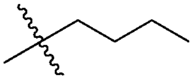,

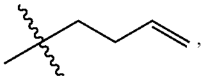, 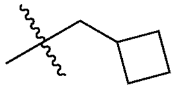,

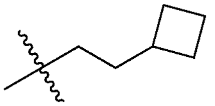, 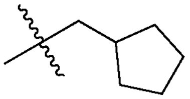,

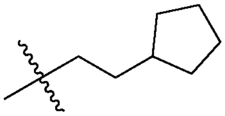, or

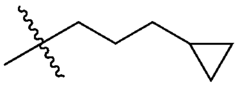.

In some embodiments, $R^3$ is 2-methylbutyl.

In some embodiments, $R^4$ is $C_6$-$C_{10}$ aryl, 5- to 10-membered heteroaryl, or 5- to 10-membered heterocyclyl, wherein the 5- to 10-membered heteroaryl or 5- to 10-membered heterocyclyl contains 1-3 heteroatoms selected from nitrogen and oxygen. In some embodiments, $R^4$ is $C_6$-$C_{10}$ aryl, such as phenyl. In some embodiments, $R^4$ is 5- to 10-membered heteroaryl containing 1-2 nitrogen atoms. In some embodiments, $R^4$ is 5- to 10-membered heterocyclyl. In some embodiments, $R^4$ is 5- to 9-membered heterocyclyl containing 1-2 nitrogen atoms. In some embodiments, $R^4$ is 5- to 9-membered heterocyclyl containing 1-2 oxygen atoms. In some embodiments, $R^4$ is 5- to 9-membered heterocyclyl containing 1 nitrogen atom and 1 oxygen atom.

In some embodiments, $R^4$ is $C_6$-$C_{10}$ aryl optionally substituted with 1-3 substituents selected from halo, hydroxyl, $C_1$-$C_6$ haloalkyl, and $C_1$-$C_6$haloalkoxy. In some embodiments, $R^4$ is phenyl substituted with 1-3 substituents selected from —$CF_3$, —$OCHF_2$, —OH, fluoro, and chloro. In some embodiments, $R^4$ is:

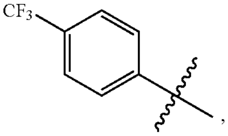, 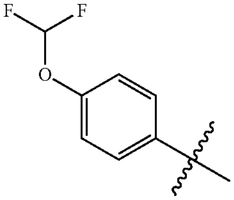,

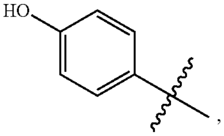, 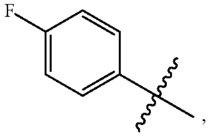,

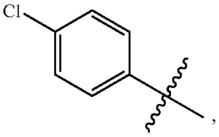, or 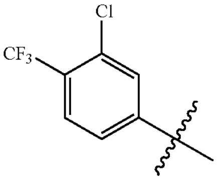.

In some embodiments, $R^4$ is:

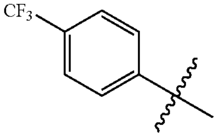,
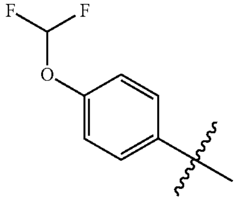,
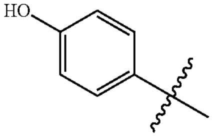,
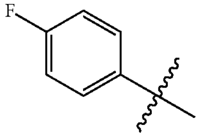, or
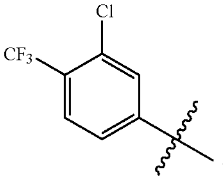.

In some embodiments, $R^4$ is 5- to 10-membered heteroaryl optionally substituted with 1-3 substituents selected from halo, hydroxyl, $C_1$-$C_6$ haloalkyl, and $C_1$-$C_6$haloalkoxy. In some embodiments, $R^4$ is pyridyl or indolyl optionally substituted with 1-3 substituents selected from halo, hydroxyl, $C_1$-$C_6$ haloalkyl, and $C_1$-$C_6$haloalkoxy. In some embodiments, $R^4$ is

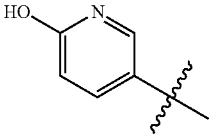 or 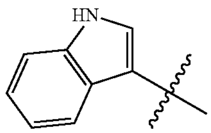.

In some embodiments, $R^4$ is pyridyl substituted with 1-3 substituents selected from halo, hydroxyl, $C_1$-$C_6$ haloalkyl, and $C_1$-$C_6$haloalkoxy. In some embodiments, $R^4$ is

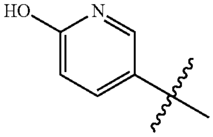.

In some embodiments, $R^4$ is 5- to 10-membered heterocyclyl optionally substituted with 1-3 substituents selected from halo, hydroxyl, $C_1$-$C_6$ haloalkyl, and $C_1$-$C_6$haloalkoxy. In some embodiments, $R^4$ is indolinyl.

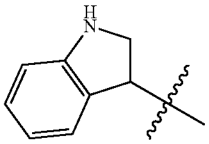.

In some embodiments, -L-$R^4$ is —$CH_2$(phenyl) or —C(O)(phenyl), wherein the phenyl is substituted by 1-3 substituents selected from $C_1$-$C_3$ haloalkyl, $C_1$-$C_3$ haloalkoxy, halo, and hydroxy. In some embodiments, -L-$R^4$ is —$CH_2$(pyridyl) or —C(O)(pyridyl), wherein the pyridyl is substituted by 1-3 substituents selected from $C_1$-$C_3$ haloalkyl, $C_1$-$C_3$ haloalkoxy, halo, and hydroxy. In some embodiments, -L-$R^4$ is:

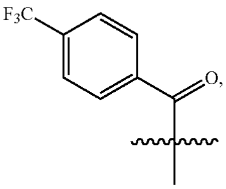,
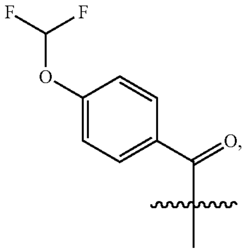,
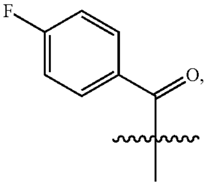,
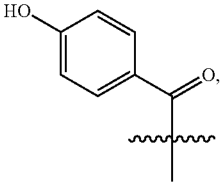,
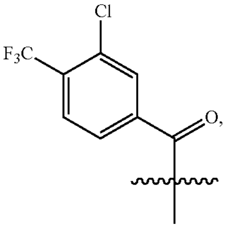,
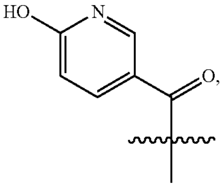,
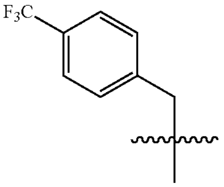,
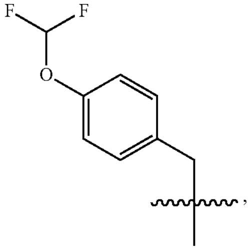,
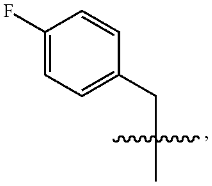,
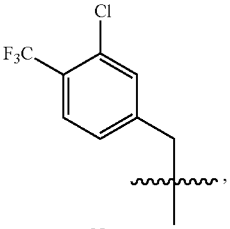, or
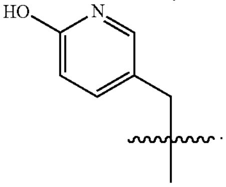.

In some embodiments, each $R^5$ is independently $C_1$-$C_6$ alkyl, oxo, or halo. In some embodiments, $R^5$ is $C_1$-$C_6$ alkyl, such as methyl, ethyl, or propyl. In some embodiments, $R^5$ is oxo. In some embodiments, $R^5$ is halo, such as fluoro, chloro, or bromo. In some embodiments, $R^5$ is oxo or halo. In some embodiments, $R^5$ is oxo or fluoro.

In some embodiments, $R^6$ is H, $C_1$-$C_6$ alkyl, or oxo. In some embodiments, $R^6$ is H. In some embodiments, $R^6$ is $C_1$-$C_6$ alkyl, such as methyl, ethyl, or propyl. In some embodiments, $R^6$ is oxo.

In some embodiments, $R^7$ is H or oxo. In some embodiments, $R^7$ is H. In some embodiments, $R^7$ is oxo.

In some embodiments, m is 1. In other embodiments, m is 2.

In some embodiments, n is 0. In other embodiments, n is an integer from 1 to 3. In some embodiments, n is 1. In some embodiments, n is 2. In some embodiments, n is 3.

In any embodiments of Formula (I), or variations thereof, each $C_1$-$C_6$ alkyl, $C_2$-$C_6$ alkenyl, $C_2$-$C_6$ alkynyl, $C_3$-$C_{12}$ cycloalkyl, $C_3$-$C_{12}$ cycloalkylalkyl, $C_6$-$C_{10}$ aryl, $C_6$-$C_{10}$ arylalkyl, 5- to 10-membered heteroaryl, 5- to 10-membered heteroarylalkyl, 5- to 10-membered heterocyclyl, and 5- to 10-membered heterocyclylalkyl is optionally substituted with one to three substituents selected from hydroxyl, halo (such as fluoro, chloro, or bromo), amino, $C_1$-$C_6$ haloalkyl (such as —$CF_3$ or —$CHF_2$), $C_1$-$C_6$ alkoxy (such as methoxy or ethoxy), $C_1$-$C_6$ haloalkoxy (such as —$OCHF_2$ or —$OCF_3$), and —(C═O)$NH_2$.

In some embodiments, the compound of Formula (I) is a compound of Formula (II), (IIa), (IIb), (IIc), (IId), or (IIe):

(II)

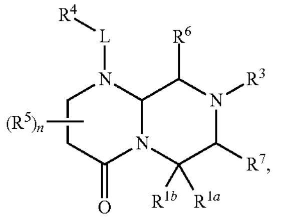

(IIa)

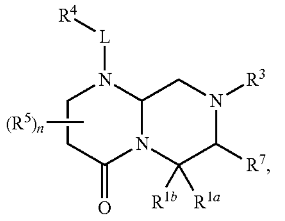

(IIb)

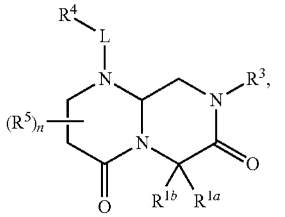

(IIc)

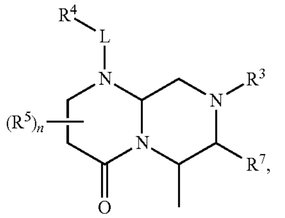

-continued (IId)

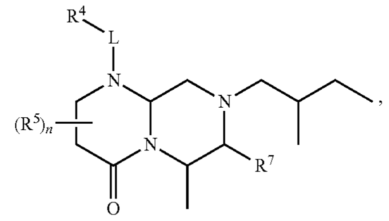

or (IIe)

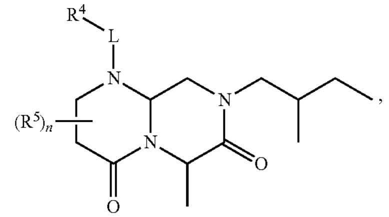

or a pharmaceutically acceptable salt thereof, wherein L, $R^{1a}$, $R^{1b}$, $R^3$, $R^4$, $R^5$, $R^6$, $R^7$, and n are as described for Formula (I). In some embodiments, the compound is of Formula (II) or a pharmaceutically acceptable salt thereof. In some embodiments, the compound is of Formula (Ha) or a pharmaceutically acceptable salt thereof. In some embodiments, the compound is of Formula (IIb) or a pharmaceutically acceptable salt thereof. In some embodiments, the compound is of Formula (IIc) or a pharmaceutically acceptable salt thereof. In some embodiments, the compound is of Formula (Hd) or a pharmaceutically acceptable salt thereof. In some embodiments, the compound is of Formula (He) or a pharmaceutically acceptable salt thereof.

In some embodiments, the compound of Formula (I) is a compound of Formula (IIIa), (IIIb), (IIIc), or (IIId):

(IIIa)

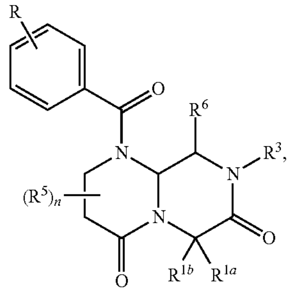

(IIIb)

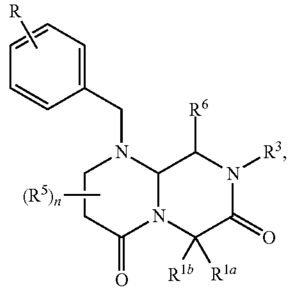

-continued (IIIc)

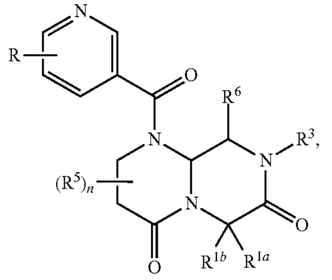

or (IIId)

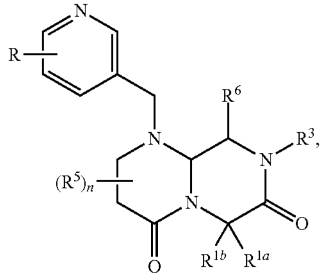

or a pharmaceutically acceptable salt thereof, wherein $R^{1a}$, $R^{1b}$, $R^3$, $R^5$, $R^6$, and n are as described for Formula (I), and R represents one or more optional substituents, such as hydroxyl, halo, amino, $C_1$-$C_6$ haloalkyl, $C_1$-$C_6$ haloalkoxy, as described for Formula (I). In some embodiments, the compound is of Formula (IIIa) or a pharmaceutically acceptable salt thereof. In some embodiments, the compound is of Formula (IIIb) or a pharmaceutically acceptable salt thereof. In some embodiments, the compound is of Formula (IIIc) or a pharmaceutically acceptable salt thereof. In some embodiments, the compound is of Formula (IIId) or a pharmaceutically acceptable salt thereof.

In some embodiments, the compound of Formula (I) is a compound of Formula (IVa), (IVb), (IVc), or (IVd):

(IVa)

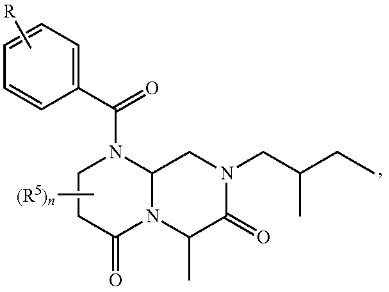

(IVb)

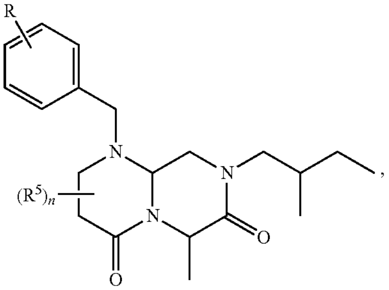

-continued (IVc)

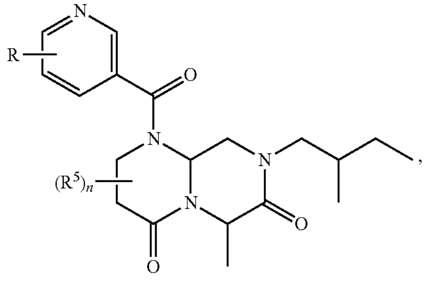

or (IVd)

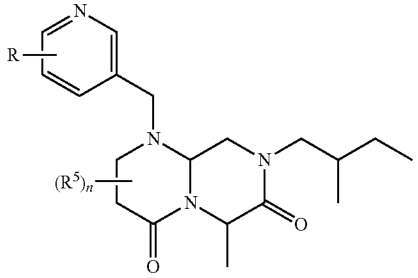

or a pharmaceutically acceptable salt thereof, wherein $R^5$ and n are as described for Formula (I), and R represents one or more optional substituents, such as hydroxyl, halo, amino, $C_1$-$C_6$ haloalkyl, $C_1$-$C_6$ haloalkoxy, as described for Formula (I). In some embodiments, the compound is of Formula (IVa) or a pharmaceutically acceptable salt thereof. In some embodiments, the compound is of Formula (IVb) or a pharmaceutically acceptable salt thereof. In some embodiments, the compound is of Formula (IVc) or a pharmaceutically acceptable salt thereof. In some embodiments, the compound is of Formula (IVd) or a pharmaceutically acceptable salt thereof.

In some embodiments, the compound of Formula (I) is a compound of Formula (V):

(V)

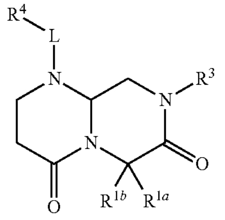

or a pharmaceutically acceptable salt thereof, wherein L, $R^{1a}$, $R^{1b}$, $R^3$, and $R^4$ are as described for Formula (I). In some embodiments, L is —C(═O)— or —$CH_2$—; $R^{1a}$ and $R^{1b}$ are independently H or $C_1$-$C_3$ alkyl optionally substituted with —$CO_2H$; $R^3$ is $C_4$-$C_5$ alkyl, $C_4$-$C_5$ alkenyl, or $C_1$-$C_3$ alkyl substituted with $C_3$-$C_5$ cycloalkyl; and $R^4$ is phenyl or pyridyl substituted with 1-3 substituents selected from —$CF_3$, —$OCHF_2$, —OH, fluoro, and chloro. In some variations, one of $R^{1a}$ and $R^{1b}$ is H and the other is $C_1$-$C_3$ alkyl, such as methyl.

In the descriptions herein, it is understood that every description, variation, embodiment, or aspect of a moiety may be combined with every description, variation, embodiment, or aspect of other moieties the same as if each and every combination of descriptions is specifically and individually listed. For example, every description, variation, embodiment, or aspect provided herein with respect to L of Formula (I) may be combined with every description, variation, embodiment, or aspect of $R^{1a}$, $R^{1b}$, $R^2$, $R^3$, $R^4$, $R^5$, $R^6$, $R^7$, and n the same as if each and every combination were specifically and individually listed. It is also understood that all descriptions, variations, embodiments, or aspects of Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (I), where applicable, apply equally to any of the formulae as detailed herein, such as Formulae (II), (IIa), (IIb), (IIc), (IId), (IIe), (IIIa), (IIIb), (IIIc), (IIId), (IVa), (IVb), (IVc), (IVd), and (V), and are equally described, the same as if each and every description, variation, embodiment, or aspect were separately and individually listed for all formulae.

In some embodiments, provided is a compound selected from the compounds in Table 1 or a pharmaceutically acceptable salt thereof. Although certain compounds described in the present disclosure, including in Table 1, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1, are herein described.

TABLE 1

| Compound | Structure | Compound | Structure |
|---|---|---|---|
| 1a | 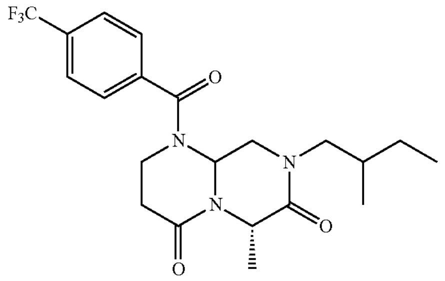 [SMILES: CCC(C)CN1CC2N(C(=O)c3ccc(C(F)(F)F)cc3)CCC(=O)N2[C@@H](C)C1=O] | 1b | 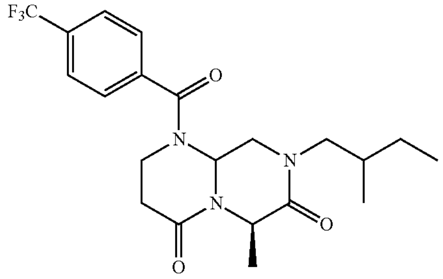 [SMILES: CCC(C)CN1CC2N(C(=O)c3ccc(C(F)(F)F)cc3)CCC(=O)N2[C@H](C)C1=O] |
| 2a | 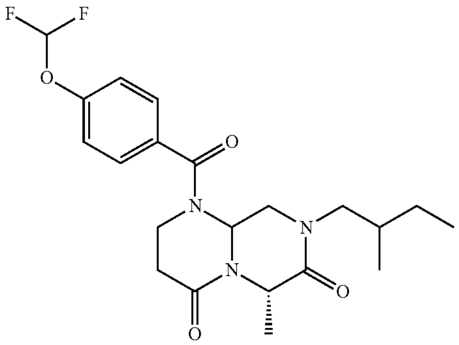 [SMILES: CCC(C)CN1CC2N(C(=O)c3ccc(OC(F)F)cc3)CCC(=O)N2[C@@H](C)C1=O] | 2b | 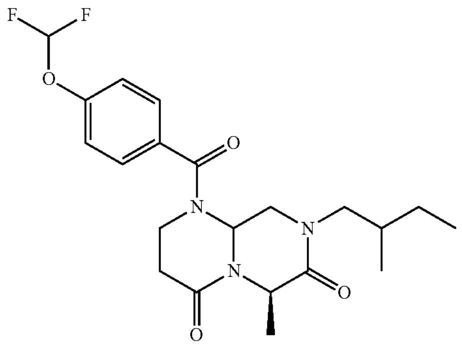 [SMILES: CCC(C)CN1CC2N(C(=O)c3ccc(OC(F)F)cc3)CCC(=O)N2[C@H](C)C1=O] |
| 3a | 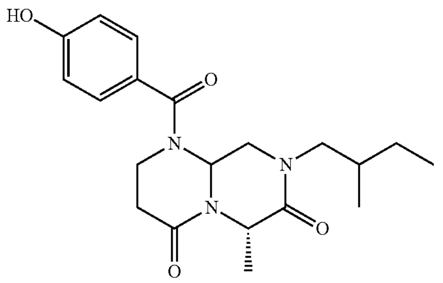 [SMILES: CCC(C)CN1CC2N(C(=O)c3ccc(O)cc3)CCC(=O)N2[C@@H](C)C1=O] | 3b | 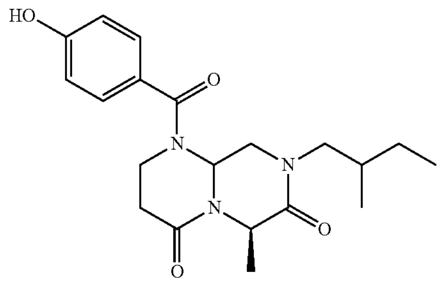 [SMILES: CCC(C)CN1CC2N(C(=O)c3ccc(O)cc3)CCC(=O)N2[C@H](C)C1=O] |
| 4a | 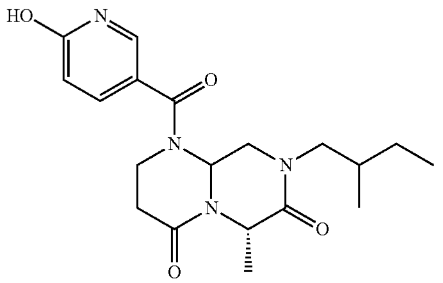 [SMILES: CCC(C)CN1CC2N(C(=O)c3ccc(O)nc3)CCC(=O)N2[C@@H](C)C1=O] | 4b | 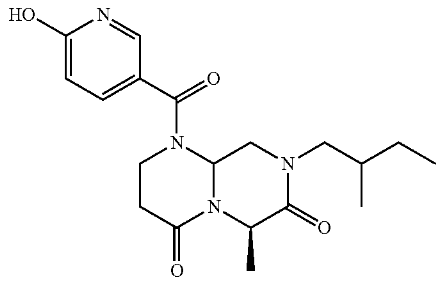 [SMILES: CCC(C)CN1CC2N(C(=O)c3ccc(O)nc3)CCC(=O)N2[C@H](C)C1=O] |

TABLE 1-continued
| Compound | Structure | Compound | Structure |
|---|---|---|---|
| 5a | 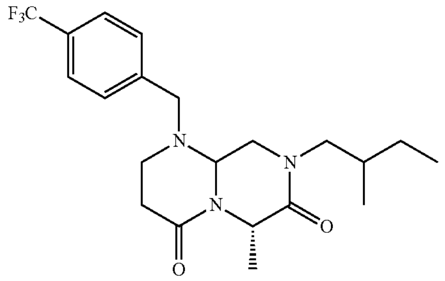 [SMILES: CCC(C)CN1CC2N(Cc3ccc(C(F)(F)F)cc3)CCC(=O)N2[C@@H](C)C1=O] | 5b | 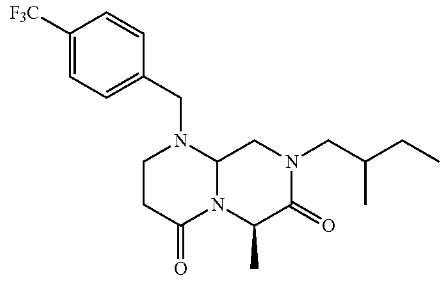 [SMILES: CCC(C)CN1CC2N(Cc3ccc(C(F)(F)F)cc3)CCC(=O)N2[C@H](C)C1=O] |
| 6a | 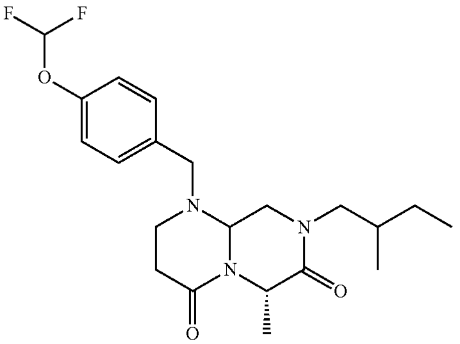 [SMILES: CCC(C)CN1CC2N(Cc3ccc(OC(F)F)cc3)CCC(=O)N2[C@@H](C)C1=O] | 6b | 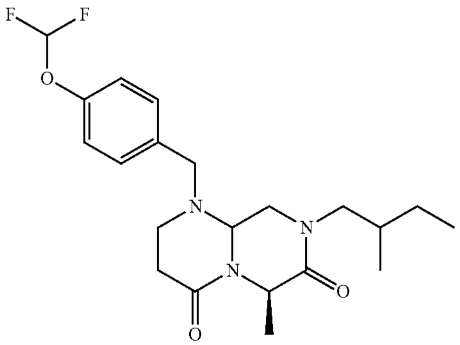 [SMILES: CCC(C)CN1CC2N(Cc3ccc(OC(F)F)cc3)CCC(=O)N2[C@H](C)C1=O] |
| 7a | 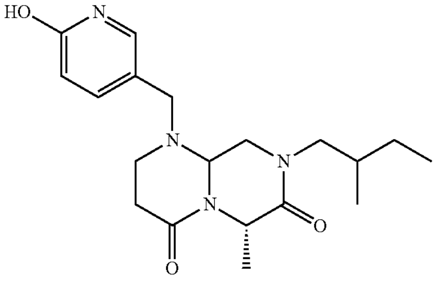 [SMILES: CCC(C)CN1CC2N(Cc3ccc(O)nc3)CCC(=O)N2[C@@H](C)C1=O] | 7b | 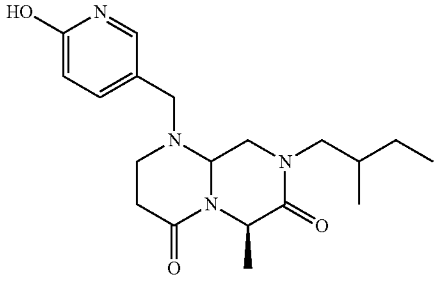 [SMILES: CCC(C)CN1CC2N(Cc3ccc(O)nc3)CCC(=O)N2[C@H](C)C1=O] |
| 8a | 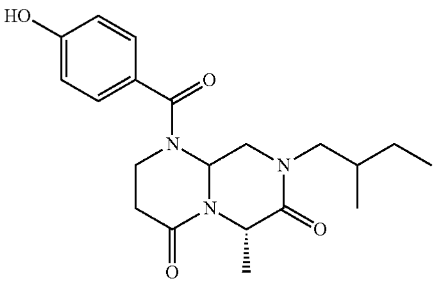 | 8b | 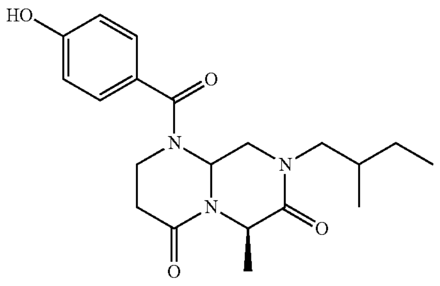 [SMILES: CCC(C)CN1CC2N(C(=O)c3ccc(O)cc3)CCC(=O)N2[C@H](C)C1=O] |
| 9 | 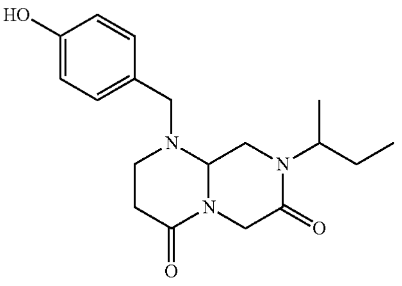 [SMILES: CCC(C)N1CC2N(Cc3ccc(O)cc3)CCC(=O)N2CC1=O] | 10 | 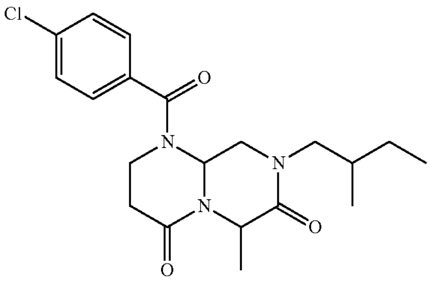 [SMILES: CCC(C)CN1CC2N(C(=O)c3ccc(Cl)cc3)CCC(=O)N2C(C)C1=O] |

TABLE 1-continued
| Compound | Structure | Compound | Structure |
|---|---|---|---|
| 11 | 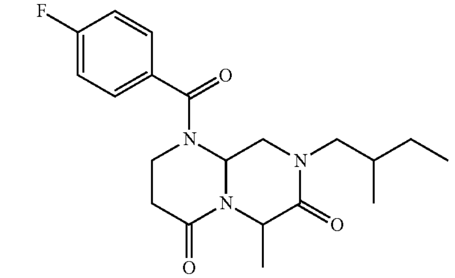 [SMILES: CCC(C)CN1CC2N(C(=O)c3ccc(F)cc3)CCC(=O)N2C(C)C1=O] | 12 | 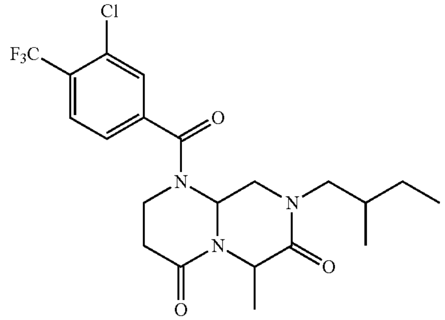 [SMILES: CCC(C)CN1CC2N(C(=O)c3ccc(C(F)(F)F)c(Cl)c3)CCC(=O)N2C(C)C1=O] |
| 13 | 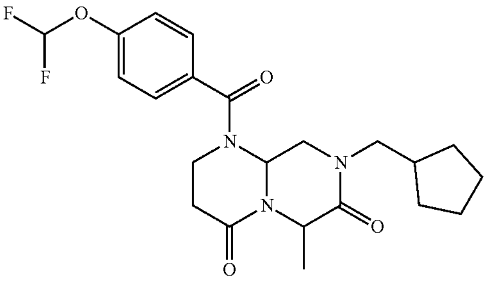 [SMILES: CC1C(=O)N(CC2CCCC2)CC2N(C(=O)c3ccc(OC(F)F)cc3)CCC(=O)N12] | 14 | 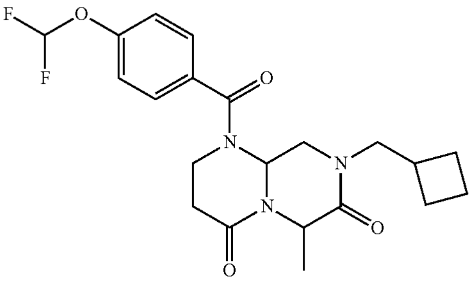 [SMILES: CC1C(=O)N(CC2CCC2)CC2N(C(=O)c3ccc(OC(F)F)cc3)CCC(=O)N12] |
| 15 | 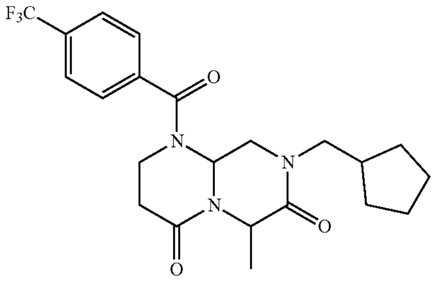 [SMILES: CC1C(=O)N(CC2CCCC2)CC2N(C(=O)c3ccc(C(F)(F)F)cc3)CCC(=O)N12] | 16 | 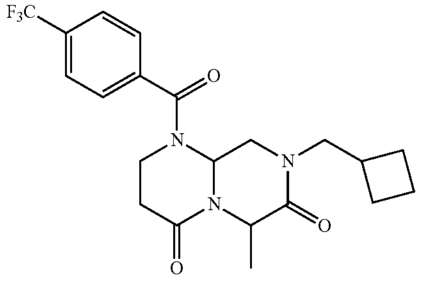 [SMILES: CC1C(=O)N(CC2CCC2)CC2N(C(=O)c3ccc(C(F)(F)F)cc3)CCC(=O)N12] |
| 17 | 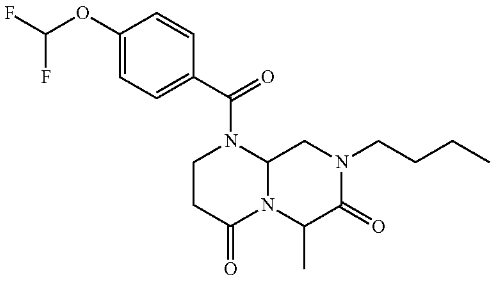 [SMILES: CCCCN1CC2N(C(=O)c3ccc(OC(F)F)cc3)CCC(=O)N2C(C)C1=O] | 18 | 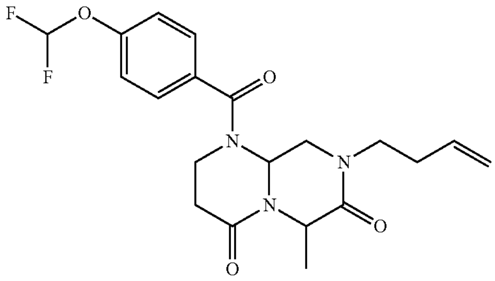 [SMILES: C=CCCN1CC2N(C(=O)c3ccc(OC(F)F)cc3)CCC(=O)N2C(C)C1=O] |
| 19 | 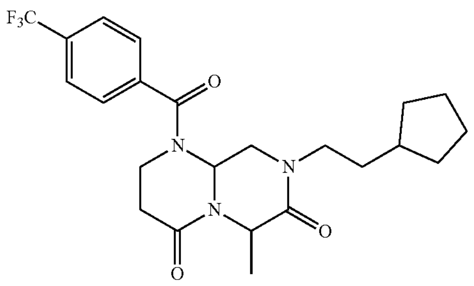 [SMILES: CC1C(=O)N(CCC2CCCC2)CC2N(C(=O)c3ccc(C(F)(F)F)cc3)CCC(=O)N12] | 20 | 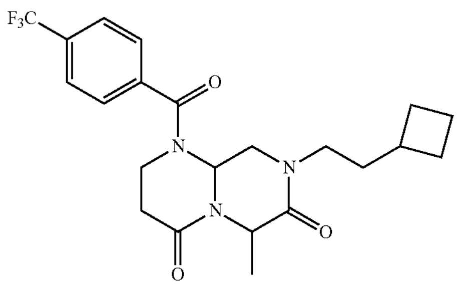 [SMILES: CC1C(=O)N(CCC2CCC2)CC2N(C(=O)c3ccc(C(F)(F)F)cc3)CCC(=O)N12] |

TABLE 1-continued
| Compound | Structure | Compound | Structure |
|---|---|---|---|
| 21 | 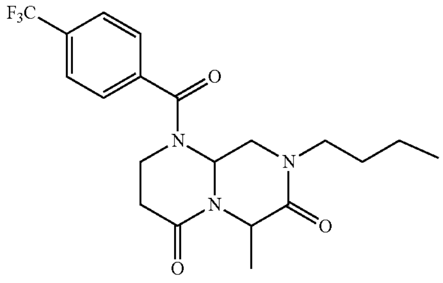 [SMILES: CCCCN1CC2N(C(=O)c3ccc(C(F)(F)F)cc3)CCC(=O)N2C(C)C1=O] | 22 | 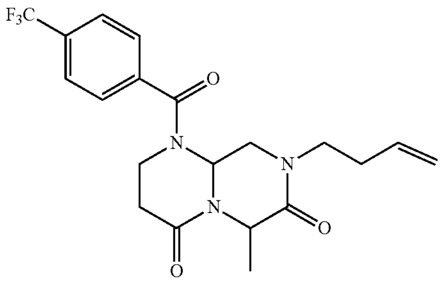 [SMILES: C=CCCN1CC2N(C(=O)c3ccc(C(F)(F)F)cc3)CCC(=O)N2C(C)C1=O] |
| 23 | 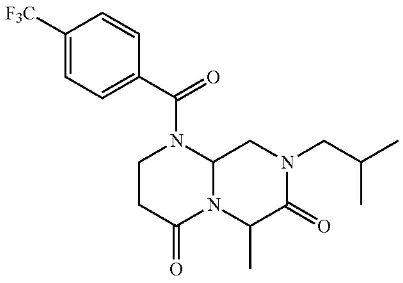 [SMILES: CC(C)CN1CC2N(C(=O)c3ccc(C(F)(F)F)cc3)CCC(=O)N2C(C)C1=O] | 24 | 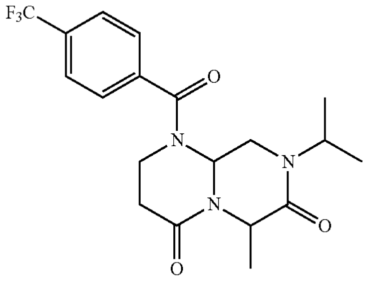 [SMILES: CC(C)N1CC2N(C(=O)c3ccc(C(F)(F)F)cc3)CCC(=O)N2C(C)C1=O] |
| 25 | 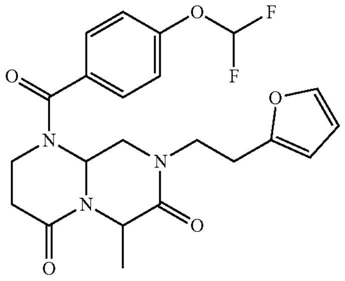 [SMILES: CC1C(=O)N(CCc2ccco2)CC2N(C(=O)c3ccc(OC(F)F)cc3)CCC(=O)N12] | 26 | 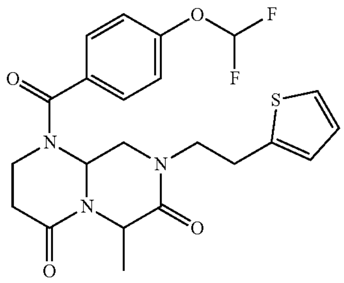 |
| 27 | 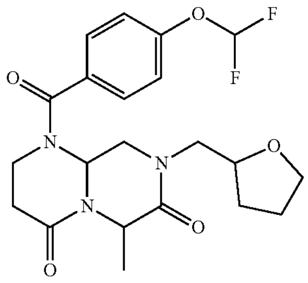 [SMILES: CC1C(=O)N(CC2CCCO2)CC2N(C(=O)c3ccc(OC(F)F)cc3)CCC(=O)N12] | 28 | 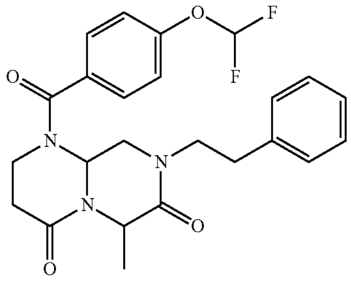 [SMILES: CC1C(=O)N(CCc2ccccc2)CC2N(C(=O)c3ccc(OC(F)F)cc3)CCC(=O)N12] |
| 29 | 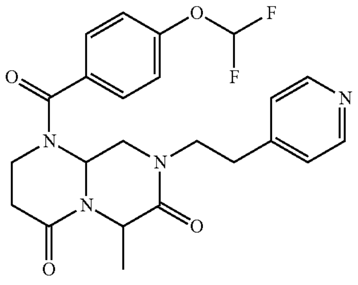 [SMILES: CC1C(=O)N(CCc2ccncc2)CC2N(C(=O)c3ccc(OC(F)F)cc3)CCC(=O)N12] | 30 | 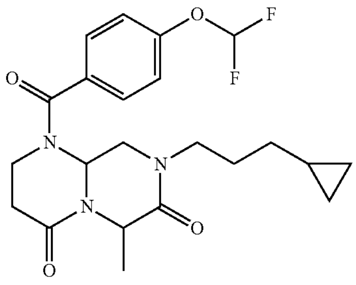 [SMILES: CC1C(=O)N(CCCC2CC2)CC2N(C(=O)c3ccc(OC(F)F)cc3)CCC(=O)N12] |

TABLE 1-continued
| Compound | Structure | Compound | Structure |
|---|---|---|---|
| 31 | 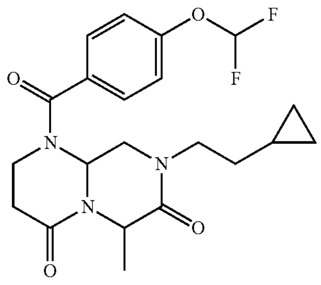 [SMILES: CC1C(=O)N(CCC2CC2)CC2N(C(=O)c3ccc(OC(F)F)cc3)CCC(=O)N12] | 32 | 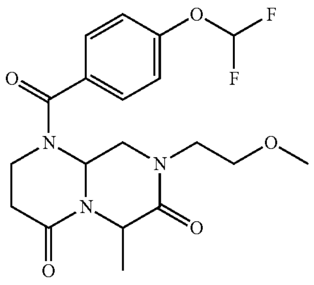 [SMILES: COCCN1CC2N(C(=O)c3ccc(OC(F)F)cc3)CCC(=O)N2C(C)C1=O] |
| 33 | 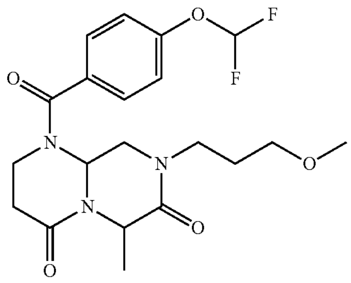 [SMILES: COCCCN1CC2N(C(=O)c3ccc(OC(F)F)cc3)CCC(=O)N2C(C)C1=O] | 34 | 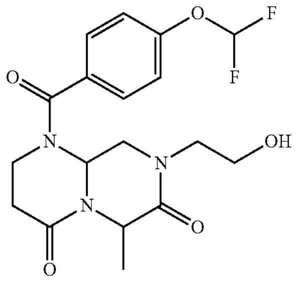 [SMILES: CC1C(=O)N(CCO)CC2N(C(=O)c3ccc(OC(F)F)cc3)CCC(=O)N12] |
| 35 | 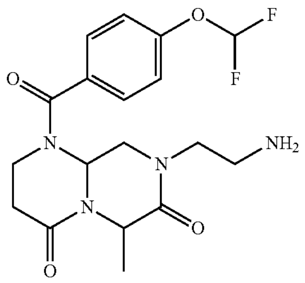 [SMILES: CC1C(=O)N(CCN)CC2N(C(=O)c3ccc(OC(F)F)cc3)CCC(=O)N12] | 36 | 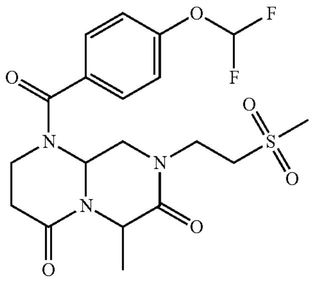 [SMILES: CC1C(=O)N(CCS(C)(=O)=O)CC2N(C(=O)c3ccc(OC(F)F)cc3)CCC(=O)N12] |
| 37 | 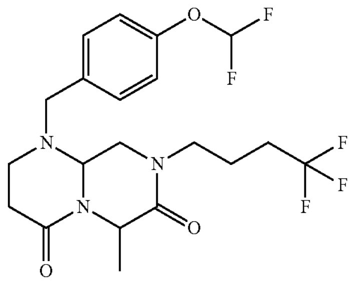 [SMILES: CC1C(=O)N(CCCC(F)(F)F)CC2N(Cc3ccc(OC(F)F)cc3)CCC(=O)N12] | 38 | 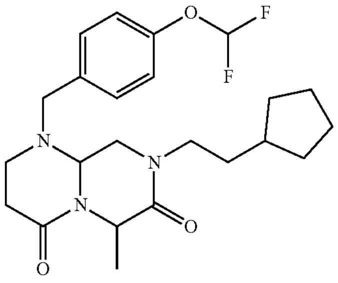 [SMILES: CC1C(=O)N(CCC2CCCC2)CC2N(Cc3ccc(OC(F)F)cc3)CCC(=O)N12] |
| 39 | 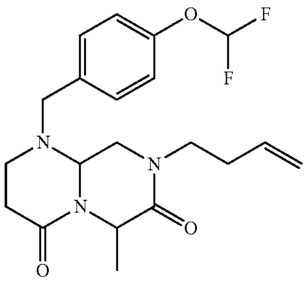 [SMILES: C=CCCN1CC2N(Cc3ccc(OC(F)F)cc3)CCC(=O)N2C(C)C1=O] | 40 | 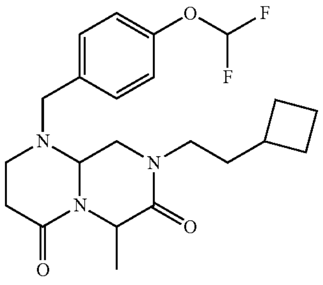 [SMILES: CC1C(=O)N(CCC2CCC2)CC2N(Cc3ccc(OC(F)F)cc3)CCC(=O)N12] |

TABLE 1-continued
| Compound | Structure | Compound | Structure |
|---|---|---|---|
| 41 | 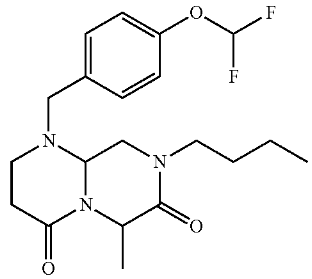 [SMILES: CCCCN1CC2N(Cc3ccc(OC(F)F)cc3)CCC(=O)N2C(C)C1=O] | 42 | 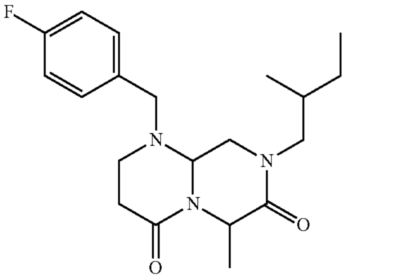 [SMILES: CCC(C)CN1CC2N(Cc3ccc(F)cc3)CCC(=O)N2C(C)C1=O] |
| 43 | 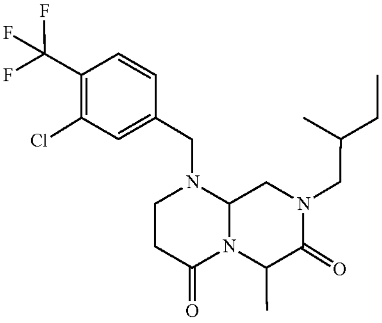 [SMILES: CCC(C)CN1CC2N(Cc3ccc(C(F)(F)F)c(Cl)c3)CCC(=O)N2C(C)C1=O] | 44 | 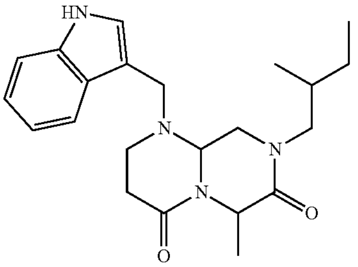 [SMILES: CCC(C)CN1CC2N(Cc3c[nH]c4ccccc34)CCC(=O)N2C(C)C1=O] |
| 45 | 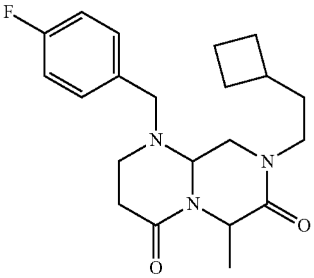 [SMILES: CC1C(=O)N(CCC2CCC2)CC2N(Cc3ccc(F)cc3)CCC(=O)N12] | 46 | 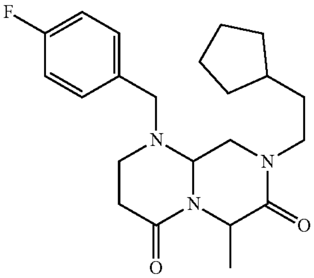 [SMILES: CC1C(=O)N(CCC2CCCC2)CC2N(Cc3ccc(F)cc3)CCC(=O)N12] |
| 47 | 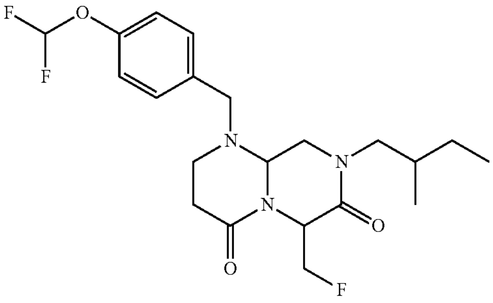 [SMILES: CCC(C)CN1CC2N(Cc3ccc(OC(F)F)cc3)CCC(=O)N2C(CF)C1=O] | 48 | 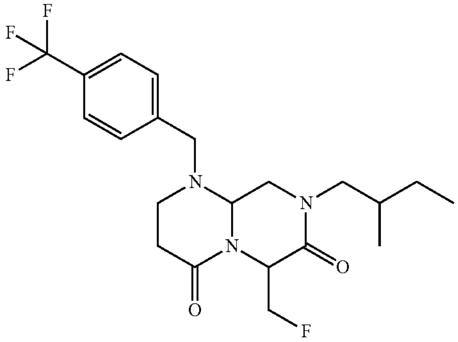 [SMILES: CCC(C)CN1CC2N(Cc3ccc(C(F)(F)F)cc3)CCC(=O)N2C(CF)C1=O] |
| 49 | 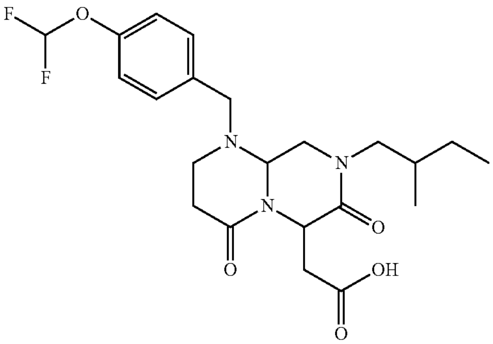 [SMILES: CCC(C)CN1CC2N(Cc3ccc(OC(F)F)cc3)CCC(=O)N2C(CC(=O)O)C1=O] | 50 | 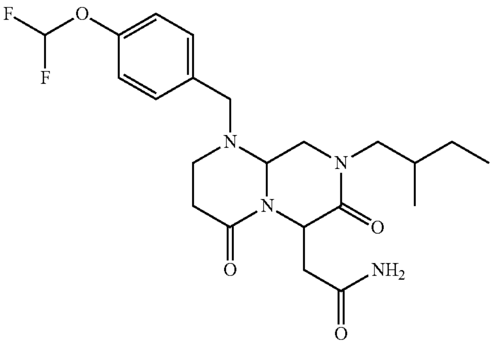 |

TABLE 1-continued
| Compound | Structure | Compound | Structure |
|---|---|---|---|
| 51 | 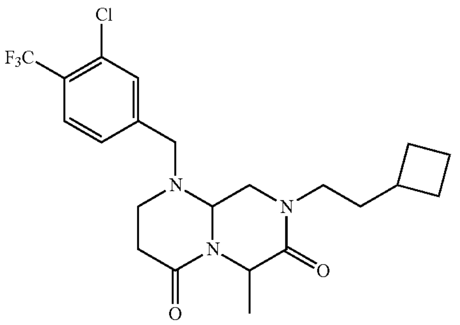 [SMILES: CC1C(=O)N(CCC2CCC2)CC2N(Cc3ccc(C(F)(F)F)c(Cl)c3)CCC(=O)N12] | 52 | 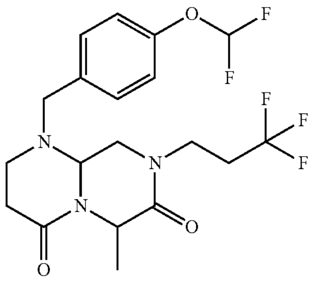 [SMILES: CC1C(=O)N(CCC(F)(F)F)CC2N(Cc3ccc(OC(F)F)cc3)CCC(=O)N12] |
| 53 | 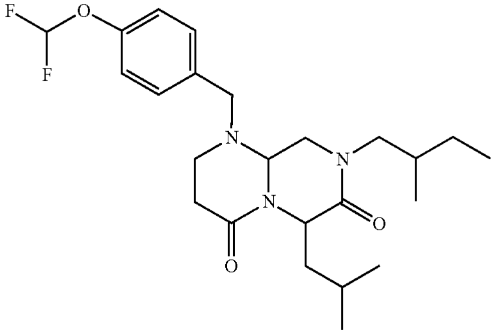 [SMILES: CCC(C)CN1CC2N(Cc3ccc(OC(F)F)cc3)CCC(=O)N2C(CC(C)C)C1=O] | 54 | 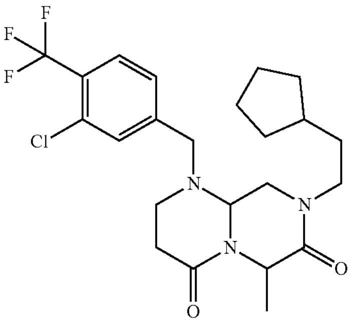 [SMILES: CC1C(=O)N(CCC2CCCC2)CC2N(Cc3ccc(C(F)(F)F)c(Cl)c3)CCC(=O)N12] |
| 55 | 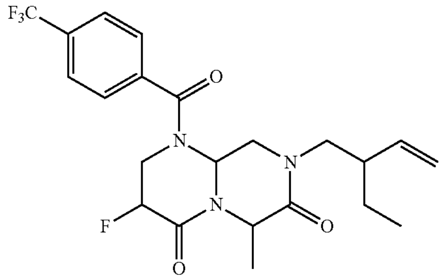 [SMILES: C=CC(CC)CN1CC2N(C(=O)c3ccc(C(F)(F)F)cc3)CC(F)C(=O)N2C(C)C1=O] | 56 | 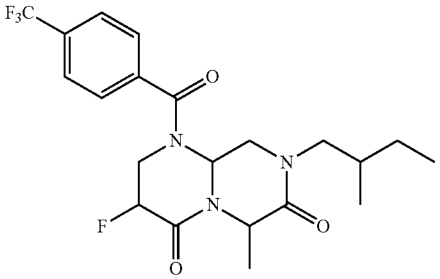 [SMILES: CCC(C)CN1CC2N(C(=O)c3ccc(C(F)(F)F)cc3)CC(F)C(=O)N2C(C)C1=O] |
| 57 | 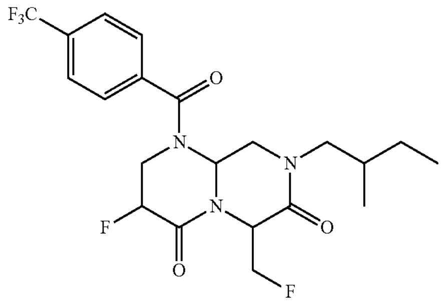 [SMILES: CCC(C)CN1CC2N(C(=O)c3ccc(C(F)(F)F)cc3)CC(F)C(=O)N2C(CF)C1=O] | 58 | 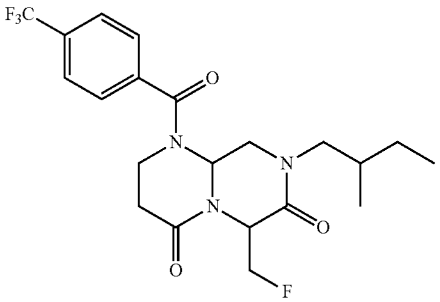 [SMILES: CCC(C)CN1CC2N(C(=O)c3ccc(C(F)(F)F)cc3)CCC(=O)N2C(CF)C1=O] |
| 59 | 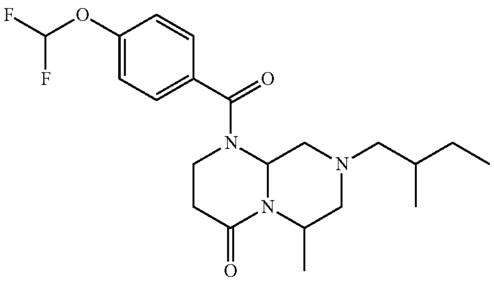 [SMILES: CCC(C)CN1CC(C)N2C(=O)CCN(C(=O)c3ccc(OC(F)F)cc3)C2C1] | 60 | 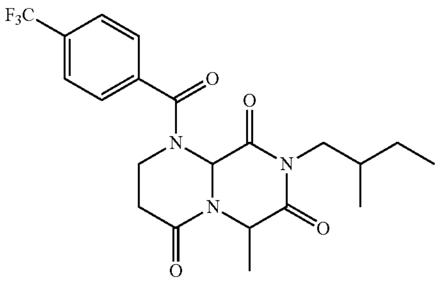 [SMILES: CCC(C)CN1C(=O)C(C)N2C(=O)CCN(C(=O)c3ccc(C(F)(F)F)cc3)C2C1=O] |

TABLE 1-continued
| Compound | Structure | Compound | Structure |
|---|---|---|---|
| 61 | 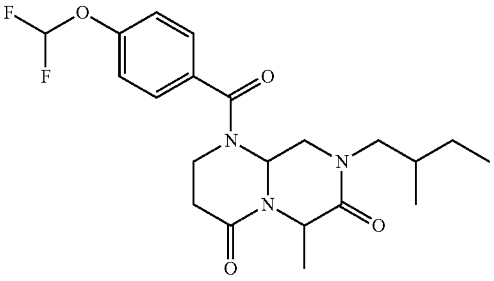 [SMILES: CCC(C)CN1CC2N(C(=O)c3ccc(OC(F)F)cc3)CCC(=O)N2C(C)C1=O] | 62 | 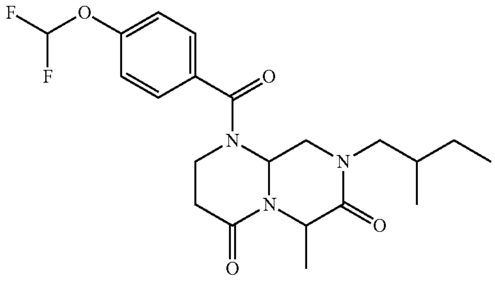 [SMILES: CCC(C)CN1CC2N(C(=O)c3ccc(OC(F)F)cc3)CCC(=O)N2C(C)C1=O] |
| 63 | 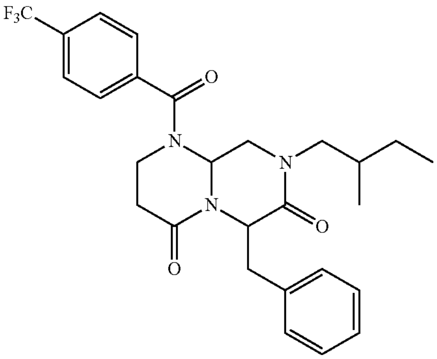 [SMILES: CCC(C)CN1CC2N(C(=O)c3ccc(C(F)(F)F)cc3)CCC(=O)N2C(Cc2ccccc2)C1=O] | 64 | 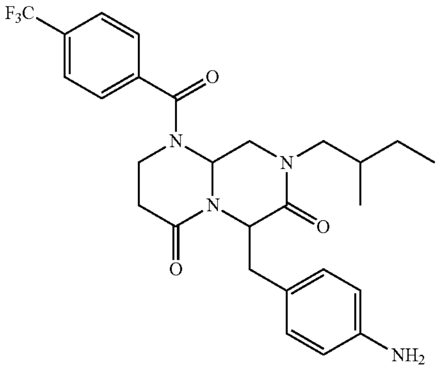 [SMILES: CCC(C)CN1CC2N(C(=O)c3ccc(C(F)(F)F)cc3)CCC(=O)N2C(Cc2ccc(N)cc2)C1=O] |
| 65 | 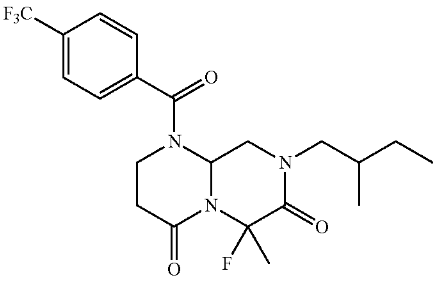 [SMILES: CCC(C)CN1CC2N(C(=O)c3ccc(C(F)(F)F)cc3)CCC(=O)N2C(C)(F)C1=O] | 66 | 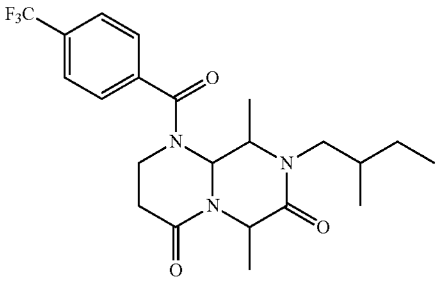 [SMILES: CCC(C)CN1C(=O)C(C)N2C(=O)CCN(C(=O)c3ccc(C(F)(F)F)cc3)C2C1C] |
| 67 | 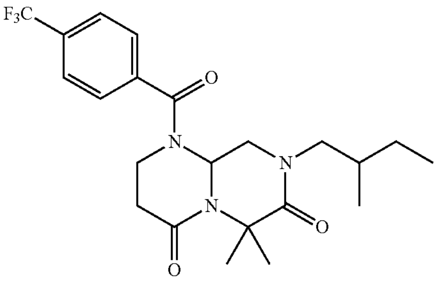 [SMILES: CCC(C)CN1CC2N(C(=O)c3ccc(C(F)(F)F)cc3)CCC(=O)N2C(C)(C)C1=O] | 68 | 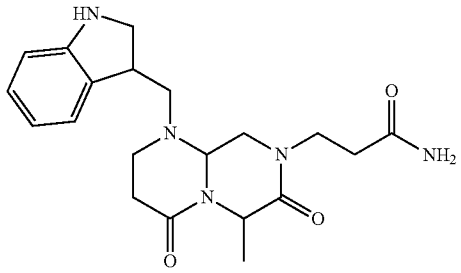 [SMILES: CC1C(=O)N(CCC(N)=O)CC2N(CC3CNc4ccccc43)CCC(=O)N12] |
| 69 | 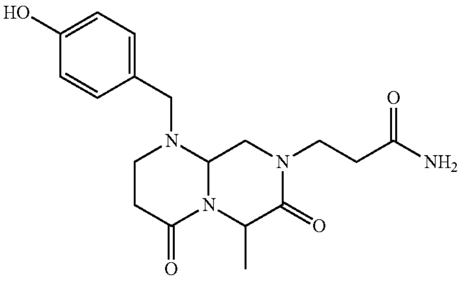 [SMILES: CC1C(=O)N(CCC(N)=O)CC2N(Cc3ccc(O)cc3)CCC(=O)N12] | 70 | 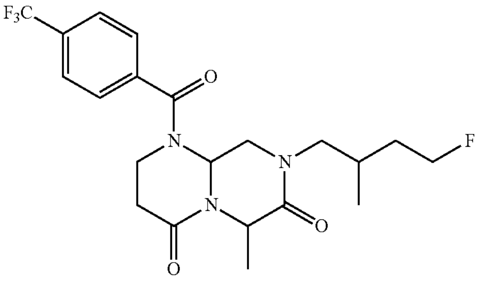 [SMILES: CC(CCF)CN1CC2N(C(=O)c3ccc(C(F)(F)F)cc3)CCC(=O)N2C(C)C1=O] |

TABLE 1-continued

| Compound | Structure | Compound | Structure |
| --- | --- | --- | --- |
| 71 | 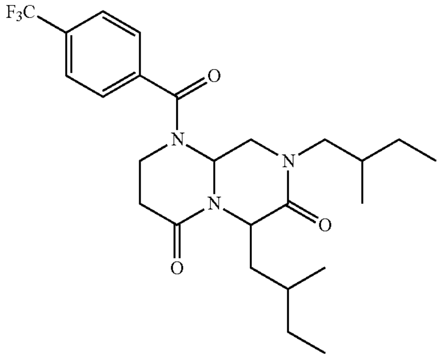 [SMILES: CCC(C)CC1C(=O)N(CC(C)CC)CC2N(C(=O)c3ccc(C(F)(F)F)cc3)CCC(=O)N12] | 72 | 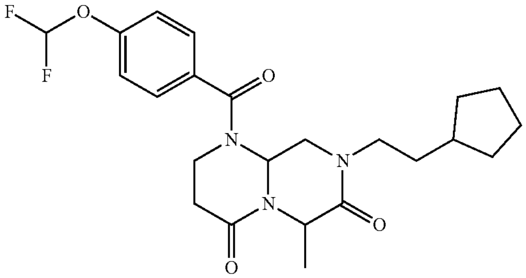 [SMILES: CC1C(=O)N(CCC2CCCC2)CC2N(C(=O)c3ccc(OC(F)F)cc3)CCC(=O)N12] |
| 73 | 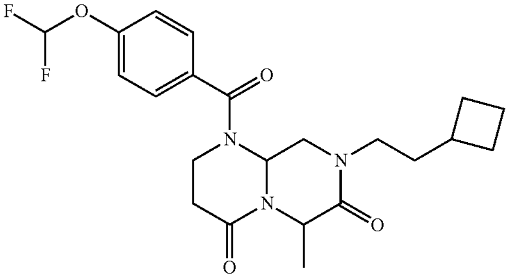 [SMILES: CC1C(=O)N(CCC2CCC2)CC2N(C(=O)c3ccc(OC(F)F)cc3)CCC(=O)N12] | 74 | 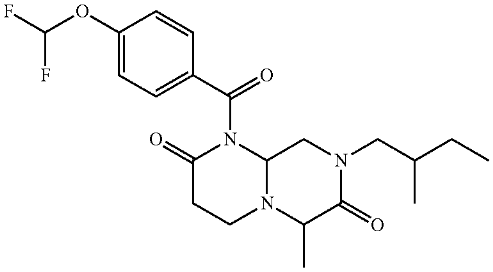 [SMILES: CCC(C)CN1CC2N(C(=O)c3ccc(OC(F)F)cc3)C(=O)CCN2C(C)C1=O] |

or a pharmaceutically acceptable salt thereof.

In some embodiments, the compound of Formula (I) is not Compound 3a, 3b, 9, 10, 13, 15, 16, 18, 21, 23-29, 31-41, 43-48, 50, 52, or 54.

In some embodiments, provided is a compound selected from the compounds in Table 1A or a pharmaceutically acceptable salt thereof. Although certain compounds described in the present disclosure, including in Table 1A, are presented as specific stereoisomers and/or in a non-stereochemical form, it is understood that any or all stereochemical forms, including any enantiomeric or diastereomeric forms, and any tautomers or other forms of any of the compounds of the present disclosure, including in Table 1A, are herein described.

TABLE 1A

| Compound | Structure | Compound | Structure |
| --- | --- | --- | --- |
| la | 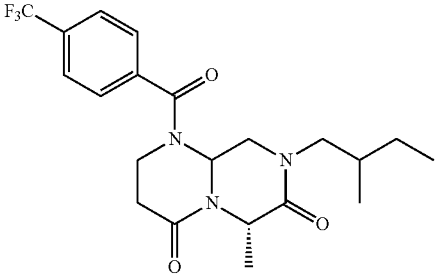 | 1b | 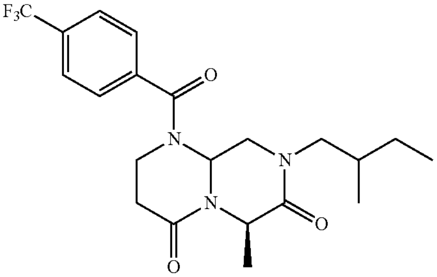 [SMILES: CCC(C)CN1CC2N(C(=O)c3ccc(C(F)(F)F)cc3)CCC(=O)N2[C@H](C)C1=O] |

TABLE 1A-continued
| Compound | Structure | Compound | Structure |
| --- | --- | --- | --- |
| 2a | 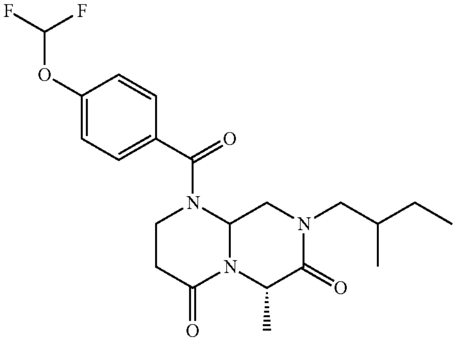 [SMILES: CCC(C)CN1CC2N(C(=O)c3ccc(OC(F)F)cc3)CCC(=O)N2[C@@H](C)C1=O] | 2b | 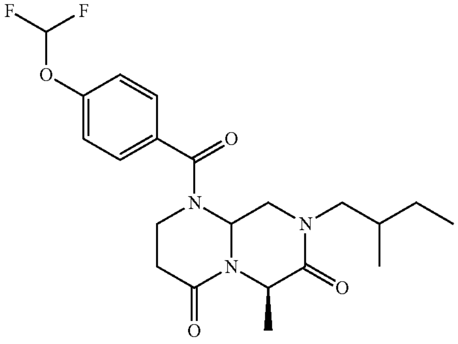 [SMILES: CCC(C)CN1CC2N(C(=O)c3ccc(OC(F)F)cc3)CCC(=O)N2[C@H](C)C1=O] |
| 4a | 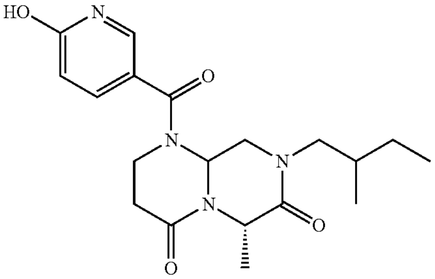 [SMILES: CCC(C)CN1CC2N(C(=O)c3ccc(O)nc3)CCC(=O)N2[C@@H](C)C1=O] | 4b | 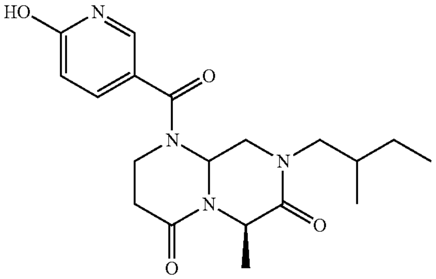 [SMILES: CCC(C)CN1CC2N(C(=O)c3ccc(O)nc3)CCC(=O)N2[C@H](C)C1=O] |
| 5a | 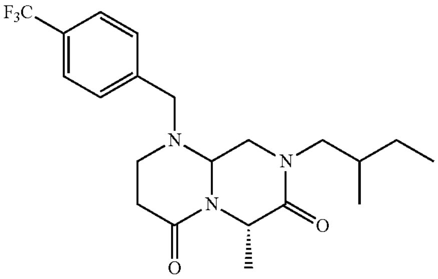 [SMILES: CCC(C)CN1CC2N(Cc3ccc(C(F)(F)F)cc3)CCC(=O)N2[C@@H](C)C1=O] | 5b | 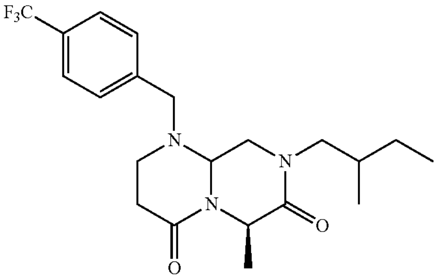 [SMILES: CCC(C)CN1CC2N(Cc3ccc(C(F)(F)F)cc3)CCC(=O)N2[C@H](C)C1=O] |
| 6a | 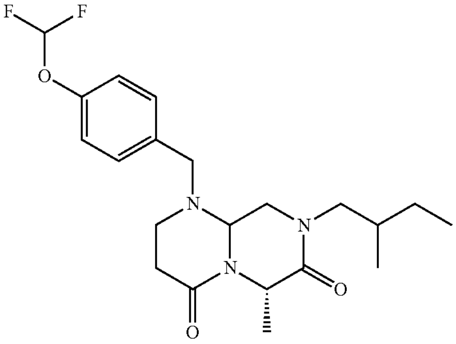 [SMILES: CCC(C)CN1CC2N(Cc3ccc(OC(F)F)cc3)CCC(=O)N2[C@@H](C)C1=O] | 6b | 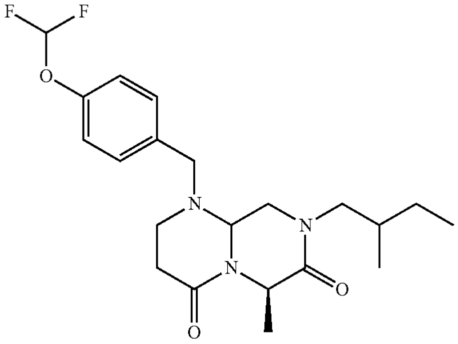 [SMILES: CCC(C)CN1CC2N(Cc3ccc(OC(F)F)cc3)CCC(=O)N2[C@H](C)C1=O] |
| 7a | 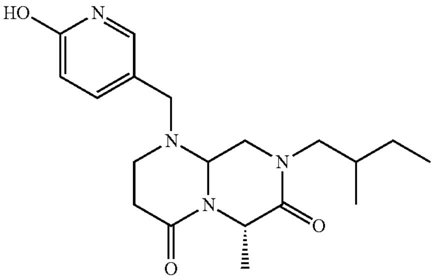 [SMILES: CCC(C)CN1CC2N(Cc3ccc(O)nc3)CCC(=O)N2[C@@H](C)C1=O] | 7b | 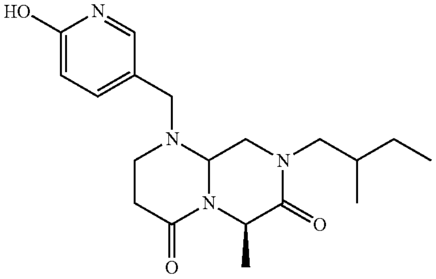 [SMILES: CCC(C)CN1CC2N(Cc3ccc(O)nc3)CCC(=O)N2[C@H](C)C1=O] |

TABLE 1A-continued
| Compound | Structure | Compound | Structure |
| --- | --- | --- | --- |
| 8a | 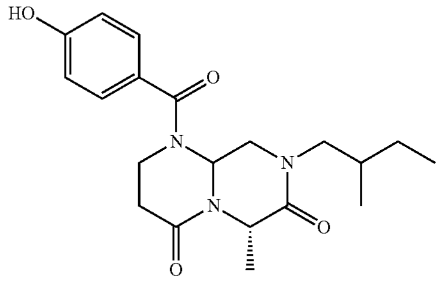 [SMILES: CCC(C)CN1CC2N(C(=O)c3ccc(O)cc3)CCC(=O)N2[C@@H](C)C1=O] | 8b | 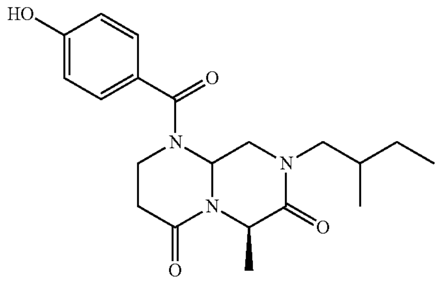 |
| 11 | 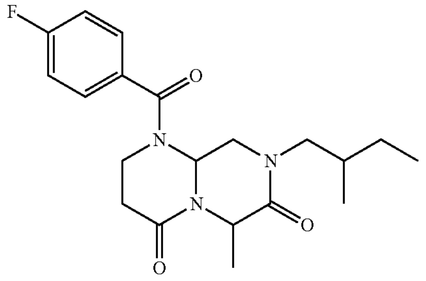 [SMILES: CCC(C)CN1CC2N(C(=O)c3ccc(F)cc3)CCC(=O)N2C(C)C1=O] | 12 | 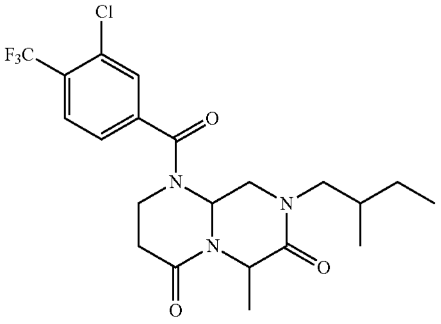 [SMILES: CCC(C)CN1CC2N(C(=O)c3ccc(C(F)(F)F)c(Cl)c3)CCC(=O)N2C(C)C1=O] |
| 14 | 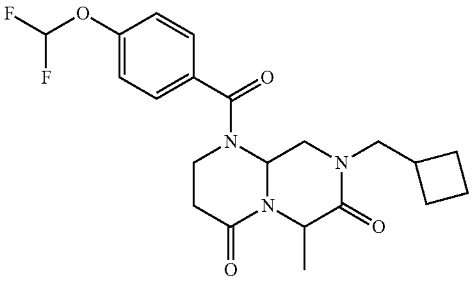 [SMILES: CC1C(=O)N(CC2CCC2)CC2N(C(=O)c3ccc(OC(F)F)cc3)CCC(=O)N12] | 17 | 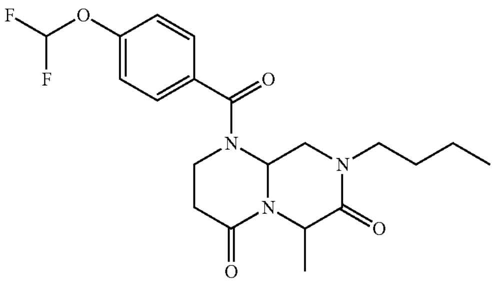 [SMILES: CCCCN1CC2N(C(=O)c3ccc(OC(F)F)cc3)CCC(=O)N2C(C)C1=O] |
| 19 | 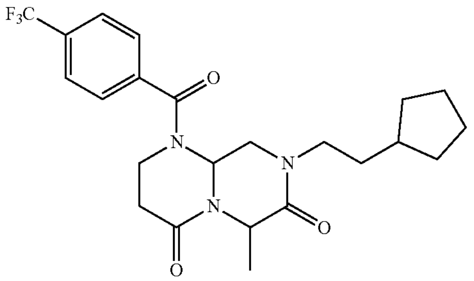 [SMILES: CC1C(=O)N(CCC2CCCC2)CC2N(C(=O)c3ccc(C(F)(F)F)cc3)CCC(=O)N12] | 20 | 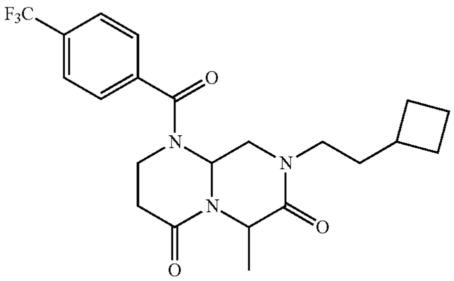 [SMILES: CC1C(=O)N(CCC2CCC2)CC2N(C(=O)c3ccc(C(F)(F)F)cc3)CCC(=O)N12] |
| 22 | 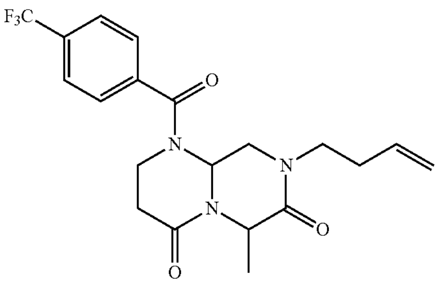 [SMILES: C=CCCN1CC2N(C(=O)c3ccc(C(F)(F)F)cc3)CCC(=O)N2C(C)C1=O] | 30 | 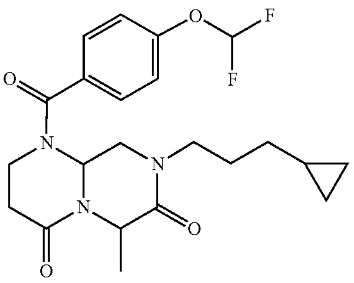 [SMILES: CC1C(=O)N(CCCC2CC2)CC2N(C(=O)c3ccc(OC(F)F)cc3)CCC(=O)N12] |

TABLE 1A-continued

| Compound | Structure | Compound | Structure |
|---|---|---|---|
| 42 | 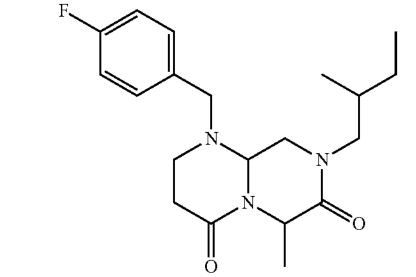 [SMILES: CCC(C)CN1CC2N(Cc3ccc(F)cc3)CCC(=O)N2C(C)C1=O] | 49 | 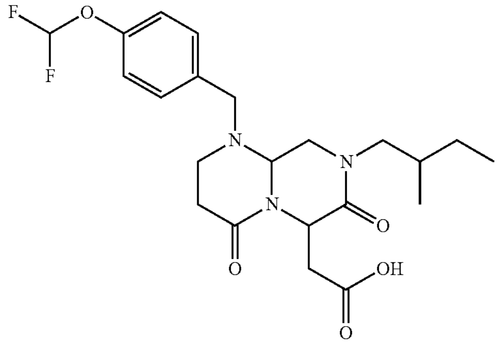 [SMILES: CCC(C)CN1CC2N(Cc3ccc(OC(F)F)cc3)CCC(=O)N2C(CC(=O)O)C1=O] |
| 51 | 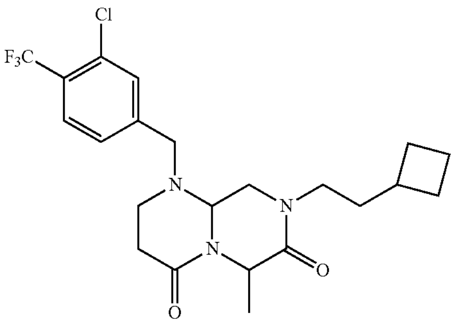 [SMILES: CC1C(=O)N(CCC2CCC2)CC2N(Cc3ccc(C(F)(F)F)c(Cl)c3)CCC(=O)N12] | 53 | 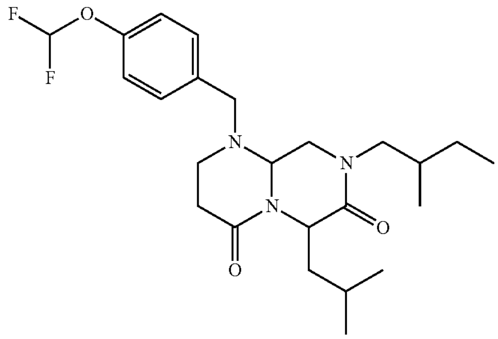 [SMILES: CCC(C)CN1CC2N(Cc3ccc(OC(F)F)cc3)CCC(=O)N2C(CC(C)C)C1=O] |

or a pharmaceutically acceptable salt thereof.

It is understood that in the present description, combinations of substituents and/or variables of the depicted formulae are permissible only if such contributions result in stable compounds.

Furthermore, all compounds of Formula (I) which exist in free base or acid form can be converted to their pharmaceutically acceptable salts by treatment with the appropriate inorganic or organic base or acid by methods known to one skilled in the art. Salts of the compounds of Formula (I) can be converted to their free base or acid form by standard techniques.

Methods of Synthesis

Compounds of Formula (I), or a pharmaceutically acceptable salt, isotopic form, or stereoisomer thereof, can be prepared by using organic chemistry synthesis methods known in the art. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

General Reaction Scheme 1.

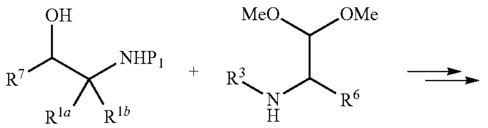

A1 A2

-continued

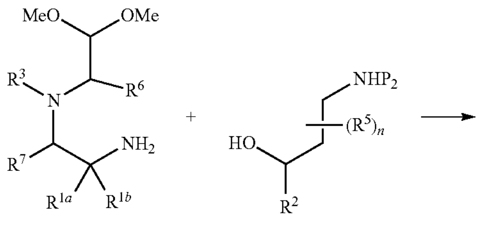

A3 A4

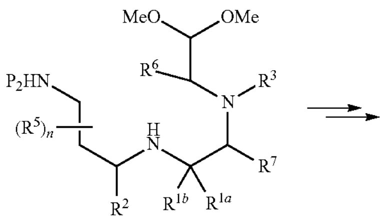

A5

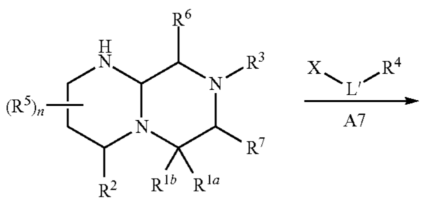

A6

-continued

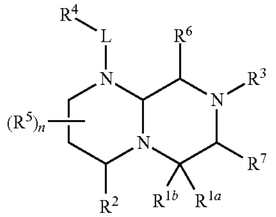

Formula (I)

General Reaction Scheme 1 provides an exemplary method for preparation of compounds of Formula (I). $R^{1a}$, $R^{1b}$, $R^2$, $R^3$, $R^4$, $R^5$, $R^6$, $R^7$, L, and n in General Reaction Scheme 1 are as defined herein. X is a reactive moiety selected to facilitate the desired reaction (e.g., halo). $P_1$ and $P_2$ are suitable protecting groups. L' is selected such that a desired L moiety results from the reaction between L'-$R^4$ and the secondary amine. Compounds of structure A1 are purchased or prepared according to methods known in the art. Reaction of A1 with A2 under appropriate coupling conditions (e.g., $T_3P$ and base) yields the product of the coupling reaction between A1 and A2, A3. A3 is then reacted with A4 under suitable coupling conditions (e.g., $T_3P$ and base) to afford compound A5. Compound A5 is then cyclized (e.g., using formic acid) and deprotected (e.g., using piperidine) to afford compound A6. Compound A6 is then reacted with compound A7 to afford the final compound of Formula (I) as shown.

General Reaction Scheme 2.

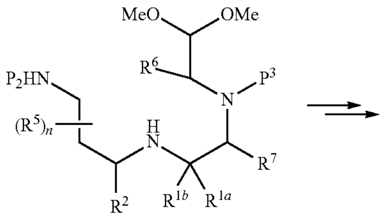

A8

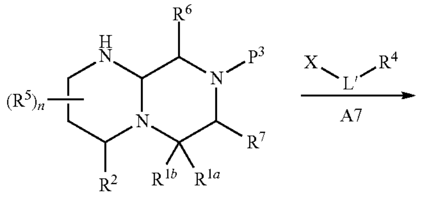

A9

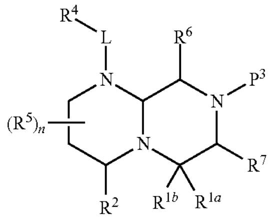

A10

-continued

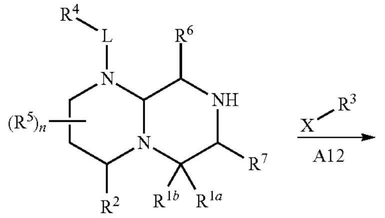

A11

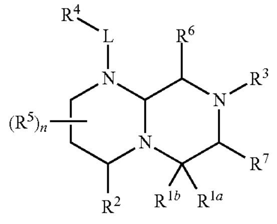

Formula (I)

An alternative method for the synthesis of compounds of Formula (I) is depicted in General Reaction Scheme 2. $R^{1a}$, $R^{1b}$, $R^2$, $R^3$, $R^4$, $R^5$, $R^6$, $R^7$, L, and n in General Reaction Scheme 2 are as defined herein. P2 is a suitable protecting group. Each X is a reactive moiety selected to facilitate the desired reaction (e.g., halo). L' is selected such that a desired L moiety results from the reaction between L'-$R^4$ and the secondary amine. Intermediate A5 is prepared with a removable protecting group P 3 (e.g. para-methoxybenzyl) as the R 3 group giving intermediate A8. A8 is then cyclized (e.g., using formic acid) and deprotected (e.g., using piperidine) to afford compound A9. Compound A9 is then reacted with A7 to give compound A10. Compound A10 is then deprotected (e.g., with cerica ammonium nitrate) to give compound A11. Compound A11 is then reacted with A12 to provide the final compound of Formula (I).

General Reaction Scheme 3.

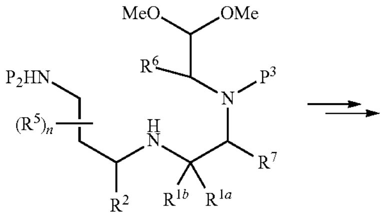

A8

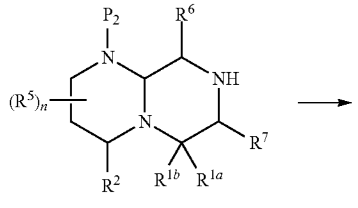

A9

-continued

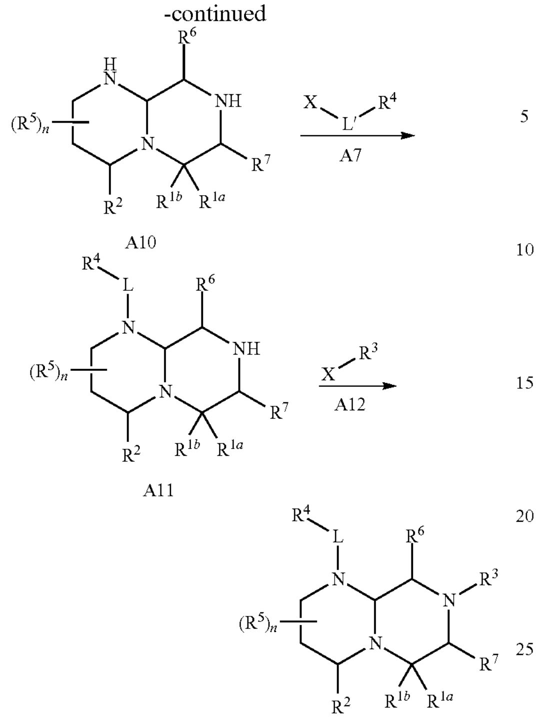

A10

A11

Formula (I)

A related method to the one shown in General Reaction Scheme 2 is depicted in General Reaction Scheme 3. In this method, the two amine nitrogen atoms of the bicyclic core are deprotected to provide compound A10, then reacted with A7 to afford compound A11. Subsequent reaction with A12 provides the final compound of Formula (I).

It should be noted that various alternative strategies for preparation of compounds of Formula (I) are available to those of ordinary skill in the art. For example, other compounds of Formula (I) can be prepared according to analogous methods using the appropriate starting material.

It will also be appreciated by those skilled in the art that in the processes for preparing the compounds described herein the functional groups of intermediate compounds may need to be protected by suitable protecting groups. Such functional groups may include hydroxy, amino, and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino and amidino include t-butoxycarbonyl, benzyloxycarbonyl, and the like. Suitable protecting groups for carboxylic acid include alkyl, aryl, or arylalkyl esters. Protecting groups are optionally added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Pharmaceutical Compositions and Formulations

In a further aspect, provided herein are pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound of Formula (I), or a pharmaceutically acceptable salt, isotopic form, or stereoisomer thereof, and an additional therapeutic agent. Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound of Formula (I), or a pharmaceutically acceptable salt, isotopic form, or stereoisomer thereof, is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound of Formula (I), or a pharmaceutically acceptable salt, isotopic form, or stereoisomer thereof, is provided in the form of a rapid release formulation, in the form of an extended release formulation, or in the form of an intermediate release formulation. In yet other embodiments, the compound described herein is administered topically.

The compounds of Formula (I), or a pharmaceutically acceptable salt, isotopic form, or stereoisomer thereof, are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of Formula (I), or a pharmaceutically acceptable salt, isotopic form, or stereoisomer thereof, is administered in a single dose. Typically, such administration will be by injection, e.g., intravenous injection, in order to introduce the agent quickly. However, other routes are used as appropriate. A single dose of a compound of the disclosure may also be used for treatment of an acute condition (e.g., traumatic brain injury).

In some embodiments, a compound of Formula (I), or a pharmaceutically acceptable salt, isotopic form, or stereoisomer thereof, is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of Formula (I), or a pharmaceutically acceptable salt, isotopic form, or stereoisomer thereof, and another therapeutic agent are administered together about once per day to about 6 times per day. In another embodiment the administration of a compound of Formula (I), or a pharmaceutically acceptable salt, isotopic form, or stereoisomer thereof, and a therapeutic agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of Formula (I), or a pharmaceutically acceptable salt, isotopic form, or stereoisomer thereof, may continue as long as necessary. In some embodiments, a compound of Formula (I), or a pharmaceutically acceptable salt, isotopic form, or stereoisomer thereof, is administered for more than 1, 2, 3, 4, 5, 6, 7, 14, or 28 days. In some embodiments, a compound of Formula (I), or a pharmaceutically acceptable salt, isotopic form, or stereoisomer thereof, is administered for less than 28, 14, 7, 6, 5, 4, 3, 2, or 1 day. In some embodiments, a compound of Formula (I), or a pharmaceutically acceptable salt, isotopic form, or stereoisomer thereof, is administered chronically on an ongoing basis, e.g., for the treatment of chronic effects (e.g., dementia).

In some embodiments, the compound of Formula (I), or a pharmaceutically acceptable salt, isotopic form, or stereoisomer thereof, is administered in dosages. It is known in the art that due to intersubject variability in compound pharmacokinetics, individualization of dosing regimen is necessary for optimal therapy. Dosing for a compound may be found by routine experimentation in light of the instant disclosure.

In some embodiments, the compounds Formula (I), or a pharmaceutically acceptable salt, isotopic form, or stereoisomer thereof, are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of Formula (I), or a pharmaceutically acceptable salt, isotopic form, or stereoisomer thereof, and a pharmaceutically acceptable diluent(s), excipient(s), or carrier(s). Also provided herein are methods for administering a pharmaceutical composition comprising a compound of Formula (I), or a pharmaceutically acceptable salt, isotopic form, or stereoisomer thereof, and a pharmaceutically acceptable diluent(s), excipient(s), or carrier(s).

In certain embodiments, the compounds are administered as pharmaceutical compositions in which compounds of Formula (I), or a pharmaceutically acceptable salt, isotopic form, or stereoisomer thereof, are mixed with other therapeutic agents, as in combination therapy. Encompassed herein are all combinations of active ingredients set forth in the methods section below and throughout this disclosure. In specific embodiments, the pharmaceutical compositions include one or more compounds of Formula (I), or a pharmaceutically acceptable salt, isotopic form, or stereoisomer thereof.

A pharmaceutical composition, as used herein, refers to a mixture of a compound of Formula (I), or a pharmaceutically acceptable salt, isotopic form, or stereoisomer thereof, with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of Formula (I), or a pharmaceutically acceptable salt, isotopic form, or stereoisomer thereof, provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of Formula (I), or a pharmaceutically acceptable salt, isotopic form, or stereoisomer thereof, are formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of Formula (I), or a pharmaceutically acceptable salt, isotopic form, or stereoisomer thereof, are formulated for transmucosal administration. In specific embodiments, transmucosal formulations include penetrants that are appropriate to the barrier to be permeated (e.g., the blood-brain barrier). In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds of Formula (I), or a pharmaceutically acceptable salt, isotopic form, or stereoisomer thereof, are formulated for oral administration. Compounds are formulated by combining the active compounds with, e.g., pharmaceutically acceptable carriers or excipients. In various embodiments, the compounds Formula (I), or a pharmaceutically acceptable salt, isotopic form, or stereoisomer thereof, are formulated in oral dosage forms that include, by way of example only, tablets, powders, pills, dragees, capsules, liquids, gels, syrups, elixirs, slurries, suspensions, and the like.

In certain embodiments, pharmaceutical preparations for oral use are obtained by mixing one or more solid excipient with one or more of the compounds of Formula (I), or a pharmaceutically acceptable salt, isotopic form, or stereoisomer thereof, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds Formula (I), or a pharmaceutically acceptable salt, isotopic form, or stereoisomer thereof, are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds of Formula (I), or a pharmaceutically acceptable salt, isotopic form, or stereoisomer thereof, described herein are formulated for buccal or sublingual administration. Formulations suitable for buccal or sublingual administration include, by way of example only, tablets, lozenges, or gels. In still other embodiments, the compounds of Formula (I), or a pharmaceutically acceptable salt, isotopic form, or stereoisomer thereof, are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, a suspension of an active compound or compounds (e.g., compounds of Formula (I), or a pharmaceutically acceptable salt, isotopic form, or stereoisomer thereof,) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of Formula (I), or a pharmaceutically acceptable salt, isotopic form, or stereoisomer thereof, are administered topically. The compounds are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of Formula (I), or a pharmaceutically acceptable salt, isotopic form, or stereoisomer thereof, are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula (I), or a pharmaceutically acceptable salt, isotopic form, or stereoisomer thereof, is accomplished by means of iontophoretic patches and the like. In certain embodiments, transdermal patches provide controlled delivery of the compounds of Formula (I), or a pharmaceutically acceptable salt, isotopic form, or stereoisomer thereof. In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of Formula (I), or a pharmaceutically acceptable salt, isotopic form, or stereoisomer thereof, are formulated for administration by inhalation. Various forms suitable for administration by inhalation include, but are not limited to, aerosols, mists or powders. Pharmaceutical compositions of any of compound of Formula (I), or a pharmaceutically acceptable salt, isotopic form, or stereoisomer thereof, are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of Formula (I), or a pharmaceutically acceptable salt, isotopic form, or stereoisomer thereof, are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of Formula (I), or a pharmaceutically acceptable salt, isotopic form, or stereoisomer thereof, are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of Formula (I), or a pharmaceutically acceptable salt, isotopic form, or stereoisomer thereof, described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds Formula (I), or a pharmaceutically acceptable salt, isotopic form, or stereoisomer thereof, encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds of Formula (I), or a pharmaceutically acceptable salt, isotopic form, or stereoisomer thereof, include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound of Formula (I), or a pharmaceutically acceptable salt, isotopic form, or stereoisomer thereof. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of Formula (I), or a pharmaceutically acceptable salt, isotopic form, or stereoisomer thereof, illustratively takes the form of a liquid where the agents are present in solution, in suspension or both. Typically, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of Formula (I), or a pharmaceutically acceptable salt, isotopic form, or stereoisomer thereof. The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate, or bisulfite anions; suitable salts include sodium chloride, potassium chloride, sodium thiosulfate, sodium bisulfite, and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds of Formula (I), or a pharmaceutically acceptable salt, isotopic form, or stereoisomer thereof, are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of the compound of Formula (I) provided in the pharmaceutical compositions of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.000 %, 0.0002%, or 0.0001% w/w, w/v or v/v.

In some embodiments, the concentration of the compound of Formula (I) provided in the pharmaceutical compositions of the present disclosure is greater than 90%, 80%, 70%, 60%, 50%, 40%, 30%, 20%, 19.75%, 19.50%, 19.25%, 19%, 18.75%, 18.50%, 18.25%, 18%, 17.75%, 17.50%, 17.25%, 17%, 16.75%, 16.50%, 16.25%, 16%, 15.75%, 15.50%, 15.25%, 15%, 14.75%, 14.50%, 14.25%, 14%, 13.75%, 13.50%, 13.25%, 13%, 12.75%, 12.50%, 12.25%, 12%, 11.75%, 11.50%, 11.25%, 11%, 10.75%, 10.50%, 10.25%, 10%, 9.75%, 9.50%, 9.25%, 9%, 8.75%, 8.50%, 8.25%, 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of the compound of Formula (I), or a pharmaceutically acceptable salt, isotopic form, or stereoisomer thereof, provided in the pharmaceutical compositions ranges from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10% w/w, w/v or v/v.

In some embodiments, the concentration of the compound of Formula (I), or a pharmaceutically acceptable salt, isotopic form, or stereoisomer thereof, provided in the pharmaceutical compositions ranges from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9% w/w, w/v or v/v.

In some embodiments, the amount the compound of Formula (I), or a pharmaceutically acceptable salt, isotopic form, or stereoisomer thereof, provided in the pharmaceutical compositions is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of the compound of Formula (I), or a pharmaceutically acceptable salt, isotopic form, or stereoisomer thereof, provided in the pharmaceutical compositions of the present disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of the compound of Formula (I), or a pharmaceutically acceptable salt, isotopic form, or stereoisomer thereof, provided in the pharmaceutical compositions ranges from 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound of Formula (I), or a pharmaceutically acceptable salt, isotopic form, or stereoisomer thereof. Non-limiting examples of such materials include, but not limited to, buffers, diluents, filters, needles, syringes, carrier, package, container, vial, and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound of Formula (I), or a pharmaceutically acceptable salt, isotopic form, or stereoisomer thereof, formulated in a compatible pharmaceutical carrier are prepared, placed in an appropriate container, and labeled for treatment of an indicated condition.

Methods of Use/Treatments

Embodiments of the present disclosure provide a method for modulating hepatocyte growth factor in a subject in need thereof, the method comprising administering to the subject an effective amount of a compound as disclosed herein (e.g., a compound of Formula (I), or a pharmaceutically acceptable salt, isotopic form, or stereoisomer thereof). In some embodiments, a compound described herein activates hepatocyte growth factor. Modulation (e.g., inhibition or activation) of hepatocyte growth factor can be assessed and demonstrated by a wide variety of ways known in the art. Kits and commercially available assays can be utilized for determining whether and to what degree hepatocyte growth factor has been modulated (e.g., inhibited or activated).

In some embodiments, provided herein are compounds of Formula (I), or a pharmaceutically acceptable salt thereof, for use in modulating hepatocyte growth factor in a subject in need thereof. In some embodiments, provided herein are compounds of Formula (I), or a pharmaceutically acceptable salt thereof, for the manufacture of a medicament for modulating hepatocyte growth factor in a subject in need thereof.

Applicant has discovered that the compounds Formula (I) show promising activity related to certain diseases of interest. Accordingly, in one aspect, provided herein is a method for modulating hepatocyte growth factor in a subject in need thereof, the method comprising administering to the subject an effective amount of a compound of Formula (I), or a pharmaceutically acceptable salt, isotopic form, or stereoisomer thereof. In some embodiments, provided herein is a method for activating hepatocyte growth factor in a subject in need thereof, the method comprising administering to the subject an effective amount of a compound of Formula (I), or a pharmaceutically acceptable salt, isotopic form, or stereoisomer thereof.

In certain more specific embodiments, the modulating comprises treating a disease, condition or injury (e.g., traumatic brain injury). By way of non-limiting examples, the disease, condition or injury includes a neurodegenerative disease, a traumatic brain injury, memory loss or function, spinal cord injury, sensorineural hearing loss, nerve damage and the like. In some embodiments, the disease, condition, or injury is a neurodegenerative disease, a spinal cord injury, a traumatic brain injury, or sensorineural hearing loss.

In one more specific embodiment, the disease, condition or injury is a neurodegenerative disease. For example, in some embodiments, the neurodegenerative disease is Alzheimer's disease, dementia, Parkinson's disease, Huntington's disease, or amyotrophic lateral sclerosis (ALS). In one more specific embodiment, the neurodegenerative disease is Alzheimer's disease or Parkinson's disease.

Also provided herein is a method for treating or slowing progression of dementia in a subject in need thereof, the method comprising administering to the subject an effective amount of a compound of Formula (I), or a pharmaceutically acceptable salt, isotopic form, or stereoisomer thereof. In a specific embodiment, the dementia is associated with Alzheimer's disease or Parkinson's disease.

In a further aspect, provided herein is a method for preventing cognitive dysfunction in a subject in need thereof, the method comprising administering to the subject an effective amount of a compound of Formula (I), or a pharmaceutically acceptable salt, isotopic form, or stereoisomer thereof.

Still another related embodiment provides a method for treating, repairing or preventing a disease, condition or injury related to nerve tissue in a subject in need thereof, the method comprising administering to the subject an effective amount of a compound of Formula (I), or a pharmaceutically acceptable salt, isotopic form, or stereoisomer thereof.

In other aspects, provided herein is a method of treating a neuropsychiatry disease or disorder, the method comprising administering to a subject in need thereof an effective amount of a compound of Formula (I), or a pharmaceutically acceptable salt, isotopic form, or stereoisomer thereof. Non-limiting examples of neuropsychiatry diseases or disorders include, without limitation, depression and anxiety.

In further aspects, provided herein is a method of treating a disease or disorder of the central nervous system, the method comprising administering to a subject in need thereof an effective amount of a compound of Formula (I), or a pharmaceutically acceptable salt, isotopic form, or stereoisomer thereof. In some embodiments, provided herein is a method of preventing a disease or disorder of the central nervous system, the method comprising administering to a subject in need thereof an effective amount of a compound of Formula (I), or a pharmaceutically acceptable salt, isotopic form, or stereoisomer thereof. A non-limiting example of a disease or disorder of the central nervous system is traumatic brain injury.

In yet other aspects, provided herein is a method of treating a disease or disorder of the peripheral nervous system, the method comprising administering to a subject in need thereof an effective amount of a compound of Formula (I), or a pharmaceutically acceptable salt, isotopic form, or stereoisomer thereof. In some embodiments, provided herein is a method of preventing a disease or disorder of the peripheral nervous system, the method comprising administering to a subject in need thereof an effective amount of a compound of Formula (I), or a pharmaceutically acceptable salt, isotopic form, or stereoisomer thereof. A non-limiting example of a disease or disorder of the peripheral nervous system is neuropathic pain.

Embodiments of the methods described above comprise administering to the mammal a therapeutically effective amount of a compound of Formula (I), or a pharmaceutically acceptable salt, isotopic form, or stereoisomer thereof. The methods disclosed herein are generally directed to administration of compounds of Formula (I), or a pharmaceutically acceptable salt, isotopic form, or stereoisomer thereof, to treat, protect from or reverse disease and injury associated with nerve cells or the nervous system. That is, embodiments of the present disclosure are directed to treatment, prevention or reversal of neurodegenerative diseases including treatment of dementia; repair of traumatic injury; and/or to prevent cognitive dysfunction.

In some embodiments, the disclosure provides methods of modulating protein activity (e.g., hepatocyte growth factor) in subject including but not limited to rodents and mammal (e.g., human) by administering into the subject an effective amount of a compound of Formula (I), or a pharmaceutically acceptable salt, isotopic form, or stereoisomer thereof. In some embodiments, modulation of hepatocyte growth factor is activation of hepatocyte growth factor. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the disclosure provides methods of modulating hepatocyte growth factor activity in a cell by contacting said cell with an amount of a compound of Formula (I), or a pharmaceutically acceptable salt, isotopic form, or stereoisomer thereof, sufficient to modulate the activity of hepatocyte growth factor. In some embodiments, the disclosure provides methods of modulating hepatocyte growth factor activity in a tissue by contacting said tissue with an amount of a compound of Formula (I), or a pharmaceutically acceptable salt, isotopic form, or stereoisomer thereof, sufficient to modulate the activity of hepatocyte growth factor in the tissue. In some embodiments, the disclosure provides methods of modulating hepatocyte growth factor activity in an organism by contacting said organism with an amount of a compound of Formula (I), or a pharmaceutically acceptable salt, isotopic form, or stereoisomer thereof, sufficient to modulate the activity of hepatocyte growth factor in the organism. In some embodiments, the disclosure provides methods of modulating hepatocyte growth factor activity in an animal by contacting the animal with an amount of a compound of Formula (I), or a pharmaceutically acceptable salt, isotopic form, or stereoisomer thereof, sufficient to modulate the activity of hepatocyte growth factor in the animal. In some embodiments, the disclosure provides methods of modulating hepatocyte growth factor activity in a mammal by contacting the mammal with an amount of a compound of Formula (I), or a pharmaceutically acceptable salt, isotopic form, or stereoisomer thereof, sufficient to modulate the activity of hepatocyte growth factor in the mammal. In some embodiments, the disclosure provides methods of modulating hepatocyte growth factor activity in a human by contacting the human with an amount of a compound of Formula (I), or a pharmaceutically acceptable salt, isotopic form, or stereoisomer thereof, sufficient to modulate the activity of hepatocyte growth factor in the human. In other embodiments, the present disclosure provides methods of treating a disease mediated by hepatocyte growth factor activity in a subject in need of such treatment. In some variations, modulation of hepatocyte growth factor by a compound of Formula (I), or a pharmaceutically acceptable salt, isotopic form, or stereoisomer thereof, involves activation of hepatocyte growth factor.

Other embodiments provide methods for combination therapies in which a therapeutic agent known to modulate other pathways, or other components of the same pathway, or even overlapping sets of target enzymes are used in combination with a compound of Formula (I), or a pharmaceutically acceptable salt, isotopic form, or stereoisomer thereof. In one aspect, such therapy includes but is not limited to the combination of one or more compounds of Formula (I), or a pharmaceutically acceptable salt, isotopic form, or stereoisomer thereof, with therapeutic agents, therapeutic antibodies, and other forms of treatment, to provide a synergistic or additive therapeutic effect.

Many therapeutic agents are presently known in the art and can be used in combination with the compounds of Formula (I), or a pharmaceutically acceptable salt, isotopic form, or stereoisomer thereof. In some embodiments, the therapeutic agent is selected from memantine, cholinesterase inhibitors, antidepressants, anxiolytics, and/or antipsychotic medicines. Some embodiments include use of therapies that include reminiscent therapy, cognitive stimulation therapy, reality orientation training, physical activity, and the like.

Exemplary cholinesterase inhibitors may include donepenzil, galantamine, and rivastigmine, which help to slow the breakdown of a brain chemical involved in memory and judgment. Memantine may help to control a different brain chemical needed for learning and memory. In certain aspects, memantine may also be used with donepezil in a combination drug for moderate to severe dementia. Antidepressants may include, but are not limited to, selective serotonin reuptake inhibitors (SSRIs). Anxiolytics may include, but are not limited to, lorazepam (Ativan) or oxazepam (Serax). Some embodiments of the methods described herein may include use or administration of antipsychotic medicines such as aripiprazole (Abilify), haloperidol (Haldol), olanzapine (Zyprexa), and risperidone (Risperdal).

In some embodiments, the compounds of Formula (I), or a pharmaceutically acceptable salt, isotopic form, or stereoisomer thereof, are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, therapeutic agents that are administered in conjunction with the compounds of Formula (I), or a pharmaceutically acceptable salt, isotopic form, or stereoisomer thereof, include any suitable therapeutic agent usefully delivered by inhalation for example, analgesics, e.g. codeine, dihydromorphine, ergotamine, fentanyl, or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics, e.g., ipratropium, atropine or oxitropium; hormones, e.g., cortisone, hydrocortisone or prednisolone; xanthines, e.g., aminophylline, choline theophyllinate, lysine theophyllinate or theophylline; and therapeutic proteins and peptides, e.g., insulin or glucagon. It will be clear to a person skilled in the art that, where appropriate, the therapeutic agents are used in the form of salts (e.g., as alkali metal or amine salts or as acid addition salts) or as esters (e.g., lower alkyl esters) or as solvates (e.g., hydrates) to optimize the activity and/or stability of the therapeutic agent.

Further therapeutic agents that can be combined with a compound of Formula (I), or a pharmaceutically acceptable salt, isotopic form, or stereoisomer thereof, are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds of Formula (I), or a pharmaceutically acceptable salt, isotopic form, or stereoisomer thereof, can be used in combination with the therapeutic agents disclosed herein depending on the condition being treated. Hence, in some embodiments the one or more compounds of Formula (I), or a pharmaceutically acceptable salt, isotopic form, or stereoisomer thereof, will be co-administered with other therapeutic agents as described above. When used in combination therapy, the compounds of Formula (I), or a pharmaceutically acceptable salt, isotopic form, or stereoisomer thereof, are administered with the second therapeutic agent simultaneously or separately. This administration in combination can include simultaneous administration in the same dosage form, simultaneous administration in separate dosage forms, and separate administration. That is, a compound of Formula (I), or a pharmaceutically acceptable salt, isotopic form, or stereoisomer thereof, and any of the therapeutic agents described above can be formulated together in the same dosage form and administered simultaneously. Alternatively, a compound of Formula (I), or a pharmaceutically acceptable salt, isotopic form, or stereoisomer thereof, and any of the therapeutic agents described above can be simultaneously administered, wherein both are present in separate formulations. In another alternative, a compound of Formula (I), or a pharmaceutically acceptable salt, isotopic form, or stereoisomer thereof, can be administered just followed by and any of the therapeutic agents described above, or vice versa. In some embodiments of the separate administration protocol, a compound of Formula (I), or a pharmaceutically acceptable salt, isotopic form, or stereoisomer thereof, and any of the therapeutic agents described above are administered a few minutes apart, or a few hours apart, or a few days apart.

The examples and preparations provided below further illustrate and exemplify the compounds of Formula (I), or a pharmaceutically acceptable salt, isotopic form, or stereoisomer thereof, and methods of preparing such compounds. It is to be understood that the scope of the present disclosure is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following example are provided for exemplary purposes. Methods for preparation of compounds of Formula (I), or a pharmaceutically acceptable salt, isotopic form, or stereoisomer thereof, are provided herein or can be derived by one of ordinary skill in the art.

The examples and preparations provided below further illustrate and exemplify the compounds of the present disclosure and methods for testing such compounds. It is to be understood that the scope of the present disclosure is not limited in any way by the scope of the following examples.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be performed by modifications apparent to those skilled in the art, for example by appropriately protecting interfering groups, by utilizing other suitable reagents known in the art other than those described, or by making routine modification of reaction conditions, reagents, and starting materials. Alternatively, other reactions disclosed herein or known in the art will be recognized as having applicability for preparing other compounds of the present disclosure.

Unless indicated otherwise in the following Examples, the compounds are isolated as a racemic mixture.

The following abbreviations may be relevant for the application.

Abbreviations

AcOH: acetic acid
CAN: ceric ammonium nitrate
DAST: diethylaminosulfur trifluoride
DCM: dichloromethane
DIPEA: N,N-diisopropylethylamine
DMEM: Dulbecco's Modified Eagle Medium
DMF: dimethylformamide
DMSO: dimethylsulfoxide
EMEM: Eagle's Minimum Essential Medium
EtOAc: ethyl acetate
EtOH: ethanol
FBS: fetal bovine serum
Fmoc: fluorenylmethoxycarbonyl
HATU: (1-[bis(dimethylamino)methylene]-1H-1,2,3-triazolo[4,5-b]pyridinium 3-oxide hexafluorophosphate
LC/MS: liquid chromatography-mass spectrometry
Me: methyl
MeOH: methanol
PBS: phosphate buffered saline
Pic-$BH_3$: picoline borane
PMB: para-methoxybenzyl ether
Prep HPLC: preparative high performance liquid chromatography
rt or RT: room temperature
TFA: trifluoroacetic acid
TLC: thin layer chromatography
$T_3P$: Propanephosphonic acid anhydride

SYNTHETIC EXAMPLES

Example S1. Synthesis of (6S)-6-methyl-8-(2-methylbutyl)hexahydro-4H-pyrazino[1,2-a]pyrimidine-4,7(6H)-dione The synthetic route for preparing this starting material compound is shown in Scheme 1.

Scheme 1.

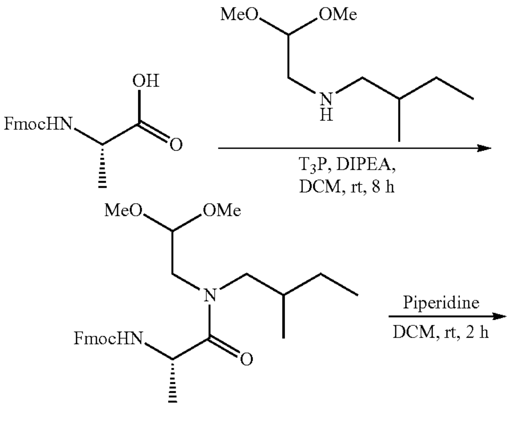

-continued

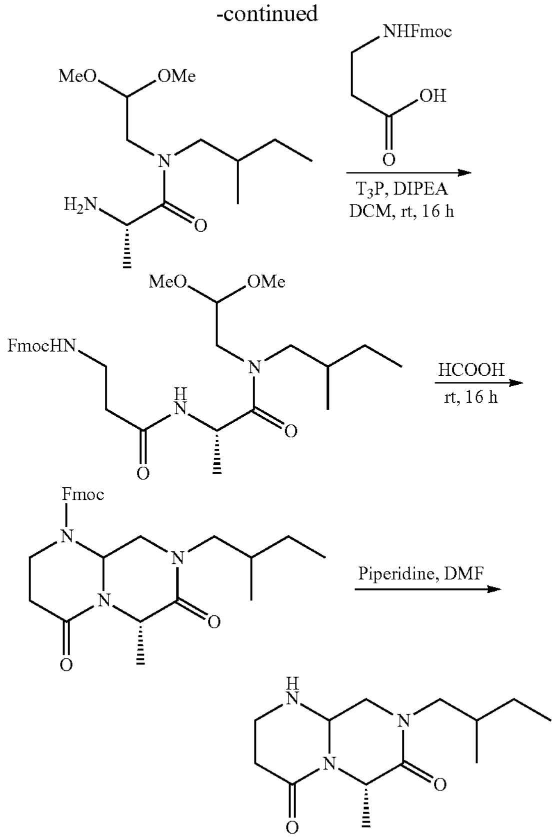

Step 1: Synthesis of (9H-fluoren-9-yl)methyl (2S)-1-((2,2-dimethoxyethyl)(2-methylbutyl)amino)-1-oxopropan-2-ylcarbamate. To a stirred solution of compound (S)-2-(((9H-fluoren-9-yl)methoxy)carbonylamino)propanoic acid (5.0 g, 16.07) in dichloromethane (100 mL) was added $T_3P$ (15.2 mL, 24.1) and DIPEA (5.6 mL, 32.1 mmol) at room temperature. The reaction mixture was stirred at room temperature for 15 min and N-(2,2-dimethoxyethyl)-2-methylbutan-1-amine (2.81 g, 32.1 mmol.) was added, and stirring was continued at room temperature for 8 hours. The reaction was monitored by TLC. After completion, the reaction mixture was quenched with ice cold water (100 mL) and extracted with dichloromethane (2×100 mL). The combined organic layers were dried over anhydrous $Na_2SO_4$, filtered and concentrated under reduced pressure to give crude compound. The crude compound was purified by flash column chromatography (100-200 mesh silica gel, eluted with 40% ethyl acetate in petroleum ether) to afford pure compound (9H-fluoren-9-yl)methyl (2S)-1-((2,2-dimethoxyethyl)(2-methylbutyl)amino)-1-oxopropan-2-ylcarbamate (5.2 g, 69.1%) as a gummy compound.

Step 2: Synthesis of (25)-2-amino-N-(2,2-dimethoxyethyl)-N-(2-methylbutyl)propenamide. To a stirred solution of (9H-fluoren-9-yl)methyl (2S)-1-((2,2-dimethoxyethyl)(2-methylbutyl)amino)-1-oxopropan-2-ylcarbamate (34.0 g, 72.6 mmol) in DMF (230 mL) was added 20% piperidine in DMF (70 mL) at 0° C. The reaction mixture was stirred at room temperature for 2 hours. The reaction was monitored by TLC. After completion of the reaction, excess DMF (100 mL) was added, then washed with excess n-hexane (3×200 mL). The DMF layer was collected and poured in ice cold water (1000 mL), then extracted with 10% methanol-dichloromethane (3×500 mL). The combined organic layers was dried over anhydrous $Na_2SO_4$, filtered and concentrated under reduced pressure to give (2S)-2-amino-N-(2,2-dimethoxyethyl)-N-(2-methylbutyl)propanamide (20.4 g, 68.4%) as a gummy solid.

Step 3: Synthesis of (9H-fluoren-9-yl)methyl3-((2S)-1-((2,2-dimethoxyethyl)(2-methylbutyl)amino)-1-oxopropan-2-ylamino)-3-oxopropylcarbamate. To a stirred solution of 3-(((9H-fluoren-9-yl) methoxy)carbonylamino)propanoic acid (20.2 g, 81.2 mmol) stirred in dichloromethane at room temperature (500 mL) was added $T_3P$ (80 mL, 121.8 mmol) and DIPEA (28.6 mL, 160.4 mmol), and the mixture was stirred for 10 minutes. To this (2S)-2-amino-N-(2,2-dimethoxyethyl)-N-(2-methylbutyl)propanamide (25.53 81.2 mmol) was added and stirring was continued at room temperature for 16 hours. The reaction progress was monitored by TLC. After completion, the reaction mixture was quenched with water (500 mL) and the mixture was extracted with dichloromethane (2×500 mL). The combined organic layers were dried over $Na_2SO_4$, filtered and concentrated under reduced pressure to give crude product. The crude compound was purified by flash column chromatography (100-200 mesh Silica gel, eluted with 70% ethyl acetate in petroleum ether) to afford pure compound (9H-fluoren-9-yl)methyl3-((2S)-1-((2,2-dimethoxyethyl)(2-methylbutyl)amino)-1-oxopropan-2-ylamino)-3-oxopropylcarbamate (21.2 g, 78.6%) as a gummy compound.

Step 4: Synthesis of (65)-(9H-fluoren-9-yl)methyl 6-methyl-8-(2-methylbutyl)-4,7-dioxooctahydro-1H-pyrazino[1,2-a]pyrimidine-1-carboxylate. To a stirred solution of (9H-fluoren-9-yl)methyl 3-((2S)-1-((2,2-dimethoxyethyl)(2-methylbutyl)amino)-1-oxopropan-2-ylamino)-3-oxopropylcarbamate (21.0 g, 38.9 mmol) was added formic acid (105 mL). The reaction mixture was stirred at room temperature for 12 hours. The reaction progress was monitored by TLC. After completion, the reaction mixture was concentrated under reduced pressure to give crude compound. The crude compound was taken up in saturated aqueous $NaHCO_3$ (200 mL) solution, then extracted with ethyl acetate (3×500 mL). The combined organic layers were washed with brine solution (500 mL), then the combined organic layers were dried over anhydrous $Na_2SO_4$, filtered and concentrated under reduced pressure. The crude compound was purified by flash column chromatography (100-200 mesh silica gel, eluted with 50% ethyl acetate in petroleum ether) to afford pure compound (6S)-(9H-fluoren-9-yl)methyl 6-methyl-8-(2-methylbutyl)-4,7-dioxooctahydro-1H-pyrazino[1,2-a]pyrimidine-1-carboxylate (25 g, 69.0%) as a gum.

Step 5: Synthesis of (6S)-6-methyl-8-(2-methylbutyl)tetrahydro-1H-pyrazino[1,2-a]pyrimidine-4,7(6H,8H)-dione. To a stirred solution of (6S)-(9H-fluoren-9-yl)methyl 6-methyl-8-(2-methylbutyl)-4,7-dioxooctahydro-1H-pyrazino[1,2-a]pyrimidine-1-carboxylate (14.0 g, 29.4 mmol) at 0° C. in DMF (70 mL) was added 20% piperidine in DMF (30 mL). The reaction mixture was allowed to warm to room temperature and stirred for 2 hours. The reaction was monitored by TLC. After complete consumption of starting material, additional DMF was added (50 mL), then the mixture was washed with excess n-hexane (3×200 mL). The DMF layer was poured into ice cold water (1000 mL) and extracted with 10% methanol-dichloromethane (3×500 mL). The combined organic layers were dried over anhydrous $Na_2SO_4$, filtered and concentrated under reduced pressure to provide the desired crude compound (6S)-6-methyl-8-(2-methylbutyl)tetrahydro-1H-pyrazino[1,2-a]pyrimidine-4,7(6H,8H)-dione (6.25 g, 83.8%) as a solid.

Example S2. Synthesis of Compound 1a

The synthetic route for preparing Compound 1a is shown in Scheme 2.

Scheme 2.

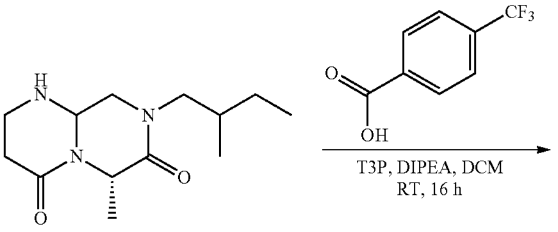

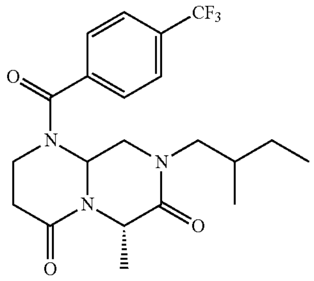

1a

To a solution of 4-(trifluoromethyl)benzoic acid (0.232 g, 0.91 mmol) stirred in dichloromethane (20 mL) at room temperature was added $T_3P$ (1.2 mL, 1.37 mmol) and DIPEA (0.42 mL, 1.82 mmol), and the mixture was stirred for 15 minutes. To this (6S)-6-methyl-8-(2-methylbutyl) tetrahydro-1H-pyrazino[1,2-a]pyrimidine-4,7(6H,8H)-dione (0.310 g, 0.91 mmol) was added and stirring was continued for 8 hours. The reaction progress was monitored by TLC. After reaction completion, the mixture was quenched with water (50 mL) and extracted with dichloromethane (2×50 mL). The combined organic layers were dried over $Na_2SO_4$, filtered and concentrated under reduced pressure. The crude compound was purified by Prep HPLC. The pure fractions were combined and concentrated under reduced pressure, then lyophilized to afford 1a (0.340 g, 65.3%) as a solid. Prep HPLC method: Mobile phase A: 10 mM ammonium bicarbonate in water; Mobile phase B: acetonitrile; Column: X-Select phenyl hexyl (150×19 mm 5μ); Flow: 16 mL/min. MS (ESI) m/z $[M+H]^+$: 426.05.

Example S3. Synthesis of Compound 2a

The synthetic route for preparing Compound 2a is shown in Scheme 3.

Scheme 3.

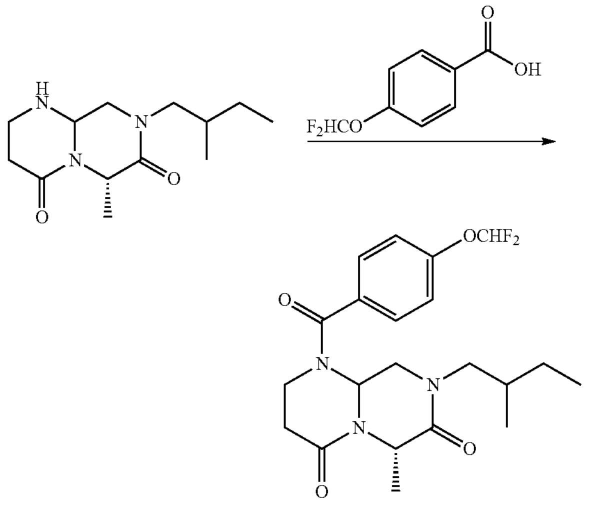

2a

To a solution of 4-(difluoromethoxy) benzoic acid (0.37 g, 1.968 mmol) in dichloromethane (15 mL) at room temperature was added DIPEA (0.8 ml, 5.904 mmol) and $T_3P$ (2.0 mL, 3.936 mmol). The mixture was stirred for 30 min, then (6S)-6-methyl-8-(2-methylbutyl)hexahydro-4H-pyrazino[1,2-a]pyrimidine-4,7(6H)-dione (0.4 g, 1.578 mmol) was added, and stirring was continued for 16 hours. Progress of the reaction was monitored by TLC and LC/MS. The reaction mixture was diluted with dichloromethane (100 mL) and washed with water (50 mL) and saturated sodium chloride solution (50 mL), then dried over sodium sulfate, filtered and concentrated under reduced pressure. The crude product was purified by Prep HPLC. The pure fractions were collected and lyophilized to afford 2a (380 mg 46%) as a solid. Prep HPLC condition: Mobile phase A: 10 mM ammonium bicarbonate in water; Mobile phase B: Acetonitrile; Column: Kromosil phenyl (150×25 mm 10μ); Flow: 25 mL/min. MS (ESI) m/z $[M+H]^+$: 424.11.

Example S4. Synthesis of Compound 3a

The synthetic route for preparing Compound 3a is shown in Scheme 4.

Scheme 4.

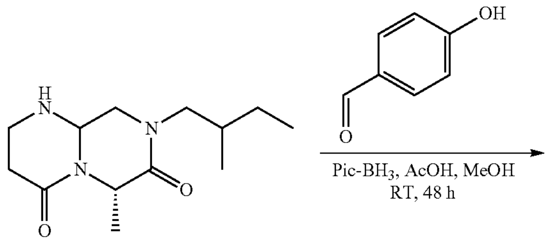

-continued

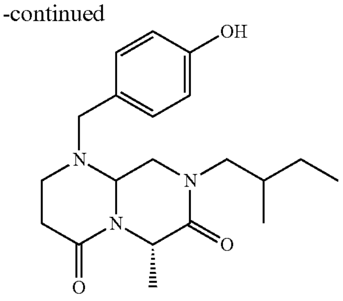

3a

To a solution of (6S)-6-methyl-8-(2-methylbutyl)tetrahydro-1H-pyrazino[1,2-a]pyrimidine-4,7(6H,8H)-dione (0.500 g, 1.97 mmol) stirred in methanol (20 mL) at room temperature was added 4-hydroxybenzaldehyde (0.289 g, 1.97 mmol) and acetic acid (0.23 mL, 3.95 mmol). The reaction mixture was stirred at room temperature for 5 minutes. To this picoline borane (0.253 g, 2.37 mmol) was added, and stirring was continued for 48 hr. The reaction progress was monitored by TLC. After completion, the reaction mixture was quenched with ice cold water (50 mL), and the mixture was extracted with 10% methanol-dichloromethane (3×40 mL). The combined organic layers were dried over $Na_2SO_4$, filtered and concentrated under reduced pressure. The crude compound was purified by Prep HPLC. The pure fractions were combined and concentrated under reduced pressure, then lyophilized to give 3a (0.180 g, 46.09%) as a solid. Prep HPLC Method: Mobile Phase A: 10 mM ammonium bicarbonate in water; Mobile Phase B: Acetonitrile; Column: Kromosil Phenyl (150×25 mm 10μ); Flow: 25 mL/min. MS (ESI) m/z $[M+H]^+$: 360.11.

Example S5. Synthesis of Compound 4a

The synthetic route for preparing Compound 4a is shown in Scheme 5.

Scheme 5.

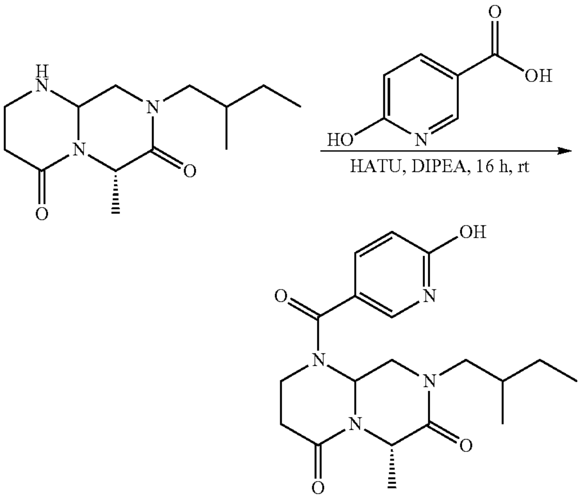

4a

To a solution of 6-hydroxynicotinic acid (0.340 g 2.446 mmol) in DMF (15 mL) at room temperature was added DIPEA (1.30 mL, 7.338 mmol) and HATU (1.39 g, 3.669 mmol). The resulting reaction mixture was stirred for 30 min, then (6S)-6-methyl-8-(2-methylbutyl)hexahydro-4H-pyrazino[1,2-a]pyrimidine-4,7(6H)-dione (0.495 g, 1.956 mmol.) was added, and the mixture was stirred for 16 hours. Progress of the reaction was monitored by TLC and LC/MS (TLC system: 10% methanol/dichloromethane, Rf: 0.15, Detection: UV). The reaction mixture was quenched with cold water (100 mL) and extracted with 10% methanol/dichloromethane (3×100 mL). The combined organic layers were washed with cold water (50 mL) and cold brine solution (50 mL), dried over sodium sulfate, filtered and concentrated under reduced pressure. The crude product was purified by Prep HPLC. The pure fractions were collected and lyophilized to afford 4a (160 mg, 21.8%) as a solid. Prep HPLC Method: Mobile Phase A: 0.01 mM ammonium bicarbonate in water; Mobile Phase B: acetonitrile; Column: X-Select phenyl hexyl (150×19 mm, 5μ); Flow: 15 mL/min. MS (ESI) m/z $[M+H]^+$: 375.05.

Example S6. Synthesis of Compound 5a

The synthetic route for preparing Compound 5a is shown in Scheme 6.

Scheme 6.

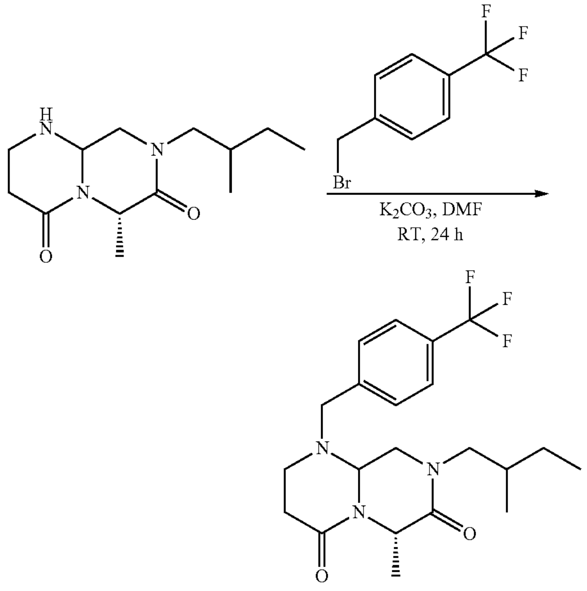

5a

To a solution of (6S)-6-methyl-8-(2-methylbutyl)tetrahydro-1H-pyrazino[1,2-a]pyrimidine-4,7(6H,8H)-dione (0.5 g, 1.97 mmol) and 1-(bromomethyl)-4-(trifluoromethyl)benzene (0.470 g, 1.97 mmol) stirred in DMF (20 mL) at room temperature was added $K_2CO_3$ (0.546 g, 3.95 mmol), and the mixture was stirred for 8 hr. The reaction progress was monitored by TLC. After completion, the mixture was quenched with water (100 mL) and extracted with ethyl acetate (3×50 mL). The combined organic layers were dried over $Na_2SO_4$, filtered and concentrated under reduced pressure. The crude compound was purified by Prep HPLC. The pure fractions were combined and concentrated under reduced pressure, then lyophilized to afford 5a (0.270 g, 63.8%) as a gum. Prep HPLC Method: Mobile Phase A: 10 mM ammonium bicarbonate in water; Mobile Phase B: Acetonitrile; Column: Kromosil $C_{18}$ (150×25 mm 10μ); Flow: 25 mL/min. MS (ESI) m/z $[M+H]^+$: 412.2.

Example S7. Synthesis of Compound 6a

The synthetic route for preparing Compound 6a is shown in Scheme 7.

Scheme 7.

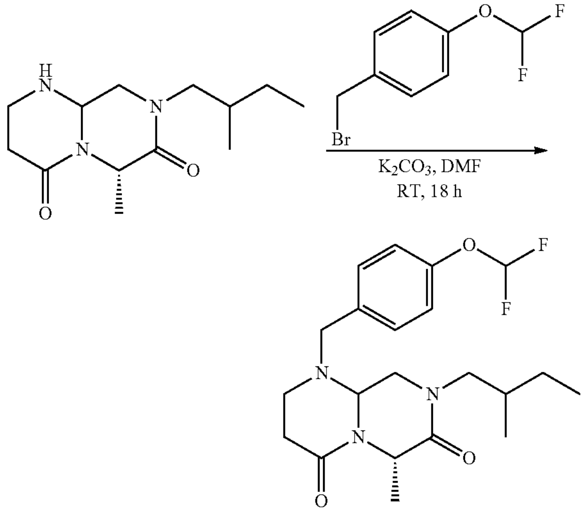

6a

To a solution of (6S)-6-methyl-8-(2-methylbutyl)tetrahydro-1H-pyrazino[1,2-a]pyrimidine-4,7(6H,8H)-dione (0.500 g, 1.97 mmol) and 1-(bromomethyl)-4-(difluoromethoxy)benzene (0.466 g, 1.97 mmol) stirred in DMF (20 mL) at room temperature was added $K_2CO_3$ (0.546 g, 9.95 mmol). The reaction mixture was stirred at room temperature for 18 hr. The reaction progress was monitored by TLC. After completion, the reaction mixture was quenched with water (100 mL) and extracted with ethyl acetate (3×50 mL). The combined organic layers were dried over $Na_2SO_4$, filtered and concentrated under reduced pressure. The crude compound was purified by Prep HPLC. The pure fractions were combined and concentrated under reduced pressure, then lyophilized to afford 6a (0.178 g, 41.5%) as a semi-solid. Prep HPLC Method: Mobile Phase A: 10 mM ammonium bicarbonate in water; Mobile Phase B: acetonitrile; Column: X-Select $C_{18}$ (250×19 mm, 5μ); Flow: 18 mL/min. MS (ESI) m/z $[M+H]^+$: 410.11.

Example S8. Synthesis of Compound 7a

The synthetic route for preparing Compound 7a is shown in Scheme 8.

Scheme 8.

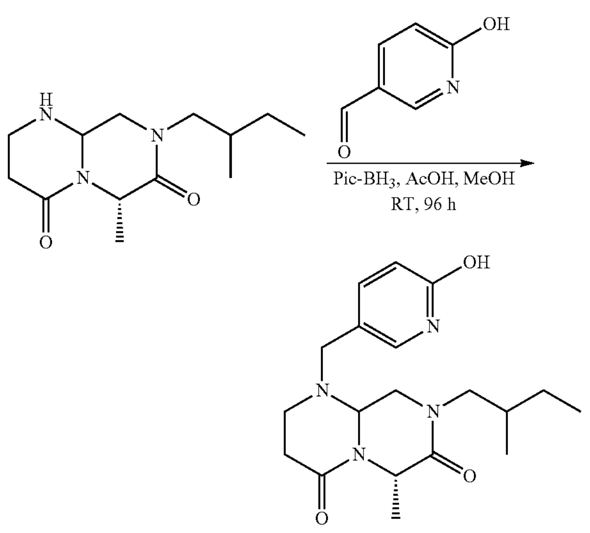

7a

To a solution of compound (6S)-6-methyl-8-(2-methylbutyl)tetrahydro-1H-pyrazino[1,2-a]pyrimidine-4,7(6H,8H)-dione (0.500 g, 1.97 mmol) stirred in methanol (20 mL) at room temperature was added 6-hydroxynicotinaldehyde (0.243 g, 1.97 mmol) and acetic acid (0.25 mL, 3.95 mmol), and the mixture was stirred for 5 min. To this picoline borane (0.318 g, 2.96 mmol) was added and stirring was continued for 96 hours. The reaction progress was monitored by TLC. After completion, the reaction mixture was quenched with ice cold water (50 mL) and extracted with 10% methanol-dichloromethane (3×40 mL). The combined organic layers were dried over $Na_2SO_4$, filtered and concentrated under reduced pressure. The crude compound was purified by Prep HPLC. The pure fractions were collected and concentrated under reduced pressure, then lyophilized to afford 7a (0.164 g, 42%) as a solid. Prep HPLC Method: Mobile Phase A: 10 mM ammonium bicarbonate in water; Mobile Phase B: acetonitrile; Column: X-BRIDGE $C_{18}$ (250×19 mm, 5μ); Flow: 18 mL/min. MS (ESI) m/z $[M+H]^+$: 361.11.

Example S9. Synthesis of Compound 8a

The synthetic route for preparing Compound 8a is shown in Scheme 9.

Scheme 9.

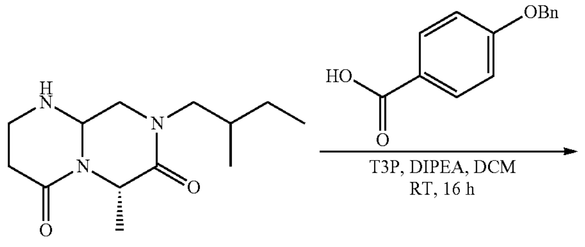

-continued

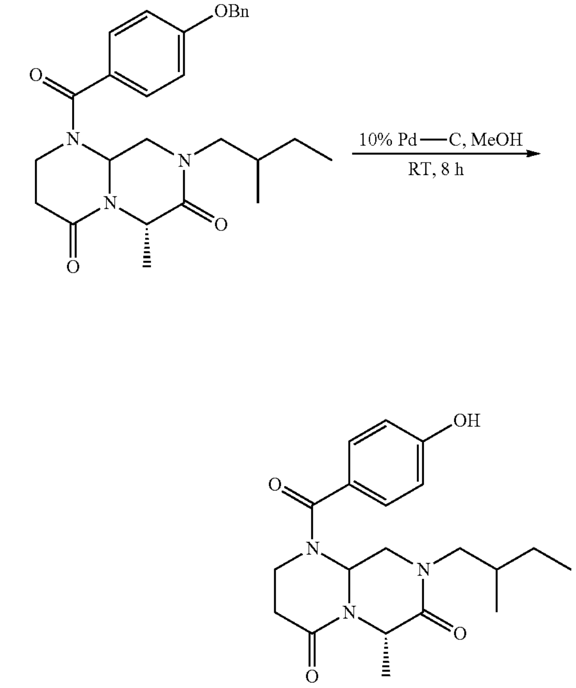

8a

Step 1: Synthesis of (6S)-1-(4-(benzyloxy)benzoyl)-6-methyl-8-(2-methylbutyl)hexahydro-4H-pyrazino[1,2-a]pyrimidine-4,7(6H)-dione. To a solution of 4-(benzyloxy)benzoic acid (0.360 g, 1.42 mmol) stirred in dichloromethane (20 mL) at room temperature was added $T_3P$ (1.2 mL, 1.7 mmol) and DIPEA (0.55 mL, 2.84 mmol), and the mixture was stirred for 15 min. To this (6S)-6-methyl-8-(2-methylbutyl)tetrahydro-1H-pyrazino[1,2-a]pyrimidine-4,7(6H,8H)-dione (0.400 g, 1.42 mmol) was added, and stirring was continued at room temperature for 16 hours. The reaction progress was monitored by TLC. After completion, the reaction mixture was quenched with water (50 mL) and extracted with dichloromethane (2×50 mL). The combined organic layers were dried over $Na_2SO_4$, filtered and concentrated under reduced pressure to give 0.9 g of crude material. Analysis of the crude material by LC/MS showed 54.59% of the desired product. The crude material was used in the next step without purification.

Step 2: Synthesis of Compound 8a. To a solution of (6S)-1-(4-(benzyloxy)benzoyl)-6-methyl-8-(2-methylbutyl)tetrahydro-1H-pyrazino[1,2-a]pyrimidine-4,7(6H,8H)-dione (0.900 g) stirred in methanol (20 mL) at room temperature was added 10% Pd—C (0.200 g), under $N_2$ atmosphere. The reaction mixture was stirred at room temperature under an $H_2$ balloon for 8 hr. The reaction progress was monitored by TLC. After completion, the reaction mixture was filtered through Celite and evaporated under reduced pressure to afford the crude compound. The crude compound was dissolved in dichloromethane (50 mL), washed with aqueous $NaHCO_3$ solution (20 mL) and brine solution (20 mL). The filtrate was dried over $Na_2SO_4$, filtered and concentrated under reduced pressure. The crude compound was triturated with diethyl ether to afford 8a (0.330 g, 82%) as a solid. MS (ESI) m/z $[M+H]^+$: 374.11.

Example S10. Synthesis of Compound 9

The synthetic route for preparing Compound 9 is shown in Scheme 10.

Scheme 10.

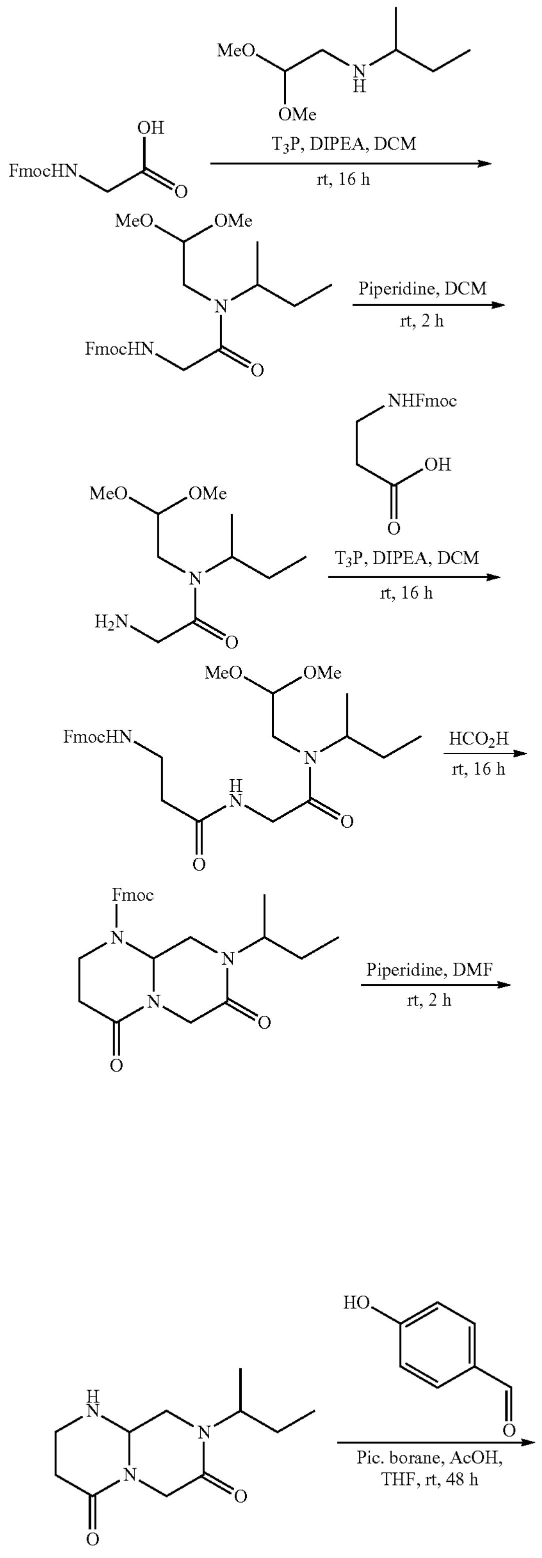

-continued

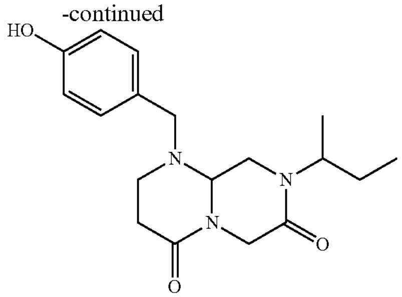

9

Step 1: Synthesis of (9H-fluoren-9-yl)methyl 2-(sec-butyl(2,2-dimethoxyethyl)amino)-2-oxoethylcarbamate. To a stirred solution of 2-(((9H-fluoren-9-yl)methoxy)carbonylamino)acetic acid (10 g, 33.6 mmol) in dichloromethane (100 mL), cooled to 0° C. were added DIPEA (11.88 mL, 67.3 mmol), N-(2,2-dimethoxyethyl)butan-2-amine (10.84 g, 67.3 mmol) and $T_3P$ (53.0 mL, 84.1 mmol), and the reaction mixture was stirred for 16 hours at room temperature. Reaction progress was monitored by TLC. After completion of the reaction, ice cold water (100 mL) was added and extracted with ethyl acetate (2×150 mL). The combined organic layers were dried over anhydrous $Na_2SO_4$, filtered and concentrated under reduced pressure to obtain the desired crude product. The crude compound was purified by flash column chromatography (100-200 mesh silica gel) and eluted with 20-25% ethyl acetate in petroleum ether to afford (9H-fluoren-9-yl)methyl 2-(sec-butyl(2,2-dimethoxyethyl)amino)-2-oxoethylcarbamate (10.8 g, 72.9%) as a solid.

Step 2: Synthesis of 2-amino-N-sec-butyl-N-(2,2-dimethoxyethyl)acetamide. To a solution of (9H-fluoren-9-yl)methyl 2-(sec-butyl(2,2-dimethoxyethyl)amino)-2-oxoethylcarbamate (10.8 g, 24.5 mmol) in DMF (20 mL), cooled to 0° C., was added piperidine (2.4 mL) and the reaction mixture was stirred at room temperature for 2 hours. Progress of the reaction was monitored by TLC. After TLC indicated complete consumption of starting material, the reaction mixture was diluted with petroleum ether (2×100 mL), then water was added and the mixture was separated. The aqueous layer was extracted with dichloromethane (2×150 mL). The combined organic layers were dried over anhydrous $Na_2SO_4$, filtered and concentrated under reduced pressure to obtain the desired pure product 2-amino-N-sec-butyl-N-(2,2-dimethoxyethyl)acetamide (3.6 g, 67.2%) as a solid.

Step 3: Synthesis of (9H-fluoren-9-yl)methyl-3-(2-(sec-butyl(2,2-dimethoxyethyl)amino)-2-oxoethylamino)-3-oxopropylcarbamate. To a stirred solution of 2-amino-N-sec-butyl-N-(2,2-dimethoxyethyl)acetamide (3.6 g, 16.5 mmol) in dichloromethane (40 mL) were added DIPEA (31.91 mL, 49.5 mmol), 3-(((9H-fluoren-9-yl)methoxy)carbonylamino)propanoic acid (5.14 g, 16.5 mmol) and $T_3P$ (39.13 g, 33 mmol) at 0° C. The reaction mixture was stirred at room temperature for 16 hours. Progress of the reaction was monitored by TLC. After completion of the reaction, the reaction water (100 mL) was added and the organic phase was separated. The aqueous phase was extracted with dichloromethane (2×150 mL). The combined organic layers were dried over $Na_2SO_4$, filtered and concentrated under reduced pressure to give the crude product. The crude product was purified by column chromatography using silica (230-400 mesh; 23-25% ethyl acetate/petroleum ether as eluent). Collected pure fractions were concentrated under reduced pressure to give (9H-fluoren-9-yl)methyl-3-(2-(sec-butyl(2,2-dimethoxyethyl)amino)-2-oxoethylamino)-3-oxopropylcarbamate (4.1 g, 48.6%) as a gum.

Step 4: Synthesis of (9H-fluoren-9-yl)methyl 8-sec-butyl-4,7-dioxooctahydro-1H-pyrazino[1,2-a]pyrimidine-1-carboxylate. To a solution of (9H-fluoren-9-yl)methyl-3-(2-(sec-butyl(2,2-dimethoxyethyl)amino)-2-oxoethylamino)-3-oxopropylcarbamate (4.1 g, 8.01 mmol) in acetic acid (2 mL) was stirred for 16 hours at room temperature. Progress of the reaction was monitored by TLC. After TLC indicated complete consumption of the starting material, the reaction mixture was concentrated and the resulting mass was diluted with water and extracted with dichloromethane (2×100 mL). The combined organic layers were dried over $Na_2SO_4$, filtered and concentrated under reduced pressure to give the product (9H-fluoren-9-yl)methyl 8-sec-butyl-4,7-dioxooctahydro-1H-pyrazino[1,2-a]pyrimidine-1-carboxylate. (3.2 g, 89.3%) as a gum.

Step 5: Synthesis of 8-sec-butyltetrahydro-1H-pyrazino[1,2-a]pyrimidine-4,7(6H,8H)-dione. To a solution of (9H-fluoren-9-yl)methyl 8-sec-butyl-4,7-dioxooctahydro-1H-pyrazino[1,2-a]pyrimidine-1-carboxylate (3.2 g, 7.1 mmol) in DMF (20 mL), cooled to 0° C., was added piperidine (0.7 mL, 1.0 eq) and the reaction mixture was stirred at room temperature for 2 hours. Progress of the reaction was monitored by TLC. After TLC indicated complete consumption of starting material, the reaction mixture was washed with petroleum ether (2×50 mL) to remove the non-polar impurities. Cold water was added and extracted with dichloromethane (2×100 mL). The combined organic layers were dried over $Na_2SO_4$, filtered and concentrated under reduced pressure to give the pure product 8-sec-butyltetrahydro-1H-pyrazino[1,2-a]pyrimidine-4,7(6H,8H)-dione (900 mg, 55.9%) as a solid.

Step 6: Synthesis of Compound 9. To a stirred solution of (8-(sec-butyl)hexahydro-4H-pyrazino[1,2-a]pyrimidine-4,7(6H)-dione (0.500 g, 2.2 mmol) and 4-hydroxybenzaldehyde (0.271 g, 2.2 mmol) in methanol (10 mL) was added acetic acid (0.27 mL, 2.0 eq.) and picoline borane (0.285 g, 2.6 mmol) at room temperature. The reaction mixture was stirred at room temperature for 48 hr. The reaction progress was monitored by TLC. After completion, the reaction mixture was quenched with ice cold water (10 mL) and extracted with ethyl acetate (2×20 mL). The combined organic layers were dried over $Na_2SO_4$, filtered and concentrated under reduced pressure to give crude product. The crude compound was analyzed by LC/MS. The crude LC/MS data showed 8.28% desired mass. The crude compound was purified by column chromatography over silica gel (100-200), and 50-70% ethyl acetate in petroleum ether eluted the desired compound. The LC/MS of the eluted fractions showed 72.16% desired mass, which was further purified by Prep HPLC. After Prep HPLC purification, the fractions were collected and concentrated under reduced pressure, then lyophilized to afford 9 (0.168 g, 22.8%) as a solid. Prep HPLC Method: Mobile Phase A: 10 mM ammonium bicarbonate in water; Mobile Phase B: acetonitrile; Column: X-BRIDGE $C_{18}$ (150×19 mm 5μ); Flow: 18 mL/min. MS (ESI) m/z $[M+H]^+$: 332.2.

Example S11. Synthesis of Compound 10

The synthetic route for preparing Compound 10 is shown in Scheme 11.

Scheme 11.

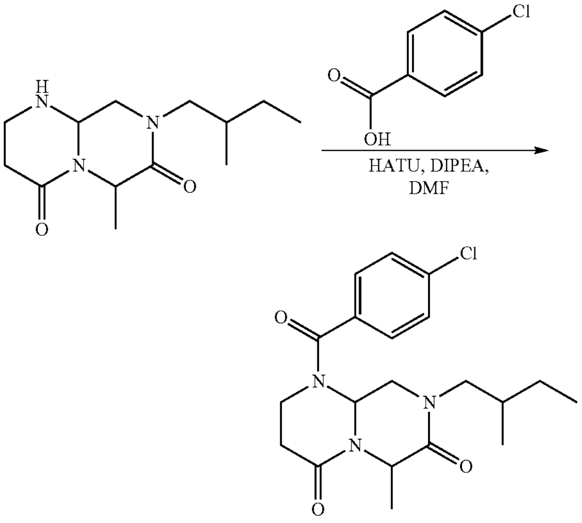

10

To a solution of 6-methyl-8-(2-methylbutyl)hexahydro-4H-pyrazino[1,2-a]pyrimidine-4,7(6H)-dione (250 mg, 0.98 mmol) and 4-chlorobenzoic acid (170 mg, 1.09 mmol) in DMF (4 mL) at 0° C. was added HATU (413 mg, 1.08 mmol) followed by DIPEA (0.35 mL, 1.97 mmol). The reaction mixture was stirred at room temperature for 12 h. After completion, the reaction mixture was quenched with ice cold water (50 mL) and the aqueous layer was extracted with EtOAc (50 mL×2). The organic layer was washed with cold $H_2O$ (30 mL) followed by saturated brine (30 mL), dried over $Na_2SO_4$ and concentrated under reduced pressure. The crude obtained was purified by column chromatography (Silica 100-200 mesh; 30% EtOAc in hexanes) to afford 1-(4-chlorobenzoyl)-6-methyl-8-(2-methylbutyl)hexahydro-4H-pyrazino[1,2-a]pyrimidine-4,7(6H)-dione 10 (150 mg, 0.383 mmol, 39.2% yield) as a solid. MS (ESI) m/z $[M+H]^+$: 392.05. $^1H$ NMR (400 MHz, DMSO-$d_6$) δ 0.66-0.89 (m, 6H) 0.91-1.42 (m, 4H) 1.57-1.78 (m, 1H) 2.16-2.35 (m, 2H) 2.55-2.65 (m, 2H) 3.08-3.23 (m, 2H) 3.28-3.40 (m, 1H) 3.51-3.64 (m, 2H) 4.76-4.89 (m, 1H) 5.88-6.02 (m, 1H) 7.46-7.56 (m, 4H).

Example S12. Synthesis of Compound 11

The synthetic route for preparing Compound 11 is shown in Scheme 12.

Scheme 12.

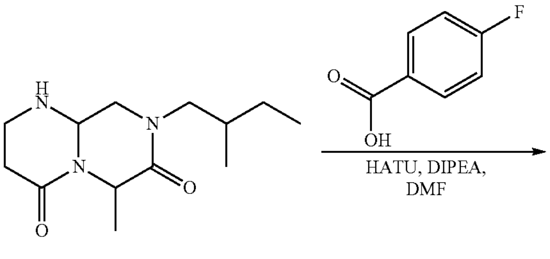

-continued

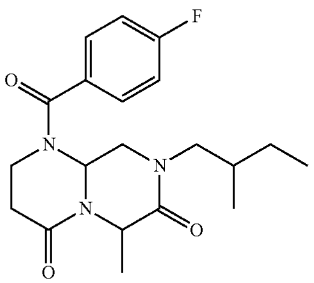

11

To a solution of 6-methyl-8-(2-methylbutyl)hexahydro-4H-pyrazino[1,2-a]pyrimidine-4,7(6H)-dione (250 mg, 0.98 mmol) and 4-fluorobenzoic acid (153 mg, 1.09 mmol) in DMF (4 mL) at 0° C. was added HATU (413 mg, 1.08 mmol) followed by DIPEA (0.35 mL, 1.97 mmol). The reaction mixture was stirred at room temperature for 12 h. After completion, the reaction mixture was quenched with ice cold water (50 mL) and the aqueous layer was extracted with EtOAc (50 mL×2). The organic layer was washed with cold $H_2O$ (30 mL) followed by saturated brine (30 mL), dried over $Na_2SO_4$ and concentrated under reduced pressure. The crude obtained was purified by column chromatography (Silica 100-200 mesh; 30% EtOAc in hexanes) to afford 1-(4-fluorobenzoyl)-6-methyl-8-(2-methylbutyl)hexahydro-4H-pyrazino[1,2-a]pyrimidine-4,7(6H)-dione 11 (140 mg, 0.37 mmol, 38.0% yield) as a solid. MS (ESI) m/z $[M+H]^+$: 376.05. $^1H$ NMR (400 MHz, DMSO-d6) δ 0.69-0.81 (m, 3H) 0.86 (t, J=7.23 Hz, 3H) 0.95-1.14 (m, 2H) 1.20-1.43 (m, 4H) 1.59-1.80 (m, 2H) 2.26 (d, J=16.95 Hz, 1H) 2.55-2.72 (m, 1H) 3.20-3.31 (m, 2H) 3.35-3.39 (m, 1H) 3.52-3.70 (m, 2H) 4.73-4.89 (m, 1H) 7.33 (t, J=8.73 Hz, 2H) 7.61 (dd, J=8.23, 5.73 Hz, 2H).

Example S13. Synthesis of Compound 12

The synthetic route for preparing Compound 12 is shown in Scheme 13.

Scheme 13.

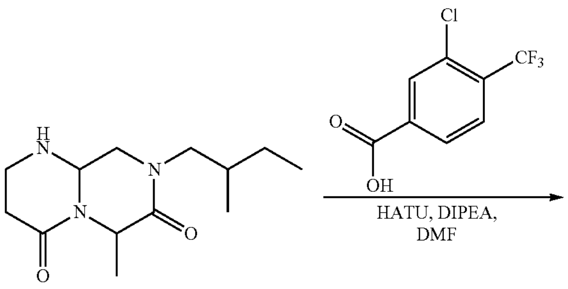

-continued

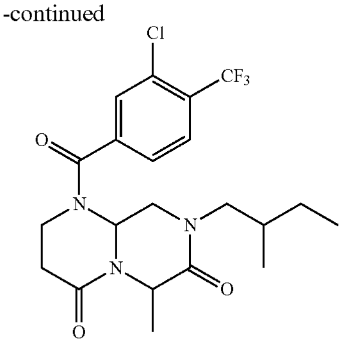

12

To a solution of 6-methyl-8-(2-methylbutyl)hexahydro-4H-pyrazino[1,2-a]pyrimidine-4,7(6H)-dione (250 mg, 0.98 mmol) and 3-chloro-4-(trifluoromethyl)benzoic acid (242 mg, 1.09 mmol) in DMF (4 mL) at 0° C. was added HATU (413 mg, 1.08 mmol) followed by DIPEA (0.35 mL, 1.97 mmol). The reaction mixture was stirred at room temperature for 12 h. After completion, the reaction mixture was quenched with ice cold water (50 mL) and the aqueous layer was extracted with EtOAc (50 mL×2). The organic layer was washed with cold $H_2O$ (30 mL) followed by saturated brine (30 mL), dried over $Na_2SO_4$ and concentrated under reduced pressure. The crude obtained was purified by column chromatography (Silica 100-200 mesh; 30% EtOAc in hexanes) to afford 1-(3-chloro-4-(trifluoromethyl)benzoyl)-6-methyl-8-(2-methylbutyl)hexahydro-4H-pyrazino[1,2-a]pyrimidine-4,7(6H)-dione 12 (250 mg, 0.55 mmol, yield) as a solid. MS (ESI) m/z $[M+H]^+$: 460.0. $^1H$ NMR (400 MHz, DMSO-d6) δ 0.74-0.93 (m, 6H) 0.98-1.19 (m, 2H) 1.28-1.46 (m, 3H) 1.64-1.81 (m, 1H) 2.22 (d, J=17.45 Hz, 1H) 2.57-2.70 (m, 1H) 3.14 (dd, J=13.21, 6.23 Hz, 1H) 3.25-3.31 (m, 2H) 3.44-3.57 (m, 1H) 3.61-3.87 (m, 2H) 4.78-4.90 (m, 1H) 5.89-6.05 (m, 1H) 7.72 (d, J=7.98 Hz, 1H) 7.90-8.02 (m, 2H).

Example S14. Synthesis of Intermediate Compound 8-(4-methoxybenzyl)-6-methylhexahydro-4H-pyrazino[1,2-a]pyrimidine-4,7(6H)-dione The synthetic route for preparing this intermediate compound is shown in Scheme 14.

Scheme 14.

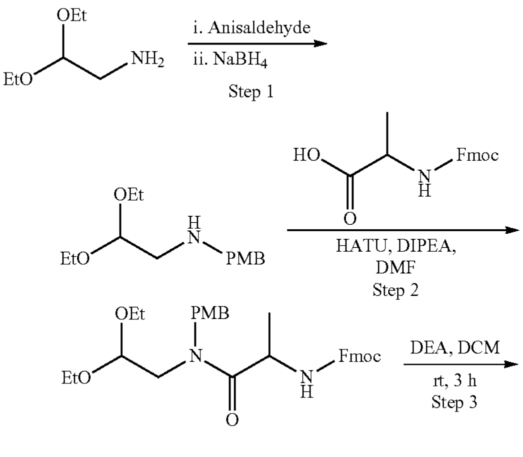

-continued

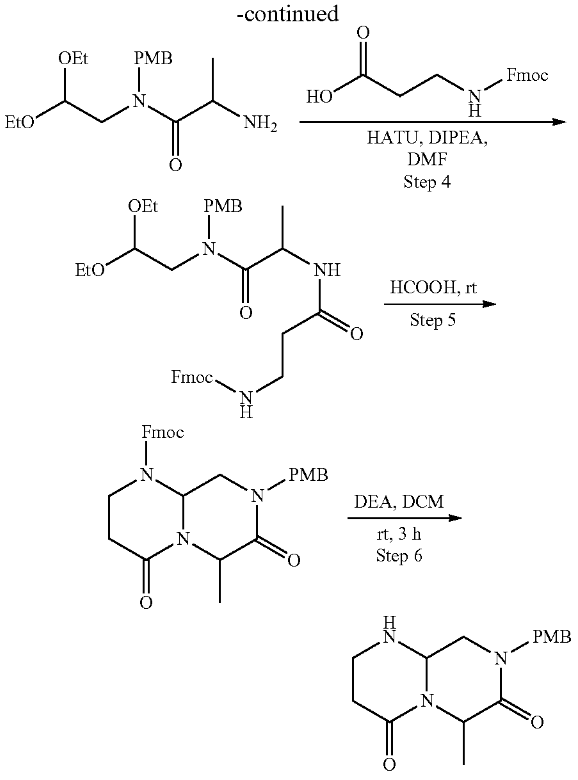

Step 1: Synthesis of 2,2-diethoxy-N-(4-methoxybenzyl)ethan-1-amine. A 500 mL round bottom flask was charged with anisaldehyde (12 mL, 90.22 mmol) and 2,2-diethoxyethanamine (10 g, 75.18 mmol). The reaction mixture was heated at 100° C. for 1 h. The reaction mixture was allowed to cool at room temperature and to this was added EtOH (100 mL) followed by $NaBH_4$ (4.28 g, 112.7 mmol). The resulting reaction mixture was stirred at room temperature for 16 h. After complete consumption of starting material (monitored by TLC), the reaction mixture was concentrated under reduced vacuum. The crude obtained was dissolved in EtOAc (300 mL). The organic layer was washed with brine (100 mL), dried over $Na_2SO_4$ and concentrated under vacuum to give crude product. The crude product obtained was purified by column chromatography (silica 100-200 mesh; 70% EtOAc in hexanes) to obtain 2,2-diethoxy-N-(4-methoxybenzyl)ethan-1-amine (15 g, 59.28 mmol, 78% yield) as a liquid. MS (ESI) m/z $[M+H]^+$: 254.3.

Step 2: (9H-fluoren-9-yl)methyl (1-((2,2-diethoxyethyl)(4-methoxybenzyl)amino)-1-oxopropan-2-yl)carbamate. To a stirred solution of (((9H-fluoren-9-yl)methoxy)carbonyl)alanine (32 g, 102.76 mmol) in dry DMF (140 mL) maintained at 0° C. was added HATU (42 g, 110.67 mmol), DIPEA (21.06 mL, 118.57 mmol), followed by 2,2-diethoxy-N-(4-methoxybenzyl)ethan-1-amine (20 g, 79.05 mmol). The reaction mixture was stirred at room temperature for 16 h. After complete consumption of starting material, the reaction mixture was quenched with ice cold water (300 mL) and the aqueous layer was extracted with EtOAc (200 mL×2). The organic layer was washed with cold $H_2O$ (200 mL) followed by brine (100 mL), dried over $Na_2SO_4$ and concentrated under reduced pressure to give crude product. The crude obtained was purified by column chromatography (Silica 100-200 mesh; 50% EtOAc in hexanes) to afford (9H-fluoren-9-yl)methyl (1-((2,2-diethoxyethyl)(4-methoxybenzyl)amino)-1-oxopropan-2-yl)carbamate (28 g, 51.22 mmol, 64.8% yield) as a gummy liquid. MS (ESI) m/z $[M+H-EtOH]^+$: 501.2.

Step 3: Synthesis of 2-amino-N-(2,2-diethoxyethyl)-N-(4-methoxybenzyl)propanamide. To a solution of (9H-fluoren-9-yl) methyl (1-((2,2-diethoxyethyl)(4-methoxybenzyl)amino)-1-oxopropan-2-yl)carbamate (28 g, 51.22 mmol) in $CH_2Cl_2$ (30 mL) was added diethylamine (200 mL). The reaction mixture was stirred at room temperature for 3 h. After complete consumption of the starting material (monitored by TLC), the reaction mixture was concentrated and the crude obtained was purified by column chromatography (Silica 100-200 mesh; 5% MeOH in DCM) to afford 2-amino-N-(2,2-diethoxyethyl)-N-(4-methoxybenzyl)propanamide (14.5 g, 44.75 mmol, 87% yield) as a viscous liquid. MS (ESI) m/z $[M+H-EtOH]^+$: 279.05.

Step 4: Synthesis of (9H-fluoren-9-yl)methyl (3-((1-((2,2-diethoxyethyl)(4-methoxybenzyl)amino)-1-oxopropan-2-yl)amino)-3-oxopropyl)carbamate. To a stirred solution of 3-((((9H-fluoren-9-yl)methoxy)carbonyl)amino)propanoic acid (14.78 g, 47.53 mmol) in dry DMF (120 mL) maintained at 0° C. was added HATU (18.06 g, 47.53 mmol), DIPEA (9.21 mL, 51.85 mmol) followed by 2-amino-N-(2,2-diethoxyethyl)-N-(4-methoxybenzyl)propanamide (14 g, 43.20 mmol). The reaction mixture was stirred for 16 h at room temperature. After completion, the reaction mixture was quenched with ice cold water (200 mL) and the aqueous layer was extracted with EtOAc (200 mL×2). The organic layer was washed with cold $H_2O$ (500 mL) followed by saturated brine (200 mL), dried over $Na_2SO_4$ and concentrated under reduced pressure. The crude obtained was purified by column chromatography (Silica 100-200 mesh; 30% EtOAc in hexanes) to afford (9H-fluoren-9-yl)methyl (3-((1-((2,2-diethoxyethyl)(4-methoxybenzyl)amino)-1-oxopropan-2-yl)amino)-3-oxopropyl)carbamate (18 g, 29.14 mmol, 67.44% yield) as a viscous liquid. MS (ESI) m/z $[M+H-EtOH]^+$: 572.

Step 5: Synthesis of (9H-fluoren-9-yl)methyl 8-(4-methoxybenzyl)-6-methyl-4,7-dioxohexahydro-2H-pyrazino[1,2-a]pyrimidine-1(6H)-carboxylate. A solution of (9H-fluoren-9-yl)methyl (3-((1-((2,2-diethoxyethyl)(4-methoxybenzyl)amino)-1-oxopropan-2-yl)amino)-3-oxopropyl)carbamate (18 g, 29.14 mmol) in formic acid (120 mL) was stirred at room temperature for 12 h. After completion, the reaction mixture was concentrated and the crude obtained was purified by column chromatography (Silica 100-200 mesh; 30% EtOAc in hexanes) to afford (9H-fluoren-9-yl)methyl 8-(4-methoxybenzyl)-6-methyl-4,7-dioxohexahydro-2H-pyrazino[1,2-a]pyrimidine-1(6H)-carboxylate (14.5 g, 27.58 mmol, 94% yield) as a solid. MS (ESI) m/z $[M+H]^+$: 526.

Step 6: Synthesis of 8-(4-methoxybenzyl)-6-methylhexahydro-4H-pyrazino[1,2-a]pyrimidine-4,7(6H)-dione. To a solution of (9H-fluoren-9-yl)methyl 8-(4-methoxybenzyl)-6-methyl-4,7-dioxohexahydro-2H-pyrazino[1,2-a]pyrimidine-1(6H)-carboxylate (14 g, 26.63 mmol) in $CH_2Cl_2$ (150 mL) was added diethyl amine (100 mL) and the reaction mixture was stirred at room temperature for 3 h. After complete consumption of the starting material (monitored by TLC), the reaction mixture was concentrated and the crude obtained was purified by column chromatography (Silica 100-200 mesh; 5% MeOH in DCM) to afford 8-(4-methoxybenzyl)-6-methylhexahydro-4H-pyrazino[1,2-a]pyrimidine-4,7(6H)-dione (7 g, 23.07 mmol, 87% yield) as a sticky solid. MS (ESI) m/z $[M+H]^+$: 304.

Example S15. Synthesis of Intermediate Compound 8-(4-methoxybenzyl)-6-methylhexahydro-4H-pyrazino[1,2-a]pyrimidine-4,7(6H)-dione The synthetic route for preparing this intermediate compound is shown in Scheme 15.

Scheme 15.

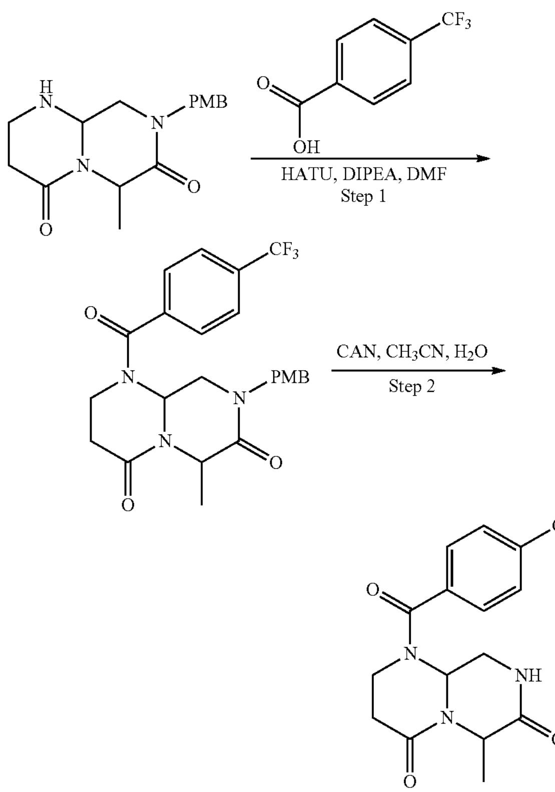

Step 1: Synthesis of 8-(4-methoxybenzyl)-6-methyl-1-(4-(trifluoromethyl)benzoyl)hexahydro-4H-pyrazino[1,2-a]pyrimidine-4,7(6H)-dione. To a solution of 4-(trifluoromethyl) benzoic acid (5.26 g, 27.69 mmol) in DMF (100 mL) maintained at 0° C. was added HATU (10.52 g, 27.69 mmol), DIPEA (12.30 mL, 69.23 mmol) followed by 8-(4-methoxybenzyl)-6-methylhexahydro-4H-pyrazino[1,2-a] pyrimidine-4,7(6H)-dione (7 g, 23.07 mmol), and the reaction mixture was stirred at room temperature for 12 h. After completion, the reaction mixture was quenched with ice cold water (200 mL) and the aqueous layer was extracted with EtOAc (200 mL×2). The organic layer was washed with cold $H_2O$ (200 mL) followed by saturated brine (150 mL), dried over $Na_2SO_4$ and concentrated under reduced pressure. The crude obtained was purified by column chromatography (Silica 100-200 mesh; 30% EtOAc in hexanes) to afford 8-(4-methoxybenzyl)-6-methyl-1-(4-(trifluoromethyl)benzoyl)hexahydro-4H-pyrazino[1,2-a]pyrimidine-4,7(6H)-dione (9 g, 18.92 mmol, 82.04% yield) as a solid. MS (ESI) m/z $[M+H]^+$: 476.15 and MS (ESI) m/z $[M+Na]^+$: 498.05.

Step 2: Synthesis of 6-methyl-1-(4-(trifluoromethyl)benzoyl)hexahydro-4H-pyrazino[1,2-a]pyrimidine-4,7(6H)-dione. To a solution of 8-(4-methoxybenzyl)-6-methyl-1-(4-(trifluoromethyl)benzoyl)hexahydro-4H-pyrazino[1,2-a] pyrimidine-4,7(6H)-dione (9 g, 18.92 mmol) in $CH_3CN$: $H_2O$ (2:1, 150 mL) maintained at 0° C., was added CAN (31.15 g, 56.82 mmol) and the reaction mixture was allowed to stir at room temperature for 3 h. Progress of the reaction was monitored by TLC. After completion, the reaction mixture was quenched with saturated solution of aq. $NaHCO_3$ (200 mL) and extracted with EtOAc (200 mL×2). Combined organic layer was washed with $H_2O$ (200 mL) followed by saturated brine solution (150 mL), dried over $Na_2SO_4$ and concentrated under reduced pressure. The crude obtained was purified by column chromatography (Silica 100-200 mesh; 10% MeOH in DCM) to afford 6-methyl-1-(4-(trifluoromethyl)benzoyl)hexahydro-4H-pyrazino[1,2-a] pyrimidine-4,7(6H)-dione (3.5 g, 9.85 mmol, 52.8% yield) as a solid. MS (ESI) m/z $[M+H+CH_3CN]^+$: 397.0. $^1H$ NMR (400 MHz, DMSO-d6) δ 1.25-1.46 (m, 3H) 2.15-2.30 (m, 1H) 2.56-2.69 (m, 1H) 3.16 (d, J=4.99 Hz, 1 H) 3.22-3.30 (m, 1H) 3.42-3.72 (m, 2H) 4.70-4.87 (m, 1H) 5.85-5.95 (m, 1H) 7.75 (d, J=7.98 Hz, 2H) 7.86 (d, J=7.98 Hz, 2H) 8.11 (brs, 1H).

Example S16. General Procedure A for the Synthesis of Final Compounds

To a solution of 6-methyl-1-(4-(trifluoromethyl)benzoyl) hexahydro-4H-pyrazino[1,2-a]pyrimidine-4,7(6H)-dione (200 mg, 0.56 mmol) in DMF (2 mL) was added KO t Bu (1M in THF, 1.69 mmol, 1.69 mL) followed by alkyl halide (1.12 mmol), and the reaction mixture was exposed to microwave irradiation at 120° C. for 1 h. The reaction mixture was cooled to room temperature and quenched with $H_2O$ (25 mL). The aqueous layer was extracted with EtOAc (10 mL×3). The combined organic layers were washed with brine and concentrated. The crude product obtained was purified by CombiFlash.

Example S17. Synthesis of Compound 15

Compound 15 was synthesized by General Procedure A using (bromomethyl)cyclopentane as the alkyl halide. MS (ESI) m/z $[M+H]^+$: 438.65. $^1H$ NMR (400 MHz, DMSO-$d_6$) δ 1.02-1.26 (m, 3H) 1.28-1.42 (m, 2H) 1.44-1.76 (m, 6H) 1.80-2.08-2.33 (m, 2H) 2.55-2.71 (m, 1H) 3.22 (dd, J=12.96, 7.48 Hz, 1H) 3.26-3.32 (m, 1H) 3.39 (d, J=6.98 Hz, 1H) 3.49-3.57 (m, 1H) 3.59-3.74 (m, 1H) 3.76-3.91 (m, 1H) 4.80-4.90 (m, 1H) 5.95-6.05 (m, 1H) 7.72-7.79 (m, 2H) 7.84-7.91 (m, 2H).

Example S18. Synthesis of Compound 16

Compound 16 was synthesized by General Procedure A using bromomethylcyclobutane as the alkyl halide. MS (ESI) m/z $[M+H]^+$: 424.15. $^1H$ NMR (400 MHz, DMSO-$d_6$) δ 1.29-1.44 (m, 2H) 1.58-1.89 (m, 4H) 1.90-2.08 (m, 2H) 2.16-2.31 (m, 1H) 2.55-2.70 (m, 2H) 3.18-3.31 (m, 1H) 3.25-3.26 (m, 1H) 3.34-3.42 (m, 1H) 3.36-3.57 (m, 2H) 3.60-3.69 (m, 1H) 3.71-3.83 (m, 1H) 4.75-4.89 (m, 1H) 5.90-6.05 (m, 1H) 7.70-7.79 (m, 2H) 7.87 (d, J=8.31 Hz, 2H).

Example S19. Synthesis of Compound 19

Compound 19 was synthesized by General Procedure A using (2-bromoethyl)cyclopentane as the alkyl halide. MS (ESI) m/z $[M+H]^+$: 452.35. $^1H$ NMR (400 MHz, DMSO-$d_6$) δ 0.94-1.18 (m, 3H) 1.26-1.61 (m, 9H) 1.66-1.83 (m, 2H) 2.16-2.31 (m, 1H) 2.56-2.70 (m, 1H) 3.16-3.28 (m, 1H)

3.35-3.56 (m, 3H) 3.60-3.73 (m, 1H) 3.77-3.90 (m, 1H) 4.72-4.92 (m, 1H) 5.94-6.06 (m, 1H) 7.77 (d, J=7.98 Hz, 2H) 7.87 (d, J=7.98 Hz, 2H).

Example S20. Synthesis of Compound 20

Compound 20 was synthesized by General Procedure A using (2-bromoethyl)cyclobutane as the alkyl halide. MS (ESI) m/z $[M+H]^+$: 438.25. $^1H$ NMR (400 MHz, DMSO-$d_6$) δ 1.27-1.44 (m, 3H) 1.50-1.71 (m, 4H) 1.71-1.88 (m, 2H) 1.93-2.09 (m, 2H) 2.13-2.34 (m, 2H) 2.56-2.70 (m, 2H) 3.25-3.32 (m, 1H) 3.35-3.42 (m, 1H) 3.45-3.55 (m, 1H) 3.59-3.72 (m, 1H) 3.74-3.90 (m, 1H) 4.75-4.89 (m, 1H) 5.94-6.05 (m, 1H) 7.71-7.79 (m, 2H) 7.87 (d, J=8.31 Hz, 2H).

Example S21. Synthesis of Compound 21

Compound 21 was synthesized by General Procedure A using 1-bromobutane as the alkyl halide. MS (ESI) m/z $[M+H]^+$: 412.20. $^1H$ NMR (400 MHz, DMSO-$d_6$) δ 0.81-0.97 (m, 3H) 1.15-1.57 (m, 7H) 2.15-2.31 (m, 1H) 2.57-2.69 (m, 1H) 3.14-3.28 (m, 1H) 3.35-3.60 (m, 3H) 3.62-3.73 (m, 1H) 3.74-3.92 (m, 1H) 4.75-4.91 (m, 1H) 5.94-6.06 (m, 1H) 7.76 (d, J=7.34 Hz, 2H) 7.87 (d, J=7.83 Hz, 2H).

Example S22. Synthesis of Compound 22

Compound 22 was synthesized by General Procedure A using 4-bromobut-1-ene as the alkyl halide. MS (ESI) m/z $[M+H]^+$: 410.20. $^1H$ NMR (400 MHz, DMSO-$d_6$) δ 1.28-1.45 (m, 3H) 2.14-2.38 (m, 3H) 2.55-2.69 (m, 1H) 3.36-3.57 (m, 4H) 3.58-3.72 (m, 1H) 3.75-3.89 (m, 1H) 4.75-4.90 (m, 1H) 4.98-5.19 (m, 2H) 5.69-5.84 (m, 1H) 5.93-6.05 (m, 1H) 7.76 (d, J=7.98 Hz, 2H) 7.88 (d, J=7.98 Hz, 2H).

Example S23. Synthesis of Compound 23

Compound 23 was synthesized by General Procedure A using 1-bromo-2-methylpropane as the alkyl halide. MS (ESI) m/z $[M+H]^+$: 412.25. $^1H$ NMR (400 MHz, DMSO-$d_6$) δ 0.80-0.96 (m, 6H) 1.30-1.48 (m, 3H) 1.85-2.03 (m, 1H) 2.15-2.31 (m, 1H) 2.57-2.70 (m, 1H) 3.06-3.16 (m, 1H) 3.18-3.28 (m, 1H) 3.36-3.45 (m, 1H) 3.44-3.57 (m, 1H) 3.60-3.74 (m, 1H) 3.73-3.87 (m, 1H) 4.77-4.92 (m, 1H) 5.93-6.07 (m, 1H) 7.76 (d, J=7.48 Hz, 2H) 7.87 (d, J=7.48 Hz, 2H).

Example S24. Synthesis of Compound 24

Compound 24 was synthesized by General Procedure A using 2-bromopropane as the alkyl halide. MS (ESI) m/z $[M+H]^+$: 398.55. $^1H$ NMR (400 MHz, DMSO-$d_6$) δ 1.10 (d, J=5.49 Hz, 6H) 1.28-1.45 (m, 3H) 2.16-2.24 (m, 1H) 2.56-2.71 (m, 1H) 3.34-3.40 (m, 1H) 3.44-3.79 (m, 3H) 4.59-4.72 (m, 1H) 4.75-4.90 (m, 1H) 5.86-6.00 (m, 1H) 7.79 (d, J=7.98 Hz, 2H) 7.83-7.92 (m, 2H).

Example S25. Synthesis of Intermediate Compound 1-(4-(difluoromethoxy)benzoyl)-6-methylhexahydro-4H-pyrazino[1,2-a]pyrimidine-4,7(6H)-dione The synthetic route for preparing this intermediate compound is shown in Scheme 16.

Scheme 16.

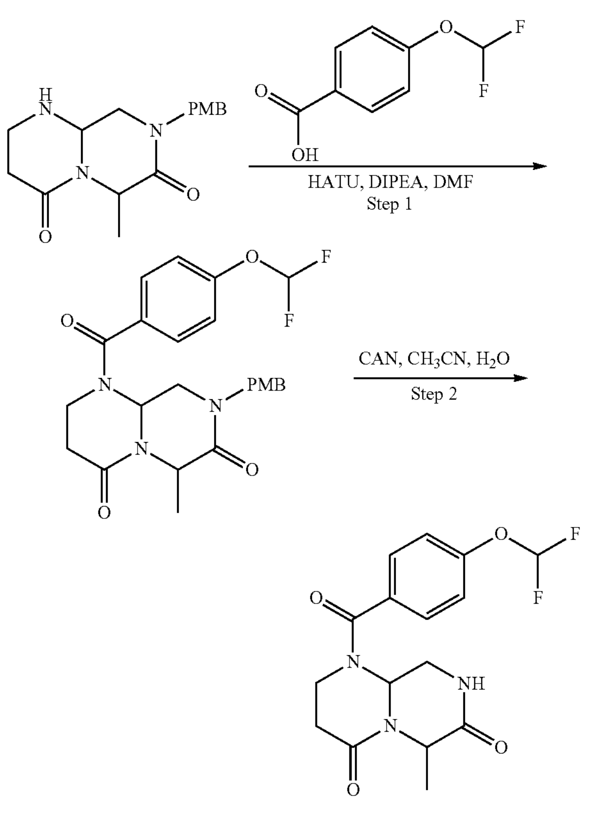

Step 1: Synthesis of 1-(4-(difluoromethoxy)benzoyl)-8-(4-methoxybenzyl)-6-methylhexahydro-4H-pyrazino[1,2-a]pyrimidine-4,7(6H)-dione. To a solution of 4-(difluoromethoxy)benzoic acid (1.71 g, 9.08 mmol) in DMF (25 mL) maintained at 0° C. was added HATU (3.45 g, 9.08 mmol), DIPEA (4.34 mL, 24.8 mmol) followed by 8-(4-methoxybenzyl)-6-methylhexahydro-4H-pyrazino[1,2-a]pyrimidine-4,7(6H)-dione (2.5 g, 8.25 mmol) and reaction mixture was stirred at room temperature for 12 h. After completion, the reaction mixture was quenched with ice cold water (50 mL) and the aqueous layer was extracted with EtOAc (100 mL×2). The organic layer was washed with cold $H_2O$ (100 mL) followed by saturated brine (100 mL), dried over $Na_2SO_4$ and concentrated under reduced pressure. The crude obtained was purified by column chromatography (Silica 100-200 mesh; 30% EtOAc in hexanes) to afford 1-(4-(difluoromethoxy)benzoyl)-8-(4-methoxybenzyl)-6-methylhexahydro-4H-pyrazino[1,2-a]pyrimidine-4,7(6H)-dione (3.5 g, 7.38 mmol, 89.5% yield) as a solid. MS (ESI) m/z $[M+H]^+$: 474.12.

Step 2: Synthesis of 1-(4-(difluoromethoxy)benzoyl)-6-methylhexahydro-4H-pyrazino[1,2-a]pyrimidine-4,7(6H)-dione. To a solution of 1-(4-(difluoromethoxy)benzoyl)-8-(4-methoxybenzyl)-6-methylhexahydro-4H-pyrazino[1,2-a]pyrimidine-4,7(6H)-dione (3.0 g, 6.34 mmol) in $CH_3CN$:$H_2O$ (2:1, 45 mL) maintained at 0° C., was added CAN (12.0 g, 21.90 mmol) and the reaction mixture was allowed to stir at room temperature for 3 h. Progress of the reaction was monitored by TLC. After completion, the reaction mixture was quenched with saturated solution of aq. $NaHCO_3$ (100 mL) and extracted with EtOAc (200 mL×2). The combined organic layer was washed with $H_2O$ (250 mL) followed by saturated brine solution (250 mL), dried over $Na_2SO_4$ and concentrated under reduced pressure. The crude obtained was purified by column chromatography (Silica 100-200 mesh; 10% MeOH in DCM) to afford 1-(4-(difluoromethoxy)benzoyl)-6-methylhexahydro-4H-pyrazino[1,2-a]pyrimidine-4,7(6H)-dione (2.0 g, 5.66 mmol, 89.6% yield) as a solid. MS (ESI) m/z $[M+H]^+$: 353.95. $^1H$ NMR (400 MHz, DMSO-$d_6$) δ 1.10-1.39 (m, 3H) 2.17-2.18 (m, 1H) 2.52-2.68 (m, 1H) 3.18-3.27 (m, 2H) 3.44-3.71 (m, 2H) 4.69-4.83 (m, 1H) 5.75-5.92 (m, 1H) 7.24 (d, J=7.83 Hz, 2H) 7.32 (t, J=72.0 Hz, 1H) 7.57 (d, J=8.31 Hz, 2H) 8.04 (brs, 1H).

Example S26. General Procedure B for the Synthesis of Final Compounds

To a solution of 1-(4-(difluoromethoxy)benzoyl)-6-methylhexahydro-4H-pyrazino[1,2-a]pyrimidine-4,7(6H)-dione (200 mg, 0.56 mmol) in DMF (4 mL) maintained at 0° C. was added NaH (122 mg, 2.8 mmol, 55% dispersion in mineral oil) and the reaction mixture was stirred at the same temperature for 15 minutes. To this reaction mixture was added alkyl halide (1.6 mmol) and the reaction mixture was allowed to warm to room temperature and stirred for 3 h. After completion, the reaction mixture was quenched with ice cold $H_2O$ (15 mL) and aqueous layer was extracted with EtOAc (15 mL×3). The combined organic layer was washed with brine and concentrated. The crude product obtained was purified by CombiFlash.

Example S27. Synthesis of Compound 13

Compound 13 was synthesized by General Procedure B using (bromomethyl)cyclopentane as the alkyl halide. MS (ESI) m/z $[M+H]^+$: 436.05. $^1H$ NMR (400 MHz, DMSO-$d_6$) δ 1.07-1.16 (m, 3H) 1.32 (d, J=6.48 Hz, 3H) 1.41-1.73 (m, 7H) 2.06-2.21 (m, 1H) 2.21-2.34 (m, 1H) 2.54-2.70 (m, 1H) 3.14-3.29 (m, 1H) 3.35-3.45 (m, 1H) 3.52-3.69 (m, 1H) 3.75-3.93 (m, 1H) 4.75-4.91 (m, 1H) 5.88-5.99 (m, 1H) 7.27 (d, J=8.48 Hz, 2H) 7.35 (t, J=72.0 Hz, 1H) 7.61 (d, J=8.98 Hz, 2H).

Example S28. Synthesis of Compound 14

Compound 14 was synthesized by General Procedure B using (bromomethyl)cyclobutane as the alkyl halide. MS (ESI) m/z $[M+H]^+$: 421.14. $^1H$ NMR (400 MHz, DMSO-$d_6$) δ 1.16-1.25 (m, 1H) 1.27-1.43 (m, 3H) 1.54-1.73 (m, 2H) 1.73-1.86 (m, 2H) 1.89-2.03 (m, 2H) 2.24 (d, J=17.12 Hz, 1H) 2.53-2.69 (m, 2H) 3.20-3.28 (m, 1H) 3.29-3.40 (m, 1H) 3.40-3.66 (m, 2H) 3.69-3.87 (m, 1H) 4.75-4.86 (m, 1H) 5.74-6.02 (m, 1H) 7.26 (d, J=8.31 Hz, 2H)) 7.33 (t, J=72.0 Hz, 1H) 7.59 (d, J=8.31 Hz, 2H).

Example S29. Synthesis of Compound 17

Compound 20 was synthesized by General Procedure B using 1-bromobutane as the alkyl halide. MS (ESI) m/z $[M+H]^+$: 410.0. $^1H$ NMR (400 MHz, DMSO-$d_6$) δ 0.81-0.96 (m, 3H) 1.15-1.39 (m, 4H) 1.40-1.55 (m, 2H) 2.26 (d, J=16.95 Hz, 1H) 2.53-2.70 (m, 2H) 3.12-3.30 (m, 2H) 3.38-3.46 (m, 1H) 3.56-3.74 (m, 2H) 3.75-3.92 (m, 1H) 4.84 (q, J=6.81 Hz, 1H) 5.86-6.06 (m, 1H) 7.28 (d, J=7.98 Hz, 2H) 7.36 (t, J=72.0 at, 1H) 7.62 (d, J=8.48 Hz, 2H).

Example S30. Synthesis of Compound 18

Compound 18 was synthesized by General Procedure B using 4-bromobut-1-ene as the alkyl halide. MS (ESI) m/z $[M+H]^+$: 408.06. $^1H$ NMR (400 MHz, DMSO-$d_6$) δ 1.16-1.45 (m, 3H) 2.18-2.33 (m, 3H) 2.53-2.70 (m, 1H) 3.36-3.46 (m, 3H) 3.51-3.72 (m, 2H) 3.74-3.90 (m, 1H) 4.84 (q, J=6.65 Hz, 1H) 4.91-5.15 (m, 2H) 5.67-5.84 (m, 1H) 5.86-6.03 (m, 1H) 7.29 (d, J=8.48 Hz, 2H) 7.36 (t. J=72.0 Hz, 1H) 7.61 (d, J=8.48 Hz, 2H).

Example S31. Synthesis of Compound 27

Compound 27 was synthesized by General Procedure B using 2-(bromomethyl)tetrahydrofuran as the alkyl halide. MS (ESI) m/z $[M+H]^+$: 438.1. $^1H$ NMR (400 MHz, $CDCl_3$) δ 7.48-7.55 (m, 2H), 7.20-7.30 (m, 2H), 6.40-6.76 (m, 1H), 5.90-6.20 (m, 1H), 5.16-5.26 (m, 1H), 4.06-4.17 (m, 2H), 3.82-3.92 (m, 4H), 3.61-3.77 (m, 2H), 2.83-2.99 (m, 1H), 2.47-2.59 (m, 2H), 2.01-2.12 (m, 4H), 1.49 (s, 3H).

Example S32. Synthesis of Compound 28

Compound 28 was synthesized by General Procedure B using (2-bromoethyl)benzene as the alkyl halide. MS (ESI) m/z $[M+H]^+$: 458.10. $^1H$ NMR (400 MHz, $CDCl_3$) δ 7.40-7.50 (m, 2H), 7.20-7.28 (m, 2H), 7.33-7.43 (m, 5H), 6.40-6.76 (m, 1H), 5.90-6.20 (m, 1H), 5.16-5.26 (m, 1H), 3.72-3.96 (m, 2H), 3.44-3.52 (m, 1H), 3.25-3.35 (m, 2H), 2.83-2.99 (m, 2H), 2.47-2.59 (m, 1H), 2.42-2.60 (m, 1H), 2.30-2.57 (m, 1H), 1.49 (s, 3H).

Example S33. Synthesis of Compound 29

Compound 29 was synthesized by General Procedure B using 4-(2-bromoethyl)pyridine as the alkyl halide. MS (ESI) m/z $[M+H]^+$: 459.10. $^1H$ NMR (400 MHz, $CDCl_3$) δ 8.50-8.58 (m, 2H), 7.24-7.46 (m, 4H), 7.18 (d, J=7.99 Hz, 2H), 6.40-6.76 (m, 1H), 5.90-6.20 (m, 1H), 5.16-5.26 (m, 1H), 3.72-3.96 (m, 2H), 3.44-3.52 (m, 1H), 3.25-3.35 (m, 2H), 2.83-2.99 (m, 2H), 2.47-2.59 (m, 1H), 2.42-2.60 (m, 1H), 2.30-2.57 (m, 1H), 1.49 (s, 3H).

Example S34. Synthesis of Compound 30

Compound 30 was synthesized by General Procedure B using (3-bromopropyl)cyclopropane as the alkyl halide. MS (ESI) m/z $[M+H]^+$: 459.10. $^1H$ NMR (400 MHz, $CDCl_3$) δ 8.50-8.58 (m, 2H), 7.24-7.46 (m, 4H), 7.18 (d, J=7.99 Hz, 2H), 6.40-6.76 (m, 1H), 5.90-6.20 (m, 1H), 5.16-5.26 (m, 1H), 3.72-3.96 (m, 2H), 3.44-3.52 (m, 1H), 3.25-3.35 (m, 2H), 2.83-2.99 (m, 2H), 2.47-2.59 (m, 1H), 2.42-2.60 (m, 1H), 2.30-2.57 (m, 1H), 1.49 (s, 3H).

Example S35. Synthesis of Compound 31

Compound 31 was synthesized by General Procedure B using (2-bromoethyl)cyclopropane as the alkyl halide. MS (ESI) m/z $[M+H]^+$: 422.2. $^1H$ NMR (400 MHz, $CDCl_3$) δ 7.48 (d, J=8.01 Hz, 2H), 7.20-7.28 (m, 2H), 6.40-6.76 (m, 1H), 5.90-6.20 (m, 1H), 5.16-5.26 (m, 1H), 3.72-3.96 (m, 1H), 3.46-3.64 (m, 5H), 2.46-2.64 (m, 2H), 1.43-1.56 (m, 5H), 0.43-0.65 (m, 2H), 0.75-0.85 (m, 2H).

Example S36. Synthesis of Compound 32

Compound 32 was synthesized by General Procedure B using 1-bromo-2-methoxyethane as the alkyl halide. MS (ESI) m/z $[M+H]^+$: 412.1. $^1H$ NMR (400 MHz, DMSO-$d_6$) δ 7.52-7.62 (m, 2H), 7.16-7.34 (m, 3H), 5.85-5.95 (m, 1H), 4.80-4.90 (m, 1H), 3.85-3.95 (m, 1H), 3.70-3.80 (m, 2H), 3.25-3.46 (m, 5H), 3.22 (s, 3H), 2.62-2.72 (m, 1H), 2.20-2.30 (m, 1H), 1.49 (s, 3H).

Example S37. Synthesis of Compound 33

Compound 33 was synthesized by General Procedure B using 1-bromo-3-methoxypropane as the alkyl halide. MS (ESI) m/z $[M+H]^+$: 426.20. $^1$H NMR (400 MHz, DMSO-$d_6$) δ 7.52-7.62 (m, 2H), 7.16-7.34 (m, 3H), 5.85-5.95 (m, 1H), 4.80-4.90 (m, 1H), 3.85-3.95 (m, 1H), 3.70-3.80 (m, 2H), 3.58-3.68 (m, 2H), 3.45-3.55 (m, 4H), 3.22 (s, 3H), 2.62-2.72 (m, 1H), 2.20-2.30 (m, 2H), 1.49 (s, 3H).

Example S38. Synthesis of Compound 36

Compound 36 was synthesized by General Procedure B using (2-bromoethyl)methylsulfone as the alkyl halide. MS (ESI) m/z $[M+H]^+$: 459.95. $^1$H NMR (400 MHz, CHLOROFORM) δ 7.49 (d, J=8.01 Hz, 2H), 7.15-7.26 (m, 2H), 6.40-6.76 (m, 1H), 5.90-6.20 (m, 1H), 5.15-5.25 (m, 1H), 3.86-3.97 (m, 3H), 3.66-3.77 (m, 2H), 3.38-3.49 (m, 3H), 2.97 (s, 3H), 2.59-2.69 (m, 2H), 1.49 (s, 3H).

Example S39. Synthesis of Compound 34

Step 1. To a solution of 1-(4-(difluoromethoxy)benzoyl)-6-methylhexahydro-4H-pyrazino[1,2-a]pyrimidine-4,7 (6H)-dione (0.300 g, 0.849 mmol) in DMF (6 mL) was added $Cs_2CO_3$ (0.827 g, 2.547 mmol) followed by (2-bromoethoxy)(tert-butyl)dimethylsilane (0.243 g, 1.018 mmol) at 0° C. and the reaction mixture was heated at 120° C. in sealed tube for 1 h. Progress of the reaction was monitored by TLC. After completion, the reaction mixture was slowly quenched with ice cold water (30 mL) and extracted with EtOAc (50 mL). Combined organic layer was washed with ice cold brine solution (3x30 mL), dried over $Na_2SO_4$ and concentrated under reduced pressure to afford 8-(2-((tert-butyldimethylsilyl)oxy)ethyl)-1-(4-(difluoromethoxy)benzoyl)-6-methylhexahydro-4H-pyrazino[1,2-a]pyrimidine-4,7(6H)-dione (0.250 g, crude). The crude compound was as such used for next reaction without carried out further purification. MS (ESI) m/z $[M+H]^+$: 512.10.

Step 2. To a solution of 8-(2-((tert-butyldimethylsilyl)oxy)ethyl)-1-(4-(difluoromethoxy)benzoyl)-6-methylhexahydro-4H-pyrazino[1,2-a]pyrimidine-4,7(6H)-dione (0.250 g, 0.4886 mmol) in THF (5 mL) was added TBAF (3 mL) 0° C. temperature. The reaction mixture was allowed to attain room temperature and stirred for 6 h. Progress of the reaction was monitored by TLC. After completion, the reaction mixture was slowly quenched with ice cold water (5 mL) and extracted with EtOAc (2x10 mL). Combined organic layer was washed with ice cold brine solution (10 mL), dried over $Na_2SO_4$ and concentrated under reduced pressure to get crude compound. The crude compound obtained was purified by column chromatography (Silicagel 60-120 mesh; 10% MeOH in DCM) to afford 1-(4-(difluoromethoxy)benzoyl)-8-(2-hydroxyethyl)-6-methylhexahydro-4H-pyrazino[1,2-a]pyrimidine-4,7(6H)-dione (0.102 g, 52% yield) white solid. MS (ESI) m/z $[M+H]^+$: 398.2. $^1$H NMR (400 MHz, DMSO-$d_6$) δ 7.52-7.62 (m, 2H), 7.16-7.34 (m, 3H), 5.92-6.02 (m, 1H), 6.78-6.88 (m, 2H), 3.86-3.92 (m, 1H), 3.47-3.62 (m, 6H), 3.21-3.31 (m, 1H), 2.57-2.67 (m, 1H), 2.25-3.35 (m, 1H), 1.49 (s, 3H).

Example S40. Synthesis of Compound 35

Step 1. To a solution of 1-(4-(difluoromethoxy)benzoyl)-6-methylhexahydro-4H-pyrazino[1,2-a]pyrimidine-4,7 (6H)-dione (0.300 g, 0.849 mmol) in DMF (6 mL) was added NaH (0.050 g, 1.274 mmol) followed by 2-bromoacetonitrile (0.112 g, 0.933 mmol) at 0° C. and the reaction mixture was allowed to stand for room temperature for 1 h. Progress of the reaction was monitored by TLC. After completion, the reaction mixture was slowly quenched with ice cold water (70 mL) and extracted with EtOAc (100 mL). Combined organic layer was washed with ice cold brine solution (100 mL), dried over $Na_2SO_4$ and concentrated under reduced pressure to get crude compound. The crude compound obtained was purified by column chromatography (Silicagel 60-120 mesh; 10% MeOH in DCM) to afford 2-(1-(4-(difluoromethoxy)benzoyl)-6-methyl-4,7-dioxooctahydro-8H-pyrazino[1,2-a]pyrimidin-8-yl)acetonitrile (0.120 g, 36% yield) white solid. MS (ESI) m/z $[M+H]^+$: 393.05.

Step 2. To a solution of 2-(1-(4-(difluoromethoxy)benzoyl)-6-methyl-4,7-dioxooctahydro-8H-pyrazino[1,2-a]pyrimidin-8-yl)acetonitrile (0.120 g, 0.305 mmol) in ethanol (5 mL) was added Conc. HCl (0.100 mL) followed by Platinum oxide (0.012 g, 0.030 mmol) at room temperature and the reaction mixture was heated under Hydrogen gas atmosphere for 3 h. Progress of the reaction was monitored by TLC. After completion, the reaction mixture was filtered through a pad of Celite. The Celite pad was washed with ethanol (20 mL) and filtrate was concentrated under reduced pressure to get crude compound. The crude compound was triturated with n pentane to afford 8-(2-aminoethyl)-1-(4-(difluoromethoxy)benzoyl)-6-methylhexahydro-4H-pyrazino[1,2-a]pyrimidine-4,7(6H)-dione (0.110 g, 90%) yield) white solid. MS (ESI) m/z $[M+H]^+$: 397.05. $^1$H NMR (400 MHz, DMSO $d_6$) δ 7.96 (s, 2H), 7.55-7.65 (m, 2H), 7.20-7.35 (m, 3H), 5.90-6.20 (m, 1H), 4.85-4.95 (m, 1H), 3.82-3.92 (m, 1H), 3.55-3.85 (m, 2H), 3.35-3.45 (m, 3H), 2.95-3.05 (m, 2H), 2.60-2.70 (m, 1H), 2.20-2.30 (m, 1H), 1.35 (s, 3H).

Example S41. General Procedure C for the Synthesis of Final Compounds

To a solution of 1-(4-(difluoromethoxy)benzoyl)-6-methylhexahydro-4H-pyrazino[1,2-a]pyrimidine-4,7(6H)-dione (0.200 g, 0.566 mmol) in DMF (5 mL) was added $Cs_2CO_3$ (0.735 g, 2.264 mmol, 4 eq) followed by alkyl halide (0.679 mmol, 1.2 eq) at 0° C. and the reaction mixture was heated at 50° C. under microwave irradiation for 1 h. Progress of the reaction was monitored by TLC. After completion, the reaction mixture was slowly quenched with ice cold water (6 mL) and extracted with EtOAc (20 mLx3). The combined organic layer was washed with saturated brine solution (10 mL), dried over $Na_2SO_4$ and concentrated under reduced pressure to get crude compound. The crude compound obtained was purified by column chromatography to provide the final compound.

Example S42. Synthesis of Compound 25

Compound 25 was synthesized by General Procedure C using 2-(2-iodoethyl)furan as the alkyl halide. MS (ESI) m/z $[M+H]^+$: 448.10. $^1$H NMR: δ 7.40-7.50 (m, 2H), 7.28-7.38 (m, 1H), 7.15-7.25 (m, 2H), 6.39-6.78 (m, 1H), 6.25-6.35 (m, 1H), 5.90-6.12 (m, 2H), 5.25-5.35 (m, 1H), 5.10-5.20 (m, 1H), 3.70-3.80 (m, 1H), 3.50-3.60 (m, 1H), 3.20-3.40 (m, 2H), 2.95-3.05 (m, 3H), 2.45-2.60 (m, 2H), 1.59 (s, 3H).

Example S43. Synthesis of Compound 26

Compound 26 was synthesized by General Procedure C using 2-(2-bromoethyl)thiophene as the alkyl halide. MS (ESI) m/z $[M+H]^+$: 464.1. $^1H$ NMR (400 MHz, $CDCl_3$) δ 7.40-7.48 (m, 2H), 7.15-7.26 (m, 3H), 6.85-6.95 (m, 2H), 6.39-6.95 (m, 2H), 5.90-6.20 (m, 1H), 5.15-5.25 (m, 1H), 3.72-3.96 (m, 2H), 3.47-3.54 (m, 1H), 3.32-3.42 (m, 3H), 3.10-3.20 (m, 2H), 2.42-2.56 (m, 2H), 1.49 (s, 3H).

Example S44. Synthesis of Intermediate Compound 1-(4-(difluoromethoxy)benzyl)-6-methylhexahydro-4H-pyrazino[1,2-a]pyrimidine-4,7(6H)-dione

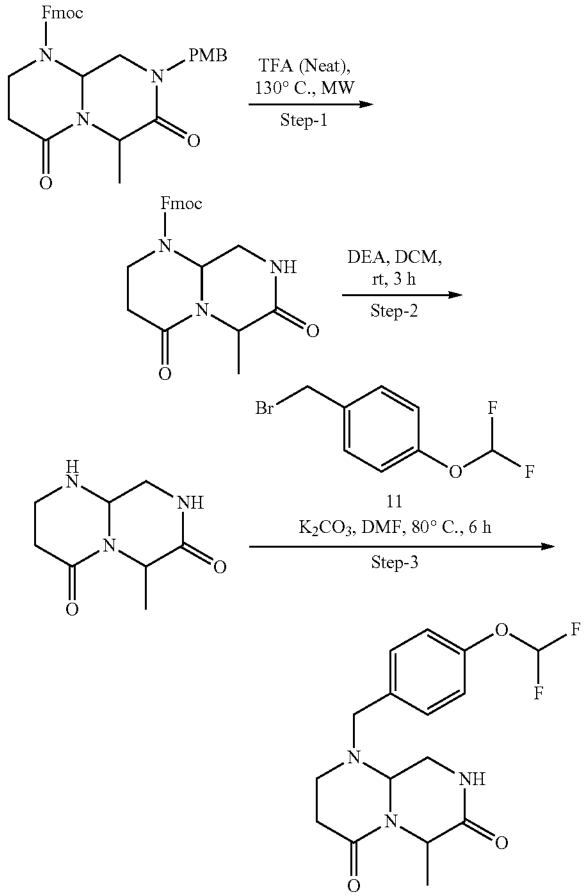

Step 1: Synthesis of (9H-fluoren-9-yl)methyl 6-methyl-4,7-dioxohexahydro-2H-pyrazino[1,2-a]pyrimidine-1(6H)-carboxylate. A solution of (9H-fluoren-9-yl)methyl 8-(4-methoxybenzyl)-6-methyl-4,7-dioxohexahydro-2H-pyrazino[1,2-a]pyrimidine-1(6H)-carboxylate (1.0 g, 26.63 mmol) in TFA (10 mL) was stirred at 130° C. for 2 h in microwave. After complete consumption of the starting material (monitored by TLC), the reaction mixture was concentrated under vacuum and the crude product was extracted with ethylacetate (100 ml) and saturated solution of sodium bicarbonate. The organic layer was dried over anhydrous $Na_2SO_4$ and concentrated under vacuum, and purified by column chromatography (Silica 100-200 mesh; 5% MeOH in DCM) to afford (9H-fluoren-9-yl)methyl 6-methyl-4,7-dioxohexahydro-2H-pyrazino[1,2-a]pyrimidine-1(6H)-carboxylate (300 mg, 42% yield) as a sticky solid. MS (ESI) m/z $[M+H]^+$: 406.

Step 2: Synthesis of 6-methylhexahydro-4H-pyrazino[1,2-a]pyrimidine-4,7(6H)-dione. To a solution of (9H-fluoren-9-yl)methyl 6-methyl-4,7-dioxohexahydro-2H-pyrazino[1,2-a]pyrimidine-1(6H)-carboxylate (300 mg, 0.74 mmol) in $CH_2Cl_2$ (5 mL) was added diethylamine (6 mL). The reaction mixture was stirred at room temperature for 3 h. After complete consumption of the starting material (monitored by TLC), the reaction mixture was concentrated and the crude product was purified by column chromatography (Silica 100-200 mesh; 10% MeOH in DCM) to afford 6-methyl-hexahydro-4H-pyrazino[1,2-a]pyrimidine-4,7(6H)-dione (120 mg, 92% yield) as a white solid. MS (ESI) m/z $[M+H]^+$: 184.

Step 3: Synthesis of 1-(4-(difluoromethoxy)benzyl)-6-methylhexahydro-4H-pyrazino[1,2-a]pyrimidine-4,7(6H)-dione. To a solution of 6-methylhexahydro-4H-pyrazino[1,2-a]pyrimidine-4,7(6H)-dione (0.700 g, 3.820 mmol) in DMF (8.0 mL) was added $K_2CO_3$ (1.58 g, 11.46 mmol) at room temperature and stirred for 10 min. To the resulting reaction mixture was added 1-(bromomethyl)-4-(difluoromethoxy)benzene (1.086 g, 4.584 mmol) and the reaction mixture was heated at 80° C. for 6 h. Progress of the reaction was monitored by TLC. After completion, the reaction mixture was cooled to room temperature, quenched with water (50 mL) and extracted with EtOAc (50 mL×2). The combined organic layers were washed with saturated brine solution (20 mL), dried over $Na_2SO_4$ and concentrated under reduced pressure. The crude product was purified by column chromatography (Silica 100-200 mesh; 5% MeOH in DCM) to afford 1-(4-(difluoromethoxy)benzyl)-6-methylhexahydro-4H-pyrazino[1,2-a]pyrimidine-4,7(6H)-dione (0.550 g, 43.0% yield) as an off-white solid. MS (ESI) m/z $[M+H]^+$: 340.34.

Example S45. General Procedure D for Synthesis of Final Compounds

To a solution of 1-(4-(difluoromethoxy)benzyl)-6-methylhexahydro-4H-pyrazino[1,2-a]pyrimidine-4,7(6H)-dione (0.100 g, 0.2949 mmol) in DMF (2 mL) was added NaH (0.021 g, 0.8847 mmol) at 0° C. followed by the appropriate alkyl halide (2 eq.) and the reaction mixture was allowed to warm to room temperature and stirred for 5 h. Progress of the reaction was monitored by TLC. After completion, the reaction mixture was slowly quenched with saturated solution of aq. $NaHCO_3$ (2 mL) and extracted with EtOAc (10 mL×2). The combined organic layers were washed with $H_2O$ (5 mL) followed by saturated brine solution (5 mL), dried over $Na_2SO_4$ and concentrated under reduced pressure. The crude material was purified by combiflash column chromatography (5% MeOH in DCM) to afford the final product.

Example S46. Synthesis of Compound 37

Compound 37 was synthesized by General Procedure D using 4-bromo-1,1,1-trifluorobutane as the alkyl halide. MS (ESI) m/z $[M+H]^+$: 354.2. $^1H$ NMR (400 MHz, $CDCl_3$): δ 1.41 (d, J=7.13 Hz, 3H), 1.71-1.86 (m, 2H), 2.01-2.15 (m, 2H), 2.26-2.35 (m, 1H), 2.60-2.67 (m, 1H), 2.89-3.01 (m, 1H), 3.07-3.15 (m, 1H), 3.21-3.34 (m, 2H), 3.46-3.65 (m, 2H), 3.81-3.95 (m, 2H), 4.35-4.41 (m, 1H), 5.20-5.29 (m, 1H), 6.53 (t, J=72.0 Hz, 1H), 7.08-7.16 (m, 2H), 7.30-7.36 (m, 2H).

Example S47. Synthesis of Compound 38

Compound 38 was synthesized by General Procedure D using (2-bromoethyl)cyclopentane as the alkyl halide. MS (ESI) m/z $[M+H]^+$: 436.2. $^1H$ NMR (400 MHz, $CDCl_3$) δ

1.01-1.15 (m, 2H), 1.41 (d, J=7.13 Hz, 3H), 1.45-1.62 (m, 8H), 1.66-1.80 (m, 2H), 2.23-2.34 (m, 1H), 2.58-2.72 (m, 1H), 2.89-2.98 (m, 1H), 3.04-3.18 (m, 2H), 3.23-3.33 (m, 1H), 3.43-3.54 (m, 1H), 3.55-3.65 (m, 1H), 3.78-3.93 (m, 1H), 4.31-4.39 (m, 1H), 5.15-5.26 (m, 1H), 6.53 (t, J=72.0 Hz, 1H), 7.13 (d, J=8.50 Hz, 2H), 7.34 (d, J=8.50 Hz, 2H).

Example S48. Synthesis of Compound 39

Compound 39 was synthesized by General Procedure D using 4-bromobut-1-ene as the alkyl halide. MS (ESI) m/z $[M+H]^+$: 394.2. $^1$H NMR (400 MHz, $CDCl_3$) δ 1.41 (d, J=7.13 Hz, 3H), 2.23-2.35 (m, 3H), 2.60-2.71 (m, 1H), 2.92-3.01 (m, 1H), 3.06-3.14 (m, 1H), 3.22-3.46 (m, 3H), 3.53-3.64 (m, 1H), 3.79-3.93 (m, 2H), 4.28-4.38 (m, 1H), 4.91-5.00 (m, 2H), 5.16-5.26 (m, 1H), 5.64-5.76 (m, 1H), 6.52 (t, J=72.0 Hz, 1H), 7.10-7.16 (m, 2H), 7.30-7.36 (m, 2H).

Example S49. Synthesis of Compound 40

Compound 40 was synthesized by General Procedure D using (2-bromoethyl)cyclobutene as the alkyl halide. MS (ESI) m/z $[M+H]^+$: 422.25 $^1$H NMR (400 MHz, $CDCl_3$) δ 1.41 (d, J=7.13 Hz, 3H), 1.56-1.65 (m, 4H), 1.73-1.92 (m, 2H), 1.95-2.07 (m, 2H), 2.14-2.25 (m, 1H), 2.26-2.35 (m, 1H), 2.59-2.72 (m, 1H), 2.91-2.99 (m, 1H), 3.04-3.14 (m, 2H), 3.23-3.43 (m, 2H), 3.53-3.63 (m, 1H), 3.87 (q, J=13.38 Hz, 2H), 4.29-4.39 (m, 1H), 5.17-5.24 (m, 1H), 6.53 (t, J=72.0 Hz, 1H), 7.13 (d, J=8.63 Hz, 2H), 7.30-7.37 (m, 2H).

Example S50. Synthesis of Compound 41

Compound 41 was synthesized by General Procedure D using 1-bromobutane as the alkyl halide. MS (ESI) m/z $[M+H]^+$: 396.05. $^1$H NMR (400 MHz, DMSO-$d_6$) δ 0.86 (t, J=7.34 Hz, 3H), 1.14-1.24 (m, 2H), 1.24-1.30 (m, 2H), 1.38-1.50 (m, 2H), 1.98-2.10 (m, 1H), 2.53-2.61 (m, 2H), 2.64-2.77 (m, 2H), 3.07-3.25 (m, 3H), 3.32-3.41 (m, 1H), 3.62-3.73 (m, 1H), 3.87-3.93 (m, 2H), 4.49-4.58 (m, 1H), 4.84-4.94 (m, 1H), 7.15 (d, J=8.56 Hz, 2H), 7.22 (t, J=72.0 Hz, 1H), 7.43 (d, J=8.56 Hz, 1H).

Example S51. Synthesis of Compound 52

Compound 52 was synthesized by General Procedure D using 2-trifluromethyl-1-bromoethane as the alkyl halide. MS (ESI) m/z $[M+H]^+$: 420.16. $^1$H NMR (400 MHz, $CDCl_3$) δ ppm 7.31-7.38 (m, 2H), 7.11-7.16 (m, 2H), 6.31-6.73 (m, 1H), 5.26 (q, J=7.21 Hz, 1H), 4.23-4.44 (m, 2H), 3.98-4.13 (m, 1H), 3.80-3.93 (m, 3H), 3.59 (t, J=11.07 Hz, 1H), 3.10 (dd, J=11.51, 3.75 Hz, 1H), 2.90-2.99 (m, 1H), 2.62-2.72 (m, 1H), 2.32 (dd, J=4.38, 2.38 Hz, 1H), 2.28 (dd, J=4.31, 2.31 Hz, 1H), 1.48 (d, J=7.25 Hz, 1H), 1.41 (d, J=7.13 Hz, 3H).

Example S52. General Procedure E for the Synthesis of Final Compounds

To a solution of 6-methyl-8-(2-methylbutyl)hexahydro-4H-pyrazino[1,2-a]pyrimidine-4,7(6H)-dione (0.300 g, 1.184 mmol) in DMF (6 mL) stirred in a flask immersed in an ice/water bath was added cesium carbonate (0.771 g, 2.368 mmol, 2 eq,) followed by the appropriate alkyl halide (1.1 eq.). The flask was removed from the bath and stirred until TLC indicated complete consumption of starting material. The reaction mixture was poured in ice-cold water (70 mL) and aqueous layer was extracted with EtOAc (100 mL). The organic layer was washed with ice cold brine (50 mL×3), dried over anhydrous $Na_2SO_4$ and concentrated under reduced pressure. The crude product was purified by preparative HPLC to afford to give the final compound.

Example S53. Synthesis of Compound 42

Compound 42 was synthesized by General Procedure E using 4-(bromomethyl)-2-chloro-1-(trifluoromethyl)benzene as the alkyl halide. MS (ESI) m/z $[M+H]^+$: 362.2. $^1$H NMR (400 MHz, DMSO-$d_6$) δ 0.75-0.89 (m, 3H), 0.82-0.87 (m, 3H), 0.96-1.13 (m, 1H), 1.23-1.31 (m, 4H), 1.64-1.75 (m, 1H), 2.06-2.09 (m, 1H), 2.55-2.62 (m, 1H), 2.65-2.76 (m, 1H), 3.05-3.15 (m, 1H), 3.15-3.26 (m, 3H), 3.64-3.74 (m, 1H), 3.84-3.95 (m, 2H), 4.52-4.60 (m, 1H), 4.86-4.94 (m, 1H), 7.17 (t, J=8.76 Hz, 2H), 7.41 (dd, J=8.19, 5.82 Hz, 2H).

Example S54. Synthesis of Compound 43

Compound 43 was synthesized by General Procedure E using 4-(bromomethyl)-2-chloro-1-(trifluoromethyl)benzene as the alkyl halide. MS (ESI) m/z $[M+H]^+$: 446.2. $^1$H NMR (400 MHz, DMSO-$d_6$) 0.72-0.80 (m, 3H), 0.80-0.87 (m, 3H), 0.96-1.10 (m, 1H), 1.21-1.27 (m, 1H), 1.28-1.34 (m, 3H), 1.62-1.79 (m, 1H), 2.00-2.13 (m, 1H), 2.53-2.65 (m, 1H), 2.66-2.76 (m, 1H), 3.00-3.10 (m, 1H), 3.17-3.29 (m, 3H), 3.62-3.72 (m, 1H), 4.00-4.08 (m, 2H), 4.55-4.65 (m, 1H), 4.85-4.95 (m, 1H), 7.52-7.60 (m, 1H), 7.73 (s, 1H), 7.80-7.88 (m, 1H).

Example S55. Synthesis of Compound 44

To a solution of 6-methyl-8-(2-methylbutyl)hexahydro-4H-pyrazino[1,2-a]pyrimidine-4,7(6H)-dione (0.420 g, 1.657 mmol) and 1H-indole-3-carbaldehyde (0.264 g, 1.823 mmol) in DCE (15 mL) was added acetic acid (1 mL, 1.657 mmol) and heated the reaction mixture at 80° C. for 1 h. To the resulting reaction mixture was added portion wise $NaBH_4$ (0.188 g, 4.973 mmol) and the reaction mixture was heated at 80° C. and stirred for 4 h. When TLC analysis (5% MeOH in DCM) indicated complete consumption of the starting material the reaction mixture was diluted with water (40 mL) and aqueous layer was extracted with DCM (100 mL). The organic layer was washed with brine (50 mL), dried over anhydrous $Na_2SO_4$ and concentrated under reduced pressure. The crude obtained was purified by column chromatography (Silica 100-200 mesh; 5% MeOH in DCM) followed by washing with water (30 mL) and dried under reduced pressure to afford compound 44 (0.250 g, 39% yield) as an off white solid. MS (ESI) m/z $[M+H]^+$: 383.4. $^1$H NMR (400 MHz, DMSO-$d_6$) δ 0.70 (t, J=7.09 Hz, 3H), 0.75-0.82 (m, 3H), 0.91-1.11 (m, 1H), 1.22-1.31 (m, 3H), 1.57-1.72 (m, 1H), 1.97-2.07 (m, 1H), 2.55-2.70 (m, 2H), 2.83 (dt, J=10.91, 2.74 Hz, 1H), 2.95-3.07 (m, 1H), 3.10-3.26 (m, 3H), 3.54-3.69 (m, 1H), 3.96-4.04 (m, 1H), 4.06-4.15 (m, 1H), 4.54-4.64 (m, 1H), 4.84-4.95 (m, 1H), 6.94-7.02 (m, 1H), 7.04-7.13 (m, 1H), 7.29-7.40 (m, 2H), 7.65 (d, J=7.95 Hz, 1H), 10.95 (s, 1H).

Example S55. Synthesis of Intermediate Compound 1-(4-fluorobenzyl)-6-methylhexahydro-4H-pyrazino [1,2-a]pyrimidine-4,7(6H) dione To a solution of 6-methylhexahydro-4H-pyrazino[1,2-a] pyrimidine-4,7(6H)-dione (250 mg, 1.40 mmol) in DMF (3 mL) was added potassium carbonate (580 mg, 4.20 mmol) followed by 4-fluorobenzylbromide (0.320 g, 1.70 mmol) and stirred at 80° C. temperature for 3 h. After completion, the reaction mixture was monitored by TLC (5% MeOH in DCM). The reaction mixture was poured in ice-cold water (50 mL) and aqueous layer was extracted with EtOAc (50 mL). The organic layer was dried over anhydrous $Na_2SO_4$ and concentrated under reduced pressure. The crude obtained was purified by column chromatography (Silica 100-200 mesh; 5% MeOH in DCM) to afford 1-(4-fluorobenzyl)-6-methylhexahydro-4H-pyrazino[1,2-a]pyrimidine-4,7(6H) dione (160 mg, 70% yield) as a white solid. MS (ESI) m/z $[M+H]^+$: 292.

Example S56. Synthesis of Compound 45

To a solution of 1-(4-fluorobenzyl)-6-methylhexahydro-4H-pyrazino[1,2-a]pyrimidine-4,7(6H) dione (80 mg, 0.2739 mmol) in DMF (3 mL) under an ice cold bath at 0° C. was added NaH (20 mg, 0.2739 mmol) and stirred for 20 min then added (2-bromoethyl)cyclobutane (67 mg, 0.41 mmol) after 3 h. After complete consumption of starting material (monitored by TLC), the reaction mixture was quenched with ice cold water and extracted with ethyl acetate. The organic layer was dried over anhydrous $Na_2SO_4$ and concentrated under reduced pressure. The crude obtained was purified by column chromatography (Silica 100-200 mesh; 5% MeOH in DCM) to afford 8-(2-cyclobutylethyl)-1-(4-fluorobenzyl)-6-methylhexahydro-4H-pyrazino[1,2-a]pyrimidine-4,7(6H)-dione (13 mg, 16% yield) as a gummy liquid. MS (ESI) m/z $[M+H]^+$: 374. $^1$H NMR (400 MHz, $CD_3Cl_3$): δ 7.30-7.40 (m, 2H), 7.00-7.10 (m, 2H), 5.15-5.25 (m, 1H), 4.25-4.35 (m, 1H), 3.80-3.95 (m, 2H), 3.55-3.65 (m, 1H), 3.25-3.45 (m, 2H), 3.05-3.20 (m, 2H), 2.90-3.0 (m, 1H), 2.60-2.70 (m, 1H), 2.15-2.40 (m, 2H), 1.75-2.10 (m, 4H), 1.55-1.65 (m, 4H), 1.20-1.30 (m, 3H).

Example S57. Synthesis of Compound 46

To a solution of 1-(4-fluorobenzyl)-6-methylhexahydro-4H-pyrazino[1,2-a]pyrimidine-4,7(6H) dione (80 mg, 0.2739 mmol) in DMF (3 mL) under an ice cold bath at 0° C. was added NaH (20 mg, 0.2739 mmol) and stirred for 20 min, then was added (2-bromoethyl)cyclopentane (72 mg, 0.41 mmol) after 3 hours, completion of starting material monitored by TLC, the reaction mixture was quenched with ice cold water and extracted with ethyl acetate. The organic layer was dried over anhydrous $Na_2SO_4$ and concentrated under reduced pressure. The crude obtained was purified by column chromatography (Silica 100-200 mesh; 5% MeOH in DCM) to afford 8-(2-cyclopentylethyl)-1-(4-fluorobenzyl)-6-methylhexahydro-4H-pyrazino[1,2-c]pyrimidine-4,7(6H)-dione as a gummy liquid.

Example S58. Synthesis of Intermediate Compound 6-(fluoromethyl)-8-(2-methylbutyl)hexahydro-4H-pyrazino[1,2-a]pyrimidine-4,7(6H)-dione Hydrochloride Salt Step 1: Synthesis of N-(2,2-diethoxyethyl)-2-methylbutan-1-amine. To stirred neat 2,2-diethoxyethan-1-amine (20.0 g, 0.137 mmol) was added 2-methylbutanal (11.60 g, mmol) at room temperature and the reaction mixture was heated to 100° C. for 3 h. To the resulting reaction mixture was slowly added ethanol (200 mL) followed by $NaBH_4$ (15.40 g, mmol) at room temperature and the reaction mixture was stirred for 16 h. After complete consumption of starting material (monitored by TLC). The reaction mixture was cooled to room temperature and slowly quenched with a saturated solution of $NH_4Cl$ (100 mL). The aq. layer was extracted with EtOAc (200 mL×2). The combined organic layer was washed with brine (400 mL), dried over $Na_2SO_4$, filtered and concentrated under reduced pressure to get crude compound. The crude obtained was purified by column chromatography (silica 100-200 mesh; 10% MeOH in DCM) to obtain N-(2,2-diethoxyethyl)-2-methylbutan-1-amine (25.8 g, 88% yield) colorless liquid. MS (ESI) m/z $[M+H]^+$: 204.3. $^1$H NMR (400 MHz, DMSO-d6) δ 0.80-0.89 (m, 6H) 1.11 (t, J=6.98 Hz, 6H) 1.35-1.48 (m, 2H) 2.28-2.32 (m, 1H) 2.41-2.45 (m, 1H) 2.55 (d, J=5.49 Hz, 2H) 3.42-3.52 (m, 2H) 3.57-3.65 (m, 2H) 4.49 (t, J=5.49 Hz, 1H).

Step 2: (9H-fluoren-9-yl)methyl (1-((2,2-diethoxyethyl)(2-methylbutyl)amino)-3-hydroxy-1-oxopropan-2-yl)carbamate. To a stirred solution of (((9H-fluoren-9-yl)methoxy)carbonyl)serine (15.0 g, 45.81 mmol) in dry DMF (150 mL) maintained at 0° C. was added HATU (26.0 g, 68.80 mmol), DIPEA (23.92 mL, 137.61 mmol) followed by N-(2,2-diethoxyethyl)-2-methylbutan-1-amine (12.10 g, 59.63 mmol). The reaction mixture was stirred at room temperature for 4 h. After complete consumption of starting material, the reaction mixture was quenched with ice cold water (500 mL) and the aqueous layer was extracted with EtOAc (250 mL×2). The combined organic layer was washed with cold $H_2O$ (200 mL) followed by brine (200 mL), dried over $Na_2SO_4$ and concentrated under reduced pressure to provide the crude product. The crude material was purified by column chromatography (Silica 100-200 mesh; 80% EtOAc in hexanes) to afford (9H-fluoren-9-yl)methyl (1-((2,2-diethoxyethyl)(2-methylbutyl)amino)-3-hydroxy-1-oxopropan-2-yl)carbamate (21.0 g, 89.43% yield) as yellow sticky solid. MS (ESI) m/z $[M+Na]^+$: 535.35.

Step 3: Synthesis of 2-amino-N-(2,2-diethoxyethyl)-3-hydroxy-N-(2-methylbutyl)propenamide. To a stirred solution of (9H-fluoren-9-yl)methyl (1-((2,2-diethoxyethyl)(2-methylbutyl)amino)-3-hydroxy-1-oxopropan-2-yl) carbamate (21.0 g, 41.01 mmol) in dry DCM (110 mL) maintained at 0° C. was added diethylamine (58 mL, 2.80 volume) and reaction mixture was stirred at room temperature for 3 h. After complete consumption of starting material (monitored by TLC), the reaction mixture was concentrated under reduced pressure to get crude product. The crude obtained was purified by column chromatography (Silica 100-200 mesh; 5% MeOH in DCM) to afford 2-amino-N-(2,2-diethoxyethyl)-3-hydroxy-N-(2-methylbutyl)propenamide (9.50 g, 80% yield) as yellow sticky solid. MS (ESI) m/z $[M+H]^+$: 291.4.

Step 4: Synthesis of (9H-fluoren-9-yl)methyl (3-((1-((2,2-diethoxyethyl)(2-methylbutyl)amino)-3-hydroxy-1-oxopropan-2-yl)amino)-3-oxopropyl)carbamate. To a stirred solution of 3-((((9H-fluoren-9-yl)methoxy)carbonyl)amino) propanoic acid (9.50 g, 30.54 mmol) in dry DMF (95 mL) maintained at 0° C. was added HATU (17.40 g, 45.81 mmol), DIPEA (16.0 mL, 91.62 mmol) followed by 2-amino-N-(2,2-diethoxyethyl)-3-hydroxy-N-(2-methylbutyl)propanamide (13.20 g, 45.81 mmol) at room temperature and the reaction mixture was stirred for 16 h. After completion, the reaction mixture was quenched with ice cold water (200 mL) and the aqueous layer was extracted with EtOAc (200 mL×2). The organic layer was washed with cold $H_2O$ (500 mL) followed by saturated brine (200 mL), dried over $Na_2SO_4$ and concentrated under reduced pressure. The crude compound was purified by column chromatography (Silica 100-200 mesh; 80% EtOAc in Hexanes) to afford (9H-fluoren-9-yl)methyl (3-((1-((2,2-diethoxyethyl)(2-methylbutyl)amino)-3-hydroxy-1-oxopropan-2-yl)amino)-3-oxopropyl)carbamate (8.0 g, 31.0% yield) as a viscous yellow oil. MS (ESI) m/z $[M-H]^-$: 582.2.

Step 5: Synthesis of (9H-fluoren-9-yl)methyl 6-(hydroxymethyl)-8-(2-methylbutyl)-4,7-dioxohexahydro-2H-pyrazino[1,2-a]pyrimidine-1(6H)-carboxylate. A stirred solution of (9H-fluoren-9-yl)methyl (3-((1-((2,2-diethoxyethyl)(2-methylbutyl)amino)-3-hydroxy-1-oxopropan-2-yl)amino)-3-oxopropyl)carbamate (8.0 g, 13.77 mmol) in formic acid (48.0 mL, 6.0 volume) at room temperature and reaction mixture was stirred for 16 h. After completion, the reaction mixture was concentrated under reduced pressure to afford (9H-fluoren-9-yl)methyl 6-(hydroxymethyl)-8-(2-methylbutyl)-4,7-dioxohexahydro-2H-pyrazino[1,2-a]pyrimidine-1(6H)-carboxylate (6.0 g, crude) as brown semi-solid. The crude compound was used as such for next reaction without further purification. MS (ESI) m/z $[M+H]^+$: 492.2.

Step 6: Synthesis of 6-(hydroxymethyl)-8-(2-methylbutyl)hexahydro-4H-pyrazino[1,2-a]pyrimidine-4,7(6H)-dione. To a solution of (9H-fluoren-9-yl)methyl 6-(hydroxymethyl)-8-(2-methylbutyl)-4,7-dioxohexahydro-2H-pyrazino[1,2-a]pyrimidine-1(6H)-carboxylate (6.0 g, 12.20 mmol) in $CH_2Cl_2$ (36.0 mL) was added diethylamine (18.0 mL) at 0° C. and the reaction mixture was stirred at room temperature for 3 h. After complete consumption of the starting material (monitored by TLC), the reaction mixture was concentrated under reduced pressure to obtain the crude compound. The crude material was purified by column chromatography (Silica 100-200 mesh; 5% MeOH in DCM) to afford 6-(hydroxymethyl)-8-(2-methylbutyl)hexahydro-4H-pyrazino[1,2-a]pyrimidine-4,7(6H)-dione (3.0 g, 93.75% yield) as a viscous colorless oil. MS (ESI) m/z $[M+H]^+$: 270.20.

Step 7: Synthesis of tert-butyl 6-(hydroxymethyl)-8-(2-methylbutyl)-4,7-dioxohexahydro-2H-pyrazino[1,2-a]pyrimidine-1(6H)-carboxylate. To a solution of 6-(hydroxymethyl)-8-(2-methylbutyl)hexahydro-4H-pyrazino[1,2-a]pyrimidine-4,7(6H)-dione (3.0 g, 11.15 mmol) in $CH_2Cl_2$ (60 mL) was added triethylamine (4.5 mL, 33.45 mmol) followed by Boc anhydride (3.78 mL, 16.72 mmol) at 0° C. and the reaction mixture was stirred at room temperature for 16 h. After complete consumption of the starting material (monitored by TLC), the reaction mixture was slowly quenched with ice cold water (30 mL) and extracted with DCM (40 mL). The organic layer was washed with brine (30 mL), dried over $Na_2SO_4$ and concentrated under reduced pressure. The crude compound was purified by column chromatography (Silica 100-200 mesh; 10% MeOH in DCM) to afford tert-butyl 6-(hydroxymethyl)-8-(2-methylbutyl)-4,7-dioxohexahydro-2H-pyrazino[1,2-a]pyrimidine-1(6H)-carboxylate (8.0 g, 31.0% yield) as a viscous yellow oil. MS (ESI) m/z $[M+H]^+$: 370.25.

Step 8: Synthesis of tert-butyl 6-(fluoromethyl)-8-(2-methylbutyl)-4,7-dioxohexahydro-2H-pyrazino[1,2-a]pyrimidine-1(6H)-carboxylate. To a solution of 6-(hydroxymethyl)-8-(2-methylbutyl)-4,7-dioxohexahydro-2H-pyrazino[1,2-a]pyrimidine-1(6H)-carboxylate (1.50 g, 4.065 mmol) in DCM (30 mL) was added DAST (1.97 g, 12.19 mmol) at −78° C. and stirred for 15 min. The reaction mixture was allowed to warm to room temperature and stirred for 3 h. After completion of the reaction (monitored by TLC), the reaction mixture was quenched with saturated $NaHCO_3$ solution (15 mL) and the aqueous layer was extracted with EtOAc (100 mL×2). The combined organic layer was washed with saturated brine (50 mL), dried over $Na_2SO_4$ and concentrated under reduced pressure to obtain crude compound. The crude material was purified by column chromatography (Silica 100-200 mesh; 5% MeOH in DCM) to afford tert-butyl 6-(fluoromethyl)-8-(2-methylbutyl)-4,7-dioxohexahydro-2H-pyrazino[1,2-a]pyrimidine-1(6H)-carboxylate (0.800 g, 72.0% yield) as a colorless viscous oil. MS (ESI) m/z $[M+H]^+$: 372.2.

Step 9: Synthesis of 6-(fluoromethyl)-8-(2-methylbutyl)hexahydro-4H-pyrazino[1,2-a]pyrimidine-4,7(6H)-dione Hydrochloride salt. To a stirred solution of tert-butyl 6-(fluoromethyl)-8-(2-methylbutyl)-4,7-dioxohexahydro-2H-pyrazino[1,2-a]pyrimidine-1(6H)-carboxylate (1.0 g, 2.695 mmol) in 1,4-dioxane (5 mL) was added 4 M HCl in dioxane (5 mL) at 0° C. and the reaction mixture was stirred at room temperature for 3 h. After complete consumption of the starting material (monitored by TLC), the reaction mixture was quenched with saturated solution of sodium bicarbonate (10 mL) and extracted with ethyl acetate (20 mL×3). The combined organic layer was washed with saturated brine (10 mL), dried over $Na_2SO_4$ and concentrated under reduced pressure to afford 6-(fluoromethyl)-8-(2-methylbutyl)hexahydro-4H-pyrazino[1,2-a]pyrimidine-4,7(6H)-dione hydrochloride salt (0.630 g, crude) as a brown sticky oil. MS (ESI) m/z $[M+H]^+$ free base: 271.00.

Example S59. Synthesis of Compound 47

To a solution of 6-(fluoromethyl)-8-(2-methylbutyl)hexahydro-4H-pyrazino[1,2-a]pyrimidine-4,7(6H)-dione hydrochloride salt (0.150 g, 0.550 mmol) in DMF (1.5 mL) was added $K_2CO_3$ (0.381 g, 2.760 mmol) followed by 1-(bromomethyl)-4-(difluoromethoxy)benzene (0.261 g, 1.100 mmol) and the reaction mixture was stirred at room temperature for 16 h. After completion (monitored by TLC), the reaction mixture was slowly quenched with ice cold water (6 mL) and extracted with EtOAc (20 mL×3). The combined organic layer was washed with saturated brine solution (10 mL), dried over $Na_2SO_4$ and concentrated under reduced pressure to get crude compound. The crude compound was purified by Prep HPLC to afford 1-(4-(difluoromethoxy)benzyl)-6-(fluoromethyl)-8-(2-methylbutyl)hexahydro-4H-pyrazino[1,2-a]pyrimidine-4,7(6H)-dione (0.040 g, 17.0% yield) as a white solid. MS (ESI) m/z $[M+H]^+$: 428.10. $^1H$ NMR (400 MHz, $CDCl_3$) δ 7.34 (d, J=8.01, 2H), 7.11 (d, J=8.01, 2H), 6.32-6.69 (m, 1H), 5.14-5.25 (m, 2H), 4.60-4.76 (m, 2H), 3.84-3.97 (m, 2H), 3.35-3.45 (m, 2H), 3.12-3.40 (m, 4H), 2.85-3.05 (m, 1H), 2.65-2.75 (m, 1H), 2.29-2.34 (m, 1H), 1.65-1.75 (m, 1H), 1.30-1.40 (m, 1H), 1.05-1.18 (m, 1H), 0.80-0.90 (m, 6H).

Example S60. Synthesis of Compound 48

To a solution of 6-(fluoromethyl)-8-(2-methylbutyl)hexahydro-4H-pyrazino[1,2-a]pyrimidine-4,7(6H)-dione hydrochloride salt (0.340 g, 1.253 mmol) in DMF (3.4 mL) was added $Cs_2CO_3$ (0.814 g, 2.506 mmol) followed by 1-(bromomethyl)-4-(trifluoromethyl)benzene (0.598 g, 2.506 mmol), and reaction mixture was stirred at room temperature for 16 h. After completion (monitored by TLC), the reaction mixture was slowly quenched with ice cold water (6 mL) and extracted with EtOAc (20 mL×3). The combined organic layer was washed with saturated brine solution (10 mL), dried over $Na_2SO_4$ and concentrated under reduced pressure to get crude compound. The crude compound was purified by prep HPLC to afford 6-(fluoromethyl)-8-(2-methylbutyl)-1-(4-(trifluoromethyl)benzyl)hexahydro-4H-pyrazino[1,2-a]pyrimidine-4,7(6H)-dione (0.045 g, 8.0% yield) as a white solid. MS (ESI) m/z $[M+H]^+$: 430.10. $^1H$ NMR (400 MHz, $CDCl_3$) δ 7.34 (d, J=8.01, 2H), 7.11 (d, J=8.01, 2H), 5.14-5.25 (m, 2H), 4.60-4.76 (m, 2H), 3.84-3.97 (m, 2H), 3.35-3.45 (m, 2H), 3.12-3.40 (m, 4H), 2.85-3.05 (m, 1H), 2.65-2.75 (m, 1H), 2.29-2.34 (m, 1H), 1.65-1.75 (m, 1H), 1.30-1.40 (m, 1H), 1.05-1.18 (m, 1H), 0.80-0.90 (m, 6H).

Example S61. Synthesis of Intermediate Compound methyl 2-(1-(4-(difluoromethoxy)benzyl)-8-(2-methylbutyl)-4,7-dioxooctahydro-2H-pyrazino[1,2-a]pyrimidin-6-yl)acetate Step 1: Synthesis of methyl 3-((((9H-fluoren-9-yl)methoxy)carbonyl)amino)-4-((2,2-diethoxyethyl)(2-methylbutyl)amino)-4-oxobutanoate. To a solution 2-((((9H-fluoren-9-yl)methoxy)carbonyl)amino)-4-methoxy-4-oxobutanoic acid (1.90 g, 9.475 mmol) stirred at 0° C. in dry DMF (30 mL) was added HATU (3.60 g, 1.137 mmol) followed by DIPEA (2.70 mL, 1.895 mmol), and the reaction mixture was stirred at same temperature for 10 min. To the resulting reaction mixture was added N-(2,2-diethoxyethyl)-2-methylbutan-1-amine (3.50 g, 9.475 mmol), then the mixture was allowed to warm to room temperature and stirred for 6 h. After complete consumption of the starting material (monitored by TLC), the reaction mixture was quenched with ice cold water (100 mL) and the aqueous layer was extracted with EtOAc (50 mL×2). The combined organic layer was washed with cold $H_2O$ (50 mL) followed by brine (50 mL), dried over $Na_2SO_4$ and concentrated under reduced pressure to get crude product. The crude material was purified by CombiFlash column chromatography using 50% EtOAc in n-hexanes to afford methyl 3-((((9H-fluoren-9-yl)methoxy)carbonyl)amino)-4-((2,2-diethoxyethyl)(2-methylbutyl)amino)-4-oxobutanoate (4.30 g, 83.0% yield) as a white solid. MS (ESI) m/z $[M+H-EtOH]^+$: 509.2.

Step 2: Synthesis of methyl 3-amino-4-((2,2-diethoxyethyl)(2-methylbutyl)amino)-4-oxobutanoate. To a solution of methyl 3-((((9H-fluoren-9-yl)methoxy)carbonyl)amino)-4-((2,2-diethoxyethyl)(2-methylbutyl)amino)-4-oxobutanoate (1.36 g, 2.451 mmol) in $CH_2Cl_2$ (27.0 mL) was added diethylamine (1.53 mL, 14.71 mmol) at room temperature and the reaction mixture was stirred for 3 h. After complete consumption of the starting material (monitored by TLC), the reaction mixture was concentrated under reduced pressure to obtained crude compound. The crude compound was purified by CombiFlash column chromatography using 5% MeOH in DCM to afford methyl 3-amino-4-((2,2-diethoxyethyl)(2-methylbutyl)amino)-4-oxobutanoate (0.700 g, 86% yield) as yellow viscous liquid. MS (ESI) m/z $[M+H-EtOH]^+$: 287.68.

Step 3: Synthesis of methyl 3-(3-((((9H-fluoren-9-yl)methoxy)carbonyl)amino)propanamido)-4-((2,2-diethoxyethyl)(2-methylbutyl)amino)-4-oxobutanoate. To a stirred solution of 3-((((9H-fluoren-9-yl)methoxy)carbonyl)amino)propanoic acid (0.490 g, 1.594 mmol) in dry DMF (10 mL) maintained at 0° C. was added HATU (0.720 g, 1.913 mmol), DIPEA (0.555 mL, 3.188 mmol) followed by the addition of methyl 3-amino-4-((2,2-diethoxyethyl)(2-methylbutyl)amino)-4-oxobutanoate (0.530 g, 1.594 mmol). The reaction mixture was allowed to warm to room temperature and stirred for 6 h. After completion, the reaction mixture was quenched with ice cold water (20 mL) and the aqueous layer was extracted with EtOAc (20 mL×2). The organic layer was washed with cold $H_2O$ (10 mL) followed by saturated brine (20 mL), dried over $Na_2SO_4$ and concentrated under reduced pressure. The crude compound was purified by Combiflash column chromatography using 5% MeOH in DCM to afford methyl 3-(3-((((9H-fluoren-9-yl)methoxy)carbonyl)amino)propanamido)-4-((2,2-diethoxyethyl)(2-methylbutyl)amino)-4-oxobutanoate (0.630 g, 70% yield) as an off-white solid. MS (ESI) m/z $[M+H-EtOH]^+$: 580.20.

Step 4: Synthesis of (9H-fluoren-9-yl)methyl 6-(2-methoxy-2-oxoethyl)-8-(2-methylbutyl)-4,7-dioxohexahydro-2H-pyrazino[1,2-a]pyrimidine-1(6H)-carboxylate. To a stirred solution of methyl 3-(3-((((9H-fluoren-9-yl)methoxy)carbonyl)amino)propanamido)-4-((2,2-diethoxyethyl)(2-methylbutyl)amino)-4-oxobutanoate (0.300 g, 0.4794 mmol) was added formic acid (1.5 mL) at room temperature and the reaction mixture was stirred for 16 h. After completion, the reaction mixture was concentrated and the crude obtained was purified by column chromatography (Silica 100-200 mesh; 0-5% MeOH in DCM) to afford (9H-fluoren-9-yl)methyl 6-(2-methoxy-2-oxoethyl)-8-(2-methylbutyl)-4,7-dioxohexahydro-2H-pyrazino[1,2-a]pyrimidine-1(6H)-carboxylate (0.200 g, 80% yield) as a yellow solid. MS (ESI) m/z $[M+H]^+$: 534.67.

Step 5: Synthesis of methyl 2-(8-(2-methylbutyl)-4,7-dioxooctahydro-2H-pyrazino[1,2-a]pyrimidin-6-yl)acetate. To a solution of (9H-fluoren-9-yl)methyl 6-(2-methoxy-2-oxoethyl)-8-(2-methylbutyl)-4,7-dioxohexahydro-2H-pyrazino[1,2-a]pyrimidine-1(6H)-carboxylate (0.240 g, 0.4499 mmol) in $CH_2Cl_2$ (0.5 mL) was added diethylamine (0.280 mL) and the reaction mixture was stirred at room temperature for 3 h. After complete consumption of the starting material (monitored by TLC), the reaction mixture was concentrated and the crude material was purified by combiflash column chromatography using 0-5% MeOH in DCM to afford methyl 2-(8-(2-methylbutyl)-4,7-dioxooctahydro-2H-pyrazino[1,2-a]pyrimidin-6-yl)acetate (0.130 g, 93% yield) as white solid. MS (ESI) m/z $[M-H]^+$: 310.4.

Step 6: Synthesis of methyl methyl 2-(1-(4-(difluoromethoxy)benzyl)-8-(2-methylbutyl)-4,7-dioxooctahydro-2H-pyrazino[1,2-a]pyrimidin-6-yl)acetate. To a solution of methyl 2-(8-(2-methylbutyl)-4,7-dioxooctahydro-2H-pyrazino[1,2-a]pyrimidin-6-yl)acetate (3.08 g, 9.890 mmol) in DMF (30 mL) was added $K_2CO_3$ (4.10 g, 29.66 mmol) at room temperature, and reaction mixture stirred at 80° C. for 15 min. To the resulting reaction mixture was added 1-(bromomethyl)-4-(difluoromethoxy)benzene (3.48 g, 14.36 mmol) and the stirred mixture was heated to 80° C. for 2 h. After completion, the reaction mixture was quenched with ice cold water (200 mL) and the aqueous layer was extracted with EtOAc (200 mL×2). The organic layer was washed with cold $H_2O$ (200 mL) followed by saturated brine (150 mL), dried over $Na_2SO_4$ and concentrated under reduced pressure. The crude compound obtained was purified by Combiflash column chromatography (5% MeOH in DCM) to afford methyl 2-(1-(4-(difluoromethoxy)benzyl)-8-(2-methylbutyl)-4,7-dioxooctahydro-2H-pyrazino[1,2-c]pyrimidin-6-yl)acetate (2.20 g, 48% yield) as a yellow solid. MS (ESI) m/z $[M-CH_3]^+$: 454.10.

Example S61. Synthesis of Compound 49

To a solution of methyl 2-(1-(4-(difluoromethoxy)benzyl)-8-(2-methylbutyl)-4,7-dioxooctahydro-2H-pyrazino[1,2-a]pyrimidin-6-yl)acetate (2.20 g, 4.705 mmol) in THF (22.0 mL) was added NaOH (0.560 g, 14.11 mmol) followed by water (4 mL) and the reaction mixture was stirred at room temperature for 3 h. Progress of the reaction was monitored by TLC. After completion, the reaction mixture was concentrated under reduced pressure. The crude residue was dissolved in water (10 mL), slowly acidified with 6N HCl (10 mL) and stirred for 5 min. The obtained solid precipitate was filtered through a Buchner funnel and dried under reduced pressure to afford 2-(1-(4-(difluoromethoxy)benzyl)-8-(2-methylbutyl)-4,7-dioxooctahydro-2H-pyrazino[1,2-a]pyrimidin-6-yl)acetic acid (0.85 g, 40% yield) as a white solid. MS (ESI) m/z $[M+H]^+$: 454.10. $^1H$ NMR (400 MHz, $CDCl_3$) δ 7.28-7.38 (m, 2H), 7.11 (d, J=7.99 Hz, 2H), 6.33-6.71 (m, 1H), 5.36-5.40 (m, 1H), 4.70-4.80 (m, 1H), 4.65-4.75 (m, 1H), 3.80-4.00 (m, 2H), 3.55-3.65 (m, 1H), 3.35-3.45 (m, 1H), 2.85-3.30 (m, 6H), 2.70-2.80 (m, 1H), 2.25-2.35 (m, 1H), 1.65-1.76 (m, 1H), 1.25-1.35 (m, 1H), 1.10-1.20 (m, 1H), 0.8-0.9 (m, 6H).

Example S62. Synthesis of Compound 50

To a solution of 2-(1-(4-(difluoromethoxy)benzyl)-8-(2-methylbutyl)-4,7-dioxooctahydro-2H-pyrazino[1,2-a]pyrimidin-6-yl)acetic acid (0.470 g, 1.036 mmol) in THF (5 mL) was added 1,1'-carbonyldiimidazole (0.500 g, 3.109 mmol) at room temperature and the reaction mixture was stirred for 15 min. To the resulting reaction mixture was added aq. $NH_3$ (10 mL) and reaction mixture was stirred at room temperature for 3 h. Progress of the reaction was monitored by TLC. After completion, the reaction mixture was slowly quenched with ice cold water (6 mL) and extracted with EtOAc (20 mL×3). The combined organic layer was washed with saturated brine solution (10 mL), dried over $Na_2SO_4$ and concentrated under reduced pressure to provide the crude compound. The crude compound obtained was purified by Combiflash column chromatography using 5% MeOH in DCM followed by PREP HPLC to afford 2-(1-(4-(difluoromethoxy)benzyl)-8-(2-methylbutyl)-4,7-dioxooctahydro-2H-pyrazino[1,2-a]pyrimidin-6-yl)acetamide (0.070 g, 15% yield) as a white solid. MS (ESI) m/z $[M+H]^+$: 453.20. $^1H$ NMR (400 MHz, $CDCl_3$) δ 7.30-7.40 (m, 2H), 7.05-7.15 (m, 2H), 6.39-6.70 (m, 1H), 5.20-5.40 (m, 2H), 4.75-4.85 (m, 1H), 3.95-4.05 (m, 1H), 3.75-3.85 (m, 1H), 3.50-3.60 (m, 1H), 3.30-3.40 (m, 1H), 3.05-3.25 (m, 2H), 2.85-2.95 (m, 2H), 2.55-2.70 (m, 1H), 2.25-2.35 (m, 1H), 1.70-1.80 (m, 2H), 1.30-1.40 (m, 2H), 1.05-1.20 (m, 2H), 0.75-0.90 (m, 6H).

Example S63. Synthesis of Intermediate Compound 1-(3-chloro-4-(trifluoromethyl)benzyl)-6-methylhexahydro-4H-pyrazino[1,2-a]pyrimidine-4,7(6H)-dione To a solution of 6-methylhexahydro-4H-pyrazino[1,2-a]pyrimidine-4,7(6H)-dione (500 mg, 2.732 mmol) in DMF (7 mL) was added potassium carbonate (1.13 g, 8.196 mmol) followed by 4-(bromomethyl)-2-chloro-1-(trifluoromethyl)benzene (0.894 g, 3.278 mmol) and stirred at 80° C. temperature for 12 h. After completion of the reaction, monitored by TLC (5% MeOH in DCM). The reaction mixture was poured in ice-cold water (50 mL) and the aqueous layer was extracted with EtOAc (50 mL). The organic layer was dried over anhydrous $Na_2SO_4$ and concentrated under reduced pressure. The crude obtained was purified by column chromatography (Silica 100-200 mesh; 5% MeOH in DCM) to afford 1-(3-chloro-4-(trifluoromethyl)benzyl)-6-methylhexahydro-4H-pyrazino[1,2-a]pyrimidine-4,7(6H)-dione (320 mg, 42% yield) as a white solid. MS (ESI) m/z $[M+H]^+$: 376.34.

Example S64. General Procedure F for the Synthesis of Final Compounds

To a solution of 1-(3-chloro-4-(trifluoromethyl)benzyl)-6-methylhexahydro-4H-pyrazino[1,2-a]pyrimidine-4,7(6H)-dione (150 mg, 0.400 mmol) in DMF (2 mL) at 0° C. was added $Cs_2CO_3$ (4 eq) and stirred for 20 min, then was added the appropriate alkyl halide (1.2 eq) at room temperature and the reaction mixture was heated at 80° C. and stirred for 12 h. After consumption of starting material (monitored by TLC), the reaction mixture was quenched with ice cold water and extracted with ethyl acetate. The organic layer was dried over anhydrous $Na_2SO_4$ and concentrated under reduced pressure. The crude obtained was purified by column chromatography (Silica 100-200 mesh; 5% MeOH in DCM) to give the final compounds.

Example S65. Synthesis of Compound 51

Compound 51 was synthesized by General Procedure F using (2-bromoethyl)cyclobutane as the alkyl halide. MS (ESI) m/z $[M+H]^+$: 458.2. $^1H$ NMR (400 MHz, $CDCl_3$) δ ppm 7.70 (d, J=8.07 Hz, 1H), 7.54 (s, 1H), 7.33 (d, J=8.68 Hz, 1H), 4.34 (dd, J=3.55 Hz, 1H), 3.87-3.99 (m, 2H), 3.61 (t, J=11.13 Hz, 1H), 3.25-3.42 (m, 2H), 3.08-3.19 (m, 2H), 2.89-2.98 (m, 1H), 2.64-2.74 (m, 1H) 2.29-2.38 (m, 1H) 2.17-2.27 (m, 1H) 1.97-2.09 (m, 2H) 1.72-1.92 (m, 3H) 1.58-1.66 (m, 4H) 1.55 (br. s, 3H).

Example S66. Synthesis of Compound 54

Compound 54 was synthesized by General Procedure F using (2-bromoethyl)cyclopentane as the alkyl halide. MS (ESI) m/z $[M+H]^+$: 472.15. $^1H$ NMR (400 MHz, $CDCl_3$) δ ppm 7.69 (d, J=8.11 Hz, 1H) 7.52-7.56 (m, 1H) 7.33 (d, J=7.89 Hz, 1H), (q, J=7.23 Hz, 1H), 4.36 (dd, J=10.52, 3.29 Hz, 1H), 3.87-3.98 (m, 2H), 3.63 (t, J=11.07 Hz, 1H), 3.46-3.56 (m, 1H), 3.25-3.35 (m, 1H), 3.12-3.23 (m, 2H), 2.87-2.97 (m, 1H), 2.60-2.70 (m, 1H), 2.29-2.37 (m, 1H), 1.66-1.82 (m, 2H), 1.54-1.63 (m, 1H), 1.51 (d, J=2.63 Hz, 2H), 1.42 (d, J=7.23 Hz, 3H), 1.26 (br. s, 2H) 1.04-1.16 (m, 2H) 0.80-0.92 (m, 2H).

Example S67. Synthesis of Compound 53

Step 1: Synthesis of (9H-fluoren-9-yl)methyl (1-((2,2-diethoxyethyl)(2-methylbutyl)amino)-4-methyl-1-oxopentan-2-yl)carbamate. To a stirred solution of (((9H-fluoren-9-yl)methoxy)carbonyl)leucine (20.0 g, 56.58 mmol) in dry DMF (200 mL) was added HATU (21.50 g, 56.58 mmol) followed by DIPEA (10.62 mL, 61.10 mmol) at 0° C. and the reaction mixture was stirred at same temperature for 10 min. To the resulting reaction mixture was added N-(2,2-diethoxyethyl)-2-methylbutan-1-amine (11.48 g, 56.58 mmol) at room temperature and the reaction mixture was stirred for 3 h. After complete consumption of the starting material (monitored by TLC), the reaction mixture was quenched with ice cold water (100 mL) and the aqueous layer was extracted with EtOAc (50 mL×4). The combined organic layers were washed with cold $H_2O$ (50 mL×2) followed by brine (50 mL), dried over $Na_2SO_4$ and concentrated under reduced pressure to get crude product. The crude product was purified by CombiFlash column chromatography using 5% MeOH in DCM to afford (9H-fluoren-9-yl)methyl (1-((2,2-diethoxyethyl)(2-methylbutyl)amino)-4-methyl-1-oxopentan-2-yl)carbamate (14.5 g, 47.57% yield) as a white solid. MS (ESI) m/z $[M+H]^+$: 539.04.

Step 2: Synthesis of 2-amino-N-(2,2-diethoxyethyl)-4-methyl-N-(2-methylbutyl)pentanamide. To a solution of (9H-fluoren-9-yl)methyl (1-((2,2-diethoxyethyl)(2-methylbutyl)amino)-4-methyl-1-oxopentan-2-yl)carbamate (8.50 g, 15.77 mmol) in $CH_2Cl_2$ (50 mL) was added diethylamine (16 mL, 157.7 mmol) at room temperature and the reaction mixture was stirred for 3 h. After complete consumption of the starting material (monitored by TLC), the reaction mixture was concentrated under reduced pressure to obtained crude compound. The crude compound was purified by CombiFlash column chromatography using 5% MeOH in DCM to afford 2-amino-N-(2,2-diethoxyethyl)-4-methyl-N-(2-methylbutyl)pentanamide (3.60 g, 72% yield) as a yellow viscous liquid. MS (ESI) m/z $[M+H-EtOH]^+$: 272.10.

Step 3: Synthesis of (9H-fluoren-9-yl)methyl (3-((1-((2,2-diethoxyethyl)(2-methylbutyl)amino)-4-methyl-1-oxopentan-2-yl)amino)-3-oxopropyl)carbamate. To a stirred solution of 3-((((9H-fluoren-9-yl)methoxy)carbonyl)amino)propanoic acid (3.80 g, 12.28 mmol) in dry DMF (35 mL) maintained at 0° C. was added HATU (6.48 g, 17.05 mmol) and DIPEA (4.90 mL, 28.42 mmol), followed by the addition of 2-amino-N-(2,2-diethoxyethyl)-4-methyl-N-(2-methylbutyl)pentanamide (3.60 g, 11.37 mmol). The reaction mixture was allowed to attain room temperature and stirred for 3 h. After completion, the reaction mixture was quenched with ice cold water (20 mL) and the aqueous layer was extracted with EtOAc (30 mL×2). The organic layer was washed with cold $H_2O$ (10 mL) followed by saturated brine (20 mL), dried over $Na_2SO_4$ and concentrated under reduced pressure. The crude compound was purified by Combiflash column chromatography using 5% MeOH in DCM to afford (9H-fluoren-9-yl)methyl (3-((1-((2,2-diethoxyethyl)(2-methylbutyl)amino)-4-methyl-1-oxopentan-2-yl)amino)-3-oxopropyl)carbamate (3.8 g, 55% yield) as an off-white solid. MS (ESI) m/z $[M+H-EtOH]^+$: 565.30.

Step 4: Synthesis of (9H-fluoren-9-yl)methyl 6-isobutyl-8-(2-methylbutyl)-4,7-dioxohexahydro-2H-pyrazino[1,2-a]pyrimidine-1(6H)-carboxylate. To a stirred solution of (9H-fluoren-9-yl)methyl 6-isobutyl-8-(2-methylbutyl)-4,7-dioxohexahydro-2H-pyrazino[1,2-a]pyrimidine-1(6H)-carboxylate (3.80 g, 6.231 mmol) was added formic acid (20 mL) at room temperature and the reaction mixture was stirred for 16 h. After completion, the reaction mixture was concentrated under reduced pressure. The crude compound was purified by column chromatography (Silica 100-200 mesh; 0-5% MeOH in DCM) to afford (9H-fluoren-9-yl)methyl 6-isobutyl-8-(2-methylbutyl)-4,7-dioxohexahydro-2H-pyrazino[1,2-a]pyrimidine-1(6H)-carboxylate (3.60 g, 94% yield) as a yellow solid. MS (ESI) m/z $[M+H]^+$: 518.23.

Step 5: Synthesis of 6-isobutyl-8-(2-methylbutyl)hexahydro-4H-pyrazino[1,2-a]pyrimidine-4,7(6H)-dione. To a solution of (9H-fluoren-9-yl)methyl 6-isobutyl-8-(2-methylbutyl)-4,7-dioxohexahydro-2H-pyrazino[1,2-a]pyrimidine-1(6H)-carboxylate (3.60 g, 6.954 mmol) in $CH_2Cl_2$ (36 mL) was added diethylamine (6.8 mL, 69.54 mmol) and the reaction mixture was stirred at room temperature for 16 h. After complete consumption of the starting material (monitored by TLC), the reaction mixture was concentrated under reduced pressure and the crude product was purified by combiflash column chromatography using 10-50% ethyl acetate in n-hexane to afford 6-isobutyl-8-(2-methylbutyl)hexahydro-4H-pyrazino[1,2-a]pyrimidine-4,7(6H)-dione (1.20 g, 60% yield) as a white solid. MS (ESI) m/z $[M+H]^+$: 296.10.

Step 6: Synthesis of 1-(4-(difluoromethoxy)benzyl)-6-isobutyl-8-(2-methylbutyl)hexahydro-4H-pyrazino[1,2-a]pyrimidine-4,7(6H)-dione. To a solution of 6-isobutyl-8-(2-methylbutyl)hexahydro-4H-pyrazino[1,2-a]pyrimidine-4,7(6H)-dione (0.170 g, mmol) in DMF (5 mL) was added $K_2CO_3$ (0.159 g, 1.152 mmol) at 0° C., and the reaction mixture was stirred for 10 min. To the resulting reaction mixture was added 1-(bromomethyl)-4-(difluoromethoxy)benzene (0.150 g, 0.632 mmol) at room temperature and stirred for 3 h. After completion, the reaction mixture was quenched with ice cold water (200 mL) and the aqueous layer was extracted with EtOAc (20 mL×2). The organic layer was washed with cold $H_2O$ (20 mL) followed by saturated brine (15 mL), dried over $Na_2SO_4$ and concentrated under reduced pressure. The resulting crude compound was purified by PREP HPLC to afford 1-(4-(difluoromethoxy)benzyl)-6-isobutyl-8-(2-methylbutyl)hexahydro-4H-pyrazino[1,2-a]pyrimidine-4,7(6H)-dione (0.103 g, 40% yield) as a white solid. MS (ESI) m/z $[M+H]^+$: 452.3. $^1H$ NMR (400 MHz, DMSO $d_6$) δ 7.42 (d, J=8.8 Hz, 2H), 7.14-7.24 (m, 3H), 5.0-5.10 (m, 1H), 4.50-4.60 (m, 1H), 3.90-4.00 (m, 2H), 3.60-3.70 (m, 1H), 3.02-3.40 (m, 4H), 2.70-2.85 (m, 2H), 2.0-2.10 (m, 1H), 1.50-1.70 (m, 4H), 1.20-1.35 (m, 1H), 1.0-1.10 (m, 1H), 0.70-0.98 (m, 12H).

BIOLOGICAL EXAMPLES

Example B1. Phospho-MET ELISA

Compounds were screened for potency towards the HGF/MET system using phospho-MET (pMET) ELISA kits (Cell Signaling). pMET levels were detected in samples having low (1 ng/mL) and high (10 ng/mL) concentrations of HGF.

HEK293 cells were prepared by passage into 6-well multi-plates and grown at 37° C. at 5% $CO_2$ in DMEM+10% FBS until approximately 90% confluent. Cells were then starved for at least 8 hours in serum-free growth media.

Exemplary compounds were prepared in DMEM+0.1% FBS, diluted and added to treatment media with 1 ng/mL recombinant HGF protein (R&D Systems). Cells were incubated in triplicate at 37° C. and 5% $CO_2$ for 15 minutes. Samples were then treated with 180 μL ice-cold RIPA (radioimmunoprecipitation assay) buffer and cells were lysed on ice for 15 minutes. Lysates were cleared by centrifugation at 16,000-g for 15 minutes and the supernatant was retained. Samples were normalized using a BCA assay of lysates to determine protein concentrations across the samples.

Between 50 and 100 μg total protein lysate was loaded into ELISA wells in pMET Sandwich ELISA kit (Cell Signaling Catalog #7227C), ensuring equal protein load in each well. The ELISA was processed according to manufacturer's instructions. After color developed, absorbance was read on an optical plate reader at 450 nm.

Potency measurements were determined using peak efficacy by scaling test compound dose treatments along a scale of 1-10 between 1 ng/mL and 10 ng/mL HGF doses according to the following formula:

$$y=1+(x-A)*(10-1)/(B-A)$$

where y is the normalized data-point, x is the raw data point, A is the mean HGF at 1 ng/mL, and B is the mean HGF at 10 ng/mL. The results for the calculated potency are shown in Table 2.

TABLE 2

Potency of Exemplary Compounds.

| Compound | Potency | Compound No. | Potency |
|---|---|---|---|
| 1a | ++++ | 2a | ++ |
| 3a | − | 4a | + |
| 5a | + | 6a | + |

TABLE 2-continued

| Potency of Exemplary Compounds. | | | |
|---|---|---|---|
| Compound | Potency | Compound No. | Potency |
| 7a | ++ | 8a | + |
| 9 | – | 10 | – |
| 11 | +++ | 12 | ++ |
| 13 | – | 14 | ++++ |
| 15 | – | 16 | – |
| 17 | +++ | 18 | – |
| 19 | +++ | 20 | + |
| 21 | – | 22 | +++ |
| 23 | – | 24 | – |
| 25 | – | 26 | – |
| 27 | – | 28 | – |
| 29 | – | 30 | +++ |
| 31 | – | 32 | – |
| 33 | – | 34 | – |
| 35 | – | 36 | – |
| 37 | – | 38 | – |
| 39 | – | 40 | – |
| 41 | – | 42 | ++++ |
| 43 | – | 44 | – |
| 45 | – | 46 | – |
| 47 | – | 48 | – |
| 49 | ++++ | 50 | – |
| 51 | +++ | 52 | – |
| 53 | ++ | 54 | – |

– indicates that the compound failed to significantly augment MET phosphorylation
+ indicates maximum potency at or above 100 nM
++ indicates maximum potency at or above 10 nM
+++ indicates maximum potency at or above 1 nM
++++ indicates maximum potency at or above 0.1 nM

Example B2. Cell Scattering Behavior Assay

MDCK cells were grown under normal conditions and observed to spontaneously form tight colonies as they proliferate. MDCK cells respond to HGF treatment by moving away from each other (scattering), which is quantified to assess the amount of HGF/MET activation in the cell population. In this experiment, MDCK cells were plated in a 96-well format, treated with HGF and exemplary compounds, fluorescently stained, imaged in large fields, and scattering behavior was quantified. Quantification was determined by analyzing the number of continuous groups of cells compared to the total stained area imaged (normalized particle counts).

MDCK cells were plated at low density in black-walled imaging plates and allowed to attach overnight at 37° C. and 5% $CO_2$ in DMEM+10% FBS. Cells were then starved to 2 hours in DMEM without FBS ("starve media"). Samples containing exemplary compounds were prepared in DMEM without FBS and included 5 ng/mL HGF protein ("treatment media"). A control curve was also prepared for each plate using HGF concentrations of 0, 5, 10, and 20 ng/mL. Starve media was replaced with treatment media and cells were incubated for 24 hours at 37° C. and 5% $CO_2$.

After incubation, cells were fixed by replacing treatment media with cold ethanol and incubating for 20 minutes at 4° C. Cells were then rehydrated by washing with PBS and then with stain solution (fluorescent wheat germ agglutinin; WGA488 at 20 μg/mL in PBS). Cells were incubated with stain solution 30 minutes at room temperature after which stain solution was replaced with fresh PBS.

Fields of cells were imaged using an iCyte high content imager in the green wavelength. Images were converted to binary and analyzed for particle size and particle count. For the purpose of analysis, an individual cell touching no other cells or separated colonies of cells were identified as particles, and particle counts were normalized by the total signal area to account for differences in cell number. An increase in the number of particles indicated that individual cells moved away from each other in a scattering behavior response. Compound potency was assessed by statistical increase in normalized particle count compared to HGF treatment alone. The results are shown in Table 3.

TABLE 3

| Cell Scattering Assay Results of Exemplary Compounds. | | | |
|---|---|---|---|
| Compound | Potency | Compound | Potency |
| 1a | ++++ | 2a | + |
| 3a | – | 4a | + |
| 5a | ++++ | 6a | +++ |
| 7a | ++ | 8a | +++ |
| 9 | – | 10 | – |
| 11 | ++ | 12 | ++ |
| 13 | – | 14 | +++ |
| 15 | – | 16 | – |
| 17 | – | 18 | – |
| 19 | +++ | 20 | +++ |
| 21 | – | 22 | ++ |
| 23 | – | 24 | – |
| 25 | – | 26 | – |
| 27 | NT | 28 | – |
| 29 | NT | 30 | ++ |
| 31 | – | 32 | – |
| 33 | – | 34 | – |
| 35 | – | 36 | – |
| 37 | – | 38 | NT |
| 39 | – | 40 | NT |
| 41 | – | 42 | +++ |
| 43 | – | 44 | – |
| 45 | NT | 46 | – |
| 47 | NT | 48 | NT |
| 49 | ++++ | 50 | – |
| 51 | +++ | 52 | – |
| 53 | +++ | 54 | – |

– indicates that the compound failed to significantly promote cell scattering behavior
+ indicates maximum potency at or above 100 nM
++ indicates maximum potency at or above 10 nM
+++ indicates maximum potency at or above 1 nM
++++ indicates maximum potency at or above 0.1 nM
NT indicates the compound was not tested

Example B3. Solubility Assay

Aqueous solubility is a critical drug property that helps to predict bioavailability. Generally, compounds with aqueous solubility <100 μg/ml are poor drugs. To assess compound solubility, a turbidimetric solubility assay was performed with exemplary compounds at a concentration range from 3-300 μM.

To assess a compound's solubility by turbidity, test compounds were first dissolved in organic solvent (DMSO) at a concentration of 10 mM. This compound solution was then diluted in aqueous solvent (PBS) in a dilution series from 3 to 30011M in a 96-well assay plate. Solutions were incubated at 37° C. for 2 hours.

In wells with test compounds over their solubility limit, the compound will precipitate, effectively blocking the passage of light and thus increasing the absorbance signal of UV light at a wavelength of 620 nm. Compounds were considered insoluble at a tested concentration if turbidity raises the absorbance more than 10% above control reads. The results are shown in Table 4.

TABLE 4

Solubility of Exemplary Compounds.

| Compound | Solubility | Compound | Solubility |
|---|---|---|---|
| 1a | ++++ | 2a | ++++ |
| 3a | ++++ | 4a | ++++ |
| 5a | ++++ | 6a | ++++ |
| 7a | ++++ | 8a | ++++ |
| 9 | ++++ | 10 | ++++ |
| 11 | ++++ | 12 | ++++ |
| 13 | ++++ | 14 | ++++ |
| 15 | ++++ | 16 | ++++ |
| 17 | ++++ | 18 | ++++ |
| 19 | ++++ | 20 | ++++ |
| 21 | ++++ | 22 | ++++ |
| 23 | ++++ | 24 | ++++ |
| 25 | ++++ | 26 | ++++ |
| 27 | +++ | 28 | +++ |
| 29 | ++++ | 30 | ++++ |
| 31 | ++++ | 32 | ++++ |
| 33 | ++++ | 34 | ++++ |
| 35 | ++++ | 36 | ++++ |
| 37 | ++++ | 38 | +++ |
| 39 | ++++ | 40 | ++++ |
| 41 | ++++ | 42 | ++++ |
| 43 | +++ | 44 | +++ |
| 45 | ++++ | 46 | ++++ |
| 47 | ++++ | 48 | +++ |
| 49 | ++++ | 50 | ++++ |
| 51 | +++ | 52 | +++ |
| 53 | +++ | 54 | ++ |

+ indicates solubility at 10 μM
++ indicates solubility at 30 μM
+++ indicates solubility at 100 μM
++++ indicates solubility at 300 μM

Example B4. Permeability Assay

Bioavailable drugs must permeate the cellular membranes of the lining of the digestive tract. To estimate the penetrability of exemplary compounds, the in vitro parallel artificial membrane permeability assay (PAMPA) was utilized.

Test compounds must have a standard curve in the final read plate to determine partitioned concentration of each drug. A 6-point standard curve was prepared for each compound from 0 to 200 μM in phosphate-buffered saline (PBS).

Test compound solution (300 μL in PBS) was added to the donor (bottom) well of the PAMPA plate in 5 replicates and PBS vehicle (200 μL) was added to the acceptor (top) wells of appropriate wells to match the loading of the donor plate. The bottom and top of the PAMPA plates were then sandwiched together. The PAMPA plates were then incubated at room temperature for 5 hours. After incubation, 150 μL of donor solution was added to a UV compatible plate containing the corresponding standard curve. 150 μL of acceptor well solution was added adjacent to the corresponding standard curve and donor well samples for that compound. The plate was then read using a UV plate reader.

Permeability and membrane retention were then calculated based on the following formulas:

$$\text{Permeability (cm/s): (Pe)(cm/s)}=\{-\ln[1-CA(t)/Ceq]\}/[A^*(1/VD+1/VA)^*t] \quad \text{(equation 1)}$$

where:

A=filter area (0.3 $cm^2$);

VD=donor well volume (0.3 mL);

VA=acceptor well volume (0.2 mL);

t=incubation time (seconds);

CA(t)=compound concentration in acceptor well at time t;

CD(t)=compound concentration in donor well at time t; and

Ceq=[CD(t)*VD+CA(t)*VA]/(VD+VA).

$$\text{Membrane Retention } (R)=1-[CD(t)^*VD+CA(t)^*VA]/(C0^*VD) \quad \text{(equation 2)}$$

where:

CD(t), VD, CA(t), and VA are as defined for equation 1, and

C0=initial concentration in donor well (200 uM).

The results are shown in Table 5.

TABLE 5

Permeability of Exemplary Compounds.

| Compound | Permeability | Compound | Permeability |
|---|---|---|---|
| 1a | ++ | 2a | +++ |
| 3a | +++ | 4a | + |
| 5a | +++ | 6a | +++ |
| 7a | + | 8a | + |
| 9 | ++ | 10 | NT |
| 11 | ++ | 12 | +++ |
| 13 | NT | 14 | ++ |
| 15 | NT | 16 | NT |
| 17 | ++ | 18 | NT |
| 19 | +++ | 20 | +++ |
| 21 | NT | 22 | +++ |
| 23 | NT | 24 | NT |
| 25 | NT | 26 | NT |
| 27 | NT | 28 | NT |
| 29 | NT | 30 | +++ |
| 31 | NT | 32 | NT |
| 33 | NT | 34 | NT |
| 35 | NT | 36 | NT |
| 37 | NT | 38 | NT |
| 39 | NT | 40 | NT |
| 41 | NT | 42 | ++ |
| 43 | NT | 44 | NT |
| 45 | NT | 46 | NT |
| 47 | NT | 48 | NT |
| 49 | ++ | 50 | NT |
| 51 | +++ | 52 | NT |
| 53 | +++ | 54 | +++ |

+ indicates permeability above 1 × $10^{-5}$ cm/s
++ indicates permeability above 2 × $10^{-6}$ cm/s
+++ indicates permeability below 2 × $10^{-6}$ cm/s
NT indicates the compound was not tested

Example B5. Cytotoxicity Assay

This experiment was designed to obtain a preliminary assessment of cytotoxicity. Compounds were tested at high concentrations to determine if any cytotoxic effects were observed in hepatocyte (HepG2) cell cultures by measuring the release of lactate dehydrogenase (LDH) into the culture media as a measurement of lysed/dead cells.

HepG2 cells were plated in 96-well cell culture plates and allowed to attach overnight at 37° C., 5% $CO_2$ in EMEM+10% FBS. Treatments were made in complete media (EMEM+10% FBS) and included a dilution series of test compounds from 0.1 to 100 μM. Known cytotoxin cerivastatin was used as a positive assay control and prepared at a final concentration of 0.5 μM.

Growth media was replaced with treatment media (EMEM+10% FBS containing test compound dissolved in DMSO) and cells were incubated with test compounds for 48 hours. At the end of the incubation period, supernatant media from each well was transferred to a new plate and LDH assay working solution was added. LDH assay solution undergoes a colorimetric reaction in proportion to the amount of lactate dehydrogenase (an intracellular protein that was only found in the media in the presence of lysed cells) in the media. Color reaction was quantified by measurement of absorbance at a wavelength of 490 nm.

The signal range of the assay was determined by no manipulation in a negative control treatment and full lysis of all cells in a lysis control sample. Compounds that increase the level of cytotoxicity more than 20% above negative control samples were considered cytotoxic in this assay. Results are shown in Table 6.

TABLE 6

Cytotoxicity of Exemplary Compounds.

| Compound | Cytotoxicity | Compound | Cytotoxicity |
|---|---|---|---|
| 1a | ++++ | 2a | ++++ |
| 3a | NT | 4a | ++++ |
| 5a | ++++ | 6a | ++++ |
| 7a | ++++ | 8a | ++++ |
| 9 | ++++ | 10 | NT |
| 11 | ++++ | 12 | ++++ |
| 13 | NT | 14 | ++++ |
| 15 | NT | 16 | NT |
| 17 | ++++ | 18 | NT |
| 19 | ++++ | 20 | ++++ |
| 21 | NT | 22 | ++++ |
| 23 | NT | 24 | NT |
| 25 | NT | 26 | NT |
| 27 | NT | 28 | NT |
| 29 | NT | 30 | ++++ |
| 31 | NT | 32 | NT |
| 33 | NT | 34 | NT |
| 35 | NT | 36 | NT |
| 37 | NT | 38 | NT |
| 39 | NT | 40 | NT |
| 41 | NT | 42 | ++++ |
| 43 | NT | 44 | NT |
| 45 | NT | 46 | NT |
| 47 | NT | 48 | NT |
| 49 | ++++ | 50 | NT |
| 51 | +++ | 52 | NT |
| 53 | +++ | 54 | +++ |

+ indicates non-toxic at 0.1 μM
++ indicates non-toxic at 1 μM
+++ indicates non-toxic at 10 μM
++++ indicates non-toxic at 100 μM
NT indicates the compound was not tested

Example B6. In Vitro Stability Assays

Bioavailability can be estimated by compound stability when exposed to conditions in the body. As an initial assessment of stability properties in a variety of conditions present in animals, exemplary compounds were tested for stability in a battery of simulated body compartments. Compounds were tested for stability in the following solutions: simulated gastric fluid (SGF: 34.2 mM NaCl, pH 1.2), simulated gastric fluid with the digestive enzyme pepsin (SGF+Enzyme: SGF with 3.2 mg/ml pepsin), simulated intestinal fluid with the mixture of enzymes in porcine pancreatin (SIF+Enzyme: 28.7 mM $NaH_2PO_4$, 105.7 mM NaCl, pH 6.8, 10 mg/ml pancreatin), rat plasma, and human plasma.

Test compounds were incubated at a final concentration of 5 μM in the above solutions at 37° C. with samples removed at the following time points: 0, 1, 2, and 4 hours. Reactions were stopped and prepared for quantification by addition of excess quench solution containing an internal standard (acetonitrile, 200 ng/mL bucetin). Test compound and internal standard in each sample was quantified by LC-MS/MS, and after internal normalization to bucetin, test compound concentration was expressed as a percentage of concentration at the 0-hour time point. Stability in the relevant test solution was then determined by the percent remaining at the 4-hour time point. Results are shown in Table 7.

TABLE 7

In Vitro Stability of Exemplary Compounds.

| Compound | SGF | SGF + Enz | SIF | Rat Plasma | Human Plasma |
|---|---|---|---|---|---|
| 1a | ++++ | ++++ | ++++ | ++ | ++ |
| 2a | ++++ | +++ | ++++ | ++ | ++ |
| 3a | NT | NT | NT | NT | NT |
| 4a | NT | NT | NT | NT | NT |
| 5a | +++ | + | +++ | ++ | ++ |
| 6a | +++ | + | ++ | +++ | ++ |
| 7a | ++++ | +++ | ++ | NT | NT |
| 8a | ++++ | +++ | +++ | ++++ | ++ |
| 9 | NT | NT | NT | NT | NT |
| 10 | NT | NT | NT | NT | NT |
| 11 | +++ | +++ | ++++ | ++++ | +++ |
| 12 | +++ | +++ | ++ | ++++ | +++ |
| 13 | NT | NT | NT | NT | NT |
| 14 | ++ | ++ | +++ | +++ | +++ |
| 15 | NT | NT | NT | NT | NT |
| 16 | NT | NT | NT | NT | NT |
| 17 | +++ | +++ | +++ | ++ | +++ |
| 18 | NT | NT | NT | NT | NT |
| 19 | +++ | ++ | + | +++ | +++ |
| 20 | +++ | +++ | +++ | ++ | +++ |
| 21 | NT | NT | NT | NT | NT |
| 22 | +++ | +++ | +++ | +++ | +++ |

+ indicates 20-39% compound remaining after 4 hours
++ indicates 40-79% compound remaining after 4 hours
+++ indicates 80-99% compound remaining after 4 hours
++++ indicates 100% compound remaining after 4 hours
NT indicates the compound was not tested

Example B7. In Vivo Pharmacokinetics

Administration of exemplary compounds by selected routes followed by blood collection and compound quantification in plasma was used to determine the pharmacokinetic (PK) profile of the compounds. Compounds were administered to mixed-sex Sprague-Dawley rats of at least 250 grams by dissolving the test compound in DMSO and then diluting the compound into an appropriate vehicle, either saline or saline and poly-ethylene glycol. Dosing was accomplished by either tail vein puncture (IV) or oral gavage (PO), and animals were administered compound according to their weight at 1 mL/kg. At selected intervals following administration (10, 20, 40, 60, 120, and 360 minutes), blood was collected by tail vein blood draw. Whole blood was then processed by centrifugation to produce plasma. Compound content in plasma samples was quantified by LC-MS/MS and compared to an internal standard and standard curves to determine concentration accurately.

Plasma concentrations were then averaged for each time point and plotted as a function of time. Area under the curve was calculated by integration of the curve, Cmax was the highest concentration achieved in plasma, and Tmax was determined by the timing of Cmax. Results are shown in Table 8.

TABLE 8

| Pharmacokinetic Parameters of Exemplary Compounds. | | | | | | |
|---|---|---|---|---|---|---|
| | AUC | | $C_{MAX}$ | | $T_{MAX}$ | |
| Compound | IV | PO | IV | PO | IV | PO |
| 1a | ++ | ++ | +++ | + | +++ | ++ |
| 2a | +++ | ++ | +++ | ++ | +++ | ++ |
| 3a | NT | NT | NT | NT | NT | NT |
| 4a | NT | NT | NT | NT | NT | NT |
| 5a | ++ | + | ++ | + | +++ | ++ |
| 6a | +++ | + | +++ | + | +++ | ++ |
| 7a | ++++ | + | ++++ | + | +++ | ++ |
| 8a | NT | NT | NT | NT | NT | NT |
| 9 | NT | NT | NT | NT | NT | NT |
| 10 | NT | NT | NT | NT | NT | NT |
| 11 | +++ | ++ | ++ | ++ | +++ | +++ |
| 12 | ++ | ++ | ++ | + | +++ | + |
| 13 | NT | NT | NT | NT | NT | NT |
| 14 | +++ | +++ | ++ | ++ | +++ | + |
| 15 | NT | NT | NT | NT | NT | NT |
| 16 | NT | NT | NT | NT | NT | NT |
| 17 | NT | NT | NT | NT | NT | NT |
| 18 | NT | NT | NT | NT | NT | NT |
| 19 | NT | NT | NT | NT | NT | NT |
| 20 | +++ | +++ | +++ | ++ | +++ | + |
| 21 | NT | NT | NT | NT | NT | NT |
| 22 | +++ | ++ | ++ | ++ | +++ | ++ |

AUC: ++++ indicates dose-corrected plasma AUC above 3000 ng*h/mL; +++ indicates dose-corrected plasma AUC between 1000-2999 ng*h/mL; ++ indicates dose-corrected plasma AUC between 100-999 ng*h/mL; + indicates dose-corrected plasma AUC between 1-100 ng*h/mL.
$C_{max}$: ++++ indicates dose-corrected plasma Cmax above 3000 ng/ml; +++ indicates dose-corrected plasma Cmax between 1000-2999 ng/ml; ++ indicates dose-corrected plasma Cmax between 100-999 ng/mL; + indicates dose-corrected plasma Cmax between 1-100 ng/mL.
$T_{max}$: +++ indicates Tmax below 30 minutes; ++ indicates Tmax between 30-60 minutes; + indicates Tmax above 60 minutes.
NT indicates the compound was not tested.

Example B8. Oral Availability Calculation

Oral bioavailability is critical to developing small molecule therapeutics for oral administration. Calculations of oral bioavailability (% F) are accomplished by comparing in vivo pharmacokinetic data (Example B7) using IV dosing as the maximum possible exposure and determining the exposure rate after PO administration. In these studies, dose corrected AUC from PO administration was divided by dose corrected AUC from IV administration and multiplied by 100 to yield the % F. Results are shown in Table 9.

TABLE 9

| Calculated Oral Availability of Exemplary Compounds. | |
|---|---|
| Compound | Oral Bioavailability |
| 1a | +++ |
| 2a | +++ |
| 3a | NT |
| 4a | NT |
| 5a | ++ |
| 6a | ++ |
| 7a | + |
| 8a | NT |
| 9 | NT |
| 10 | NT |
| 11 | +++ |
| 12 | +++ |
| 13 | NT |
| 14 | ++++ |
| 15 | NT |
| 16 | NT |
| 17 | NT |
| 18 | NT |
| 19 | NT |

TABLE 9-continued

| Calculated Oral Availability of Exemplary Compounds. | |
|---|---|
| Compound | Oral Bioavailability |
| 20 | ++++ |
| 21 | NT |
| 22 | +++ |

++++ indicates oral bioavailability above 50%
+++ indicates oral bioavailability between 25-50%
++ indicates oral bioavailability between 1-25%
+ indicates oral bioavailability below 1%
NT indicates the compound was not tested

Example B9. Non-Specific Protein Binding

Plasma and tissue exposures of exemplary compounds were scaled by their non-specific affinity for protein binding in target tissues or fluids to determine the fraction of compound available for interaction with the target. Non-specific binding was determined in blood plasma and brain homogenate collected from mixed-sex Sprague-Dawley rats.

Known concentrations of test compounds were mixed with plasma or brain homogenate and incubated in the donor chamber of a rapid equilibrium dialysis (RED) device with empty PBS buffer in the receiving chamber. After a 4-hour incubation at 37° C. in an orbital shaking incubator, compound in each chamber was quantified by LC-MS/MS. The unbound fraction ($f_{u,tissue}$) was calculated using the following formula:

$$f_{u,tissue} = \frac{1}{1 + \left(\frac{1}{f_{u,homogenate}} - 1\right) * D}$$

where:

$f_{u,tissue}$ is the unbound fraction in the tissue;

$f_{u,homogenate}$ is the ratio of concentration in the buffer chamber to concentration in the sample chamber; and D is the dilution factor used to produce the sample.

Results are shown in Table 10.

TABLE 10

| Non-Specific Protein Binding of Exemplary Compounds. | | |
|---|---|---|
| | Unbound Fraction | |
| Compound | Plasma | Brain |
| 1a | +++ | ++ |
| 2a | +++ | ++ |
| 3a | NT | NT |
| 4a | NT | NT |
| 5a | + | + |
| 6a | ++ | + |
| 7a | ++++ | +++ |
| 8a | NT | NT |
| 9 | NT | NT |
| 10 | NT | NT |
| 11 | + | ++ |
| 12 | ++ | ++ |
| 13 | NT | NT |
| 14 | ++ | ++++ |
| 15 | NT | NT |
| 16 | NT | NT |
| 17 | NT | NT |
| 18 | NT | NT |
| 19 | NT | NT |

TABLE 10-continued

Non-Specific Protein Binding of Exemplary Compounds.

| Compound | Unbound Fraction Plasma | Unbound Fraction Brain |
|---|---|---|
| 20 | ++ | +++ |
| 21 | NT | NT |
| 22 | ++ | ++++ |

++++ indicates unbound fraction above 0.9
+++ indicates unbound fraction between 0.5 and 0.9
++ indicates unbound fraction between 0.1 and 0.5
+ indicates unbound fraction below 0.1
NT indicates the compound was not tested

Example B10. In Vivo Tissue Distribution

The rate of distribution to target tissues is an important feature of therapeutic molecules. Tissue distribution of exemplary compounds was performed in mixed-sex Sprague-dawley rats. Test compounds were delivered via tail vein injection (IV) and tissues were collected at Tmax (10 minutes post administration). Animals were deeply anesthetized with isoflurane and whole blood was collected from the right atrium and processed by centrifugation to produce plasma. Animals were then fully perfused with PBS administered to the left ventricle to prevent blood contamination of tissues.

Tissues were collected and homogenized, and compound content in the target tissue was quantified by LC-MS/MS. Tissue distribution rates were determined by dividing the tissue concentration of compound by the plasma concentration and multiplying by 100. Results are shown in Table 11.

TABLE 11

In Vivo Tissue Distribution of Exemplary Compounds.

| Compound | Tissue Distribution (% Plasma exposure at 10 min post IV dose) Muscle | Sciatic Nerve | Brain | Hippocampus | Cerebellum | Cortex |
|---|---|---|---|---|---|---|
| 1a | NT | NT | ++ | ++ | ++ | ++ |
| 2a | ++++ | ++++ | ++ | ++ | + | ++ |
| 3a | NT | NT | NT | NT | NT | NT |
| 4a | NT | NT | NT | NT | NT | NT |
| 5a | NT | NT | ++++ | ++++ | ++++ | ++++ |
| 6a | ++++ | ++++ | ++ | ++ | ++ | ++ |
| 7a | ++ | ++++ | + | + | + | + |
| 8a | NT | NT | NT | NT | NT | NT |
| 9 | NT | NT | NT | NT | NT | NT |
| 10 | NT | NT | NT | NT | NT | NT |
| 11 | NT | ++ | ++ | + | + | + |
| 12 | NT | +++ | ++ | ++ | ++ | ++ |
| 13 | NT | NT | NT | NT | NT | NT |
| 14 | NT | ++ | ++ | ++ | ++ | ++ |
| 15 | NT | NT | NT | NT | NT | NT |
| 16 | NT | NT | NT | NT | NT | NT |
| 17 | NT | NT | NT | NT | NT | NT |
| 18 | NT | NT | NT | NT | NT | NT |
| 19 | NT | NT | NT | NT | NT | NT |
| 20 | NT | ++++ | ++++ | +++ | ++++ | ++++ |
| 21 | NT | NT | NT | NT | NT | NT |
| 22 | NT | +++ | ++ | ++ | ++ | ++ |

++++ indicates distribution above 70%
+++ indicates distribution between 40 and 69%
++ indicates distribution between 5 and 39%
+ indicates distribution between 0.05 and 5%
NT indicates the compound was not tested

Example B11. In Vivo Efficacy: Scopolamine-Induced Spatial Memory Deficit in the Morris Water Maze Exemplary compounds 2a and 6a were evaluated for their ability to reverse chemically-induced spatial memory deficits in rats in the Morris water maze. The water maze consists of a large round tank (diameter 2.1 m) filled with 26-28° C. water to a depth of −30 cm and the water was clouded with white paint. A round platform (13 cm diameter) was fixed such that it rested 2-3 cm below the surface of the water. High-contrast visual cues were placed around the tank to aid spatial orientation of test animals. Testing consisted of placing an animal into the water facing the tank wall at one of three randomly assigned starting locations and allowing the animal to swim and search for the hidden platform for up to 120 seconds. The time taken for the animal to locate the platform was recorded as the escape latency. Animals were tested 5 times per day with a 30 second rest period between trials. Testing was completed for a total of 8 consecutive days.

Animals were divided into groups (N=8 per group) depending on treatment. Control animals received only empty vehicle. Scopolamine groups received 3 mg/kg scopolamine dissolved in sterile saline by intraperitoneal (IP) injection 30 minutes prior to testing. Test compound groups received test compound at various concentrations by oral gavage (PO) dissolved in 48% sterile saline, 50% polyethylene glycol (PEG-400), and 2% DMSO 40 minutes prior to testing. Escape latencies were recorded for each animal for 5 trials each day for 8 consecutive days. Changes in escape latency curves were statistically analyzed by 2-way ANOVA with Bonferoni post-test. Results are shown in Table 12.

Exemplary compound 1a was evaluated for its ability to reverse chemically-induced spatial memory deficits in rats in the Morris water maze. The water maze consists of a large round tank (diameter 1.5 m) filled with 23-26° C. water to a depth of −30 cm and the water was clouded with white paint. A round platform was fixed such that it rested 2-3 cm below the surface of the water. High-contrast visual cues were placed around the tank to aid spatial orientation of test animals. Testing consisted of placing an animal into the water facing the tank wall at one of three randomly assigned starting locations and allowing the animal to swim and search for the hidden platform for up to 90 seconds. The time taken for the animal to locate the platform was recorded as the escape latency. Animals were tested 5 times per day with a 30 second rest period between trials. Testing was completed for a total of 5 consecutive days.

Animals were divided into groups (N=12 per group) depending on treatment. Control animals received only empty vehicle. Scopolamine groups received 2 mg/kg scopolamine dissolved in sterile saline by intraperitoneal (IP) injection 30 minutes prior to testing. Test compound groups received test compound at various concentrations by oral gavage (PO) dissolved in 78% sterile saline, 20% polyethylene glycol (PEG-400), and 2% DMSO 40 minutes prior to testing. Escape latencies were recorded for each animal for 5 trials each day for 5 consecutive days. Changes in escape latency curves were statistically analyzed by 2-way ANOVA with Bonferoni post-test. Results are shown in Table 12.

TABLE 12

In Vivo Efficacy of Exemplary Compounds.

| Compound | Dose (mg/kg) | Cognitive Improvement |
|---|---|---|
| 1a | 8 | – |
| | 2 | – |
| | 0.5 | + |
| 2a | 10 | – |
| | 1 | +++ |
| | 0.1 | – |
| 6a | 10 | ++ |
| | 1 | – |

+++ indicates post-test p-value below 0.01
++ indicates post-test p-value between 0.05 and 0.01
+ indicates post-test p-value between 0.06 and 0.05
– indicates post-test p-value above 0.06

Although the present invention has been described in some detail by way of illustration and example for purposes of clarity of understanding, the descriptions and examples should not be construed as limiting the scope of the invention. The disclosures of all patent and scientific literature cited herein are expressly incorporated herein in their entirety by reference.

The invention claimed is:

1. A compound of Formula (V):

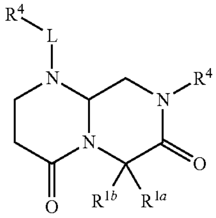

(V)

or a pharmaceutically acceptable salt thereof, wherein:

L is —C(═O)— or —$CH_2$—;

$R^{1a}$ and $R^{1b}$ are independently H or $C_1$-$C_3$ alkyl optionally substituted with —$CO_2$H;

$R^3$ is $C_4$-$C_5$ alkyl, $C_4$-$C_5$ alkenyl, or $C_1$-$C_3$ alkyl substituted with $C_3$-$C_5$ cycloalkyl; and $R^4$ is phenyl or pyridyl substituted with 1-3 substituents selected from —$CF_3$, —$OCHF_2$, —OH, fluoro, and chloro.

2. The compound of claim 1, or a pharmaceutically acceptable salt thereof, wherein L is a —C(═O)—.

3. The compound of claim 1, or a pharmaceutically acceptable salt thereof, wherein L is —$CH_2$—.

4. The compound of claim 1, or a pharmaceutically acceptable salt thereof, wherein $R^{1a}$ and $R^{1b}$ are each independently H or $C_1$-$C_3$ alkyl.

5. The compound of claim 1, or a pharmaceutically acceptable salt thereof, wherein $R^{1a}$ is methyl and $R^{1b}$ is H.

6. The compound of claim 1, or a pharmaceutically acceptable salt thereof, wherein $R^3$ is:

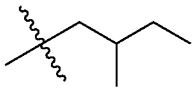, 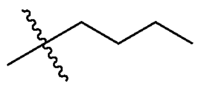,

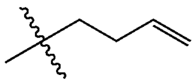, 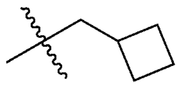,

-continued

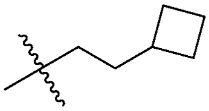, 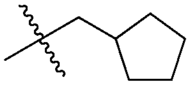,

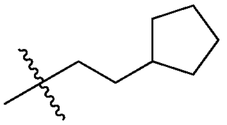, or 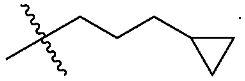.

7. The compound of claim 1, or a pharmaceutically acceptable salt thereof, wherein $R^4$ is phenyl substituted with 1-3 substituents selected from —$CF_3$, —$OCHF_2$, —OH, fluoro, and chloro.

8. The compound of claim 7, or a pharmaceutically acceptable salt thereof, wherein $R^4$ is:

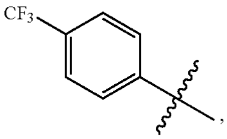, 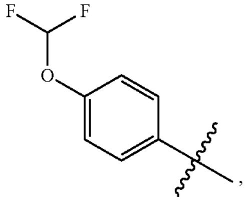,

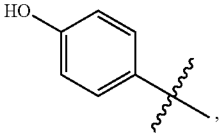, 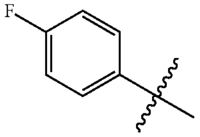, or

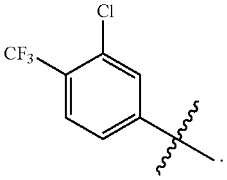.

9. The compound of claim 1, or a pharmaceutically acceptable salt thereof, wherein $R^4$ is pyridyl optionally substituted with 1-3 substituents selected from —$CF_3$, —$OCHF_2$, —OH, fluoro, and chloro.

10. The compound of claim 9, or a pharmaceutically acceptable salt thereof, wherein $R^4$ is

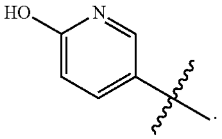.

11. The compound of claim 1, or a pharmaceutically acceptable salt thereof, wherein -L-$R^4$ is:
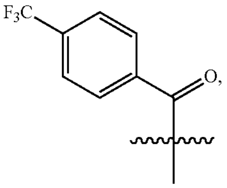,
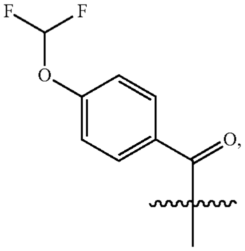,
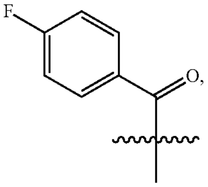,
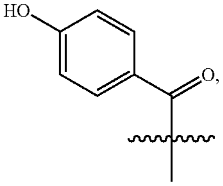,
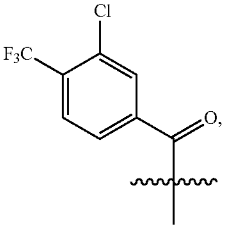,
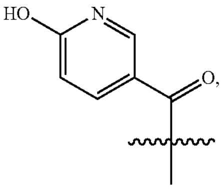,
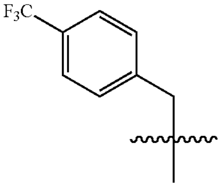,
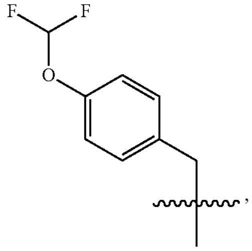,
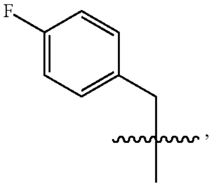,
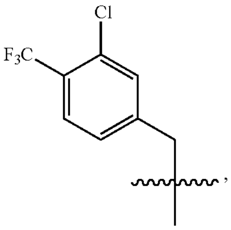, or
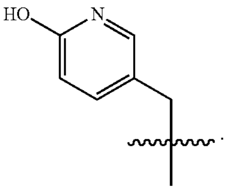.
12. A compound selected from:
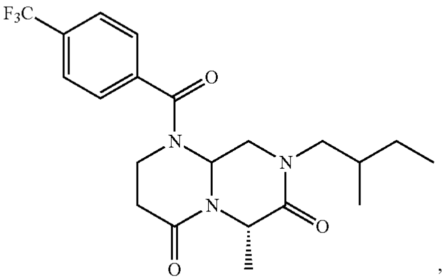 [SMILES: CCC(C)CN1CC2N(C(=O)c3ccc(C(F)(F)F)cc3)CCC(=O)N2[C@@H](C)C1=O],
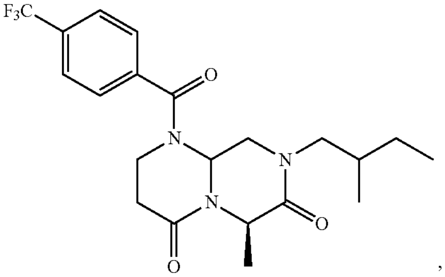,
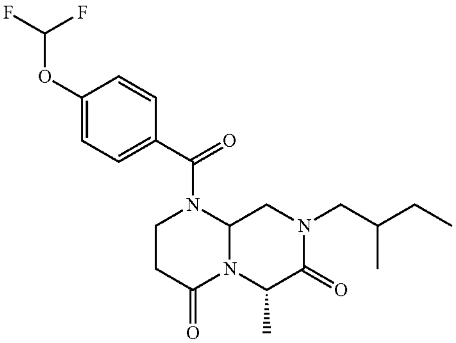,
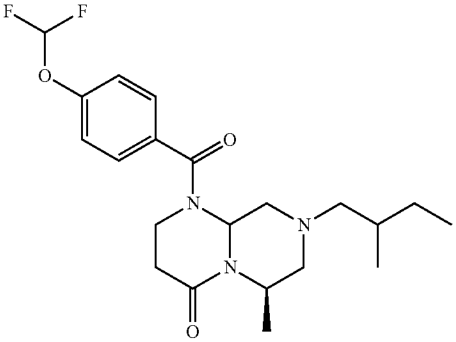,
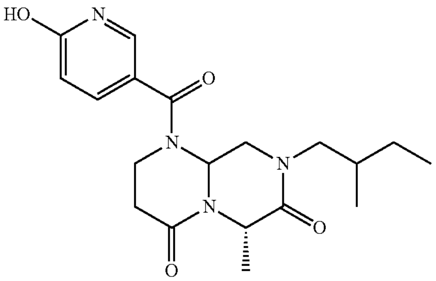, -continued
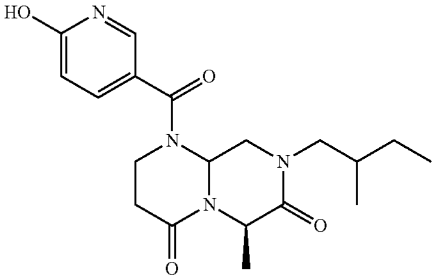
,
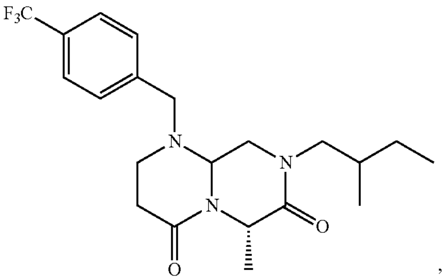 [SMILES: CCC(C)CN1CC2N(Cc3ccc(C(F)(F)F)cc3)CCC(=O)N2[C@@H](C)C1=O]
,
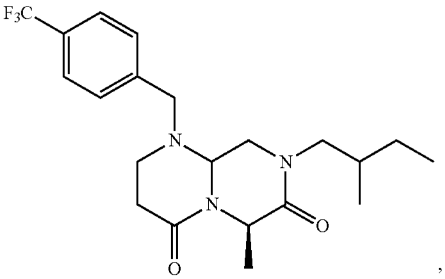
,
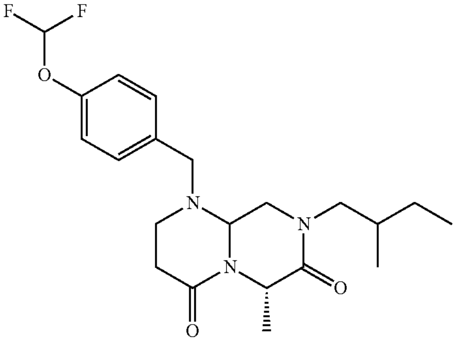
,
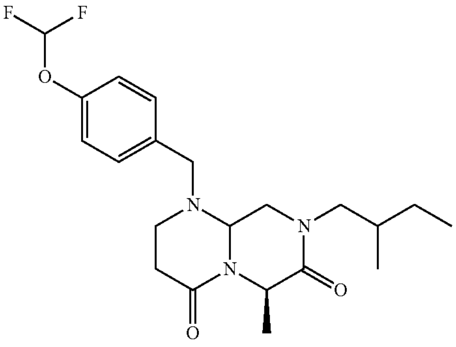
,
-continued
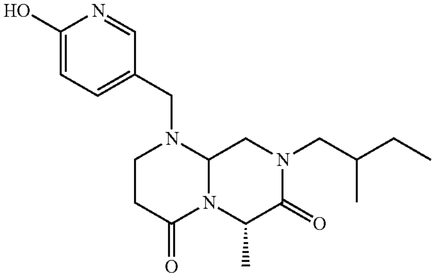
,
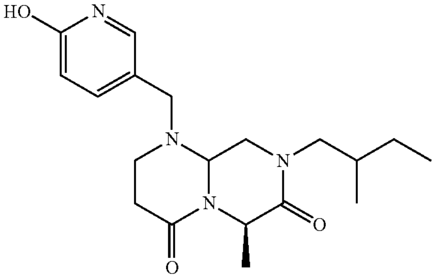
,
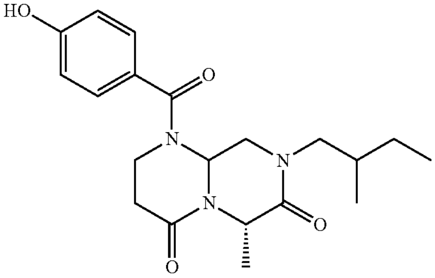
,
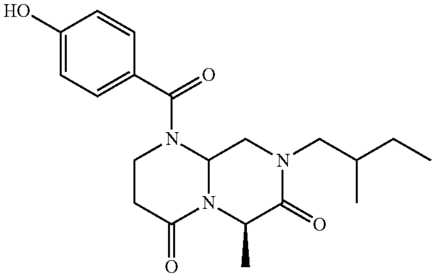
,
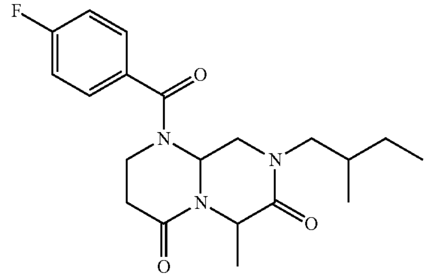
,
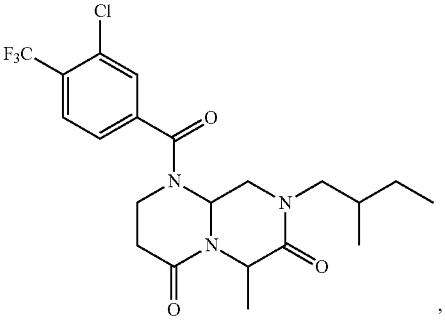
, -continued
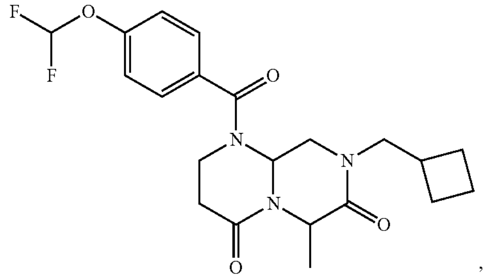
,
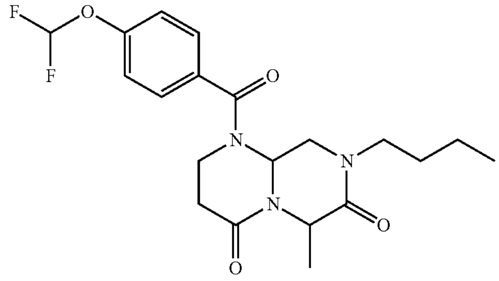
,
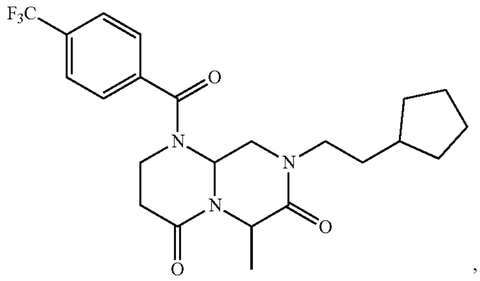
,
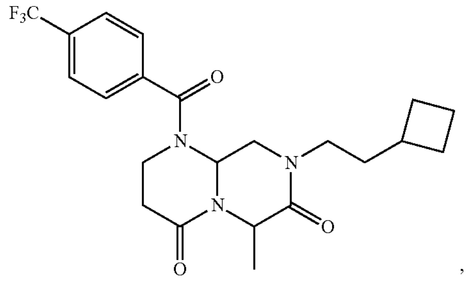
,
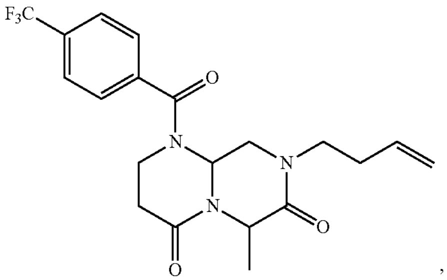
,
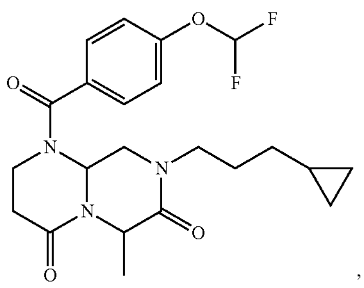
,
-continued
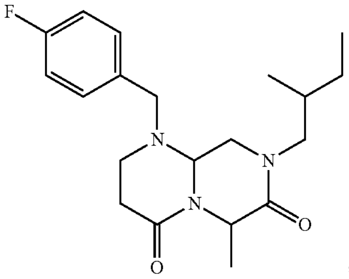
,
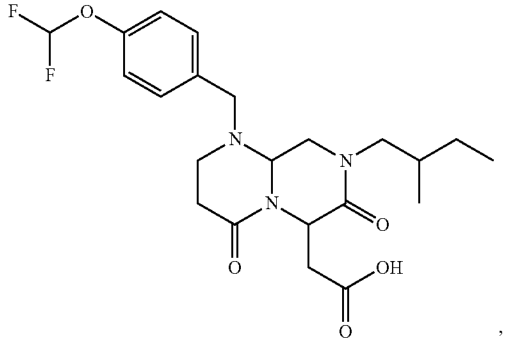
,
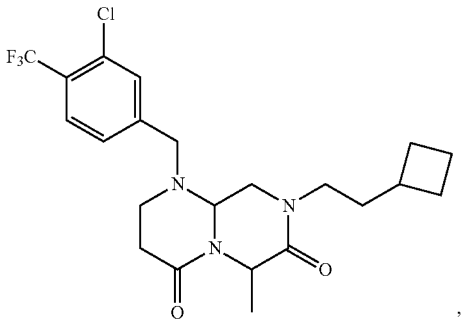
, and
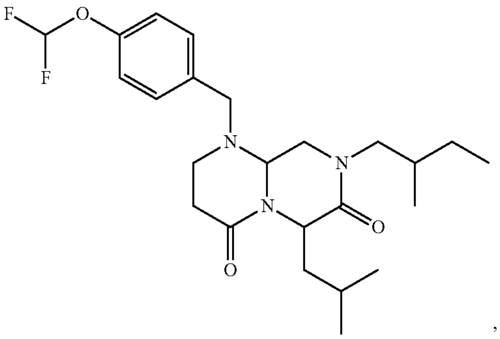
,
or a pharmaceutically acceptable salt thereof.
13. A pharmaceutical composition comprising the compound of claim 1, or a pharmaceutically acceptable salt thereof, and a pharmaceutically acceptable carrier.

14. The compound of claim 12, of the following formula:

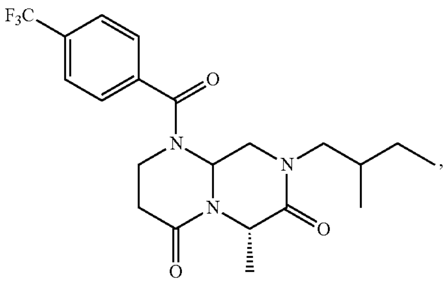, or a pharmaceutically acceptable salt thereof.

15. The compound of claim 12, of the following formula:

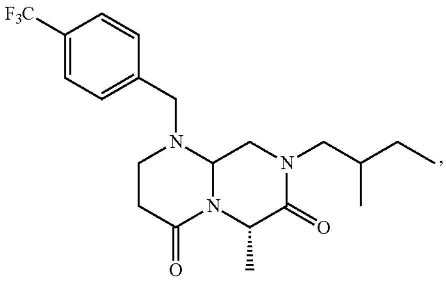, or a pharmaceutically acceptable salt thereof.

16. The compound of claim 12, of the following formula:

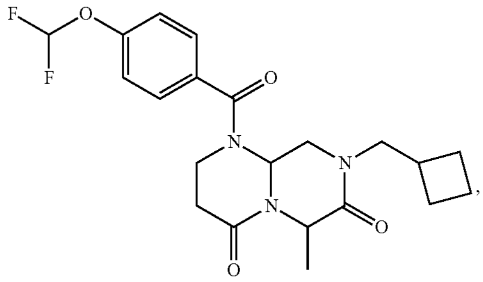 [SMILES: CC1C(=O)N(CC2CCC2)CC2N(C(=O)c3ccc(OC(F)F)cc3)CCC(=O)N12], or a pharmaceutically acceptable salt thereof.

17. The compound of claim 12, of the following formula:

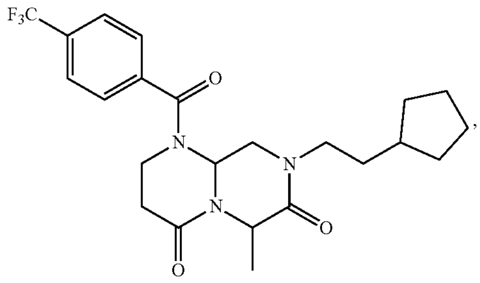 [SMILES: CC1C(=O)N(CCC2CCCC2)CC2N(C(=O)c3ccc(C(F)(F)F)cc3)CCC(=O)N12], or a pharmaceutically acceptable salt thereof.

18. The compound of claim 12, of the following formula:

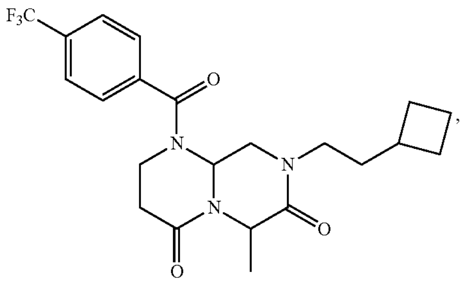 [SMILES: CC1C(=O)N(CCC2CCC2)CC2N(C(=O)c3ccc(C(F)(F)F)cc3)CCC(=O)N12], or a pharmaceutically acceptable salt thereof.

19. A pharmaceutical composition comprising the compound of claim 12, or a pharmaceutically acceptable salt thereof, and a pharmaceutically acceptable carrier.

20. A pharmaceutical composition comprising the compound of claim 14, or a pharmaceutically acceptable salt thereof, and a pharmaceutically acceptable carrier.

21. A pharmaceutical composition comprising the compound of claim 15, or a pharmaceutically acceptable salt thereof, and a pharmaceutically acceptable carrier.

22. A pharmaceutical composition comprising the compound of claim 16, or a pharmaceutically acceptable salt thereof, and a pharmaceutically acceptable carrier.

23. A pharmaceutical composition comprising the compound of claim 17, or a pharmaceutically acceptable salt thereof, and a pharmaceutically acceptable carrier.

24. A pharmaceutical composition comprising the compound of claim 18, or a pharmaceutically acceptable salt thereof, and a pharmaceutically acceptable carrier.

* * * * *